US012738355B2

(12) United States Patent
Nath et al.

(10) Patent No.: US 12,738,355 B2
(45) Date of Patent: Sep. 15, 2026

(54) METHODS OF TREATING BREAST CANCER

(71) Applicant: City of Hope, Duarte, CA (US)

(72) Inventors: Aritro Nath, Duarte, CA (US); Andrea Bild, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 511 days.

(21) Appl. No.: 18/031,855

(22) PCT Filed: Oct. 15, 2021

(86) PCT No.: PCT/US2021/055285
§ 371 (c)(1),
(2) Date: Apr. 13, 2023

(87) PCT Pub. No.: WO2022/082048
PCT Pub. Date: Apr. 21, 2022

(65) Prior Publication Data

US 2025/0201370 A1 Jun. 19, 2025

Related U.S. Application Data

(60) Provisional application No. 63/092,255, filed on Oct. 15, 2020.

(51) Int. Cl.

| | |
|---|---|
| ***C12Q 1/68*** | (2018.01) |
| ***A61K 31/282*** | (2006.01) |
| ***A61K 31/337*** | (2006.01) |
| ***A61K 31/475*** | (2006.01) |
| ***A61K 31/513*** | (2006.01) |
| ***A61K 31/519*** | (2006.01) |
| ***A61K 31/675*** | (2006.01) |
| ***A61K 31/704*** | (2006.01) |
| ***A61K 31/7068*** | (2006.01) |
| ***A61K 33/243*** | (2019.01) |
| ***C07H 21/04*** | (2006.01) |
| ***G16B 25/10*** | (2019.01) |
| ***G16B 40/20*** | (2019.01) |
| ***G16H 20/10*** | (2018.01) |

(52) U.S. Cl.
CPC ........... *G16H 20/10* (2018.01); *A61K 31/282* (2013.01); *A61K 31/337* (2013.01); *A61K 31/475* (2013.01); *A61K 31/513* (2013.01); *A61K 31/519* (2013.01); *A61K 31/675* (2013.01); *A61K 31/704* (2013.01); *A61K 31/7068* (2013.01); *A61K 33/243* (2019.01); *G16B 25/10* (2019.02); *G16B 40/20* (2019.02)

(58) Field of Classification Search
None
See application file for complete search history.

(56) References Cited

U.S. PATENT DOCUMENTS

2014/0018253 A1 1/2014 Griffith et al.
2019/0390280 A1* 12/2019 Liu ................. G01N 33/57415

OTHER PUBLICATIONS

Bourdeau, V. et al. (Jan. 2008, e-published Nov. 5, 2007). "Mechanisms of primary and secondary estrogen target gene regulation in breast cancer cells," *Nucleic Acids Res* 36(1):76-93.
Cardoso, F. et al. (Aug. 25, 2016). "70-Gene Signature as an Aid to Treatment Decisions in Early-Stage Breast Cancer," *N Engl J Med* 375(8):717-729.
Curtis, C. et al. (Apr. 18, 2012). "The genomic and transcriptomic architecture of 2,000 breast tumours reveals novel subgroups," *Nature* 486(7403):346-352.
Fu, Y. et al. (Nov. 23, 2019). "Identification of Hub Genes Using Co-Expression Network Analysis in Breast Cancer as a Tool to Predict Different Stages," *Med Sci Monit* 25:8873-8888.
International Search Report mailed on Mar. 10, 2022, for PCT Application No. PCT/US2021/055285, filed Oct. 15, 2021, 6 pages.
Jeselsohn, R. et al. (Dec. 1, 2016, e-published May 16, 2016). "TransCONFIRM: Identification of a Genetic Signature of Response to Fulvestrant in Advanced Hormone Receptor-Positive Breast Cancer," *Clin Cancer Res* 22(23):5755-5764.
Paik, S. et al. (Dec. 2004). "A multigene assay to predict recurrence of tamoxifen-treated, node-negative breast cancer," *N Engl J Med* 351(27):2817-2826.
Parker, J.S. et al. (Mar. 10, 2009, e-published Feb. 9, 2009). "Supervised risk predictor of breast cancer based on intrinsic subtypes," *J Clin Oncol* 27(8):1160-1167.
Ramaker, R.C. et al. (Jun. 13, 2017). "RNA sequencing-based cell proliferation analysis across 19 cancers identifies a subset of proliferation-informative cancers with a common survival signature," *Oncotarget* 8(24):38668-38681.
Sinn, B.V. et al. (May 30, 2019). "SETER/PR: a robust 18-gene predictor for sensitivity to endocrine therapy for metastatic breast cancer," *NPJ Breast Cancer* 5:16.
Sotiriou, C. et al. (Sep. 2, 2003, e-published Aug. 13, 2003). "Breast cancer classification and prognosis based on gene expression profiles from a population-based study," *PNAS USA* 100(18):10393-10398.
Sparano, J.A. et al. (Jul. 12, 2018, e-published Jun. 3, 2018). "Adjuvant Chemotherapy Guided by a 21-Gene Expression Assay in Breast Cancer," *N Engl J Med* 379(2):111-121.
Written Opinion mailed on Mar. 10, 2022, for PCT Application No. PCT/US2021/055285, filed Oct. 15, 2021, 8 pages.

* cited by examiner

*Primary Examiner* — Jeanine A Goldberg
(74) *Attorney, Agent, or Firm* — Mintz, Levin, Cohn, Ferris, Glovsky and Popeo, P.C.

(57) ABSTRACT

The present disclosure provides methods and compositions useful for treating metastatic breast cancer in a subject in need thereof. The methods include measuring gene expression in breast cancer cells obtained from the subject, and administering an anticancer therapeutic to the subject.

16 Claims, 50 Drawing Sheets

Specification includes a Sequence Listing.

Training concordance = 0.785
(0.783 - 0.787 95% C.I.)

Test concordance = 0.926
(0.920 - 0.932 95% C.I.)

Training concordance = 0.734
(0.734 - 0.735 95% C.I.)

Test concordance = 0.793
(0.789 - 0.797 95% C.I.)

Training concordance = 0.802
(0.801 - 0.803 95% C.I.)

Test concordance = 0.927
(0.922 - 0.932 95% C.I.)

Training concordance = 0.685
(0.685 - 0.686 95% C.I.)

Test concordance = 0.693
(0.689 - 0.697 95% C.I.)

Actual vs. predicted risk correlation

Median $\rho$ = 0.41

0.00 0.25 0.50 0.75 1.00

Actual vs. predicted risk correlation

Actual vs. predicted risk correlation

Actual vs. predicted risk correlation

RAMASWAMY METASTASIS UP
ssGSEA score
0.44
0.40
0.36
Low/Med
High
P = 1.7x10-20
SARRIO EPITHELIAL MESENCHYMAL TRANSITION UP
ssGSEA score
0.40
0.35
0.30
0.25
0.20
0.15
Low/Med
High
P = 5.1x10-31
YU MYC TARGETS UP
ssGSEA score
0.5
0.4
0.3
0.2
Low/Med
High
P = 9.8x10-33
STEIN ESRRA TARGETS RESPONSIVE TO ESTROGEN DN
ssGSEA score
0.4
0.3
0.2
Low/Med
High
P = 2.2x10-18

Number at Risk

| ENDORSE | 0 | 60 | 120 | 180 | 240 | 300 |
|---|---|---|---|---|---|---|
| Low risk | 402 | 350 | 235 | 146 | 52 | 3 |
| Medium risk | 364 | 277 | 169 | 99 | 44 | 3 |
| High risk | 67 | 40 | 25 | 13 | 5 | 2 |

FIGS. 8A

METABRIC cohort (ER+/HER2-, n = 833)
Prediction model validation (bootstrap resampling, B=150)

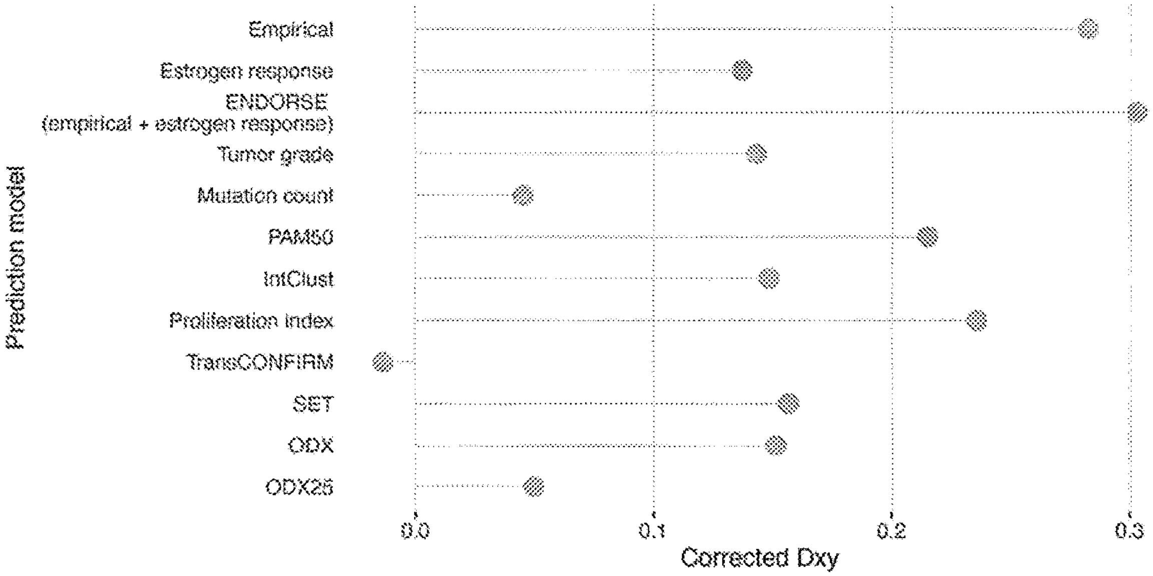

FIGS. 8B

Model comparisons

| *Model 1* | *Model 2* | *Variance test* H1: Model 1 and Model 2 are distinguishable | *Likelihood ratio test (nested)* H1A: Full model fits better than reduced model | *Partial likelihood ratio test (non-nested)* H1A: Model 1 fits better than Model 2 |
|---|---|---|---|---|
| *ENDORSE* | Empirical | $1.47 \times 10^{-3}$ | $1.09 \times 10^{-3}$ | |
| | Estrogen response | $3.83 \times 10^{-6}$ | $3.93 \times 10^{-14}$ | |
| | ***METABRIC tumor characteristics and signatures*** | | | |
| | Tumor grade | $< 2 \times 10^{-16}$ | | 2.08 x 10-3 |
| | Mutation count | $< 2 \times 10^{-16}$ | | 9.76 x 10-6 |
| | PAM50 | 2.22 x 10-8 | | 0.033 |
| | IntClust | $< 2 \times 10^{-16}$ | | 0.02 |
| | Proliferation index | $3.73 \times 10^{-5}$ | | $4.42 \times 10^{-5}$ |
| | ***External signatures*** | | | |
| | TransCONFIRM | $1.67 \times 10^{-7}$ | | $9.73 \times 10^{-6}$ |
| | SET | $< 2 \times 10^{-16}$ | | $3.53 \times 10^{-5}$ |
| | ODX | $2.18 \times 10^{-7}$ | | $6.15 \times 10^{-5}$ |
| | ODX25 | $1.49 \times 10^{-6}$ | | $1.32 \times 10^{-5}$ |

FIG. 9A
FIG. 9B
TransCONFIRM cohort (ER+ metastatic breast cancer, n = 112)
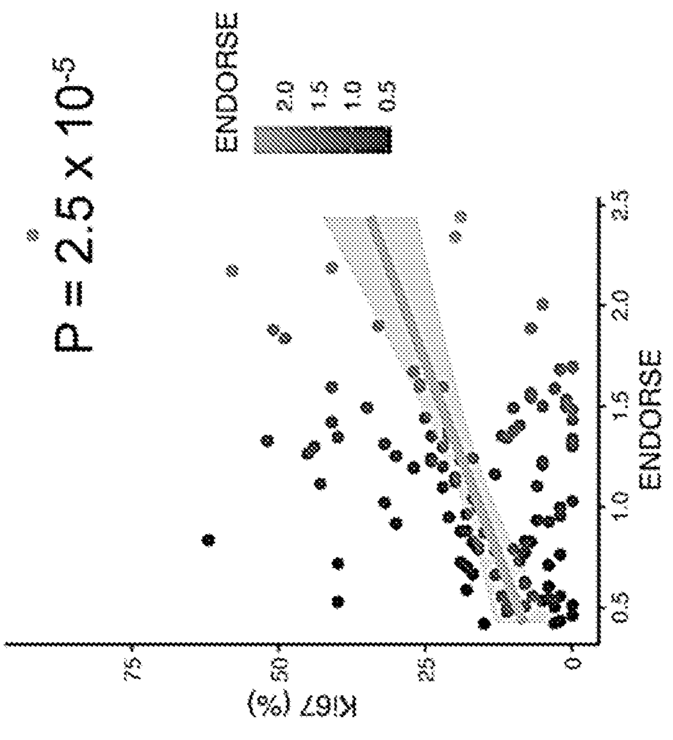
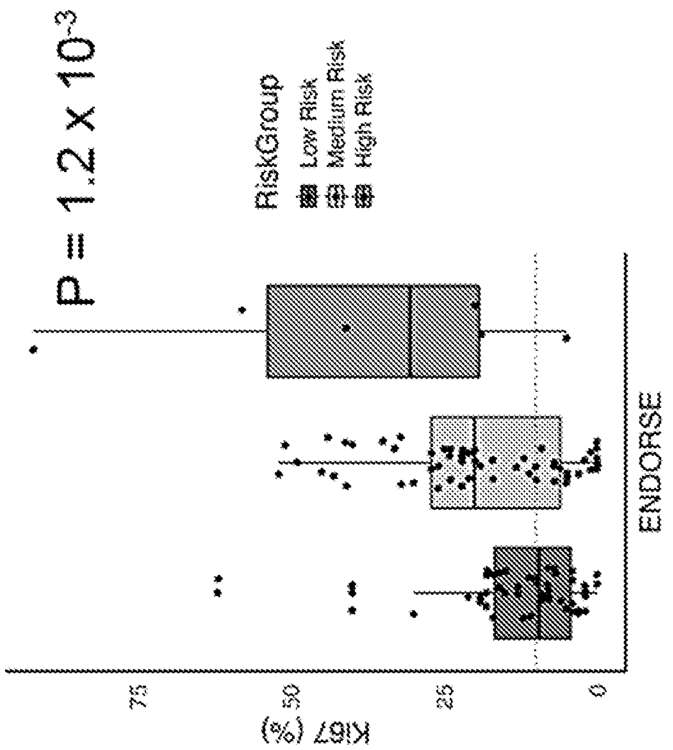

FIGS. 10G

| Model 1 | Model 2 | Variance test<br>*H1: Model 1 and Model 2 are distinguishable* | Partial likelihood ratio test (non-nested)<br>*H1A: Model 1 fits better than Model 2* |
|---|---|---|---|
| | ***Overall survival*** | | |
| *ENDORSE* | SET | $2.1 \times 10^{-4}$ | 0.667 |
| | TransCONFIRM | $2.6 \times 10^{-3}$ | 0.046 |
| | ***Progression free survival*** | | |
| | SET | $1.2 \times 10^{-5}$ | 0.258 |
| | TransCONFIRM | $9 \times 10^{-6}$ | 0.038 |

PIK3CA reference biomarkers

| Amino acid change | Coding variant | Protein variant |
|---|---|---|
| C420R | c.1258T>C | p.Cys420Arg |
| E542K | c.1624G>A | p.Glu542Lys |
| E545A | c.1634A>C | p.Glu545Ala |
| E545D | c.1635G>T | p.Glu545Asp |
| E545G | c.1634A>G | p.Glu545Gly |
| E545K | c.1633G>A | p.Glu545Lys |
| H1047L | c.3140A>T | p.His1047Leu |
| H1047R | c.3140A>G | p.His1047Arg |
| H1047Y | c.3139C>T | p.His1047Tyr |
| Q546E | c.1636C>G | p.Gln546Glu |
| Q546R | c.1637A>G | p.Gln546Arg |

METHODS OF TREATING BREAST CANCER

CROSS-REFERENCE TO RELATED APPLICATIONS

This application is a national stage filing under U.S.C. 371 of international application PCT/US2021/055285, filed Oct. 15, 2021, which claims priority to U.S. Provisional Application No. 63/092,255, filed Oct. 15, 2020, which are hereby incorporated by reference in their entirety and for all purposes.

STATEMENT AS TO RIGHTS TO INVENTIONS MADE UNDER FEDERALLY SPONSORED RESEARCH AND DEVELOPMENT

This invention was made with government support under U54 CA209978 awarded by the National Institutes of Health. The government has certain rights in the invention.

REFERENCE TO A SEQUENCE LISTING, A TABLE OR A COMPUTER PROGRAM LISTING APPENDIX SUBMITTED AS AN ASCII TEXT FILE

The Sequence Listing written in file 048440-756001WO_SequenceListing_ST25.TXT, created on Oct. 15, 2021, 9,408 bytes, machine format IBM-PC, MS Windows operating system, is hereby incorporated by reference.

BACKGROUND

Estrogen receptor (ER)-positive tumors are the most prevalent form of newly diagnosed and metastatic breast cancers. ER+ tumors are heterogeneous, both in terms of dependence on estrogen signaling for growth and survival, and intrinsic or acquired resistance to endocrine therapy. Therefore, optimal clinical management of each individual ER+ breast cancer depends on accurate prediction of response to endocrine therapy. However, there are no recommended genomic tests or prognostic biomarkers for advanced, metastatic breast cancers that could aid in therapeutic decision making.

Provided herein, inter alia, are solutions to these and other problems in the art.

BRIEF SUMMARY OF THE INVENTION

In view of the foregoing, there is a need for a tumor expression-based prognostic biomarker for ER+ breast cancers, independent of the tumor stage or lymph node status. Aspects of the present disclosure addresses this need, and provide additional benefits as well.

In an aspect is provided a method of treating cancer in a metastatic estrogen receptor positive breast cancer subject, the method including: (a) measuring an expression level of a transcriptome set of RNA transcripts in a plurality of cells obtained from a tumor from the metastatic estrogen receptor positive breast cancer subject, wherein the transcriptome set of RNA transcripts includes RNA transcripts expressed from: (i) an endocrine signaling negative gene set, wherein the endocrine signaling negative gene set includes a gene selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25; (ii) an endocrine signaling positive gene set, wherein the endocrine signaling positive gene set includes a gene selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1; and (ii) a remainder gene set, wherein the remainder gene set consists of all genes expressing the transcriptome set of RNA transcripts except the endocrine signaling positive gene set and the endocrine signaling negative gene set; (b) determining a high level of expression of the endocrine signaling negative gene set relative to a first standard control; (c) determining a low level of expression of the endocrine signaling positive gene set relative to a second standard control; and (d) administering a chemotherapy to the metastatic estrogen receptor positive breast cancer subject and not administering anticancer endocrine therapy to the metastatic estrogen receptor positive breast cancer subject.

In an aspect is provided a method of treating cancer in a metastatic estrogen receptor positive breast cancer subject, the method including: (a) measuring an expression level of a transcriptome set of RNA transcripts in a plurality of cells obtained from a tumor from the metastatic estrogen receptor positive breast cancer subject, wherein the transcriptome set of RNA transcripts includes RNA transcripts expressed from: (i) an endocrine signaling negative gene set, wherein the endocrine signaling negative gene set includes a gene selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25; (ii) an endocrine signaling positive gene set, wherein the endocrine signaling negative gene set includes a gene selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1; and (iii) a remainder gene set, wherein the remainder gene set consists of all genes expressing the transcriptome set of RNA transcripts except the endocrine signaling positive gene set and the endocrine signaling negative gene set; (b) determining a low level of expression of the endocrine signaling negative gene set relative to a third standard control; (c) determining a high level of expression of the endocrine signaling positive gene set relative to a fourth standard control; and; and (d) administering anticancer endocrine therapy to the metastatic estrogen receptor positive breast cancer subject and not administering chemotherapy to the metastatic estrogen receptor positive breast cancer subject.

In an aspect a method of treating cancer in a metastatic estrogen receptor positive breast cancer subject is provided, the method including: (a) measuring an expression level of a transcriptome set of RNA transcripts in a plurality of cells obtained from a tumor from the metastatic estrogen receptor positive breast cancer subject, wherein the transcriptome set of RNA transcripts includes RNA transcripts expressed from: (i) an endocrine signaling negative gene set, wherein the endocrine signaling negative gene set includes a gene selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25; (ii) an endocrine signaling positive gene set, wherein the endocrine signaling negative gene set includes a gene selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1; and (iii) a remainder gene set, wherein the remainder gene set consists of all genes expressing the transcriptome set of RNA transcripts except the endocrine signaling positive gene set and the endocrine signaling negative gene set; (a) determining a first aggregate rank of the expression level of RNA transcripts from the endocrine signaling negative gene set relative to the expression level of RNA transcripts from the remainder gene set and calculating an empirical gene set enrichment score ($GES_{emp}$); (b) determining a second aggregate rank of the expression level of RNA transcripts from an endocrine signaling positive gene set relative to the expression level of RNA transcripts from said remainder gene set and calculating an estrogen response gene set enrichment score ($GES_{er}$); and (c) calculating a risk score according to according to the function:

$$\exp(1.54 \times GES_{emp} + -2.72 \times GES_{er})$$

when the risk score is greater than or equal to 2, administering chemotherapy to the metastatic estrogen receptor positive breast cancer subject and not administering anticancer endocrine therapy to the metastatic estrogen receptor positive breast cancer subject, and when said risk score is less than 2, administering anticancer endocrine therapy to the metastatic estrogen receptor positive breast cancer subject and not administering chemotherapy to the metastatic estrogen receptor positive breast cancer subject.

In an aspect, provided herein is a method of detecting a breast cancer of a subject, the method including measuring levels of a plurality of target RNA molecules of a tumor of the subject, wherein the tumor is a breast cancer tumor, and further wherein the plurality of target RNA molecules are selected from transcripts of Table 1 genes. In embodiments, the method includes detecting endocrine therapy responsive cancer cells or endocrine therapy resistant cancer cells of the tumor, where (i) endocrine therapy resistant cancer cells are detected when the transcript levels are greater than a threshold, or (ii) endocrine therapy responsive cancer cells are detected when the transcript levels are below the threshold.

In an aspect, provided herein is a method of detecting a breast cancer of a subject, the method including (a) measuring levels of a plurality of target RNA molecules of a tumor of the subject, wherein the tumor is a breast cancer tumor, and further wherein the plurality of target RNA molecules are selected from transcripts of Table 1 genes; (b) aggregating the levels to produce an aggregate measure; and (c) detecting endocrine therapy responsive cancer cells or endocrine therapy resistant cancer cells of the tumor, where (i) endocrine therapy resistant cancer cells are detected when the aggregate measure is equal to or greater than a threshold, or (ii) endocrine therapy responsive cancer cells are detected when the aggregate measure is below the threshold.

In an aspect, provided herein are methods of preparing a sample from a female subject with estrogen receptor positive (ER+) breast cancer, the method including: (a) extracting RNA from a breast cancer tumor of the subject; (b) hybridizing oligonucleotides to a plurality of target RNA molecules in the extracted RNA, where the plurality of target RNA molecules are selected from transcripts of Table 1 genes; and (c) measuring levels of the target RNA molecules.

In an aspect, provided herein are methods of treating breast cancer in a subject, including detecting a breast cancer of the subject, where detecting includes (a) measuring levels of a plurality of target RNA molecules of a tumor of the subject, wherein the tumor is a breast cancer tumor, and further wherein the plurality of target RNA molecules are selected from transcripts of Table 1; (b) aggregating the levels to produce an aggregate measure; and (c) administering a cancer therapy to the subject, where (i) the cancer therapy is not endocrine therapy when the aggregate measure is equal to or greater than a threshold, or (ii) the cancer therapy is endocrine therapy when the aggregate measure is below the threshold.

In an aspect, provided herein are methods of treating an estrogen receptor positive (ER+) breast cancer in a female subject, the method including (a) detecting an increased level of a plurality of target RNA molecules of a breast cancer tumor of the subject, wherein the plurality of target RNA molecules are selected from transcripts of Table 1, and where the increased level is increased relative to a control; and (b) administering a cancer therapy to the subject, wherein the cancer therapy is not an endocrine therapy.

In an aspect, provided herein are systems including (a) at least one processor; and (b) at least one memory including program code which when executed by the at least one processor provides operations for performing one or more steps in the methods described herein.

BRIEF DESCRIPTION OF THE DRAWINGS

FIG. 2A are density plots showing distribution of concordance indices from Cox proportional hazards model fit in training (red) and test (blue) dataset across 50×10-fold cross-validations. The solid vertical line indicates mean concordance, also listed inside the boxes along with the 95% confidence intervals (CI). FIG. 2B are boxplots representing Spearman's correlation between actual risk of adverse event vs. predicted risk of event in the test dataset. Risk predictions were performed using coefficients determined in the training dataset applied to the test dataset.

" FIG. 3A. Kaplan-Meier survival curves and accompanying risk table of METABRIC ER+ breast cancers stratified into low, medium and high-risk groups based on hazard ratios estimated using ENDORSE scores. FIG. 3B are histogram and cumulative density function plots showing frequency distribution of samples based on estimated ENDORSE risk. FIG. 3C and FIG. 3D. are a series of Kaplan-Meier survival curves showing stratification of METABRIC ER+ breast cancers based on reduced number of available genes (FIG. 3C) or samples (FIG. 3D) for calculating ENDORSE scores.

FIG. 4A are Kaplan-Meier survival curves of ER+ breast cancer metastases stratified based on ENDORSE risk estimates, along with survival risk table. FIGS. 4B and 4C: right panels show violin plots for ER+ breast cancers stratified based on ENDORSE risk estimates (X-axis) and Ki67% (Y-axis). The dotted line indicates a Ki67 staining level of 10%, a threshold used in both studies to classify cancers as sensitive or resistant to therapy. The scatter plots in the left panel show correlation between continuous ENDORSE risk estimates (X-axis) and Ki67% staining (Y-axis). Liner fit along with 95% confidence intervals (CI) are also shown. FIG. 4D are violin plots comparing ENDORSE risk scores in patients stratified based on trial-reported clinical response. The left panel represents ER+/IER2+ cancers while the right panel represents ER−/HER2+ cancers. FIG. 4E. Kaplan-Meier curves of ER− METABRIC breast cancers stratified based on ENDORSE risk estimates.

FIGS. 5A-C are violin plots comparing the single sample gene set enrichment scores of various pathways (Y-axis) in METABRIC tumors stratified by estimated ENDORSE risk. The low and medium risk tumors were combined in one category for comparison. FIG. 5A are representative signatures for p53 loss, Rb loss, DNA damage repair and cell cycle. FIG. 5B are representative signatures for metastasis and related signaling pathways. FIG. 5C show tumor-extra cellular matrix interaction pathways. FIG. 5D are bar plots representing gene-level mutation frequencies of various cancer-associated genes in low/medium vs. high-risk METABRIC tumors. The p-values from Chi-square test are shown above the bars, with bold letters indicating comparison significant at an FDR>0.05 threshold.

FIG. 7A. Inclusion criteria and overall schematic of ENDORSE model development. Samples for training were selected based on ER+ status and excluded from the analysis if they were either HER2+, received chemotherapy in addition to hormone therapy, died due to other causes besides breast cancer, or were missing transcriptomic or survival data. The empirical signature was developed using a repeated cross-validation analysis framework. Each iteration of the lasso-regularized proportional hazards model generated a feature set (seed genes) predictive of OS. The seed genes were expanded to a network of intercorrelated genes, and the final empirical signature was defined by identifying a consensus set across all iterations. The two-feature ENDORSE model was then constructed using the gene set enrichment scores of the empirical signature and estrogen response signature. FIG. 7B. Predicted 10-year survival probabilities of the 833 ER+/HER2− METABRIC breast cancers based on a Cox proportional hazards model of gene signature enrichment scores of the empirical and estrogen response signatures as predictor variables. FIG. 7C. Kaplan-Meier curves and risk tables of METABRIC ER+/HER2− tumors stratified by ENDORSE. The tumors were stratified according to an ENDORSE risk score (hazard ratio) threshold of ≥2 to define high-risk, ≤1 as low risk and all other intermediate values as medium risk.

FIGS. 8A-8B. Model evaluation and comparison with other predictors FIG. 8A. Lollipop plots displaying corrected Somer's $D_{xy}$ indices of ENDORSE and various other univariate Cox proportional hazards models. The indices were calculated using 150-fold bootstrap resampling of the training dataset. FIG. 8B. Table comparing the ENDORSE model with various other univariate Cox models using partial likelihood ratio tests. The comparison between the nested ENDORSE model and its two components were performed using a likelihood ratio test, while other non-nested univariate models were compared using a partial likelihood ratio test.

FIGS. 9A-9D. Model validation in TransCONFIRM cohort. FIG. 9A. Scatter plot comparing ENDORSE scores (X-axis) with trial-reported percentage of cells stained positive for Ki67 (Y-axis). Linear fit is shown as a grey line with shaded region showing 95% confidence intervals (C.I.). P-value indicates significance of the linear fit. FIG. 9B. Boxplot comparing Ki67% across ENDORSE-guided patient strata. P-value indicates significance of the ANOVA model and the horizontal dotted line at 10% indicates threshold of resistance. FIG. 9C. Scatter plot comparing SET scores (X-axis) Ki67% (Y-axis). Linear fit is shown as a grey line with shaded region showing 95% confidence intervals (C.I.). P-value indicates significance of the linear fit. FIG. 9D. Boxplot comparing Ki67% across TransCONFIRM predicted patient strata. P-value indicates significance of the ANOVA model and the horizontal dotted line at 10% indicates threshold of resistance.

FIGS. 10A-10G. Model validation in $SET_{ER/PR}$ cohort. FIGS. 10A-10C. OS Kaplan-Meir curves and risk tables of $SET_{ER/PR}$ patients. The patients were stratified according to FIG. 10A. ENDORSE FIG. 10B. SET and FIG. 10C. TransCONFIRM predicted scores. P-values indicate significance of difference in survival curves based on log-rank tests. FIGS. 10D-10F. PFS Kaplan-Meir curves and risk tables of $SET_{ER/PR}$ patients. The patients were stratified according to FIG. 10D ENDORSE FIG. 10E SET and FIG. 10F. TransCONFIRM scores. P-values indicate significance of difference in survival curves based on log-rank tests. FIG. 10G. Table comparing the ENDORSE overall and PFS models with SET and TransCONFIRM models using partial likelihood ratio tests for non-nested Cox models.

FIG. 11A. Boxplots comparing Ki67% at the baseline (left panel) and end of treatment (right panel) across ENDORSE-predicted patient strata. P-value indicates significance of the ANOVA model and the horizontal dotted line at 10% indicates threshold of resistance. FIG. 11B. Scatter plot comparing ENDORSE scores (X-axis) and Ki67% (Y-axis) at the baseline (left panel) and end of treatment (right panel). Linear fit is shown as a grey line with shaded region showing 95% confidence intervals (C.I.). P-value indicates significance of the linear fit. FIG. 11C. Boxplots comparing ENDORSE scores between patients classified as resistant or sensitive clinical response. P-value indicates significance of the ANOVA model. FIG. 11D. Scatter plot comparing SET scores (X-axis) and Ki67% (Y-axis) at the baseline (left panel) and end of treatment (right panel). Linear fit is shown as a grey line with shaded region showing 95% confidence intervals (C.I.). P-value indicates significance of the linear fit. FIG. 11E. Boxplots comparing SET scores between patients classified as resistant or sensitive clinical response. P-value indicates significance of ANOVA model. FIG. 11F. Boxplots comparing Ki67% at the baseline (left panel) and end of treatment (right panel) across TransCONFIRM-predicted patient strata. P-value indicates significance of the ANOVA model and the horizontal dotted line at 10% indicates threshold of resistance. FIG. 11G. Boxplots comparing TransCONFIRM predictions between patients classified as resistant or sensitive clinical response. P-value indicates significance of ANOVA model.

FIGS. 12A-12L. Scatter plots displaying gene set enrichment scores (GES) of key pathways (X-axis) and ENDORSE scores (Y-axis). The cell cycle progression panel represents the hallmark G2M checkpoint signature, the E2F1 upregulation panel represents E2F1_UP.V1_UP oncogenic (C6) signature and the MTOR upregulation panel represents MTOR_UP.V1_UP oncogenic (C6) signature. Blue lines with shading indicate generalized additive model fits with 95% C.I., with $R^2$ and p-values of the significant of the fit annotated on the panels.

FIGS. 13A-13B show the comparison of the two models in overall survival (OS) probability (likelihood ratio test P-values) with the full model having P=4.184e-06, Empirical signature having P=7.735e-05 (FIG. 13A), and the Estrogen response having P=0.01597 (FIG. 13B). FIGS. 13C-13D show the comparison of the two models in progression-free survival (PFS) probability (likelihood ratio test P-values) with the full model having P=4.782e-05, Empirical signature having P=0.0003096 (FIG. 13C), and the Estrogen response having P=0.0254 (FIG. 13D). The robust likelihood ratio tests comparing ENDORSE vs. empirical OS models show that the models are different are different, and that the ENDORSE score is a better fit than the empirical signature alone. Similarly, the likelihood ratio tests comparing ENDORSE vs. estrogen response PFS models show that ENDORSE is a better fit than empirical signature alone.

FIG. 14A-14F. Schematics illustrating example treatment methods for metastatic breast cancer patients. FIG. 14A. An example treatment decision tree developed to stratify patients based on the biomarkers. A cloud-based application on the DNAnexus platform can take raw sequencing reads from the patient tumor, and generate a report containing information about the biomarkers and recommended treatment based on the decision tree. FIG. 14B. shows an example Biomarker analysis and therapeutic approach for aromatase inhibitor plus CDK4/6 resistant metastatic breast cancer patients. FIG. 14C. A treatment timeline showing that the analysis and treatment methods described herein include a 2 week plan. The final step, which results in administration of the anticancer therapeutic (e.g. anticancer endocrine therapeutic, chemotherapeutic) to the metastatic breast cancer subject, can be completed in under two hours. FIG. 14D. An example treatment method including a whole exome sequencing. FIG. 14E. An example interface for the treatment method provided herein.

FIG. 15A. A patient is classified as sensitive to endocrine therapy if the ENDORSE score is below 2. Endocrine biomarker. ENDORSE score=1.04. Patient is likely sensitive to endocrine therapy. FIG. 15B. PIK3CA biomarker. A patient is classified as sensitive to PI3K inhibitor if one or more biomarkers in the table are present in the tumor. Patient is positive for PIK3CA biomarker: c.3140A>G, p.His1047Arg. FIG. 15C. MTOR biomarker. A patient is classified as sensitive to mTOR inhibitor if predicted response is greater than 0.7. Probability of MTOR response=0.59. Patient is likely resistant to mTOR inhibitor. Thus, the report indicates that a recommended treatment can be Alpelisib and Fulvestrant.

$$(Pr(\text{non-responder}) = 1 - Pr(\text{responder})).$$

DETAILED DESCRIPTION

Figure 1:
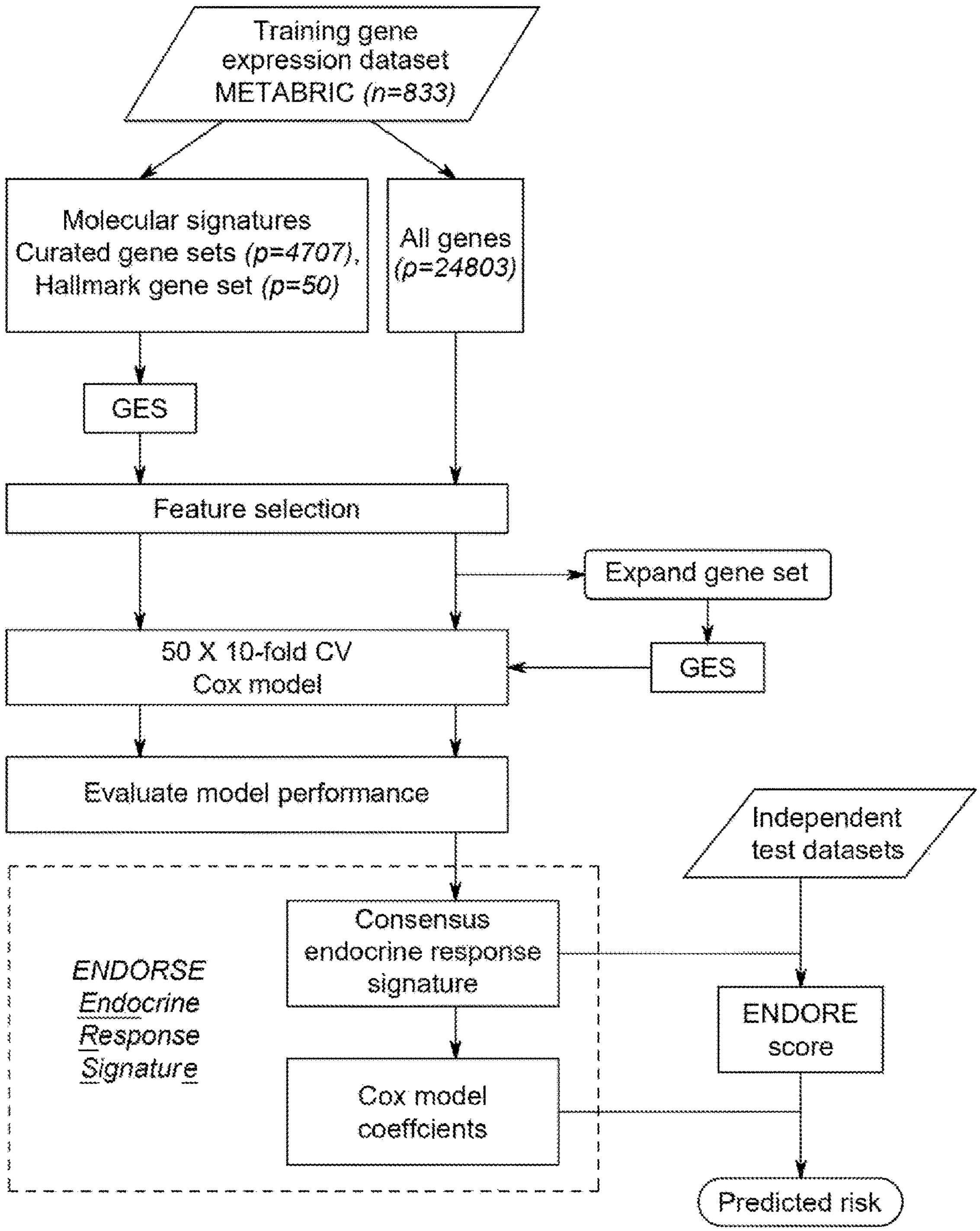
FIG. 1 illustrates model construction, performance evaluation and validation in accordance with an embodiment. The flow chart shows the framework to construct and evaluate various expression-based candidate biomarkers for endocrine response using METABRIC data.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art.

As used herein, the singular terms "a", "an", and "the" include the plural reference unless the context clearly indicates otherwise.

Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

"Nucleic acid" refers to nucleotides (e.g., deoxyribonucleotides or ribonucleotides) and polymers thereof in either single-, double- or multiple-stranded form, or complements thereof, or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. In embodiments, the target polynucleotide is an RNA molecule (or amplification product thereof) of a gene of interest (referred to herein as a "target gene"). RNA molecules transcribed from a target gene are referred to herein as "transcripts." Transcripts derived from a particular gene are identified by reference to the gene from which they were transcribed. A transcript can be a primary transcript, an mRNA, or a portion of either of these of sufficient length to identify the gene from which the transcript was transcribed. In embodiments, target RNA molecules comprise a plurality of different target RNA molecules comprising a plurality of different transcripts derived from different genes (e.g., a plurality of different genes from Table 1).

In general, an "oligonucleotide probe" or "probe" refers to a polynucleotide used for detecting or identifying its corresponding target polynucleotide in a hybridization reaction by specific hybridization with a corresponding target sequence. Thus, a nucleotide probe is hybridizable to one or more target polynucleotides, and preferably specifically hybridizable to one target polynucleotide. Oligonucleotide probes can contain a region that is perfectly complementary to one or more target polynucleotides in a sample, and may optionally contain one or more nucleotides that are not complemented by a corresponding nucleotide in the one or more target polynucleotides in a sample. By "specific hybridization," "specifically hybridizable," and the like is meant hybridization that is determinative of the presence of the corresponding target polynucleotide, often in a heterogeneous population of polynucleotides, which may include other target polynucleotides recognized by other probes, as well as non-target polynucleotides. Thus, under designated assay conditions, the specified oligonucleotide probe binds to a particular target polynucleotide at least two times the background and more typically more than 10 to 100 times background, or higher. In embodiments, an oligonucleotide probe specifically hybridizes to a target polynucleotide under stringent conditions. Stringent conditions are generally sequence-dependent, and vary depending on a number of factors. In general, the longer the sequence, the higher the temperature at which the sequence specifically hybridizes to its target sequence. Non-limiting examples of stringent conditions include hybridization at 65° C. in 0.5×SSC and 0.1% SDS, and hybridization at 42° C. in 50% formamide, 4×SSC and 0.1% SDS. Further non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

The terms "amplify," "amplifies," "amplified," "amplification," as used herein, generally refer to any process by which one or more copies are made of a target polynucleotide or a portion thereof. A variety of methods of amplifying polynucleotides (e.g. DNA and/or RNA) are available, some examples of which are described herein. Amplification may be linear, exponential, or involve both linear and exponential phases in a multi-phase amplification process. Amplification methods may involve changes in temperature, such as a heat denaturation step, or may be isothermal processes that do not require heat denaturation. In embodiments, amplification comprises extension of a primer oligonucleotide by a polymerase. A primer oligonucleotide used in an amplification reaction is referred to as an "amplification primer."

The term "antisense nucleic acid" as used herein refers to a nucleic acid (e.g., DNA or RNA molecule) that is complementary to at least a portion of a specific target nucleic acid. In embodiments, an antisense nucleic acid is capable of reducing transcription of the target nucleic acid (e.g. mRNA from DNA), reducing the translation of the target nucleic acid (e.g. mRNA), altering transcript splicing (e.g. single stranded morpholino oligo), or interfering with the endogenous activity of the target nucleic acid. See, e.g., [16]. Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid. In embodiments, the antisense nucleic acid hybridizes to the target nucleic acid in vitro. In embodiments, the antisense nucleic acid hybridizes to the target nucleic acid in a cell. In embodiments, the antisense nucleic acid hybridizes to the target nucleic acid in an organism. In embodiments, the antisense nucleic acid hybridizes to the target nucleic acid under physiological conditions. Antisense nucleic acids may comprise naturally occurring nucleotides or modified nucleotides such as, e.g., phosphorothioate, methylphosphonate, and anomeric sugar-phosphate, backbone-modified nucleotides.

In a cell, an antisense nucleic acid may hybridize to a corresponding RNA forming a double-stranded molecule. The antisense nucleic acids interfere with the endogenous behavior of the RNA and inhibit its function relative to the absence of the antisense nucleic acid. Furthermore, the double-stranded molecule may be degraded via the RNAi pathway. Further, antisense molecules which bind directly to the DNA may be used. Antisense nucleic acids may be single or double stranded nucleic acids. Non-limiting examples of antisense nucleic acids include siRNAs (including their derivatives or pre-cursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence, only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

The terms "polypeptide," "peptide" and "protein" used interchangeably herein, refer to a polymeric form of amino acids of any length, which can include coded and non-coded amino acids, chemically or biochemically modified or derivatized amino acids, and polypeptides having modified peptide backbones. In various embodiments, detecting the concentrations of naturally occurring protein in a biological sample is contemplated for use within diagnostic, prognostic, or monitoring methods disclosed herein. The term also includes fusion proteins, including, but not limited to, naturally occurring fusion proteins with a heterologous amino acid sequence, fusions with heterologous and homologous leader sequences, with or without N-terminal methionine residues; immunologically tagged proteins; and the like. The terms also include polymers that may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., Current Protocols in Molecular Biology (1995 supplement)).

The terms "identical" or percent "identity" in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection (see, e.g., NCBI web site http://www.ncbi.nlm.nih.gov/BLAST/ or the like). In embodiments, sequences that are "substantially identical" are at least 80%, 90%, 95%, 99%, or more identical. This definition also refers to, or may be applied to, the complement of a test sequence. The definition also includes sequences that have deletions and/or additions, as well as those that have substitutions. Alignment algorithms can account for gaps and the like. Preferably, identity exists over a region that is at least about 10, 15, 25, or more amino acids or nucleotides in length.

"Percentage of sequence identity" is determined by comparing two optimally aligned sequences over a comparison window, wherein the portion of the polynucleotide or polypeptide sequence in the comparison window may comprise additions or deletions as compared to the reference sequence (which does not comprise the additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison (e.g., with respect to the reference sequence), and multiplying the result by 100 to yield the percentage of sequence identity. Programs for determining sequence identify are known to those skilled in the art, and include, without limitation, BLAST (as noted above, optionally using default parameters), the Needleman-Wunsch algorithm (see e.g. the EMBOSS Needle aligner available at https://www.ebi.ac.uk/Tools/psa/emboss_needle, optionally with default settings).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

For specific proteins described herein, the named protein includes any of the protein's naturally occurring forms, variants or homologs that maintain the protein activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. Genes and their corresponding proteins are identified by designations commonly used in the art according to their plain and ordinary meaning. Additional information relating to recited gene designations, including sequence information (e.g., DNA, RNA, and amino acid sequences), full names of genes commonly identified by way of acronym, and the like are available in publicly accessible databases known to those skilled in the art, such as databases available from the National Center for Biotechnology Information (www.ncbi.nlm.nih.gov/), including GenBank (www.ncbi.nlm.nih.gov/genbank/) and the NCBI Protein database (www.ncbi.nlm.nih.gov/protein/), and UniProt (www.uniprot.org).

The term "PI3 Kinase" or "PI3K" as used herein includes any of the recombinant or PI3 Kinase, also known as Phosphatidylinositol 4,5-bisphosphate 3-kinase catalytic subunit alpha, Phosphoinositide-3-kinase and PI3-kinase subunit alpha, or variants or homologs thereof that maintain PI3K activity (e.g. within at least 50%, 80%, 90%, 95%, 96%, 97%, 98%, 99% or 100% activity compared to PI3K). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PI3K protein. In embodiments, the PI3K protein is substantially identical to the protein identified by the UniProt reference number P42336 or a variant or homolog having substantial identity thereto. In embodiments, the PI3K protein is substantially identical to the protein having the amino acid sequence of SEQ ID NO:1 or a variant or homolog having substantial identity thereto.

The term "aromatase protein" or "aromatase" as used herein includes any of the recombinant or aromatase, also known as CYPXIX, Cytochrome P-450AROM, Cytochrome P450 19A1, Estrogen synthase or variants or homologs thereof that maintain aromatase activity (e.g. within at least 50%, 80%, 90%, 95%, 96%, 97%, 98%, 99% or 100% activity compared to aromatase). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring aromatase protein. In embodiments, the aromatase protein is substantially identical to the protein identified by the UniProt reference number P11511 or a variant or homolog having substantial identity thereto.

The term "Serine/threonine-protein kinase mTOR protein" or "Serine/threonine-protein kinase mTOR" as used herein includes any of the recombinant or Serine/threonine-protein kinase mTOR (mTOR), also known as FK506-binding protein 12-rapamycin complex-associated protein 1, FKBP12-rapamycin complex-associated protein, Mammalian target of rapamycin or variants or homologs thereof that maintain mTOR activity (e.g. within at least 50%, 80%, 90%, 95%, 96%, 97%, 98%, 99% or 100% activity compared to mTOR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring mTOR protein. In embodiments, the mTOR protein is substantially identical to the protein identified by the UniProt reference number P42345 or a variant or homolog having substantial identity thereto.

A "substantially isolated" or "isolated" substance is one that is substantially free of one or more components of its associated surrounding materials in nature. The term "substantially free" is used herein to mean at least 50%, preferably at least 70%, more preferably at least 80%, and even more preferably, at least 90% free of the materials with which it is associated in nature. As used herein, "isolated" can refer to polynucleotides, polypeptides, antibodies, cells, samples, and the like.

The terms "disease" or "condition" refer to a state of being or health status of a patient or subject capable of being diagnosed and/or treated with compounds or methods provided herein. The disease may be a cancer. The disease may be breast cancer. The disease may be estrogen receptor positive (ER+) cancer.

As used herein, the term "breast cancer" refers to all types of cancer, neoplasm or malignant tumors found in or originating from breast tissue of a mammal (e.g. a human). In embodiments, the cancer is estrogen receptor positive (ER+) breast cancer. In embodiments, the breast cancer is metastatic breast cancer. In embodiments, the cancer is triple-negative breast cancer, metaplastic breast cancer, or a subtype thereof.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" may also be referred to as "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to as metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

As used herein, the term "adverse event" or "AE" refers to any untoward medical occurrence in a subject or clinical investigation subject administered a pharmaceutical product, and which does not necessarily have to have a causal relationship with this treatment. An adverse event (AE) can therefore be any unfavorable and unintended sign (including an abnormal laboratory finding, for example), symptom, or disease temporally associated with the use of a medicinal product, whether considered related to the medicinal product. In embodiments, the adverse event is continued tumor growth. In embodiments, the adverse event is metastasis. In embodiments, the adverse event is death.

As used herein, the term "diagnosis" refers to an identification or likelihood of the presence of a particular type of cancer or outcome in a subject. As also used herein, the term "prognosis" refers to the likelihood or risk of a subject developing a particular outcome or particular event.

As used herein, a "biological sample" encompasses essentially any sample type obtained from a subject that can be used in a diagnostic or prognostic method described herein.

The biological sample may be any bodily fluid, tissue or any other suitable sample. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as cells (e.g., cancer cells), polypeptides, nucleic acids, or proteins. The term "biological sample" encompasses a clinical sample, but also, in some instances, includes cells in culture, cell supernatants, cell lysates, blood, serum, plasma, urine, cerebral spinal fluid, biological fluid, and tissue samples. The sample may be pretreated by dilution in an appropriate buffer solution or concentrated, if desired. Any of a number of standard aqueous buffer solutions, employing one of a variety of buffers, such as phosphate, Tris, or the like, preferably at physiological pH can be used. Biological samples can be derived from patients using well-known techniques such as venipuncture, lumbar puncture, fluid sample such as saliva or urine, or tissue biopsy and the like. In embodiments, the sample is a cancer sample (e.g., containing or suspected of containing cancer cells, such as from a tumor).

"Treating" or "treatment" as used herein includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. "Treating" or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. In other words, "treatment" as used herein includes any cure, amelioration, or prevention of a disease.

"Treating" or "treatment" as used herein may include prophylactic treatment. Treatment may prevent the disease from occurring; inhibit the disease's spread; relieve the disease's symptoms, fully or partially remove the disease's underlying cause, shorten a disease's duration, or do a combination of these things. The term "treating" and conjugations thereof may include prevention of an injury, pathology, condition, or disease. In embodiments, treating is preventing. In embodiments, treating does not include preventing. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by diagnostic assays (e.g., assays described herein or known in the art). In some instances, chronic administration may be required. For example, the compositions are administered to the subject in an amount and for a duration sufficient to treat the patient. In embodiments, treatment or treating does not include prophylactic treatment.

The term "prevent" refers to a decrease in the occurrence of disease symptoms in a patient. The prevention may be complete (no detectable symptoms) or partial, such that fewer symptoms are observed than would likely occur absent treatment.

The term "patient" or "subject" refers to a living organism suffering from or prone to a disease or condition that can be treated by administration of a pharmaceutical composition or other therapeutic intervention. Non-limiting examples include humans, other mammals, bovines, rats, mice, dogs, monkeys, goat, sheep, cows, and deer. In some embodiments, a subject is human.

The term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is a measurement of a reference sample or aggregate of a plurality of reference samples (e.g., breast tissue of one or more subjects that do not have breast cancer, or breast tissue of a subject suspected of having breast cancer that is pathologically non-cancerous (e.g., normal breast tissue) for comparison to suspicious tissue of the subject) as described herein (including embodiments and examples). In some instances, the control is a synthetic quantification standard used as a reference for assay measurements.

As described herein, the terms "marker" and "biomarker" are used interchangeably throughout the disclosure. As used herein, a marker refers generally to one or more target RNA molecules, the level or concentration of which is associated with a particular biological state.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques.

The term "administering" as used herein refers to oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

The term "co-administer" as used herein refers to a composition described herein administered at the same time, just prior to, or just after the administration of one or more additional therapies. The compounds provided herein can be administered alone or can be coadministered to the patient. Co-administration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

The term "cancer therapy" is used in accordance with its plan ordinary meaning, and refers to a therapy used to treat cancer. Non-limiting examples of cancer therapy include chemotherapy, immunotherapy, radiation therapy, surgery, or a combination thereof. In embodiments, the cancer therapy is an anticancer agent. The term "anticancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer, such as breast cancer. In some embodiments, an anti-cancer agent is an agent having utility in methods of treating metastatic estrogen receptor positive breast cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5- azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*Pseudomonas* exotoxin conjugate, etc.), radioimmunotherapy (e.g., anti-CD20 monoclonal antibody conjugated to $^{111}In$, $^{90}Y$, or $^{131}I$, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like The term "multi-kinase inhibitor" as used herein refers to a small molecule inhibitor of at least one protein kinase, including tyrosine protein kinases and serine/threonine kinases. A multi-kinase inhibitor may include a single kinase inhibitor. Multi-kinase inhibitors may block phosphorylation. Multi-kinases inhibitors may act as covalent modifiers of protein kinases. Multi-kinase inhibitors may bind to the kinase active site or to a secondary or tertiary site inhibiting protein kinase activity. A multi-kinase inhibitor may be an anti-cancer multi-kinase inhibitor. Exemplary anti-cancer multi-kinase inhibitors include dasatinib, sunitinib, erlotinib, bevacizumab, vatalanib, vemurafenib, vandetanib, cabozantinib, poatinib, axitinib, ruxolitinib, regorafenib, crizotinib, bosutinib, cetuximab, gefitinib, imatinib, lapatinib, lenvatinib, mubritinib, nilotinib, panitumumab, pazopanib, trastuzumab, or sorafenib.

The terms "endocrine treatment," "endocrine therapy," "hormonal treatment," or "hormone therapy" (sometimes also referred to as "anti-hormonal treatment") denotes a treatment which targets hormone signaling, e.g. hormone inhibition, hormone receptor inhibition, use of hormone receptor agonists or antagonists, use of scavenger- or orphan receptors, use of hormone derivatives and interference with hormone production. Particular non-limiting examples are tamoxifen therapy, which modulates signaling of the estrogen receptor, or aromatase inhibitor treatment, which interferes with steroid hormone production. Other endocrine therapies include selective estrogen receptor modulator (SERM) and a selective estrogen receptor down-regulator (SERD). Example hormone therapy drugs for breast cancer treatment include: Anastrozole (Arimidex), Exemestane (Aromasin), Fulvestrant (Faslodex), Goserelin (Zoladex), Letrozole (Femara), Leuprorelin, leuprolideacetate (Lupron), Megestrol (Megace), Tamoxifen (Nolvadex, Soltamox), Toremifene (Fareston).

"Selective estrogen receptor modulator" or "SERM" is used in accordance with its plain ordinary meaning and refers to a compound that blocks the estrogen receptor, particularly in breast tissue cells. For example, if a SERM is in the estrogen receptor, estrogen is blocked from binding to the receptor. In embodiments, the SERM is tamoxifen, raloxifene, or toremifene. Tamoxifen is an orally active selective estrogen receptor modulator (SERM) that is used in the treatment of breast cancer and is currently the world's largest selling drug for that purpose. Tamoxifen is sold under the trade names Nolvadex, Istubal, and Valodex. However, the drug, even before its patent expiration, was and still is widely referred to by its generic name "tamoxifen." Tamoxifen and Tamoxifen derivatives competitively bind to estrogen receptors on tumors and other tissue targets, producing a nuclear complex that decreases RNA synthesis and inhibits estrogen effects.

"Selective estrogen receptor down-regulator" or "SERD" is used in accordance with its plain ordinary meaning and refers to a compound that binds the estrogen receptor and further causes the receptor to be degraded and/or downregulated. In embodiments, the SERD is fulvestrant, giredestrant, amcenestrant, AZD9833, rintodestrant, LSZ102, LY3484356, ZN-c5, D-0502, or SHR9549.

"Aromatase inhibitor" is used in accordance with its plain ordinary meaning and refers to a compound that can inhibit or downregulate the production of estrogen, or block the action of estrogen on receptors. Aromatase inhibitors may function by inhibiting the action of the enzyme aromatase. In embodiments, the aromatase inhibitor is exemestane, anastrozole, or letrozole.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

As used herein, the term "resistance" refers to lack of sensitivity or intended response of a cancer cell or cancer to a therapeutic agent. In embodiments, the therapeutic agent is an anticancer endocrine therapy. For example, resistance to an anticancer endocrine therapy may refer to loss of the anti-cancer effects (e.g. reduction in tumor volume, tumor volume growth, tumor cell death, etc.) of the anticancer endocrine therapy. In embodiments, resistance to an anticancer endocrine therapy refers to persistence of symptoms caused by the cancer. In embodiments, resistance to an anticancer endocrine therapy can refer to continued progression of the cancer.

The term "sensitive" or "sensitivity" is used herein to refer to the intended response of a cell or population of cells to a therapeutic agent (e.g. an anticancer endocrine therapy, chemotherapeutic, mTor inhibitor, PI3K inhibitor, etc.). In embodiments, the cell or population of cells may be cancer cell(s). Sensitivity may be measured as growth arrest, quiescence, senescence, apoptosis, or other forms of programmed cell death in response to the therapeutic agent; for example, cell apoptosis in response to a cytotoxic agent. Sensitivity to a therapeutic agent may be measured as inhibition or modulation of tumor growth. Sensitivity to a therapeutic agent may be measured as modulation of the metastasis of the cancer.

The terms "specific", "specifically", "specificity", or the like of a compound refers to the compound's ability to cause a particular action, such as inhibition, to a particular molecular target with minimal or no action to other proteins in the cell. In the context of nucleic acids, a "target-specific sequence" preferentially hybridizes to a target nucleic acid sequence under reaction conditions for a given assay or sub-step thereof (e.g., binding of a detection or capture probe oligonucleotide, or PCR primer binding).

The terms "substrate," "solid support," and "solid surface" are used interchangeably, and refer to any material that can serve as a solid or semi-solid foundation for creation of features such as wells for the deposition of biopolymers, including nucleic acids, polypeptide and/or other polymers. A solid surface may be modified to accommodate attachment of biopolymers by a variety of methods. Exemplary types of substrate materials include glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, a variety of polymers other than those exemplified above and multiwell microtiter plates. Specific types of exemplary plastics include acrylics, polystyrene, copolymers of styrene and other materials, polypropylene, polyethylene, polybutylene, and polyurethanes. Specific types of exemplary silica-based materials include silicon and various forms of modified silicon.

The term “contacting” is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term “contacting” may include allowing two species to react, interact, or physically touch, wherein the two species may be a compound as described herein and a protein or enzyme. In some embodiments, contacting includes allowing a compound described herein to interact with a protein or enzyme that is involved in a signaling pathway.

As defined herein, the term “activation”, “activate”, “activating”, “activator” and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms “agonist,” “activator,” “upregulator,” etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term “inhibition”, “inhibit”, “inhibiting” and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms “inhibitor,” “repressor” or “antagonist” or “downregulator” interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term “expression” includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term “gene” means the segment of DNA involved in producing a protein; a gene may include regions preceding and following the coding region (leader and trailer) as well as intervening sequences (introns) between individual coding segments (exons). The leader, the trailer as well as the introns include regulatory elements that are necessary during the transcription and the translation of a gene. Further, a “protein gene product” is a protein expressed from a particular gene.

The term “gene expression” refers to any step in the process by which information from a gene is used in the synthesis of a functional gene product. These products are often proteins, but in non-protein coding genes such as transfer RNA (tRNA) or small nuclear RNA (snRNA) genes, the product is a functional RNA. In embodiments, gene expression measurements for a plurality of genes is aggregated. In general, aggregation comprises combining the plurality of individual measurements into a single value representative of the combination. Aggregation is not limited to any particular mode of combination. Example processes for aggregating gene expression measurements, such as for comparison to a reference value, are provided herein.

The term “reference value” as used herein refers to a value to which a measured quantity is compared. In embodiments, a reference value is assigned to genes in order to compare measured gene expression levels and make a comparison of whether the measured value is greater, equal, or less than the reference value, which then enables a determination of increased, no change, or decreased expression level of the gene. In embodiments, a reference value is assigned to an activity level representing the collective reference expression levels of several genes (such as genes associated with a particular signature). In embodiments, reference values are pre-determined values, such as from previous measurements for which expression levels were previously measured. In embodiments, a reference value is a control value for a known sample or condition that was previously measured, or is measured in parallel with a test sample. In embodiments, a reference value is a value for a sample from a subject at an earlier timepoint, to which a value for a test sample at a later timepoint may be compared, and which may be measured separately or simultaneously with the test sample. In embodiments, a known sample providing the reference value is a non-cancerous tissue of the same type from which a test cancer cell originated, or a cell line of the same type as a test cancer cell. In embodiments, a reference value represents a "threshold." In general, a threshold is a reference value below which, at which, or above which some characteristic is assigned, e.g., type or responsiveness of a cancer.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

The term "fluorophore" or "fluorescent marker" as used herein refers to a fluorescent chemical compound that can re-emit light upon light excitation.

The terms "nucleotide sequencing" and "sequencing" as used herein refers to a process of determining the order of nucleotides in a polynucleotide. In embodiments, the polynucleotide may be a gene, a portion of a gene, a transcript of a gene, or a portion of a gene transcript. A variety of sequencing processes are available and known to those skilled in the art. Typically, sequencing is an iterative process (e.g., sequencing by synthesis), in which nucleotides are successively added and identified by progressively polymerizing a polynucleotide hybridized to a template being sequenced. While hybridization of a probe to a target sequence may identify the sequence to which it is hybridized by virtue of its specificity for that target sequence, such probe hybridization reactions are not "nucleotide sequencing," as used herein. In embodiments, sequencing comprises hybridizing a primer oligonucleotide to a target polynucleotide, extending the primer with a polymerase, and identifying one or more nucleotides adding in the extension. A primer oligonucleotide extended in a sequencing reaction is referred to as a "sequencing primer."

The term "associated" or "associated with" in the context of a substance, substance activity, or function associated with a disease (e.g. a protein associated disease, such as a cancer (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. As used herein, what is described as being associated with a disease, if a causative agent, could be a target for treatment of the disease.

The term "signaling pathway" or "pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components. In embodiments, a signaling pathway is identified by a particular gene (e.g., the PI3K pathways), which refers to the pathway identified by signaling changes induced by activity of the indicated gene or corresponding protein (e.g., PI3K). In embodiments, the signaling pathway includes genes whose expression is statistically significantly increased and/or decreased in response to overexpression of a particular gene that identifies the pathway. A collection of genes identified as being characteristic of a particular pathway is referred to herein as a "signature" for that pathway. Genes that are characteristic of a particular signature may be genes that are expressed at a higher level (e.g., a statistically significantly higher level) and/or expressed at a lower level (e.g., a statistically significantly lower level) when the pathway having the particular signature is activated.

In embodiments, methods disclosed herein do not comprise whole transcriptome measurement. The term "whole transcriptome measurement" refers to methods for measuring every mRNA transcript in a sample, or suspected of being in a sample. Various methods for performing "whole transcriptome measurement" are available. Non-limiting examples include the use of arrays to probe for expression of all known mRNAs associated with a sample (e.g., all human genes), and the use of high-throughput sequencing methodologies to sequence all mRNA in a sample. In general, methodologies for whole transcriptome measurement are directed at identifying all genes expressed in a given sample (e.g., a particular tissue or type of cell), or measuring their expression level. In certain sequencing methodologies, all mRNAs are subjected to a common procedure that does not select for any particular target sequence, but instead non-selectively amplifies and sequences all mRNA using common structural features (e.g., presence of a poly-A tail, or adapter ligation that does not depend on the presence of any particular sequence). Procedures for whole transcriptome measurement are therefore distinct from procedures described in embodiments herein directed to measuring expression of specific target genes, which represent a subset of transcripts in any sample in which they may occur.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Methods of Treatment

Provided herein, inter alia, are methods for treating cancer in a subject having metastatic estrogen receptor positive (ER+) breast cancer. Where the cancer cells of a breast cancer grow in response to estrogen, the breast cancer is referred to herein as an estrogen receptor positive breast cancer. The methods provided herein are contemplated to be effective, inter alia, for treating metastatic ER+ breast cancer in subjects who may be resistant to anticancer endocrine therapies. In embodiments, the methods include administering alternative anti-cancer therapeutics (e.g. not anticancer endocrine therapeutics) to subjects having metastatic ER+ breast cancer. The methods provided herein may include measuring expression levels of an RNA transcriptome set (e.g. RNA transcripts) from tumor cells of a metastatic breast cancer subject (e.g. metastatic ER+ breast cancer subject). In embodiments, the RNA transcripts in the RNA transcriptome set include transcripts from: an endocrine signaling negative gene set, an endocine signaling positive gene set, and a remainder gene set (e.g. all genes in the RNA transcriptome set excluding the endocrine signaling negative gene set and endocine signaling positive gene set). In embodiments, the genes included in the endocrine signaling negative gene set and endocine signaling positive gene set have accurate expression signatures for use in treating metastatic ER+ breast cancer.

Thus, in an aspect is provided a method of treating cancer in a metastatic estrogen receptor positive breast cancer subject, the method including: (a) measuring an expression level of a transcriptome set of RNA transcripts in a plurality of cells obtained from a tumor from the metastatic estrogen receptor positive breast cancer subject, wherein the transcriptome set of RNA transcripts includes RNA transcripts expressed from: (i) an endocrine signaling negative gene set, wherein the endocrine signaling negative gene set includes a gene (e.g. at least 5 genes) selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25; (ii) an endocrine signaling positive gene set, wherein the endocrine signaling positive gene set includes a gene (e.g. at least 5 genes) selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1; and (iii) a remainder gene set, wherein the remainder gene set consists of all genes expressing the transcriptome set of RNA transcripts except the endocrine signaling positive gene set and the endocrine signaling negative gene set; (b) determining a high level of expression of the endocrine signaling negative gene set relative to a first standard control; (c) determining a low level of expression of the endocrine signaling positive gene set relative to a second standard control; and (d) administering a chemotherapy to the metastatic estrogen receptor positive breast cancer subject and not administering anticancer endocrine therapy to the metastatic estrogen receptor positive breast cancer subject.

As used herein, the “plurality of cells obtained from a tumor” refers to breast cancer cells found in breast tissue or elsewhere as the result of metastasis to another tissue. For example, breast cancer cells may travel from the original tumor in the breast tissue to other parts of the body by way of the bloodstream or the lymphatic system. Thus, in embodiments, the plurality of cells obtained from a tumor are breast cancer cells obtained from the liver, brain, bones, or lungs. In embodiments, the plurality of cells are breast cancer cells obtained from the liver. In embodiments, the plurality of cells are breast cancer cells obtained from the brain. In embodiments, the plurality of cells are breast cancer cells obtained from the bones. In embodiments, the plurality of cells are breast cancer cells obtained from the lungs.

As used herein, “transcriptome set of RNA transcripts” refers to all RNA transcripts from a cell or a plurality of cells for which gene expression is measured. In embodiments, the transcriptome set of RNA transcripts includes the endocrine signaling negative gene set, the endocrine signaling positive gene set, and a remainder gene set.

Thus, as used herein, “remainder gene set” refers to genes expressed in the RNA transcriptome set, that do not include any of the genes within the endocrine signaling negative gene set or the endocrine signaling positive gene set. In embodiments, the remainder gene set includes at least 50 genes that do not include genes within the endocrine signaling negative gene set, or genes within the endocrine signaling positive gene set. In embodiments, the remainder gene set includes at least 100 genes that do not include genes within the endocrine signaling negative gene set, or genes within the endocrine signaling positive gene set. In embodiments, the remainder gene set includes at least 200 genes that do not include genes within the endocrine signaling negative gene set, or genes within the endocrine signaling positive gene set. In embodiments, the remainder gene set includes at least 300 genes that do not include genes within the endocrine signaling negative gene set, or genes within the endocrine signaling positive gene set. In embodiments, the remainder gene set includes at least 400 genes that do not include genes within the endocrine signaling negative gene set, or genes within the endocrine signaling positive gene set. In embodiments, the remainder gene set includes from about 500 to about 40,000 genes that do not include genes within the endocrine signaling negative gene set, or genes within the endocrine signaling positive gene set. In embodiments, the remainder gene set includes from about 1000 to about 40,000 genes. In embodiments, the remainder gene set includes from about 1500 to about 40,000 genes. In embodiments, the remainder gene set includes from about 2000 to about 40,000 genes. In embodiments, the remainder gene set includes from about 2500 to about 40,000 genes. In embodiments, the remainder gene set includes from about 3000 to about 40,000 genes. In embodiments, the remainder gene set includes from about 3500 to about 40,000 genes. In embodiments, the remainder gene set includes from about 4000 to about 40,000 genes. In embodiments, the remainder gene set includes from about 4500 to about 40,000 genes. In embodiments, the remainder gene set includes from about 5000 to about 40,000 genes. In embodiments, the remainder gene set includes from about 5500 to about 40,000 genes. In embodiments, the remainder gene set includes from about 6000 to about 40,000 genes. In embodiments, the remainder gene set includes from about 6500 to about 40,000 genes. In embodiments, the remainder gene set includes from about 7000 to about 40,000 genes. In embodiments, the remainder gene set includes from about 7500 to about 40,000 genes. In embodiments, the remainder gene set includes from about 8000 to about 40,000 genes. In embodiments, the remainder gene set includes from about 8500 to about 40,000 genes. In embodiments, the remainder gene set includes from about 9000 to about 40,000 genes. In embodiments, the remainder gene set includes from about 9500 to about 40,000 genes. In embodiments, the remainder gene set includes from about 10,000 to about 40,000 genes. In embodiments, the remainder gene set includes from about 10,500 to about 40,000 genes. In embodiments, the remainder gene set includes from about 11,000 to about 40,000 genes. In embodiments, the remainder gene set includes from about 11,500 to about 40,000 genes. In embodiments, the remainder gene set includes from about 12,000 to about 40,000 genes. In embodiments, the remainder gene set includes from about 12,500 to about 40,000 genes. In embodiments, the remainder gene set includes from about 13,000 to about 40,000 genes. In embodiments, the remainder gene set includes from about 13,500 to about 40,000 genes. In embodiments, the remainder gene set includes from about 14,000 to about 40,000 genes. In embodiments, the remainder gene set includes from about 14,500 to about 40,000 genes. In embodiments, the remainder gene set includes from about 15,000 to about 40,000 genes. In embodiments, the remainder gene set includes from about 15,500 to about 40,000 genes. In embodiments, the remainder gene set includes from about 16,000 to about 40,000 genes. In embodiments, the remainder gene set includes from about 16,500 to about 40,000 genes. In embodiments, the remainder gene set includes from about 17,000 to about 40,000 genes. In embodiments, the remainder gene set includes from about 17,500 to about 40,000 genes. In embodiments, the remainder gene set includes from about 18,000 to about 40,000 genes. In embodiments, the remainder gene set includes from about 18,500 to about 40,000 genes. In embodiments, the remainder gene set includes from about 19,000 to about 40,000 genes. In embodiments, the remainder gene set includes from about 19,500 to about 40,000 genes. In embodiments, the remainder gene set includes from about 20,000 to about 40,000 genes. In embodiments, the remainder gene set includes from about 20,500 to about 40,000 genes. In embodiments, the remainder gene set includes from about 21,000 to about 40,000 genes. In embodiments, the remainder gene set includes from about 21,500 to about 40,000 genes. In embodiments, the remainder gene set includes from about 22,000 to about 40,000 genes. In embodiments, the remainder gene set includes from about 22,500 to about 40,000 genes. In embodiments, the remainder gene set includes from about 23,000 to about 40,000 genes. In embodiments, the remainder gene set includes from about 23,500 to about 40,000 genes. In embodiments, the remainder gene set includes from about 24,000 to about 40,000 genes. In embodiments, the remainder gene set includes from about 24,500 to about 40,000 genes. In embodiments, the remainder gene set includes from about 24,000 to about 40,000 genes. In embodiments, the remainder gene set includes from about 24,500 to about 40,000 genes. In embodiments, the remainder gene set includes from about 25,000 to about 40,000 genes. In embodiments, the remainder gene set includes from about 25,500 to about 40,000 genes. In embodiments, the remainder gene set includes from about 26,000 to about 40,000 genes. In embodiments, the remainder gene set includes from about 26,500 to about 40,000 genes. In embodiments, the remainder gene set includes from about 27,000 to about 40,000 genes. In embodiments, the remainder gene set includes from about 27,500 to about 40,000 genes. In embodiments, the remainder gene set includes from about 28,000 to about 40,000 genes. In embodiments, the remainder gene set includes from about 28,500 to about 40,000 genes. In embodiments, the remainder gene set includes from about 29,000 to about 40,000 genes. In embodiments, the remainder gene set includes from about 29,500 to about 40,000 genes. In embodiments, the remainder gene set includes from about 30,000 to about 40,000 genes. In embodiments, the remainder gene set includes from about 30,500 to about 40,000 genes. In embodiments, the remainder gene set includes from about 31,000 to about 40,000 genes. In embodiments, the remainder gene set includes from about 31,500 to about 40,000 genes. In embodiments, the remainder gene set includes from about 32,000 to about 40,000 genes. In embodiments, the remainder gene set includes from about 32,500 to about 40,000 genes. In embodiments, the remainder gene set includes from about 33,000 to about 40,000 genes. In embodiments, the remainder gene set includes from about 33,500 to about 40,000 genes. In embodiments, the remainder gene set includes from about 34,000 to about 40,000 genes. In embodiments, the remainder gene set includes from about 34,500 to about 40,000 genes. In embodiments, the remainder gene set includes from about 35,000 to about 40,000 genes. In embodiments, the remainder gene set includes from about 35,500 to about 40,000 genes. In embodiments, the remainder gene set includes from about 36,000 to about 40,000 genes. In embodiments, the remainder gene set includes from about 36,500 to about 40,000 genes. In embodiments, the remainder gene set includes from about 37,000 to about 40,000 genes. In embodiments, the remainder gene set includes from about 37,500 to about 40,000 genes. In embodiments, the remainder gene set includes from about 38,000 to about 40,000 genes. In embodiments, the remainder gene set includes from about 38,500 to about 40,000 genes. In embodiments, the remainder gene set includes from about 39,000 to about 40,000 genes. In embodiments, the remainder gene set includes from about 39,500 to about 40,000 genes.

In embodiments, the remainder gene set includes from about 500 to about 39,500 genes that do not include genes within the endocrine signaling negative gene set, or genes within the endocrine signaling positive gene set. In embodiments, the remainder gene set includes from about 500 to about 38,000 genes. In embodiments, the remainder gene set includes from about 500 to about 37,500 genes. In embodiments, the remainder gene set includes from about 500 to about 37,000 genes. In embodiments, the remainder gene set includes from about 500 to about 36,500 genes. In embodiments, the remainder gene set includes from about 500 to about 36,000 genes. In embodiments, the remainder gene set includes from about 500 to about 35,500 genes. In embodiments, the remainder gene set includes from about 500 to about 35,000 genes. In embodiments, the remainder gene set includes from about 500 to about 34,500 genes. In embodiments, the remainder gene set includes from about 500 to about 34,000 genes. In embodiments, the remainder gene set includes from about 500 to about 33,500 genes. In embodiments, the remainder gene set includes from about 500 to about 33,000 genes. In embodiments, the remainder gene set includes from about 500 to about 32,500 genes. In embodiments, the remainder gene set includes from about 500 to about 32,000 genes. In embodiments, the remainder gene set includes from about 500 to about 31,500 genes. In embodiments, the remainder gene set includes from about 500 to about 31,000 genes. In embodiments, the remainder gene set includes from about 500 to about 30,500 genes. In embodiments, the remainder gene set includes from about 500 to about 30,000 genes. In embodiments, the remainder gene set includes from about 500 to about 29,500 genes. In embodiments, the remainder gene set includes from about 500 to about 29,000 genes. In embodiments, the remainder gene set includes from about 500 to about 28,500 genes. In embodiments, the remainder gene set includes from about 500 to about 28,000 genes. In embodiments, the remainder gene set includes from about 500 to about 27,500 genes. In embodiments, the remainder gene set includes from about 500 to about 27,000 genes. In embodiments, the remainder gene set includes from about 500 to about 26,500 genes. In embodiments, the remainder gene set includes from about 500 to about 26,000 genes. In embodiments, the remainder gene set includes from about 500 to about 25,500 genes. In embodiments, the remainder gene set includes from about 500 to about 25,000 genes. In embodiments, the remainder gene set includes from about 500 to about 24,500 genes. In embodiments, the remainder gene set includes from about 500 to about 24,000 genes. In embodiments, the remainder gene set includes from about 500 to about 23,500 genes. In embodiments, the remainder gene set includes from about 500 to about 23,000 genes. In embodiments, the remainder gene set includes from about 500 to about 22,500 genes. In embodiments, the remainder gene set includes from about 500 to about 22,000 genes. In embodiments, the remainder gene set includes from about 500 to about 21,500 genes. In embodiments, the remainder gene set includes from about 500 to about 21,000 genes. In embodiments, the remainder gene set includes from about 500 to about 20,500 genes. In embodiments, the remainder gene set includes from about 500 to about 20,000 genes. In embodiments, the remainder gene set includes from about 500 to about 19,500 genes. In embodiments, the remainder gene set includes from about 500 to about 19,000 genes. In embodiments, the remainder gene set includes from about 500 to about 18,500 genes. In embodiments, the remainder gene set includes from about 500 to about 18,000 genes. In embodiments, the remainder gene set includes from about 500 to about 17,500 genes. In embodiments, the remainder gene set includes from about 500 to about 17,000 genes. In embodiments, the remainder gene set includes from about 500 to about 16,500 genes. In embodiments, the remainder gene set includes from about 500 to about 16,000 genes. In embodiments, the remainder gene set includes from about 500 to about 15,500 genes. In embodiments, the remainder gene set includes from about 500 to about 15,000 genes. In embodiments, the remainder gene set includes from about 500 to about 14,500 genes. In embodiments, the remainder gene set includes from about 500 to about 14,000 genes. In embodiments, the remainder gene set includes from about 500 to about 13,500 genes. In embodiments, the remainder gene set includes from about 500 to about 13,000 genes. In embodiments, the remainder gene set includes from about 500 to about 12,500 genes. In embodiments, the remainder gene set includes from about 500 to about 12,000 genes. In embodiments, the remainder gene set includes from about 500 to about 11,500 genes. In embodiments, the remainder gene set includes from about 500 to about 11,000 genes. In embodiments, the remainder gene set includes from about 500 to about 10,500 genes. In embodiments, the remainder gene set includes from about 500 to about 10,000 genes. In embodiments, the remainder gene set includes from about 500 to about 9,500 genes. In embodiments, the remainder gene set includes from about 500 to about 9,000 genes. In embodiments, the remainder gene set includes from about 500 to about 8,500 genes. In embodiments, the remainder gene set includes from about 500 to about 8,000 genes. In embodiments, the remainder gene set includes from about 500 to about 7,500 genes. In embodiments, the remainder gene set includes from about 500 to about 7,000 genes. In embodiments, the remainder gene set includes from about 500 to about 6,500 genes. In embodiments, the remainder gene set includes from about 500 to about 6,000 genes. In embodiments, the remainder gene set includes from about 500 to about 5,500 genes. In embodiments, the remainder gene set includes from about 500 to about 5,000 genes. In embodiments, the remainder gene set includes from about 500 to about 4,500 genes. In embodiments, the remainder gene set includes from about 500 to about 4,000 genes. In embodiments, the remainder gene set includes from about 500 to about 3,500 genes. In embodiments, the remainder gene set includes from about 500 to about 3,000 genes. In embodiments, the remainder gene set includes from about 500 to about 2,500 genes. In embodiments, the remainder gene set includes from about 500 to about 2,000 genes. In embodiments, the remainder gene set includes from about 500 to about 1,500 genes. In embodiments, the remainder gene set includes from about 500 to about 1,000 genes. In embodiments, the remainder gene set includes about 500, 1000, 1500, 2000, 2500, 3000, 3500, 4000, 4500, 5000, 5500, 6000, 6500, 7000, 7500, 8000, 8500, 9000, 9500, 10000, 10500, 11000, 11500, 12000, 12500, 13000, 13500, 14000, 14500, 15000, 15500, 16000, 16500, 17000, 17500, 18000, 18500, 19000, 19500, 20000, 20500, 21000, 21500, 22000, 22500, 23000, 23500, 24000, 24500, 25000, 25500, 26000, 26500, 27000, 27500, 28000, 28500, 29000, 29500, 30000, 3500, 31000, 31500, 32000, 32500, 33000, 33500, 34000, 34500, 35000, 35500, 36000, 36500, 37000, 37500, 38000, 38500, 39000, 39500, or 40000 genes that do not include any of the genes within the endocrine signaling negative gene set or the endocrine signaling positive gene set.

In embodiments, the remainder gene set includes from about 18,000 to about 24,000 genes that do not include genes within the endocrine signaling negative gene set, or genes within the endocrine signaling positive gene set. In embodiments, the remainder gene set includes from about 18,500 to about 24,000 genes. In embodiments, the remainder gene set includes from about 19,000 to about 24,000 genes. In embodiments, the remainder gene set includes from about 19,500 to about 24,000 genes. In embodiments, the remainder gene set includes from about 20,000 to about 24,000 genes. In embodiments, the remainder gene set includes from about 20,500 to about 24,000 genes. In embodiments, the remainder gene set includes from about 21,000 to about 24,000 genes. In embodiments, the remainder gene set includes from about 21,500 to about 24,000 genes. In embodiments, the remainder gene set includes from about 22,000 to about 24,000 genes. In embodiments, the remainder gene set includes from about 22,500 to about 24,000 genes. In embodiments, the remainder gene set includes from about 23,000 to about 24,000 genes. In embodiments, the remainder gene set includes from about 23,500 to about 24,000 genes.

In embodiments, the remainder gene set includes from about 18,000 to about 23,500 genes that do not include genes within the endocrine signaling negative gene set, or genes within the endocrine signaling positive gene set. In embodiments, the remainder gene set includes from about 18,000 to about 23,000 genes. In embodiments, the remainder gene set includes from about 18,000 to about 22,500 genes. In embodiments, the remainder gene set includes from about 18,000 to about 22,000 genes. In embodiments, the remainder gene set includes from about 18,000 to about 21,500 genes. In embodiments, the remainder gene set includes from about 18,000 to about 21,000 genes. In embodiments, the remainder gene set includes from about 18,000 to about 20,500 genes. In embodiments, the remainder gene set includes from about 18,000 to about 20,000 genes. In embodiments, the remainder gene set includes from about 18,000 to about 19,500 genes. In embodiments, the remainder gene set includes from about 18,000 to about 19,000 genes. In embodiments, the remainder gene set includes from about 18,000 to about 19,500 genes. In embodiments, the remainder gene set includes about 18,000, 18,500, 19,000, 19,500, 20,000, 20,500, 21,000, 21,500, 22,000, 22,500, 23,000, 23,500, or 24,000 genes that do not include genes within the endocrine signaling negative gene set, or genes within the endocrine signaling positive gene set.

For the methods provided herein, in embodiments, the first standard control is the average expression level of RNA transcripts from the endocrine signaling negative gene set of a population of metastatic ER+ breast cancer patients. In embodiments, the first standard control is the average expression level of RNA transcripts from the endocrine signaling negative gene set of a population of metastatic ER+ breast cancer patients that are not responsive to endocrine therapy.

In embodiments, a population of metastatic ER+ breast cancer patients includes at least 50 patients having metastatic ER+ breast cancer. In embodiments, a population of metastatic ER+ breast cancer patients includes at least 100 patients having metastatic ER+ breast cancer. In embodiments, a population of metastatic ER+ breast cancer patients includes at least 200 patients having metastatic ER+ breast cancer. In embodiments, a population of metastatic ER+ breast cancer patients includes at least 300 patients having metastatic ER+ breast cancer. In embodiments, a population of metastatic ER+ breast cancer patients includes at least 400 patients having metastatic ER+ breast cancer. In embodiments, a population of metastatic ER+ breast cancer patients includes at least 500 patients having metastatic ER+ breast cancer. In embodiments, a population of metastatic ER+ breast cancer patients includes from about 250 to about 20,500 patients having metastatic ER+ breast cancer. In embodiments, a population of of metastatic ER+ breast cancer patients includes at least about 250 patients having metastatic ER+ breast cancer. In embodiments, a population of metastatic ER+ breast cancer patients includes at least about 500 patients having metastatic ER+ breast cancer. In embodiments, a population of metastatic ER+ breast cancer patients includes at least about 1,500 patients having metastatic ER+ breast cancer. In embodiments, a population of metastatic ER+ breast cancer patients includes at least about 2,000 patients having metastatic ER+ breast cancer. In embodiments, a population of metastatic ER+ breast cancer patients includes at least about 5,000 patients having metastatic ER+ breast cancer. In embodiments, a population of of metastatic ER+ breast cancer patients includes at least about 10,000 patients having metastatic ER+ breast cancer. In embodiments, a population of metastatic ER+ breast cancer patients includes at least about 15,000 patients having metastatic ER+ breast cancer. In embodiments, a population of metastatic ER+ breast cancer patients includes at least about 20,000 patients having metastatic ER+ breast cancer. In embodiments, a population of metastatic ER+ breast cancer patients includes at least 250, 500, 1,000, 1,500, 2,500, 5,000, 10,000 or 20,000 patients having metastatic ER+ breast cancer.

In embodiments, the first standard control is the $30^{th}$ percentile of the expression level of RNA transcripts from the endocrine signaling negative gene set of a population of metastatic ER+ breast cancer patients. Where a "percentile" of expression level of RNA transcripts is referred to herein, the $100^{th}$ percentile is the highest level of expression. Thus, a low percentile correlates to lower RNA transcript levels and a high percentile correlates to higher RNA transcripts levels. In embodiments, the first standard control is the $40^{th}$ percentile of the expression level of RNA transcripts from the endocrine signaling negative gene set of a population of metastatic ER+ breast cancer patients. In embodiments, the first standard control is the $50^{th}$ percentile of the expression level of RNA transcripts from the endocrine signaling negative gene set of a population of metastatic ER+ breast cancer patients. In embodiments, the first standard control is the $60^{th}$ percentile of the expression level of RNA transcripts from the endocrine signaling negative gene set of a population of metastatic ER+ breast cancer patients. In embodiments, the first standard control is the $61^{st}$ percentile of the expression level of RNA transcripts from the endocrine signaling negative gene set of a population of metastatic ER+ breast cancer patients. In embodiments, the first standard control is the $62^{nd}$ percentile of the expression level of RNA transcripts from the endocrine signaling negative gene set of a population of metastatic ER+ breast cancer patients. In embodiments, the first standard control is the $63^{rd}$ percentile of the expression level of RNA transcripts from the endocrine signaling negative gene set of a population of metastatic ER+ breast cancer patients. In embodiments, the first standard control is the $64^{th}$ percentile of the expression level of RNA transcripts from the endocrine signaling negative gene set of a population of metastatic ER+ breast cancer patients. In embodiments, the first standard control is the $65^{th}$ percentile of the expression level of RNA transcripts from the endocrine signaling negative gene set of a population of metastatic ER+ breast cancer patients. In embodiments, the first standard control is the $66^{th}$ percentile of the expression level of RNA transcripts from the endocrine signaling negative gene set of a population of metastatic ER+ breast cancer patients. In embodiments, the first standard control is the $67^{th}$ percentile of the expression level of RNA transcripts from the endocrine signaling negative gene set of a population of metastatic ER+ breast cancer patients. In embodiments, the first standard control is the $68^{th}$ percentile of the expression level of RNA transcripts from the endocrine signaling negative gene set of a population of metastatic ER+ breast cancer patients. In embodiments, the first standard control is the $69^{th}$ percentile of the expression level of RNA transcripts from the endocrine signaling negative gene set of a population of metastatic ER+ breast cancer patients. In embodiments, the first standard control is the $70^{th}$ percentile of the expression level of RNA transcripts from the endocrine signaling negative gene set of a population of metastatic ER+ breast cancer patients. In embodiments, the first standard control is the $70^{th}$ percentile of the expression level of RNA transcripts from the endocrine signaling negative gene set of a population of metastatic ER+ breast cancer patients. In embodiments, the first standard control is the $71^{st}$ percentile of the expression level of RNA transcripts from the endocrine signaling negative gene set of a population of metastatic ER+ breast cancer patients. In embodiments, the first standard control is the $72^{nd}$ percentile of the expression level of RNA transcripts from the endocrine signaling negative gene set of a population of metastatic ER+ breast cancer patients. In embodiments, the first standard control is the $73^{rd}$ percentile of the expression level of RNA transcripts from the endocrine signaling negative gene set of a population of metastatic ER+ breast cancer patients. In embodiments, the first standard control is the $74^{th}$ percentile of the expression level of RNA transcripts from the endocrine signaling negative gene set of a population of metastatic ER+ breast cancer patients. In embodiments, the first standard control is the $75^{th}$ percentile of the expression level of RNA transcripts from the endocrine signaling negative gene set of a population of metastatic ER+ breast cancer patients. In embodiments, the first standard control is the $76^{th}$ percentile of the expression level of RNA transcripts from the endocrine signaling negative gene set of a population of metastatic ER+ breast cancer patients. In embodiments, the first standard control is the $77^{th}$ percentile of the expression level of RNA transcripts from the endocrine signaling negative gene set of a population of metastatic ER+ breast cancer patients. In embodiments, the first standard control is the $78^{th}$ percentile of the expression level of RNA transcripts from the endocrine signaling negative gene set of a population of metastatic ER+ breast cancer patients. In embodiments, the first standard control is the $79^{th}$ percentile of the expression level of RNA transcripts from the endocrine signaling negative gene set of a population of metastatic ER+ breast cancer patients. In embodiments, the first standard control is the $80^{th}$ percentile of the expression level of RNA transcripts from the endocrine signaling negative gene set of a population of metastatic ER+ breast cancer patients. In embodiments, the first standard control is the $81^{st}$ percentile of the expression level of RNA transcripts from the endocrine signaling negative gene set of a population of metastatic ER+ breast cancer patients. In embodiments, the first standard control is the $82^{nd}$ percentile of the expression level of RNA transcripts from the endocrine signaling negative gene set of a population of metastatic ER+ breast cancer patients. In embodiments, the first standard control is the $83^{rd}$ percentile of the expression level of RNA transcripts from the endocrine signaling negative gene set of a population of metastatic ER+ breast cancer patients. In embodiments, the first standard control is the $84^{th}$ percentile of the expression level of RNA transcripts from the endocrine signaling negative gene set of a population of metastatic ER+ breast cancer patients. In embodiments, the first standard control is the $85^{th}$ percentile of the expression level of RNA transcripts from the endocrine signaling negative gene set of a population of metastatic ER+ breast cancer patients. In embodiments, the first standard control is the $86^{th}$ percentile of the expression level of RNA transcripts from the endocrine signaling negative gene set of a population of metastatic ER+ breast cancer patients. In embodiments, the first standard control is the $87^{th}$ percentile of the expression level of RNA transcripts from the endocrine signaling negative gene set of a population of metastatic ER+ breast cancer patients. In embodiments, the first standard control is the $88^{th}$ percentile of the expression level of RNA transcripts from the endocrine signaling negative gene set of a population of metastatic ER+ breast cancer patients. In embodiments, the first standard control is the $89^{th}$ percentile of the expression level of RNA transcripts from the endocrine signaling negative gene set of a population of metastatic ER+ breast cancer patients. In embodiments, the first standard control is the $90^{th}$ percentile of the expression level of RNA transcripts from the endocrine signaling negative gene set of a population of metastatic ER+ breast cancer patients. In embodiments, the first standard control is the $91^{st}$ percentile of expression level of RNA transcripts from the endocrine signaling negative gene set of a population of metastatic ER+ breast cancer patients. In embodiments, the first standard control is the $92^{nd}$ percentile of the expression level of RNA transcripts from the endocrine signaling negative gene set of a population of metastatic ER+ breast cancer patients. In embodiments, the first standard control is the $93^{rd}$ percentile of the expression level of RNA transcripts from the endocrine signaling negative gene set of a population of metastatic ER+ breast cancer patients. In embodiments, the first standard control is the $94^{th}$ percentile of the expression level of RNA transcripts from the endocrine signaling negative gene set of a population of metastatic ER+ breast cancer patients. In embodiments, the first standard control is the $95^{th}$ percentile of the expression level of RNA transcripts from the endocrine signaling negative gene set of a population of metastatic ER+ breast cancer patients.

In embodiments, the high level of expression is higher than the $30^{th}$ percentile of the expression level of RNA transcripts from the endocrine signaling negative gene set of a population of metastatic ER+ breast cancer patients. In embodiments, the high level of expression is higher than the $40^{th}$ percentile of the expression level of RNA transcripts from the endocrine signaling negative gene set of a population of metastatic ER+ breast cancer patients. In embodiments, the high level of expression is higher than the $50^{th}$ percentile of the expression level of RNA transcripts from the endocrine signaling negative gene set of a population of metastatic ER+ breast cancer patients. In embodiments, the high level of expression is higher than the $60^{th}$ percentile of the expression level of RNA transcripts from the endocrine signaling negative gene set of a population of metastatic ER+ breast cancer patients. In embodiments, the high level of expression is higher than the $61^{st}$ percentile of the expression level of RNA transcripts from the endocrine signaling negative gene set of a population of metastatic ER+ breast cancer patients. In embodiments, the high level of expression is higher than the $62^{nd}$ percentile of the expression level of RNA transcripts from the endocrine signaling negative gene set of a population of metastatic ER+ breast cancer patients. In embodiments, the high level of expression is higher than the $63^{rd}$ percentile of the expression level of RNA transcripts from the endocrine signaling negative gene set of a population of metastatic ER+ breast cancer patients. In embodiments, the high level of expression is higher than the $64^{th}$ percentile of the expression level of RNA transcripts from the endocrine signaling negative gene set of a population of metastatic ER+ breast cancer patients. In embodiments, the high level of expression is higher than the $65^{th}$ percentile of the expression level of RNA transcripts from the endocrine signaling negative gene set of a population of metastatic ER+ breast cancer patients. In embodiments, the high level of expression is higher than the $66^{th}$ percentile of the expression level of RNA transcripts from the endocrine signaling negative gene set of a population of metastatic ER+ breast cancer patients. In embodiments, the high level of expression is higher than the $67^{th}$ percentile of the expression level of RNA transcripts from the endocrine signaling negative gene set of a population of metastatic ER+ breast cancer patients. In embodiments, the high level of expression is higher than the $68^{th}$ percentile of the expression level of RNA transcripts from the endocrine signaling negative gene set of a population of metastatic ER+ breast cancer patients. In embodiments, the high level of expression is higher than the $69^{th}$ percentile of the expression level of RNA transcripts from the endocrine signaling negative gene set of a population of metastatic ER+ breast cancer patients. In embodiments, the high level of expression is higher than the $70^{th}$ percentile of the expression level of RNA transcripts from the endocrine signaling negative gene set of a population of metastatic ER+ breast cancer patients. In embodiments, the high level of expression is higher than the $71^{st}$ percentile of the expression level of RNA transcripts from the endocrine signaling negative gene set of a population of metastatic ER+ breast cancer patients. In embodiments, the high level of expression is higher than the $72^{nd}$ percentile of the expression level of RNA transcripts from the endocrine signaling negative gene set of a population of metastatic ER+ breast cancer patients. In embodiments, the high level of expression is higher than the $73^{rd}$ percentile of the expression level of RNA transcripts from the endocrine signaling negative gene set of a population of metastatic ER+ breast cancer patients. In embodiments, the high level of expression is higher than the $74^{th}$ percentile of the expression level of RNA transcripts from the endocrine signaling negative gene set of a population of metastatic ER+ breast cancer patients. In embodiments, the high level of expression is higher than the $75^{th}$ percentile of the expression level of RNA transcripts from the endocrine signaling negative gene set of a population of metastatic ER+ breast cancer patients. In embodiments, the high level of expression is higher than the $76^{th}$ percentile of the expression level of RNA transcripts from the endocrine signaling negative gene set of a population of metastatic ER+ breast cancer patients. In embodiments, the high level of expression is higher than the $77^{th}$ percentile of the expression level of RNA transcripts from the endocrine signaling negative gene set of a population of metastatic ER+ breast cancer patients. In embodiments, the high level of expression is higher than the $78^{th}$ percentile of the expression level of RNA transcripts from the endocrine signaling negative gene set of a population of metastatic ER+ breast cancer patients. In embodiments, the high level of expression is higher than the $79^{th}$ percentile of the expression level of RNA transcripts from the endocrine signaling negative gene set of a population of metastatic ER+ breast cancer patients. In embodiments, the high level of expression is higher than the $80^{th}$ percentile of the expression level of RNA transcripts from the endocrine signaling negative gene set of a population of metastatic ER+ breast cancer patients. In embodiments, the high level of expression is higher than the $81^{st}$ percentile of the expression level of RNA transcripts from the endocrine signaling negative gene set of a population of metastatic ER+ breast cancer patients. In embodiments, the high level of expression is higher than the $82^{nd}$ percentile of the expression level of RNA transcripts from the endocrine signaling negative gene set of a population of metastatic ER+ breast cancer patients. In embodiments, the high level of expression is higher than the $83^{rd}$ percentile of the expression level of RNA transcripts from the endocrine signaling negative gene set of a population of metastatic ER+ breast cancer patients. In embodiments, the high level of expression is higher than the $84^{th}$ percentile of the expression level of RNA transcripts from the endocrine signaling negative gene set of a population of metastatic ER+ breast cancer patients. In embodiments, the high level of expression is higher than the $85^{th}$ percentile of the expression level of RNA transcripts from the endocrine signaling negative gene set of a population of metastatic ER+ breast cancer patients. In embodiments, the high level of expression is higher than the $86^{th}$ percentile of the expression level of RNA transcripts from the endocrine signaling negative gene set of a population of metastatic ER+ breast cancer patients. In embodiments, the high level of expression is higher than the $87^{th}$ percentile of the expression level of RNA transcripts from the endocrine signaling negative gene set of a population of metastatic ER+ breast cancer patients. In embodiments, the high level of expression is higher than the $88^{th}$ percentile of the expression level of RNA transcripts from the endocrine signaling negative gene set of a population of metastatic ER+ breast cancer patients. In embodiments, the high level of expression is higher than the $89^{th}$ percentile of the expression level of RNA transcripts from the endocrine signaling negative gene set of a population of metastatic ER+ breast cancer patients. In embodiments, the high level of expression is higher than the $90^{th}$ percentile of the expression level of RNA transcripts from the endocrine signaling negative gene set of a population of metastatic ER+ breast cancer patients. In embodiments, the high level of expression is higher than the $91^{st}$ percentile of the expression level of RNA transcripts from the endocrine signaling negative gene set of a population of metastatic ER+ breast cancer patients. In embodiments, the high level of expression is higher than the $92^{nd}$ percentile of the expression level of RNA transcripts from the endocrine signaling negative gene set of a population of metastatic ER+ breast cancer patients. In embodiments, the high level of expression is higher than the $93^{rd}$ percentile of the expression level of RNA transcripts from the endocrine signaling negative gene set of a population of metastatic ER+ breast cancer patients. In embodiments, the high level of expression is higher than the $94^{th}$ percentile of the expression level of RNA transcripts from the endocrine signaling negative gene set of a population of metastatic ER+ breast cancer patients. In embodiments, the high level of expression is higher than the $95^{th}$ percentile of the expression level of RNA transcripts from the endocrine signaling negative gene set of a population of metastatic ER+ breast cancer patients.

In embodiments, the second standard control is the average expression level of RNA transcripts from the endocrine signaling positive gene set of a population of metastatic ER+ breast cancer patients that are responsive to endocrine therapy. In embodiments, the second standard control is the average expression level of RNA transcripts from the endocrine signaling positive gene set of a population of metastatic ER+ breast cancer patients that are not responsive to endocrine therapy.

In embodiments, the second standard control is the $30^{th}$ percentile of the expression level of RNA transcripts from the endocrine signaling positive gene set of a population of metastatic ER+ breast cancer patients. In embodiments, the second standard control is the $31^{st}$ percentile of the expression level of RNA transcripts from the endocrine signaling positive gene set of a population of metastatic ER+ breast cancer patients. In embodiments, the second standard control is the $32^{nd}$ percentile of the expression level of RNA transcripts from the endocrine signaling positive gene set of a population of metastatic ER+ breast cancer patients. In embodiments, the second standard control is the $33^{rd}$ percentile of the expression level of RNA transcripts from the endocrine signaling positive gene set of a population of metastatic ER+ breast cancer patients. In embodiments, the second standard control is the $34^{th}$ percentile of the expression level of RNA transcripts from the endocrine signaling positive gene set of a population of metastatic ER+ breast cancer patients. In embodiments, the second standard control is the $35^{th}$ percentile of the expression level of RNA transcripts from the endocrine signaling positive gene set of a population of metastatic ER+ breast cancer patients. In embodiments, the second standard control is the $36^{th}$ percentile of the expression level of RNA transcripts from the endocrine signaling positive gene set of a population of metastatic ER+ breast cancer patients. In embodiments, the second standard control is the $37^{th}$ percentile of the expression level of RNA transcripts from the endocrine signaling positive gene set of a population of metastatic ER+ breast cancer patients. In embodiments, the second standard control is the $38^{th}$ percentile of the expression level of RNA transcripts from the endocrine signaling positive gene set of a population of metastatic ER+ breast cancer patients. In embodiments, the second standard control is the $39^{th}$ percentile of the expression level of RNA transcripts from the endocrine signaling positive gene set of a population of metastatic ER+ breast cancer patients. In embodiments, the second standard control is the $40^{th}$ percentile of the expression level of RNA transcripts from the endocrine signaling positive gene set of a population of metastatic ER+ breast cancer patients. In embodiments, the second standard control is the $41^{st}$ percentile of the expression level of RNA transcripts from the endocrine signaling positive gene set of a population of metastatic ER+ breast cancer patients. In embodiments, the second standard control is the $42^{nd}$ percentile of the expression level of RNA transcripts from the endocrine signaling positive gene set of a population of metastatic ER+ breast cancer patients. In embodiments, the second standard control is the $43^{rd}$ percentile of the expression level of RNA transcripts from the endocrine signaling positive gene set of a population of metastatic ER+ breast cancer patients. In embodiments, the second standard control is the $44^{th}$ percentile of the expression level of RNA transcripts from the endocrine signaling positive gene set of a population of metastatic ER+ breast cancer patients. In embodiments, the second standard control is the $45^{th}$ percentile of the expression level of RNA transcripts from the endocrine signaling positive gene set of a population of metastatic ER+ breast cancer patients. In embodiments, the second standard control is the $46^{th}$ percentile of the expression level of RNA transcripts from the endocrine signaling positive gene set of a population of metastatic ER+ breast cancer patients. In embodiments, the second standard control is the $47^{th}$ percentile of the expression level of RNA transcripts from the endocrine signaling positive gene set of a population of metastatic ER+ breast cancer patients. In embodiments, the second standard control is the $48^{th}$ percentile of the expression level of RNA transcripts from the endocrine signaling positive gene set of a population of metastatic ER+ breast cancer patients. In embodiments, the second standard control is the $49^{th}$ percentile of the expression level of RNA transcripts from the endocrine signaling positive gene set of a population of metastatic ER+ breast cancer patients. In embodiments, the second standard control is the $50^{th}$ percentile of the expression level of RNA transcripts from the endocrine signaling positive gene set of a population of metastatic ER+ breast cancer patients In embodiments, the second standard control is the $50^{th}$ percentile of the expression level of RNA transcripts from the endocrine signaling positive gene set of a population of metastatic ER+ breast cancer patients. In embodiments, the second standard control is the $51^{st}$ percentile of the expression level of RNA transcripts from the endocrine signaling positive gene set of a population of metastatic ER+ breast cancer patients. In embodiments, the second standard control is the $52^{nd}$ percentile of the expression level of RNA transcripts from the endocrine signaling positive gene set of a population of metastatic ER+ breast cancer patients. In embodiments, the second standard control is the $53^{rd}$ percentile of the expression level of RNA transcripts from the endocrine signaling positive gene set of a population of metastatic ER+ breast cancer patients. In embodiments, the second standard control is the $54^{th}$ percentile of the expression level of RNA transcripts from the endocrine signaling positive gene set of a population of metastatic ER+ breast cancer patients. In embodiments, the second standard control is the $55^{th}$ percentile of the expression level of RNA transcripts from the endocrine signaling positive gene set of a population of metastatic ER+ breast cancer patients. In embodiments, the second standard control is the $56^{th}$ percentile of the expression level of RNA transcripts from the endocrine signaling positive gene set of a population of metastatic ER+ breast cancer patients. In embodiments, the second standard control is the $57^{th}$ percentile of the expression level of RNA transcripts from the endocrine signaling positive gene set of a population of metastatic ER+ breast cancer patients. In embodiments, the second standard control is the $58^{th}$ percentile of the expression level of RNA transcripts from the endocrine signaling positive gene set of a population of metastatic ER+ breast cancer patients. In embodiments, the second standard control is the $59^{th}$ percentile of the expression level of RNA transcripts from the endocrine signaling positive gene set of a population of metastatic ER+ breast cancer patients. In embodiments, the second standard control is the $60^{th}$ percentile of the expression level of RNA transcripts from the endocrine signaling positive gene set of a population of metastatic ER+ breast cancer patients. In embodiments, the second standard control is the $61^{st}$ percentile of the expression level of RNA transcripts from the endocrine signaling positive gene set of a population of metastatic ER+ breast cancer patients. In embodiments, the second standard control is the $62^{nd}$ percentile of the expression level of RNA transcripts from the endocrine signaling positive gene set of a population of metastatic ER+ breast cancer patients. In embodiments, the second standard control is the $63^{rd}$ percentile of the expression level of RNA transcripts from the endocrine signaling positive gene set of a population of metastatic ER+ breast cancer patients. In embodiments, the second standard control is the $64^{th}$ percentile of the expression level of RNA transcripts from the endocrine signaling positive gene set of a population of metastatic ER+ breast cancer patients. In embodiments, the second standard control is the $65^{th}$ percentile of the expression level of RNA transcripts from the endocrine signaling positive gene set of a population of metastatic ER+ breast cancer patients. In embodiments, the second standard control is the $66^{th}$ percentile of the expression level of RNA transcripts from the endocrine signaling positive gene set of a population of metastatic ER+ breast cancer patients. In embodiments, the second standard control is the $67^{th}$ percentile of the expression level of RNA transcripts from the endocrine signaling positive gene set of a population of metastatic ER+ breast cancer patients. In embodiments, the second standard control is the $68^{th}$ percentile of the expression level of RNA transcripts from the endocrine signaling positive gene set of a population of metastatic ER+ breast cancer patients. In embodiments, the second standard control is the $69^{th}$ percentile of the expression level of RNA transcripts from the endocrine signaling positive gene set of a population of metastatic ER+ breast cancer patients. In embodiments, the second standard control is the $70^{th}$ percentile of the expression level of RNA transcripts from the endocrine signaling positive gene set of a population of metastatic ER+ breast cancer patients. In embodiments, the second standard control is the $71^{st}$ percentile of the expression level of RNA transcripts from the endocrine signaling positive gene set of a population of metastatic ER+ breast cancer patients. In embodiments, the second standard control is the $72^{nd}$ percentile of the expression level of RNA transcripts from the endocrine signaling positive gene set of a population of metastatic ER+ breast cancer patients. In embodiments, the second standard control is the $73^{rd}$ percentile of the expression level of RNA transcripts from the endocrine signaling positive gene set of a population of metastatic ER+ breast cancer patients. In embodiments, the second standard control is the $74^{th}$ percentile of the expression level of RNA transcripts from the endocrine signaling positive gene set of a population of metastatic ER+ breast cancer patients. In embodiments, the second standard control is the $75^{th}$ percentile of the expression level of RNA transcripts from the endocrine signaling positive gene set of a population of metastatic ER+ breast cancer patients. In embodiments, the second standard control is the $76^{th}$ percentile of the expression level of RNA transcripts from the endocrine signaling positive gene set of a population of metastatic ER+ breast cancer patients. In embodiments, the second standard control is the $77^{th}$ percentile of the expression level of RNA transcripts from the endocrine signaling positive gene set of a population of metastatic ER+ breast cancer patients. In embodiments, the second standard control is the $78^{th}$ percentile of the expression level of RNA transcripts from the endocrine signaling positive gene set of a population of metastatic ER+ breast cancer patients. In embodiments, the second standard control is the $79^{th}$ percentile of the expression level of RNA transcripts from the endocrine signaling positive gene set of a population of metastatic ER+ breast cancer patients. In embodiments, the second standard control is the $80^{th}$ percentile of the expression level of RNA transcripts from the endocrine signaling positive gene set of a population of metastatic ER+ breast cancer patients.

In embodiments, the low level of expression is lower than the $30^{th}$ percentile of the expression level of RNA transcripts from the endocrine signaling positive gene set of a population of metastatic ER+ breast cancer patients. In embodiments, the low level of expression is lower than the $31^{st}$ percentile of the expression level of RNA transcripts from the endocrine signaling positive gene set of a population of metastatic ER+ breast cancer patients. In embodiments, the low level of expression is lower than the $32^{nd}$ percentile of the expression level of RNA transcripts from the endocrine signaling positive gene set of a population of metastatic ER+ breast cancer patients. In embodiments, the low level of expression is lower than the $33^{rd}$ percentile of the expression level of RNA transcripts from the endocrine signaling positive gene set of a population of metastatic ER+ breast cancer patients. In embodiments, the low level of expression is lower than the $34^{th}$ percentile of the expression level of RNA transcripts from the endocrine signaling positive gene set of a population of metastatic ER+ breast cancer patients. In embodiments, the low level of expression is lower than the $35^{th}$ percentile of the expression level of RNA transcripts from the endocrine signaling positive gene set of a population of metastatic ER+ breast cancer patients. In embodiments, the low level of expression is lower than the $36^{th}$ percentile of the expression level of RNA transcripts from the endocrine signaling positive gene set of a population of metastatic ER+ breast cancer patients. In embodiments, the low level of expression is lower than the $37^{th}$ percentile of the expression level of RNA transcripts from the endocrine signaling positive gene set of a population of metastatic ER+ breast cancer patients. In embodiments, the low level of expression is lower than the $38^{th}$ percentile of the expression level of RNA transcripts from the endocrine signaling positive gene set of a population of metastatic ER+ breast cancer patients. In embodiments, the low level of expression is lower than the $39^{th}$ percentile of the expression level of RNA transcripts from the endocrine signaling positive gene set of a population of metastatic ER+ breast cancer patients. In embodiments, the low level of expression is lower than the $40^{th}$ percentile of the expression level of RNA transcripts from the endocrine signaling positive gene set of a population of metastatic ER+ breast cancer patients. In embodiments, the low level of expression is lower than the $41^{st}$ percentile of the expression level of RNA transcripts from the endocrine signaling positive gene set of a population of metastatic ER+ breast cancer patients. In embodiments, the low level of expression is lower than the $42^{nd}$ percentile of the expression level of RNA transcripts from the endocrine signaling positive gene set of a population of metastatic ER+ breast cancer patients. In embodiments, the low level of expression is lower than the $43^{rd}$ percentile of the expression level of RNA transcripts from the endocrine signaling positive gene set of a population of metastatic ER+ breast cancer patients. In embodiments, the low level of expression is lower than the $44^{th}$ percentile of the expression level of RNA transcripts from the endocrine signaling positive gene set of a population of metastatic ER+ breast cancer patients. In embodiments, the low level of expression is lower than the $45^{th}$ percentile of the expression level of RNA transcripts from the endocrine signaling positive gene set of a population of metastatic ER+ breast cancer patients. In embodiments, the low level of expression is lower than the $46^{th}$ percentile of the expression level of RNA transcripts from the endocrine signaling positive gene set of a population of metastatic ER+ breast cancer patients. In embodiments, the low level of expression is lower than the $47^{th}$ percentile of the expression level of RNA transcripts from the endocrine signaling positive gene set of a population of metastatic ER+ breast cancer patients. In embodiments, the low level of expression is lower than the $48^{th}$ percentile of the expression level of RNA transcripts from the endocrine signaling positive gene set of a population of metastatic ER+ breast cancer patients. In embodiments, the low level of expression is lower than the $49^{th}$ percentile of the expression level of RNA transcripts from the endocrine signaling positive gene set of a population of metastatic ER+ breast cancer patients. In embodiments, the low level of expression is lower than the $50^{th}$ percentile of the expression level of RNA transcripts from the endocrine signaling positive gene set of a population of metastatic ER+ breast cancer patients In embodiments, the low level of expression is lower than the $50^{th}$ percentile of the expression level of RNA transcripts from the endocrine signaling positive gene set of a population of metastatic ER+ breast cancer patients. In embodiments, the low level of expression is lower than the $51^{st}$ percentile of the expression level of RNA transcripts from the endocrine signaling positive gene set of a population of metastatic ER+ breast cancer patients. In embodiments, the low level of expression is lower than the $52^{nd}$ percentile of the expression level of RNA transcripts from the endocrine signaling positive gene set of a population of metastatic ER+ breast cancer patients. In embodiments, the low level of expression is lower than the $53^{rd}$ percentile of the expression level of RNA transcripts from the endocrine signaling positive gene set of a population of metastatic ER+ breast cancer patients. In embodiments, the low level of expression is lower than the $54^{th}$ percentile of the expression level of RNA transcripts from the endocrine signaling positive gene set of a population of metastatic ER+ breast cancer patients. In embodiments, the low level of expression is lower than the $55^{th}$ percentile of the expression level of RNA transcripts from the endocrine signaling positive gene set of a population of metastatic ER+ breast cancer patients. In embodiments, the low level of expression is lower than the $56^{th}$ percentile of the expression level of RNA transcripts from the endocrine signaling positive gene set of a population of metastatic ER+ breast cancer patients. In embodiments, the low level of expression is lower than the $57^{th}$ percentile of the expression level of RNA transcripts from the endocrine signaling positive gene set of a population of metastatic ER+ breast cancer patients. In embodiments, the low level of expression is lower than the $58^{th}$ percentile of the expression level of RNA transcripts from the endocrine signaling positive gene set of a population of metastatic ER+ breast cancer patients. In embodiments, the low level of expression is lower than the $59^{th}$ percentile of the expression level of RNA transcripts from the endocrine signaling positive gene set of a population of metastatic ER+ breast cancer patients. In embodiments, the low level of expression is lower than the $60^{th}$ percentile of the expression level of RNA transcripts from the endocrine signaling positive gene set of a population of metastatic ER+ breast cancer patients. In embodiments, the low level of expression is lower than the $61^{st}$ percentile of the expression level of RNA transcripts from the endocrine signaling positive gene set of a population of metastatic ER+ breast cancer patients. In embodiments, the low level of expression is lower than the $62^{nd}$ percentile of the expression level of RNA transcripts from the endocrine signaling positive gene set of a population of metastatic ER+ breast cancer patients. In embodiments, the low level of expression is lower than the $63^{rd}$ percentile of the expression level of RNA transcripts from the endocrine signaling positive gene set of a population of metastatic ER+ breast cancer patients. In embodiments, the low level of expression is lower than the $64^{th}$ percentile of the expression level of RNA transcripts from the endocrine signaling positive gene set of a population of metastatic ER+ breast cancer patients. In embodiments, the low level of expression is lower than the $65^{th}$ percentile of the expression level of RNA transcripts from the endocrine signaling positive gene set of a population of metastatic ER+ breast cancer patients. In embodiments, the low level of expression is lower than the $66^{th}$ percentile of the expression level of RNA transcripts from the endocrine signaling positive gene set of a population of metastatic ER+ breast cancer patients. In embodiments, the low level of expression is lower than the $67^{th}$ percentile of the expression level of RNA transcripts from the endocrine signaling positive gene set of a population of metastatic ER+ breast cancer patients. In embodiments, the low level of expression is lower than the $68^{th}$ percentile of the expression level of RNA transcripts from the endocrine signaling positive gene set of a population of metastatic ER+ breast cancer patients. In embodiments, the low level of expression is lower than the $69^{th}$ percentile of the expression level of RNA transcripts from the endocrine signaling positive gene set of a population of metastatic ER+ breast cancer patients. In embodiments, the low level of expression is lower than the $70^{th}$ percentile of the expression level of RNA transcripts from the endocrine signaling positive gene set of a population of metastatic ER+ breast cancer patients. In embodiments, the low level of expression is lower than the $71^{st}$ percentile of the expression level of RNA transcripts from the endocrine signaling positive gene set of a population of metastatic ER+ breast cancer patients. In embodiments, the low level of expression is lower than the $72^{nd}$ percentile of the expression level of RNA transcripts from the endocrine signaling positive gene set of a population of metastatic ER+ breast cancer patients. In embodiments, the low level of expression is lower than the $73^{rd}$ percentile of the expression level of RNA transcripts from the endocrine signaling positive gene set of a population of metastatic ER+ breast cancer patients. In embodiments, the low level of expression is lower than the $74^{th}$ percentile of the expression level of RNA transcripts from the endocrine signaling positive gene set of a population of metastatic ER+ breast cancer patients. In embodiments, the low level of expression is lower than the $75^{th}$ percentile of the expression level of RNA transcripts from the endocrine signaling positive gene set of a population of metastatic ER+ breast cancer patients. In embodiments, the low level of expression is lower than the $76^{th}$ percentile of the expression level of RNA transcripts from the endocrine signaling positive gene set of a population of metastatic ER+ breast cancer patients. In embodiments, the low level of expression is lower than the $77^{th}$ percentile of the expression level of RNA transcripts from the endocrine signaling positive gene set of a population of metastatic ER+ breast cancer patients. In embodiments, the low level of expression is lower than the $78^{th}$ percentile of the expression level of RNA transcripts from the endocrine signaling positive gene set of a population of metastatic ER+ breast cancer patients. In embodiments, the low level of expression is lower than the 791 percentile of the expression level of RNA transcripts from the endocrine signaling positive gene set of a population of metastatic ER+ breast cancer patients. In embodiments, the low level of expression is lower than the $80^{th}$ percentile of the expression level of RNA transcripts from the endocrine signaling positive gene set of a population of metastatic ER+ breast cancer patients.

In embodiments, the determining a high level of expression of the endocrine signaling negative gene set relative to a first standard control includes determining a first aggregate rank of the expression level of RNA transcripts from the endocrine signaling negative gene set relative to the expression level of RNA transcripts from the remainder gene set, wherein the first aggregate rank is high relative to the first standard control; and determining a low level of expression of the endocrine signaling positive gene set relative to a second standard control includes determining a second aggregate rank of the expression level of RNA transcripts from an endocrine signaling positive gene set relative to the expression level of RNA transcripts from the remainder gene set, wherein the second aggregate rank is low relative to the second standard control. Thus, in embodiments, the absolute values of the RNA transcript levels within the transcriptome set (e.g. transcripts expressed from the endocrine signaling negative gene set, transcripts expressed from the endocine signaling positive gene set, and transcripts expressed from the remainder gene set) are ranked. For example, the RNA transcripts from the RNA transcriptome set may be ranked by expression level. In embodiments, the expression levels may be ranked from lowest expression to highest expression. It is contemplated that ranking the expression levels of RNA transcripts allows for consistency across different methods (e.g. microarray, RNA-sequencing, PCR, etc.) of measuring gene expression levels, for example, as compared to taking the absolute values of RNA expression levels.

As used herein, "aggregate rank" refers to a value that is representative of a combination of ranked measurements. In embodiments, the aggregate rank may be a cumulative number resulting from adding individual ranks. In embodiments, aggregate ranking includes ranking expression levels (e.g. levels of RNA transcripts) of specific genes (e.g. endocrine signaling negative gene set, endocrine signaling positive gene set) within all gene expression levels measured, and combining the individual ranks to produce an aggregate rank. In embodiments, the aggregate rank is the combined rank of expression levels of genes from the endocrine signaling negative gene set. In embodiments, the aggregate rank is the combined rank of expression levels of genes from the endocrine signaling positive gene set.

For the methods provided herein, in embodiments, the first standard control is the average aggregate rank of the expression level of RNA transcripts from the endocrine signaling negative gene set of a population of metastatic ER+ breast cancer patients. In embodiments, the first standard control is the average aggregate rank of the expression level of RNA transcripts from the endocrine signaling negative gene set of a population of metastatic ER+ breast cancer patients that are not responsive to endocrine therapy.

In embodiments, the first standard control is the $30^{th}$ percentile of the aggregate rank of RNA transcripts from the endocrine signaling negative gene set of a population of metastatic ER+ breast cancer patients. Where a "percentile" of aggregate rank is referred to herein, the $100^{th}$ percentile is the highest aggregate rank. Thus, a low percentile correlates to lower aggregate rank of RNA transcripts and a high percentile correlates to higher aggregate rank of RNA transcripts. In embodiments, the first standard control is the $40^{th}$ percentile of the aggregate rank of RNA transcripts from the endocrine signaling negative gene set of a population of metastatic ER+ breast cancer patients. In embodiments, the first standard control is the $50^{th}$ percentile of the aggregate rank of RNA transcripts from the endocrine signaling negative gene set of a population of metastatic ER+ breast cancer patients. In embodiments, the first standard control is the $60^{th}$ percentile of the aggregate rank of RNA transcripts from the endocrine signaling negative gene set of a population of metastatic ER+ breast cancer patients. In embodiments, the first standard control is the $61^{st}$ percentile of the aggregate rank of RNA transcripts from the endocrine signaling negative gene set of a population of metastatic ER+ breast cancer patients. In embodiments, the first standard control is the $62^{nd}$ percentile of the aggregate rank of RNA transcripts from the endocrine signaling negative gene set of a population of metastatic ER+ breast cancer patients. In embodiments, the first standard control is the $63^{rd}$ percentile of the aggregate rank of RNA transcripts from the endocrine signaling negative gene set of a population of metastatic ER+ breast cancer patients. In embodiments, the first standard control is the $64^{th}$ percentile of the aggregate rank of RNA transcripts from the endocrine signaling negative gene set of a population of metastatic ER+ breast cancer patients. In embodiments, the first standard control is the $65^{th}$ percentile of the aggregate rank of RNA transcripts from the endocrine signaling negative gene set of a population of metastatic ER+ breast cancer patients. In embodiments, the first standard control is the $66^{th}$ percentile of the aggregate rank of RNA transcripts from the endocrine signaling negative gene set of a population of metastatic ER+ breast cancer patients. In embodiments, the first standard control is the $67^{th}$ percentile of the aggregate rank of RNA transcripts from the endocrine signaling negative gene set of a population of metastatic ER+ breast cancer patients. In embodiments, the first standard control is the $68^{th}$ percentile of the aggregate rank of RNA transcripts from the endocrine signaling negative gene set of a population of metastatic ER+ breast cancer patients. In embodiments, the first standard control is the $69^{th}$ percentile of the aggregate rank of RNA transcripts from the endocrine signaling negative gene set of a population of metastatic ER+ breast cancer patients. In embodiments, the first standard control is the $70^{th}$ percentile of the aggregate rank of RNA transcripts from the endocrine signaling negative gene set of a population of metastatic ER+ breast cancer patients. In embodiments, the first standard control is the $70^{th}$ percentile of the aggregate rank of RNA transcripts from the endocrine signaling negative gene set of a population of metastatic ER+ breast cancer patients. In embodiments, the first standard control is the $71^{st}$ percentile of the aggregate rank of RNA transcripts from the endocrine signaling negative gene set of a population of metastatic ER+ breast cancer patients. In embodiments, the first standard control is the $72^{nd}$ percentile of the aggregate rank of RNA transcripts from the endocrine signaling negative gene set of a population of metastatic ER+ breast cancer patients. In embodiments, the first standard control is the $73^{rd}$ percentile of the aggregate rank of RNA transcripts from the endocrine signaling negative gene set of a population of metastatic ER+ breast cancer patients. In embodiments, the first standard control is the $74^{th}$ percentile of the aggregate rank of RNA transcripts from the endocrine signaling negative gene set of a population of metastatic ER+ breast cancer patients. In embodiments, the first standard control is the $75^{th}$ percentile of the aggregate rank of RNA transcripts from the endocrine signaling negative gene set of a population of metastatic ER+ breast cancer patients. In embodiments, the first standard control is the $76^{th}$ percentile of the aggregate rank of RNA transcripts from the endocrine signaling negative gene set of a population of metastatic ER+ breast cancer patients. In embodiments, the first standard control is the $77^{th}$ percentile of the aggregate rank of RNA transcripts from the endocrine signaling negative gene set of a population of metastatic ER+ breast cancer patients. In embodiments, the first standard control is the $78^{th}$ percentile of the aggregate rank of RNA transcripts from the endocrine signaling negative gene set of a population of metastatic ER+ breast cancer patients. In embodiments, the first standard control is the $79^{th}$ percentile of the aggregate rank of RNA transcripts from the endocrine signaling negative gene set of a population of metastatic ER+ breast cancer patients. In embodiments, the first standard control is the $80^{th}$ percentile of the aggregate rank of RNA transcripts from the endocrine signaling negative gene set of a population of metastatic ER+ breast cancer patients. In embodiments, the first standard control is the $81^{st}$ percentile of the aggregate rank of the expression level of RNA transcripts from the endocrine signaling negative gene set of a population of metastatic ER+ breast cancer patients. In embodiments, the first standard control is the $82^{nd}$ percentile of the aggregate rank of RNA transcripts from the endocrine signaling negative gene set of a population of metastatic ER+ breast cancer patients. In embodiments, the first standard control is the $83^{rd}$ percentile of the aggregate rank of RNA transcripts from the endocrine signaling negative gene set of a population of metastatic ER+ breast cancer patients. In embodiments, the first standard control is the $84^{th}$ percentile of the aggregate rank of RNA transcripts from the endocrine signaling negative gene set of a population of metastatic ER+ breast cancer patients. In embodiments, the first standard control is the $85^{th}$ percentile of the aggregate rank of RNA transcripts from the endocrine signaling negative gene set of a population of metastatic ER+ breast cancer patients. In embodiments, the first standard control is the $86^{th}$ percentile of the aggregate rank of RNA transcripts from the endocrine signaling negative gene set of a population of metastatic ER+ breast cancer patients. In embodiments, the first standard control is the $87^{th}$ percentile of the aggregate rank of RNA transcripts from the endocrine signaling negative gene set of a population of metastatic ER+ breast cancer patients. In embodiments, the first standard control is the $88^{th}$ percentile of the aggregate rank of RNA transcripts from the endocrine signaling negative gene set of a population of metastatic ER+ breast cancer patients. In embodiments, the first standard control is the $89^{th}$ percentile of the aggregate rank of RNA transcripts from the endocrine signaling negative gene set of a population of metastatic ER+ breast cancer patients. In embodiments, the first standard control is the $90^{th}$ percentile of the aggregate rank of RNA transcripts from the endocrine signaling negative gene set of a population of metastatic ER+ breast cancer patients. In embodiments, the first standard control is the $91^{st}$ percentile of the aggregate rank of the expression level of RNA transcripts from the endocrine signaling negative gene set of a population of metastatic ER+ breast cancer patients. In embodiments, the first standard control is the $92^{nd}$ percentile of the aggregate rank of RNA transcripts from the endocrine signaling negative gene set of a population of metastatic ER+ breast cancer patients. In embodiments, the first standard control is the $93^{rd}$ percentile of the aggregate rank of RNA transcripts from the endocrine signaling negative gene set of a population of metastatic ER+ breast cancer patients. In embodiments, the first standard control is the $94^{th}$ percentile of the aggregate rank of RNA transcripts from the endocrine signaling negative gene set of a population of metastatic ER+ breast cancer patients. In embodiments, the first standard control is the $95^{th}$ percentile of the aggregate rank of RNA transcripts from the endocrine signaling negative gene set of a population of metastatic ER+ breast cancer patients.

In embodiments, the first aggregate rank is higher than the $30^{th}$ percentile of the expression level of RNA transcripts from the endocrine signaling negative gene set of a population of metastatic ER+ breast cancer patients. In embodiments, the first aggregate rank is higher than the $40^{th}$ percentile of the expression level of RNA transcripts from the endocrine signaling negative gene set of a population of metastatic ER+ breast cancer patients. In embodiments, the first aggregate rank is higher than the $50^{th}$ percentile of the expression level of RNA transcripts from the endocrine signaling negative gene set of a population of metastatic ER+ breast cancer patients. In embodiments, the first aggregate rank is higher than the $60^{th}$ percentile of the aggregate rank of RNA transcripts from the endocrine signaling negative gene set of a population of metastatic ER+ breast cancer patients. In embodiments, the first aggregate rank is higher than the $61^{st}$ percentile of the aggregate rank of RNA transcripts from the endocrine signaling negative gene set of a population of metastatic ER+ breast cancer patients. In embodiments, the first aggregate rank is higher than the $62^{nd}$ percentile of the aggregate rank of RNA transcripts from the endocrine signaling negative gene set of a population of metastatic ER+ breast cancer patients. In embodiments, the first aggregate rank is higher than the $63^{rd}$ percentile of the aggregate rank of RNA transcripts from the endocrine signaling negative gene set of a population of metastatic ER+ breast cancer patients. In embodiments, the first aggregate rank is higher than the $64^{th}$ percentile of the aggregate rank of RNA transcripts from the endocrine signaling negative gene set of a population of metastatic ER+ breast cancer patients. In embodiments, the first aggregate rank is higher than the $65^{th}$ percentile of the aggregate rank of RNA transcripts from the endocrine signaling negative gene set of a population of metastatic ER+ breast cancer patients. In embodiments, the first aggregate rank is higher than the $66^{th}$ percentile of the aggregate rank of RNA transcripts from the endocrine signaling negative gene set of a population of metastatic ER+ breast cancer patients. In embodiments, the first aggregate rank is higher than the $67^{th}$ percentile of the aggregate rank of RNA transcripts from the endocrine signaling negative gene set of a population of metastatic ER+ breast cancer patients. In embodiments, the first aggregate rank is higher than the $68^{th}$ percentile of the aggregate rank of RNA transcripts from the endocrine signaling negative gene set of a population of metastatic ER+ breast cancer patients. In embodiments, the first aggregate rank is higher than the $69^{th}$ percentile of the aggregate rank of RNA transcripts from the endocrine signaling negative gene set of a population of metastatic ER+ breast cancer patients. In embodiments, the first aggregate rank is higher than the $70^{th}$ percentile of the aggregate rank of RNA transcripts from the endocrine signaling negative gene set of a population of metastatic ER+ breast cancer patients. In embodiments, the first aggregate rank is higher than the $71^{st}$ percentile of the aggregate rank of RNA transcripts from the endocrine signaling negative gene set of a population of metastatic ER+ breast cancer patients. In embodiments, the first aggregate rank is higher than the $72^{nd}$ percentile of the aggregate rank of RNA transcripts from the endocrine signaling negative gene set of a population of metastatic ER+ breast cancer patients. In embodiments, the first aggregate rank is higher than the $73^{rd}$ percentile of the aggregate rank of RNA transcripts from the endocrine signaling negative gene set of a population of metastatic ER+ breast cancer patients. In embodiments, the first aggregate rank is higher than the $74^{th}$ percentile of the aggregate rank of RNA transcripts from the endocrine signaling negative gene set of a population of metastatic ER+ breast cancer patients. In embodiments, the first aggregate rank is higher than the $75^{th}$ percentile of the aggregate rank of RNA transcripts from the endocrine signaling negative gene set of a population of metastatic ER+ breast cancer patients. In embodiments, the first aggregate rank is higher than the $76^{th}$ percentile of the aggregate rank of RNA transcripts from the endocrine signaling negative gene set of a population of metastatic ER+ breast cancer patients. In embodiments, the first aggregate rank is higher than the $77^{th}$ percentile of the aggregate rank of RNA transcripts from the endocrine signaling negative gene set of a population of metastatic ER+ breast cancer patients. In embodiments, the first aggregate rank is higher than the $78^{th}$ percentile of the aggregate rank of RNA transcripts from the endocrine signaling negative gene set of a population of metastatic ER+ breast cancer patients. In embodiments, the first aggregate rank is higher than the $79^{th}$ percentile of the aggregate rank of RNA transcripts from the endocrine signaling negative gene set of a population of metastatic ER+ breast cancer patients. In embodiments, the first aggregate rank is higher than the $80^{th}$ percentile of the aggregate rank of RNA transcripts from the endocrine signaling negative gene set of a population of metastatic ER+ breast cancer patients. In embodiments, the first aggregate rank is higher than the $81^{st}$ percentile of the aggregate rank of the expression level of RNA transcripts from the endocrine signaling negative gene set of a population of metastatic ER+ breast cancer patients. In embodiments, the first aggregate rank is higher than the $82^{nd}$ percentile of the aggregate rank of RNA transcripts from the endocrine signaling negative gene set of a population of metastatic ER+ breast cancer patients. In embodiments, the first aggregate rank is higher than the $83^{rd}$ percentile of the aggregate rank of RNA transcripts from the endocrine signaling negative gene set of a population of metastatic ER+ breast cancer patients. In embodiments, the first aggregate rank is higher than the $84^{th}$ percentile of the aggregate rank of RNA transcripts from the endocrine signaling negative gene set of a population of metastatic ER+ breast cancer patients. In embodiments, the first aggregate rank is higher than the $85^{th}$ percentile of the aggregate rank of RNA transcripts from the endocrine signaling negative gene set of a population of metastatic ER+ breast cancer patients. In embodiments, the first aggregate rank is higher than the $86^{th}$ percentile of the aggregate rank of RNA transcripts from the endocrine signaling negative gene set of a population of metastatic ER+ breast cancer patients. In embodiments, the first aggregate rank is higher than the $87^{th}$ percentile of the aggregate rank of RNA transcripts from the endocrine signaling negative gene set of a population of metastatic ER+ breast cancer patients. In embodiments, the first aggregate rank is higher than the $88^{th}$ percentile of the aggregate rank of RNA transcripts from the endocrine signaling negative gene set of a population of metastatic ER+ breast cancer patients. In embodiments, the first aggregate rank is higher than the $89^{th}$ percentile of the aggregate rank of RNA transcripts from the endocrine signaling negative gene set of a population of metastatic ER+ breast cancer patients. In embodiments, the first aggregate rank is higher than the $90^{th}$ percentile of the aggregate rank of RNA transcripts from the endocrine signaling negative gene set of a population of metastatic ER+ breast cancer patients. In embodiments, the first aggregate rank is higher than the $91^{st}$ percentile of the aggregate rank of the expression level of RNA transcripts from the endocrine signaling negative gene set of a population of metastatic ER+ breast cancer patients. In embodiments, the first aggregate rank is higher than the $92^{th}$ percentile of the aggregate rank of RNA transcripts from the endocrine signaling negative gene set of a population of metastatic ER+ breast cancer patients. In embodiments, the first aggregate rank is higher than the $93^{rd}$ percentile of the aggregate rank of RNA transcripts from the endocrine signaling negative gene set of a population of metastatic ER+ breast cancer patients. In embodiments, the first aggregate rank is higher than the $94^{th}$ percentile of the aggregate rank of RNA transcripts from the endocrine signaling negative gene set of a population of metastatic ER+ breast cancer patients. In embodiments, the first aggregate rank is higher than the $95^{th}$ percentile of the aggregate rank of RNA transcripts from the endocrine signaling negative gene set of a population of metastatic ER+ breast cancer patients.

For the methods provided herein, in embodiments, the second standard control is the average aggregate rank of the expression level of RNA transcripts from the endocrine signaling positive gene set of a population of metastatic ER+ breast cancer patients. In embodiments, the second standard control is the average aggregate rank of the expression level of RNA transcripts from the endocrine signaling positive gene set of a population of metastatic ER+ breast cancer patients that are not responsive to endocrine therapy.

In embodiments, the second standard control is the $30^{th}$ percentile of the aggregate rank of RNA transcripts from the endocrine signaling positive gene set of a population of metastatic ER+ breast cancer patients. In embodiments, the second standard control is the $31^{st}$ percentile of the aggregate rank of RNA transcripts from the endocrine signaling positive gene set of a population of metastatic ER+ breast cancer patients. In embodiments, the second standard control is the $32^{nd}$ percentile of the aggregate rank of RNA transcripts from the endocrine signaling positive gene set of a population of metastatic ER+ breast cancer patients. In embodiments, the second standard control is the $33^{rd}$ percentile of the aggregate rank of RNA transcripts from the endocrine signaling positive gene set of a population of metastatic ER+ breast cancer patients. In embodiments, the second standard control is the $34^{th}$ percentile of the aggregate rank of RNA transcripts from the endocrine signaling positive gene set of a population of metastatic ER+ breast cancer patients. In embodiments, the second standard control is the $35^{th}$ percentile of the aggregate rank of RNA transcripts from the endocrine signaling positive gene set of a population of metastatic ER+ breast cancer patients. In embodiments, the second standard control is the $36^{th}$ percentile of the aggregate rank of RNA transcripts from the endocrine signaling positive gene set of a population of metastatic ER+ breast cancer patients. In embodiments, the second standard control is the $37^{th}$ percentile of the aggregate rank of RNA transcripts from the endocrine signaling positive gene set of a population of metastatic ER+ breast cancer patients. In embodiments, the second standard control is the $38^{th}$ percentile of the aggregate rank of RNA transcripts from the endocrine signaling positive gene set of a population of metastatic ER+ breast cancer patients. In embodiments, the second standard control is the $39^{th}$ percentile of the aggregate rank of RNA transcripts from the endocrine signaling positive gene set of a population of metastatic ER+ breast cancer patients. In embodiments, the second standard control is the $40^{th}$ percentile of the aggregate rank of RNA transcripts from the endocrine signaling positive gene set of a population of metastatic ER+ breast cancer patients. In embodiments, the second standard control is the $41^{st}$ percentile of the aggregate rank of RNA transcripts from the endocrine signaling positive gene set of a population of metastatic ER+ breast cancer patients. In embodiments, the second standard control is the $42^{nd}$ percentile of the aggregate rank of RNA transcripts from the endocrine signaling positive gene set of a population of metastatic ER+ breast cancer patients. In embodiments, the second standard control is the $43^{rd}$ percentile of the aggregate rank of RNA transcripts from the endocrine signaling positive gene set of a population of metastatic ER+ breast cancer patients. In embodiments, the second standard control is the $44^{th}$ percentile of the aggregate rank of RNA transcripts from the endocrine signaling positive gene set of a population of metastatic ER+ breast cancer patients. In embodiments, the second standard control is the $45^{th}$ percentile of the aggregate rank of RNA transcripts from the endocrine signaling positive gene set of a population of metastatic ER+ breast cancer patients. In embodiments, the second standard control is the $46^{th}$ percentile of the aggregate rank of RNA transcripts from the endocrine signaling positive gene set of a population of metastatic ER+ breast cancer patients. In embodiments, the second standard control is the $47^{th}$ percentile of the aggregate rank of RNA transcripts from the endocrine signaling positive gene set of a population of metastatic ER+ breast cancer patients. In embodiments, the second standard control is the $48^{th}$ percentile of the aggregate rank of RNA transcripts from the endocrine signaling positive gene set of a population of metastatic ER+ breast cancer patients. In embodiments, the second standard control is the $49^{th}$ percentile of the aggregate rank of RNA transcripts from the endocrine signaling positive gene set of a population of metastatic ER+ breast cancer patients. In embodiments, the second standard control is the $50^{th}$ percentile of the aggregate rank of RNA transcripts from the endocrine signaling positive gene set of a population of metastatic ER+ breast cancer patients In embodiments, the second standard control is the 50th percentile of the aggregate rank of RNA transcripts from the endocrine signaling positive gene set of a population of metastatic ER+ breast cancer patients. In embodiments, the second standard control is the $51^{st}$ percentile of the aggregate rank of RNA transcripts from the endocrine signaling positive gene set of a population of metastatic ER+ breast cancer patients. In embodiments, the second standard control is the $52^{nd}$ percentile of the aggregate rank of RNA transcripts from the endocrine signaling positive gene set of a population of metastatic ER+ breast cancer patients. In embodiments, the second standard control is the $53^{rd}$ percentile of the aggregate rank of RNA transcripts from the endocrine signaling positive gene set of a population of metastatic ER+ breast cancer patients. In embodiments, the second standard control is the $54^{th}$ percentile of the aggregate rank of RNA transcripts from the endocrine signaling positive gene set of a population of metastatic ER+ breast cancer patients. In embodiments, the second standard control is the $55^{th}$ percentile of the aggregate rank of RNA transcripts from the endocrine signaling positive gene set of a population of metastatic ER+ breast cancer patients. In embodiments, the second standard control is the $56^{th}$ percentile of the aggregate rank of RNA transcripts from the endocrine signaling positive gene set of a population of metastatic ER+ breast cancer patients. In embodiments, the second standard control is the $57^{th}$ percentile of the aggregate rank of RNA transcripts from the endocrine signaling positive gene set of a population of metastatic ER+ breast cancer patients. In embodiments, the second standard control is the $58^{th}$ percentile of the aggregate rank of RNA transcripts from the endocrine signaling positive gene set of a population of metastatic ER+ breast cancer patients. In embodiments, the second standard control is the $59^{th}$ percentile of the aggregate rank of RNA transcripts from the endocrine signaling positive gene set of a population of metastatic ER+ breast cancer patients. In embodiments, the second standard control is the $60^{th}$ percentile of the aggregate rank of RNA transcripts from the endocrine signaling positive gene set of a population of metastatic ER+ breast cancer patients. In embodiments, the second standard control is the $61^{st}$ percentile of the aggregate rank of RNA transcripts from the endocrine signaling positive gene set of a population of metastatic ER+ breast cancer patients. In embodiments, the second standard control is the $62^{nd}$ percentile of the aggregate rank of RNA transcripts from the endocrine signaling positive gene set of a population of metastatic ER+ breast cancer patients. In embodiments, the second standard control is the $63^{rd}$ percentile of the aggregate rank of RNA transcripts from the endocrine signaling positive gene set of a population of metastatic ER+ breast cancer patients. In embodiments, the second standard control is the $64^{th}$ percentile of the aggregate rank of RNA transcripts from the endocrine signaling positive gene set of a population of metastatic ER+ breast cancer patients. In embodiments, the second standard control is the $65^{th}$ percentile of the aggregate rank of RNA transcripts from the endocrine signaling positive gene set of a population of metastatic ER+ breast cancer patients. In embodiments, the second standard control is the $66^{th}$ percentile of the aggregate rank of RNA transcripts from the endocrine signaling positive gene set of a population of metastatic ER+ breast cancer patients. In embodiments, the second standard control is the $67^{th}$ percentile of the aggregate rank of RNA transcripts from the endocrine signaling positive gene set of a population of metastatic ER+ breast cancer patients. In embodiments, the second standard control is the $68^{th}$ percentile of the aggregate rank of RNA transcripts from the endocrine signaling positive gene set of a population of metastatic ER+ breast cancer patients. In embodiments, the second standard control is the $69^{th}$ percentile of the aggregate rank of RNA transcripts from the endocrine signaling positive gene set of a population of metastatic ER+ breast cancer patients. In embodiments, the second standard control is the $70^{th}$ percentile of the aggregate rank of RNA transcripts from the endocrine signaling positive gene set of a population of metastatic ER+ breast cancer patients. In embodiments, the second standard control is the $71^{st}$ percentile of the aggregate rank of RNA transcripts from the endocrine signaling positive gene set of a population of metastatic ER+ breast cancer patients. In embodiments, the second standard control is the $72^{nd}$ percentile of the aggregate rank of RNA transcripts from the endocrine signaling positive gene set of a population of metastatic ER+ breast cancer patients. In embodiments, the second standard control is the $73^{rd}$ percentile of the aggregate rank of RNA transcripts from the endocrine signaling positive gene set of a population of metastatic ER+ breast cancer patients. In embodiments, the second standard control is the $74^{th}$ percentile of the aggregate rank of RNA transcripts from the endocrine signaling positive gene set of a population of metastatic ER+ breast cancer patients. In embodiments, the second standard control is the $75^{th}$ percentile of the aggregate rank of RNA transcripts from the endocrine signaling positive gene set of a population of metastatic ER+ breast cancer patients. In embodiments, the second standard control is the $76^{th}$ percentile of the aggregate rank of RNA transcripts from the endocrine signaling positive gene set of a population of metastatic ER+ breast cancer patients. In embodiments, the second standard control is the $77^{th}$ percentile of the aggregate rank of RNA transcripts from the endocrine signaling positive gene set of a population of metastatic ER+ breast cancer patients. In embodiments, the second standard control is the $78^{th}$ percentile of the aggregate rank of RNA transcripts from the endocrine signaling positive gene set of a population of metastatic ER+ breast cancer patients. In embodiments, the second standard control is the $79^{th}$ percentile of the aggregate rank of RNA transcripts from the endocrine signaling positive gene set of a population of metastatic ER+ breast cancer patients. In embodiments, the second standard control is the $80^{th}$ percentile of the aggregate rank of RNA transcripts from the endocrine signaling positive gene set of a population of metastatic ER+ breast cancer patients.

In embodiments, the second aggregate rank is lower than the $30^{th}$ percentile of the aggregate rank of RNA transcripts from the endocrine signaling positive gene set of a population of metastatic ER+ breast cancer patients. In embodiments, the second aggregate rank is lower than the $31^{st}$ percentile of the aggregate rank of RNA transcripts from the endocrine signaling positive gene set of a population of metastatic ER+ breast cancer patients. In embodiments, the second aggregate rank is lower than the $32^{nd}$ percentile of the aggregate rank of RNA transcripts from the endocrine signaling positive gene set of a population of metastatic ER+ breast cancer patients. In embodiments, the second aggregate rank is lower than the $33^{rd}$ percentile of the aggregate rank of RNA transcripts from the endocrine signaling positive gene set of a population of metastatic ER+ breast cancer patients. In embodiments, the second aggregate rank is lower than the $34^{th}$ percentile of the aggregate rank of RNA transcripts from the endocrine signaling positive gene set of a population of metastatic ER+ breast cancer patients. In embodiments, the second aggregate rank is lower than the $35^{th}$ percentile of the aggregate rank of RNA transcripts from the endocrine signaling positive gene set of a population of metastatic ER+ breast cancer patients. In embodiments, the second aggregate rank is lower than the $36^{th}$ percentile of the aggregate rank of RNA transcripts from the endocrine signaling positive gene set of a population of metastatic ER+ breast cancer patients. In embodiments, the second aggregate rank is lower than the $37^{th}$ percentile of the aggregate rank of RNA transcripts from the endocrine signaling positive gene set of a population of metastatic ER+ breast cancer patients. In embodiments, the second aggregate rank is lower than the $38^{th}$ percentile of the aggregate rank of RNA transcripts from the endocrine signaling positive gene set of a population of metastatic ER+ breast cancer patients. In embodiments, the second aggregate rank is lower than the $39^{th}$ percentile of the aggregate rank of RNA transcripts from the endocrine signaling positive gene set of a population of metastatic ER+ breast cancer patients. In embodiments, the second aggregate rank is lower than the $40^{th}$ percentile of the aggregate rank of RNA transcripts from the endocrine signaling positive gene set of a population of metastatic ER+ breast cancer patients. In embodiments, the second aggregate rank is lower than the $41^{st}$ percentile of the aggregate rank of RNA transcripts from the endocrine signaling positive gene set of a population of metastatic ER+ breast cancer patients. In embodiments, the second aggregate rank is lower than the $42^{nd}$ percentile of the aggregate rank of RNA transcripts from the endocrine signaling positive gene set of a population of metastatic ER+ breast cancer patients. In embodiments, the second aggregate rank is lower than the $43^{rd}$ percentile of the aggregate rank of RNA transcripts from the endocrine signaling positive gene set of a population of metastatic ER+ breast cancer patients. In embodiments, the second aggregate rank is lower than the $44^{th}$ percentile of the aggregate rank of RNA transcripts from the endocrine signaling positive gene set of a population of metastatic ER+ breast cancer patients. In embodiments, the second aggregate rank is lower than the $45^{th}$ percentile of the aggregate rank of RNA transcripts from the endocrine signaling positive gene set of a population of metastatic ER+ breast cancer patients. In embodiments, the second aggregate rank is lower than the $46^{th}$ percentile of the aggregate rank of RNA transcripts from the endocrine signaling positive gene set of a population of metastatic ER+ breast cancer patients. In embodiments, the second aggregate rank is lower than the $47^{th}$ percentile of the aggregate rank of RNA transcripts from the endocrine signaling positive gene set of a population of metastatic ER+ breast cancer patients. In embodiments, the second aggregate rank is lower than the $48^{th}$ percentile of the aggregate rank of RNA transcripts from the endocrine signaling positive gene set of a population of metastatic ER+ breast cancer patients. In embodiments, the second aggregate rank is lower than the $49^{th}$ percentile of the aggregate rank of RNA transcripts from the endocrine signaling positive gene set of a population of metastatic ER+ breast cancer patients. In embodiments, the second aggregate rank is lower than the $50^{th}$ percentile of the aggregate rank of RNA transcripts from the endocrine signaling positive gene set of a population of metastatic ER+ breast cancer patients In embodiments, the second aggregate rank is lower than the $50^{th}$ percentile of the aggregate rank of RNA transcripts from the endocrine signaling positive gene set of a population of metastatic ER+ breast cancer patients. In embodiments, the second aggregate rank is lower than the $51^{st}$ percentile of the aggregate rank of RNA transcripts from the endocrine signaling positive gene set of a population of metastatic ER+ breast cancer patients. In embodiments, the second aggregate rank is lower than the $52^{nd}$ percentile of the aggregate rank of RNA transcripts from the endocrine signaling positive gene set of a population of metastatic ER+ breast cancer patients. In embodiments, the second aggregate rank is lower than the $53^{rd}$ percentile of the aggregate rank of RNA transcripts from the endocrine signaling positive gene set of a population of metastatic ER+ breast cancer patients. In embodiments, the second aggregate rank is lower than the $54^{th}$ percentile of the aggregate rank of RNA transcripts from the endocrine signaling positive gene set of a population of metastatic ER+ breast cancer patients. In embodiments, the second aggregate rank is lower than the $55^{th}$ percentile of the aggregate rank of RNA transcripts from the endocrine signaling positive gene set of a population of metastatic ER+ breast cancer patients. In embodiments, the second aggregate rank is lower than the $56^{th}$ percentile of the aggregate rank of RNA transcripts from the endocrine signaling positive gene set of a population of metastatic ER+ breast cancer patients. In embodiments, the second aggregate rank is lower than the $57^{th}$ percentile of the aggregate rank of RNA transcripts from the endocrine signaling positive gene set of a population of metastatic ER+ breast cancer patients. In embodiments, the second aggregate rank is lower than the $58^{th}$ percentile of the aggregate rank of RNA transcripts from the endocrine signaling positive gene set of a population of metastatic ER+ breast cancer patients. In embodiments, the second aggregate rank is lower than the $59^{th}$ percentile of the aggregate rank of RNA transcripts from the endocrine signaling positive gene set of a population of metastatic ER+ breast cancer patients. In embodiments, the second aggregate rank is lower than the $60^{th}$ percentile of the aggregate rank of RNA transcripts from the endocrine signaling positive gene set of a population of metastatic ER+ breast cancer patients. In embodiments, the second aggregate rank is lower than the $61^{st}$ percentile of the aggregate rank of RNA transcripts from the endocrine signaling positive gene set of a population of metastatic ER+ breast cancer patients. In embodiments, the second aggregate rank is lower than the $62^{nd}$ percentile of the aggregate rank of RNA transcripts from the endocrine signaling positive gene set of a population of metastatic ER+ breast cancer patients. In embodiments, the second aggregate rank is lower than the $63^{rd}$ percentile of the aggregate rank of RNA transcripts from the endocrine signaling positive gene set of a population of metastatic ER+ breast cancer patients. In embodiments, the second aggregate rank is lower than the $64^{th}$ percentile of the aggregate rank of RNA transcripts from the endocrine signaling positive gene set of a population of metastatic ER+ breast cancer patients. In embodiments, the second aggregate rank is lower than the $65^{th}$ percentile of the aggregate rank of RNA transcripts from the endocrine signaling positive gene set of a population of metastatic ER+ breast cancer patients. In embodiments, the second aggregate rank is lower than the $66^{th}$ percentile of the aggregate rank of RNA transcripts from the endocrine signaling positive gene set of a population of metastatic ER+ breast cancer patients. In embodiments, the second aggregate rank is lower than the $67^{th}$ percentile of the aggregate rank of RNA transcripts from the endocrine signaling positive gene set of a population of metastatic ER+ breast cancer patients. In embodiments, the second aggregate rank is lower than the $68^{th}$ percentile of the aggregate rank of RNA transcripts from the endocrine signaling positive gene set of a population of metastatic ER+ breast cancer patients. In embodiments, the second aggregate rank is lower than the $69^{th}$ percentile of the aggregate rank of RNA transcripts from the endocrine signaling positive gene set of a population of metastatic ER+ breast cancer patients. In embodiments, the second aggregate rank is lower than the $70^{th}$ percentile of the aggregate rank of RNA transcripts from the endocrine signaling positive gene set of a population of metastatic ER+ breast cancer patients. In embodiments, the second aggregate rank is lower than the $71^{st}$ percentile of the aggregate rank of RNA transcripts from the endocrine signaling positive gene set of a population of metastatic ER+ breast cancer patients. In embodiments, the second aggregate rank is lower than the $72^{nd}$ percentile of the aggregate rank of RNA transcripts from the endocrine signaling positive gene set of a population of metastatic ER+ breast cancer patients. In embodiments, the second aggregate rank is lower than the $73^{rd}$ percentile of the aggregate rank of RNA transcripts from the endocrine signaling positive gene set of a population of metastatic ER+ breast cancer patients. In embodiments, the second aggregate rank is lower than the $74^{th}$ percentile of the aggregate rank of RNA transcripts from the endocrine signaling positive gene set of a population of metastatic ER+ breast cancer patients. In embodiments, the second aggregate rank is lower than the $75^{th}$ percentile of the aggregate rank of RNA transcripts from the endocrine signaling positive gene set of a population of metastatic ER+ breast cancer patients. In embodiments, the second aggregate rank is lower than the $76^{th}$ percentile of the aggregate rank of RNA transcripts from the endocrine signaling positive gene set of a population of metastatic ER+ breast cancer patients. In embodiments, the second aggregate rank is lower than the $77^{th}$ percentile of the aggregate rank of RNA transcripts from the endocrine signaling positive gene set of a population of metastatic ER+ breast cancer patients. In embodiments, the second aggregate rank is lower than the $78^{th}$ percentile of the aggregate rank of RNA transcripts from the endocrine signaling positive gene set of a population of metastatic ER+ breast cancer patients. In embodiments, the second aggregate rank is lower than the $79^{th}$ percentile of the aggregate rank of RNA transcripts from the endocrine signaling positive gene set of a population of metastatic ER+ breast cancer patients. In embodiments, the second aggregate rank is lower than the $80^{th}$ percentile of the aggregate rank of RNA transcripts from the endocrine signaling positive gene set of a population of metastatic ER+ breast cancer patients.

For the methods provided herein, in embodiments, the endocrine signaling negative gene set includes a plurality of genes set forth in Table 1. In embodiments, the endocrine signaling negative gene set includes at least about 2, 3, 4, 5, 10, 20, 30, 40, 50 genes set forth in Table 1. In embodiments, the endocrine signaling negative gene set includes the genes set forth in Table 1 and no other genes.

In embodiments, the endocrine signaling negative gene set includes at least 1, 2, 3, 4, 5, 10, 20, 30, 40, or 50 of the following genes: ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, and SPC25.

In embodiments, the endocrine signaling negative gene set includes at least 1, 2, 3, 4, 5, 10, 20, 30, 40, or 50 of the following genes: ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, and SPC25 and no other genes.

In embodiments, the endocrine signaling negative gene set includes at least 5 of the following genes: ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, and SPC25.

In embodiments, the endocrine signaling negative gene set includes at least 10 of the following genes: ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, and SPC25.

In embodiments, the endocrine signaling negative gene set includes at least 20 of the following genes: ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, and SPC25.

In embodiments, the endocrine signaling negative gene set includes at least 50 of the following genes: ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, and SPC25.

In embodiments, the endocrine signaling negative gene set includes at least one gene selected from KIF20A, ZC3H11A, RABGAP1, HARS, LARP1, TROAP, PPARGC1B, COL4A1, CKAP2L, GSK3B, DBN1, ENC1, APLN, or NKX2-2.

In embodiments, the endocrine signaling negative gene set includes at least five or at least ten genes selected from KIF20A, ZC3H11A, RABGAP1, HARS, LARP1, TROAP, PPARGC1B, COL4A1, CKAP2L, GSK3B, DBN1, ENC1, APLN, or NKX2-2.

For the methods provided herein, in embodiments, the endocrine signaling positive gene set includes a plurality of genes set forth in Table 13. In embodiments, the endocrine signaling positive gene set includes at least about 2, 3, 4, 5, 10, 20, 30, 40, 50, 100 or 150 genes set forth in Table 13. In embodiments, the endocrine signaling positive gene set includes the genes set forth in Table 13 and no other genes.

In embodiments, the endocrine signaling positive gene set includes at least 1, 2, 3, 4, 5, 10, 20, 30, 40, 50, 100 or 150 of the following genes: GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, and LAD1.

In embodiments, the endocrine signaling positive gene set includes at least 1, 2, 3, 4, 5, 10, 20, 30, 40, 50, 100 or 150 of the following genes: GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1 and no other genes.

In embodiments, the endocrine signaling positive gene set includes at least 5 of the following genes: GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1.

In embodiments, the endocrine signaling positive gene set includes at least 10 of the following genes: GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, and LAD1.

In embodiments, the endocrine signaling positive gene set includes at least 20 of the following genes: GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1.

In embodiments, the endocrine signaling positive gene set includes at least 50 of the following genes: GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, and LAD1.

Measuring an expression level of RNA transcripts may be accomplished by a number of methods known in the art including but not limited to Northern blotting, Southern blotting, Western blotting, fluorescent in situ hybridization, reverse transcriptase-polymerase chain reaction, serial analysis of gene expression (SAGE), microarray analysis, tiling arrays, NanoString Assays, and the like. In embodiments, isolated mRNA (or derivatives thereof, such as cDNA) is used in hybridization or amplification assays, examples of which include, but are not limited to, Southern or Northern analyses, PCR analyses, probe arrays, and NanoString Assays. One method for the detection of mRNA levels involves contacting the isolated mRNA or synthesized cDNA with an oligonucleotide probe that can hybridize to the mRNA encoded by the gene being detected. The oligonucleotide probe can be, for example, a cDNA, or a portion thereof, such as an oligonucleotide of at least 7, 15, 30, 50, 100, 250, or 500 nucleotides in length and sufficient to specifically hybridize under the assay conditions, and/or under stringent conditions, to the RNA (or corresponding cDNA) of the gene whose expression is to be measured. In embodiments, polynucleotide probes are attached to a solid support forming an array, with one or more polynucleotide probes targeting each of the RNA (or corresponding cDNA) of the genes whose expression are to be measured. In embodiments, RNA obtained from a sample is converted to complementary DNA (cDNA) in a hybridization reaction, which optionally may be further amplified prior to measuring expression (e.g., by PCR amplification). In embodiments, RNA from a sample is measured without conversion to cDNA, and/or without amplification prior to measuring expression.

In embodiments, measuring expression levels of RNA transcripts includes hybridizing a plurality of oligonucleotide probes to the RNA obtained from a sample. Each oligonucleotide probe includes a target-specific sequence and a tag, such as a label or barcode. The barcode is unique to the target-specific sequence to which it is attached. In embodiments, there are multiple copies of each probe, such that measuring the number of probes bound to a particular target sequence provides a measure of the expression level of the corresponding gene. Identification of the target sequence (and corresponding target gene) is facilitated by detecting the label or identifying the barcode. In embodiments, measuring expression levels does not include nucleotide sequencing.

In embodiments, measuring an expression level includes sequencing, microarray, PCR, or a combination thereof. In embodiments, measuring an expression level includes sequencing. In embodiments, measuring an expression level includes microarray. In embodiments, measuring an expression level includes PCR. In embodiments, measuring an expression level includes hybridizing one or more oligonucleotide probes to one or more of the RNA transcripts, wherein each oligonucleotide probe comprises a sequence specific to the RNA transcript.

For the methods provided herein, in embodiments, the chemotherapy includes capecitabine, gemicitabine, vinorelbine, doxorubicin, epirubicin, paclitaxel, docetaxel, eribulin, cyclophosphamide, carboplatin, cisplatin, ixabepilone, fluorouracil, methotrexate, or a combination thereof. In embodiments, the chemotherapy includes capecitabine. In embodiments, the chemotherapy includes gemicitabine. In embodiments, the chemotherapy includes vinorelbine. In embodiments, the chemotherapy includes doxorubicin. In embodiments, the chemotherapy includes epirubicin. In embodiments, the chemotherapy includes paclitaxel. In embodiments, the chemotherapy includes docetaxel. In embodiments, the chemotherapy includes eribulin. In embodiments, the chemotherapy includes cyclophosphamide. In embodiments, the chemotherapy includes carboplatin. In embodiments, the chemotherapy includes cisplatin. In embodiments, the chemotherapy includes ixabepilone. In embodiments, the chemotherapy includes fluorouracil. In embodiments, the chemotherapy includes methotrexate. Exemplary chemotherapeutic agents include without limitation any chemotherapeutic agent known in the art that is effective for treating metatstatic ER+ breast cancer. Chemotherapeutic agents for treating metastatic ER+ breast cancer are described, for example, by Barrios, C. H. et al. What is the role of chemotherapy in estrogen receptorpositive, advanced breast cancer?; Ann. Oncol. 2009, 20: 1157-1162; doi:10.1093/annonc/mdn756.; McAndrew. N. P et al. Management of ER positive metastatic breast cancer; Semin. Oncol. 2020, Volume 47, Issue 5: 270-277; https://doi.org/10.1053/j.seminoncol.2020.07.005.; which are incorporated by reference herein in their entirety and for all purposes.

For the methods provided herein, in embodiments, the breast cancer is a human epidermal growth factor receptor 2 negative breast cancer. In embodiments, the metastatic estrogen receptor positive breast cancer subject previously received anticancer endocrine therapy. In embodiments, the subject was previously sensitive to anticancer endocrine therapy and is no longer sensitive to anticancer endocrine therapy.

The methods provided herein, including embodiments thereof are contemplated to be effective for treating metastatic ER+ breast cancer in patients who are responsive to anticancer endocrine therapy. Thus, in an aspect is provided a method of treating cancer in a metastatic estrogen receptor positive breast cancer subject, the method including: (a) measuring an expression level of a transcriptome set of RNA transcripts in a plurality of cells obtained from a tumor from the metastatic estrogen receptor positive breast cancer subject, wherein the transcriptome set of RNA transcripts includes RNA transcripts expressed from: (i) an endocrine signaling negative gene set, wherein the endocrine signaling negative gene set includes a gene (e.g. at least 5 genes) selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25; (ii) an endocrine signaling positive gene set, wherein the endocrine signaling negative gene set includes a gene (e.g. at least 5 genes) selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1; and (iii) a remainder gene set, wherein the remainder gene set consists of all genes expressing the transcriptome set of RNA transcripts except the endocrine signaling positive gene set and the endocrine signaling negative gene set; (b) determining a low level of expression of the endocrine signaling negative gene set relative to a third standard control; (c) determining a high level of expression of the endocrine signaling positive gene set relative to a fourth standard control; and; and (d) administering anticancer endocrine therapy to the metastatic estrogen receptor positive breast cancer subject and not administering chemotherapy to the metastatic estrogen receptor positive breast cancer subject. In embodiments, not administering a chemotherapy includes not administering a therapeutic that is not an anticancer endocrine therapy (e.g. a SERM, SERD, an aromatase inhibitor, etc.) to the metastatic estrogen receptor positive breast cancer subject. In embodiments, not administering chemotherapy includes not administering any one of capecitabine, gemicitabine, vinorelbine, doxorubicin, epirubicin, paclitaxel, docetaxel, eribulin, cyclophosphamide, carboplatin, cisplatin, ixabepilone, fluorouracil, or methotrexate to the metastatic estrogen receptor positive breast cancer subject. In embodiments, not administering a chemotherapy includes not administering an mTor inhibitor to the metastatic estrogen receptor positive breast cancer subject.

In embodiments, the third standard control is the average expression level of RNA transcripts from the endocrine signaling negative gene set of a population of metastatic ER+ breast cancer patients. In embodiments, the third standard control is the average expression level of RNA transcripts from the endocrine signaling negative gene set of a population of metastatic ER+ breast cancer patients that are responsive to endocrine therapy.

In embodiments, the third standard control is the 30$^{th}$ percentile of the expression level of RNA transcripts from the endocrine signaling negative gene set of a population of metastatic ER+ breast cancer patients. In embodiments, the third standard control is the 40$^{th}$ percentile of the expression level of RNA transcripts from the endocrine signaling negative gene set of a population of metastatic ER+ breast cancer patients. In embodiments, the third standard control is the 50$^{th}$ percentile of the expression level of RNA transcripts from the endocrine signaling negative gene set of a population of metastatic ER+ breast cancer patients. In embodiments, the third standard control is the 60$^{th}$ percentile of the expression level of RNA transcripts from the endocrine signaling negative gene set of a population of metastatic ER+ breast cancer patients. In embodiments, the third standard control is the 61$^{st}$ percentile of the expression level of RNA transcripts from the endocrine signaling negative gene set of a population of metastatic ER+ breast cancer patients. In embodiments, the third standard control is the 62$^{nd}$ percentile of the expression level of RNA transcripts from the endocrine signaling negative gene set of a population of metastatic ER+ breast cancer patients. In embodiments, the third standard control is the 63$^{rd}$ percentile of the expression level of RNA transcripts from the endocrine signaling negative gene set of a population of metastatic ER+ breast cancer patients. In embodiments, the third standard control is the 64$^{th}$ percentile of the expression level of RNA transcripts from the endocrine signaling negative gene set of a population of metastatic ER+ breast cancer patients. In embodiments, the third standard control is the 65$^{th}$ percentile of the expression level of RNA transcripts from the endocrine signaling negative gene set of a population of metastatic ER+ breast cancer patients. In embodiments, the third standard control is the 66$^{th}$ percentile of the expression level of RNA transcripts from the endocrine signaling negative gene set of a population of metastatic ER+ breast cancer patients. In embodiments, the third standard control is the 67$^{th}$ percentile of the expression level of RNA transcripts from the endocrine signaling negative gene set of a population of metastatic ER+ breast cancer patients. In embodiments, the third standard control is the 68$^{th}$ percentile of the expression level of RNA transcripts from the endocrine signaling negative gene set of a population of metastatic ER+ breast cancer patients. In embodiments, the third standard control is the 69$^{th}$ percentile of the expression level of RNA transcripts from the endocrine signaling negative gene set of a population of metastatic ER+ breast cancer patients. In embodiments, the third standard control is the 70$^{th}$ percentile of the expression level of RNA transcripts from the endocrine signaling negative gene set of a population of metastatic ER+ breast cancer patients. In embodiments, the third standard control is the 70$^{th}$ percentile of the expression level of RNA transcripts from the endocrine signaling negative gene set of a population of metastatic ER+ breast cancer patients. In embodiments, the third standard control is the 71$^{st}$ percentile of the expression level of RNA transcripts from the endocrine signaling negative gene set of a population of metastatic ER+ breast cancer patients. In embodiments, the third standard control is the 72$^{nd}$ percentile of the expression level of RNA transcripts from the endocrine signaling negative gene set of a population of metastatic ER+ breast cancer patients. In embodiments, the third standard control is the 73$^{d}$ percentile of the expression level of RNA transcripts from the endocrine signaling negative gene set of a population of metastatic ER+ breast cancer patients. In embodiments, the third standard control is the 74$^{th}$ percentile of the expression level of RNA transcripts from the endocrine signaling negative gene set of a population of metastatic ER+ breast cancer patients. In embodiments, the third standard control is the 75$^{th}$ percentile of the expression level of RNA transcripts from the endocrine signaling negative gene set of a population of metastatic ER+ breast cancer patients. In embodiments, the third standard control is the 76$^{th}$ percentile of the expression level of RNA transcripts from the endocrine signaling negative gene set of a population of metastatic ER+ breast cancer patients. In embodiments, the third standard control is the 77$^{th}$ percentile of the expression level of RNA transcripts from the endocrine signaling negative gene set of a population of metastatic ER+ breast cancer patients. In embodiments, the third standard control is the 78$^{th}$ percentile of the expression level of RNA transcripts from the endocrine signaling negative gene set of a population of metastatic ER+ breast cancer patients. In embodiments, the third standard control is the 79$^{th}$ percentile of the expression level of RNA transcripts from the endocrine signaling negative gene set of a population of metastatic ER+ breast cancer patients. In embodiments, the third standard control is the 80$^{th}$ percentile of the expression level of RNA transcripts from the endocrine signaling negative gene set of a population of metastatic ER+ breast cancer patients. In embodiments, the third standard control is the 81$^{st}$ percentile of the expression level of RNA transcripts from the endocrine signaling negative gene set of a population of metastatic ER+ breast cancer patients. In embodiments, the third standard control is the 82$^{nd}$ percentile of the expression level of RNA transcripts from the endocrine signaling negative gene set of a population of metastatic ER+ breast cancer patients. In embodiments, the third standard control is the 83$^{rd}$ percentile of the expression level of RNA transcripts from the endocrine signaling negative gene set of a population of metastatic ER+ breast cancer patients. In embodiments, the third standard control is the 84$^{th}$ percentile of the expression level of RNA transcripts from the endocrine signaling negative gene set of a population of metastatic ER+ breast cancer patients. In embodiments, the third standard control is the 85$^{th}$ percentile of the expression level of RNA transcripts from the endocrine signaling negative gene set of a population of metastatic ER+ breast cancer patients. In embodiments, the third standard control is the 86$^{th}$ percentile of the expression level of RNA transcripts from the endocrine signaling negative gene set of a population of metastatic ER+ breast cancer patients. In embodiments, the third standard control is the 87$^{th}$ percentile of the expression level of RNA transcripts from the endocrine signaling negative gene set of a population of metastatic ER+ breast cancer patients. In embodiments, the third standard control is the 88$^{th}$ percentile of the expression level of RNA transcripts from the endocrine signaling negative gene set of a population of metastatic ER+ breast cancer patients. In embodiments, the third standard control is the 89$^{th}$ percentile of the expression level of RNA transcripts from the endocrine signaling negative gene set of a population of metastatic ER+ breast cancer patients. In embodiments, the third standard control is the $90^{th}$ percentile of the expression level of RNA transcripts from the endocrine signaling negative gene set of a population of metastatic ER+ breast cancer patients. In embodiments, the third standard control is the $91^{st}$ percentile of expression level of RNA transcripts from the endocrine signaling negative gene set of a population of metastatic ER+ breast cancer patients. In embodiments, the third standard control is the $92^{nd}$ percentile of the expression level of RNA transcripts from the endocrine signaling negative gene set of a population of metastatic ER+ breast cancer patients. In embodiments, the third standard control is the $93^{d}$ percentile of the expression level of RNA transcripts from the endocrine signaling negative gene set of a population of metastatic ER+ breast cancer patients. In embodiments, the third standard control is the $94^{th}$ percentile of the expression level of RNA transcripts from the endocrine signaling negative gene set of a population of metastatic ER+ breast cancer patients. In embodiments, the third standard control is the $95^{th}$ percentile of the expression level of RNA transcripts from the endocrine signaling negative gene set of a population of metastatic ER+ breast cancer patients.

In embodiments, the low level of expression is lower than the $30^{th}$ percentile of the expression level of RNA transcripts from the endocrine signaling negative gene set of a population of metastatic ER+ breast cancer patients. In embodiments, the low level of expression is lower than the $40^{th}$ percentile of the expression level of RNA transcripts from the endocrine signaling negative gene set of a population of metastatic ER+ breast cancer patients. In embodiments, the low level of expression is lower than the $50^{th}$ percentile of the expression level of RNA transcripts from the endocrine signaling negative gene set of a population of metastatic ER+ breast cancer patients. In embodiments, the low level of expression is lower than the $60^{th}$ percentile of the expression level of RNA transcripts from the endocrine signaling negative gene set of a population of metastatic ER+ breast cancer patients. In embodiments, the low level of expression is lower than the $61^{st}$ percentile of the expression level of RNA transcripts from the endocrine signaling negative gene set of a population of metastatic ER+ breast cancer patients. In embodiments, the low level of expression is lower than the $62^{nd}$ percentile of the expression level of RNA transcripts from the endocrine signaling negative gene set of a population of metastatic ER+ breast cancer patients. In embodiments, the low level of expression is lower than the $63^{rd}$ percentile of the expression level of RNA transcripts from the endocrine signaling negative gene set of a population of metastatic ER+ breast cancer patients. In embodiments, the low level of expression is lower than the $64^{th}$ percentile of the expression level of RNA transcripts from the endocrine signaling negative gene set of a population of metastatic ER+ breast cancer patients. In embodiments, the low level of expression is lower than the $65^{th}$ percentile of the expression level of RNA transcripts from the endocrine signaling negative gene set of a population of metastatic ER+ breast cancer patients. In embodiments, the low level of expression is lower than the $66^{th}$ percentile of the expression level of RNA transcripts from the endocrine signaling negative gene set of a population of metastatic ER+ breast cancer patients. In embodiments, the low level of expression is lower than the $67^{th}$ percentile of the expression level of RNA transcripts from the endocrine signaling negative gene set of a population of metastatic ER+ breast cancer patients. In embodiments, the low level of expression is lower than the $68^{th}$ percentile of the expression level of RNA transcripts from the endocrine signaling negative gene set of a population of metastatic ER+ breast cancer patients. In embodiments, the low level of expression is lower than the $69^{th}$ percentile of the expression level of RNA transcripts from the endocrine signaling negative gene set of a population of metastatic ER+ breast cancer patients. In embodiments, the low level of expression is lower than the $70^{th}$ percentile of the expression level of RNA transcripts from the endocrine signaling negative gene set of a population of metastatic ER+ breast cancer patients. In embodiments, the low level of expression is lower than the $71^{st}$ percentile of the expression level of RNA transcripts from the endocrine signaling negative gene set of a population of metastatic ER+ breast cancer patients. In embodiments, the low level of expression is lower than the $72^{nd}$ percentile of the expression level of RNA transcripts from the endocrine signaling negative gene set of a population of metastatic ER+ breast cancer patients. In embodiments, the low level of expression is lower than the $73^{rd}$ percentile of the expression level of RNA transcripts from the endocrine signaling negative gene set of a population of metastatic ER+ breast cancer patients. In embodiments, the low level of expression is lower than the $74^{th}$ percentile of the expression level of RNA transcripts from the endocrine signaling negative gene set of a population of metastatic ER+ breast cancer patients. In embodiments, the low level of expression is lower than the $75^{th}$ percentile of the expression level of RNA transcripts from the endocrine signaling negative gene set of a population of metastatic ER+ breast cancer patients. In embodiments, the low level of expression is lower than the $76^{th}$ percentile of the expression level of RNA transcripts from the endocrine signaling negative gene set of a population of metastatic ER+ breast cancer patients. In embodiments, the low level of expression is lower than the $77^{th}$ percentile of the expression level of RNA transcripts from the endocrine signaling negative gene set of a population of metastatic ER+ breast cancer patients. In embodiments, the low level of expression is lower than the $78^{th}$ percentile of the expression level of RNA transcripts from the endocrine signaling negative gene set of a population of metastatic ER+ breast cancer patients. In embodiments, the low level of expression is lower than the $79^{th}$ percentile of the expression level of RNA transcripts from the endocrine signaling negative gene set of a population of metastatic ER+ breast cancer patients. In embodiments, the low level of expression is lower than the 80th percentile of the expression level of RNA transcripts from the endocrine signaling negative gene set of a population of metastatic ER+ breast cancer patients. In embodiments, the low level of expression is lower than the $81^{st}$ percentile of the expression level of RNA transcripts from the endocrine signaling negative gene set of a population of metastatic ER+ breast cancer patients. In embodiments, the low level of expression is lower than the $82^{nd}$ percentile of the expression level of RNA transcripts from the endocrine signaling negative gene set of a population of metastatic ER+ breast cancer patients. In embodiments, the low level of expression is lower than the $83^{rd}$ percentile of the expression level of RNA transcripts from the endocrine signaling negative gene set of a population of metastatic ER+ breast cancer patients. In embodiments, the low level of expression is lower than the $84^{th}$ percentile of the expression level of RNA transcripts from the endocrine signaling negative gene set of a population of metastatic ER+ breast cancer patients. In embodiments, the low level of expression is lower than the $85^{th}$ percentile of the expression level of RNA transcripts from the endocrine signaling negative gene set of a population of metastatic ER+ breast cancer patients. In embodiments, the low level of expression is lower than the $86^{th}$ percentile of the expression level of RNA transcripts from the endocrine signaling negative gene set of a population of metastatic ER+ breast cancer patients. In embodiments, the low level of expression is lower than the $87^{th}$ percentile of the expression level of RNA transcripts from the endocrine signaling negative gene set of a population of metastatic ER+ breast cancer patients. In embodiments, the low level of expression is lower than the $88^{th}$ percentile of the expression level of RNA transcripts from the endocrine signaling negative gene set of a population of metastatic ER+ breast cancer patients. In embodiments, the low level of expression is lower than the $89^{th}$ percentile of the expression level of RNA transcripts from the endocrine signaling negative gene set of a population of metastatic ER+ breast cancer patients. In embodiments, the low level of expression is lower than the $90^{th}$ percentile of the expression level of RNA transcripts from the endocrine signaling negative gene set of a population of metastatic ER+ breast cancer patients. In embodiments, the low level of expression is lower than the $91^{st}$ percentile of the expression level of RNA transcripts from the endocrine signaling negative gene set of a population of metastatic ER+ breast cancer patients. In embodiments, the low level of expression is lower than the $92^{nd}$ percentile of the expression level of RNA transcripts from the endocrine signaling negative gene set of a population of metastatic ER+ breast cancer patients. In embodiments, the low level of expression is lower than the $93^{rd}$ percentile of the expression level of RNA transcripts from the endocrine signaling negative gene set of a population of metastatic ER+ breast cancer patients. In embodiments, the low level of expression is lower than the $94^{th}$ percentile of the expression level of RNA transcripts from the endocrine signaling negative gene set of a population of metastatic ER+ breast cancer patients. In embodiments, the low level of expression is lower than the $95^{th}$ percentile of the expression level of RNA transcripts from the endocrine signaling negative gene set of a population of metastatic ER+ breast cancer patients.

In embodiments, the fourth standard control is the expression level of RNA transcripts from the endocrine signaling positive gene set of a population of metastatic ER+ breast cancer patients. In embodiments, the fourth standard control is the average expression level of RNA transcripts from the endocrine signaling positive gene set of a population of metastatic ER+ breast cancer patients that are responsive to endocrine therapy.

In embodiments, the fourth standard control is the $30^{th}$ percentile of the expression level of RNA transcripts from the endocrine signaling positive gene set of a population of metastatic ER+ breast cancer patients. In embodiments, the fourth standard control is the $31^{st}$ percentile of the expression level of RNA transcripts from the endocrine signaling positive gene set of a population of metastatic ER+ breast cancer patients. In embodiments, the fourth standard control is the $32^{nd}$ percentile of the expression level of RNA transcripts from the endocrine signaling positive gene set of a population of metastatic ER+ breast cancer patients. In embodiments, the fourth standard control is the $33^{rd}$ percentile of the expression level of RNA transcripts from the endocrine signaling positive gene set of a population of metastatic ER+ breast cancer patients. In embodiments, the fourth standard control is the $34^{th}$ percentile of the expression level of RNA transcripts from the endocrine signaling positive gene set of a population of metastatic ER+ breast cancer patients. In embodiments, the fourth standard control is the $35^{th}$ percentile of the expression level of RNA transcripts from the endocrine signaling positive gene set of a population of metastatic ER+ breast cancer patients. In embodiments, the fourth standard control is the $36^{th}$ percentile of the expression level of RNA transcripts from the endocrine signaling positive gene set of a population of metastatic ER+ breast cancer patients. In embodiments, the fourth standard control is the $37^{th}$ percentile of the expression level of RNA transcripts from the endocrine signaling positive gene set of a population of metastatic ER+ breast cancer patients. In embodiments, the fourth standard control is the $38^{th}$ percentile of the expression level of RNA transcripts from the endocrine signaling positive gene set of a population of metastatic ER+ breast cancer patients. In embodiments, the fourth standard control is the $39^{th}$ percentile of the expression level of RNA transcripts from the endocrine signaling positive gene set of a population of metastatic ER+ breast cancer patients. In embodiments, the fourth standard control is the $40^{th}$ percentile of the expression level of RNA transcripts from the endocrine signaling positive gene set of a population of metastatic ER+ breast cancer patients. In embodiments, the fourth standard control is the $41^{st}$ percentile of the expression level of RNA transcripts from the endocrine signaling positive gene set of a population of metastatic ER+ breast cancer patients. In embodiments, the fourth standard control is the $42^{nd}$ percentile of the expression level of RNA transcripts from the endocrine signaling positive gene set of a population of metastatic ER+ breast cancer patients. In embodiments, the fourth standard control is the $43^{rd}$ percentile of the expression level of RNA transcripts from the endocrine signaling positive gene set of a population of metastatic ER+ breast cancer patients. In embodiments, the fourth standard control is the $44^{th}$ percentile of the expression level of RNA transcripts from the endocrine signaling positive gene set of a population of metastatic ER+ breast cancer patients. In embodiments, the fourth standard control is the $45^{th}$ percentile of the expression level of RNA transcripts from the endocrine signaling positive gene set of a population of metastatic ER+ breast cancer patients. In embodiments, the fourth standard control is the $46^{th}$ percentile of the expression level of RNA transcripts from the endocrine signaling positive gene set of a population of metastatic ER+ breast cancer patients. In embodiments, the fourth standard control is the $47^{th}$ percentile of the expression level of RNA transcripts from the endocrine signaling positive gene set of a population of metastatic ER+ breast cancer patients. In embodiments, the fourth standard control is the $48^{th}$ percentile of the expression level of RNA transcripts from the endocrine signaling positive gene set of a population of metastatic ER+ breast cancer patients. In embodiments, the fourth standard control is the $49^{th}$ percentile of the expression level of RNA transcripts from the endocrine signaling positive gene set of a population of metastatic ER+ breast cancer patients. In embodiments, the fourth standard control is the $50^{th}$ percentile of the expression level of RNA transcripts from the endocrine signaling positive gene set of a population of metastatic ER+ breast cancer patients In embodiments, the fourth standard control is the $50^{th}$ percentile of the expression level of RNA transcripts from the endocrine signaling positive gene set of a population of metastatic ER+ breast cancer patients. In embodiments, the fourth standard control is the $51^{st}$ percentile of the expression level of RNA transcripts from the endocrine signaling positive gene set of a population of metastatic ER+ breast cancer patients. In embodiments, the fourth standard control is the $52^{nd}$ percentile of the expression level of RNA transcripts from the endocrine signaling positive gene set of a population of metastatic ER+ breast cancer patients. In embodiments, the fourth standard control is the $53^{rd}$ percentile of the expression level of RNA transcripts from the endocrine signaling positive gene set of a population of metastatic ER+ breast cancer patients. In embodiments, the fourth standard control is the $54^{th}$ percentile of the expression level of RNA transcripts from the endocrine signaling positive gene set of a population of metastatic ER+ breast cancer patients. In embodiments, the fourth standard control is the $55^{th}$ percentile of the expression level of RNA transcripts from the endocrine signaling positive gene set of a population of metastatic ER+ breast cancer patients. In embodiments, the fourth standard control is the $56^{th}$ percentile of the expression level of RNA transcripts from the endocrine signaling positive gene set of a population of metastatic ER+ breast cancer patients. In embodiments, the fourth standard control is the $57^{th}$ percentile of the expression level of RNA transcripts from the endocrine signaling positive gene set of a population of metastatic ER+ breast cancer patients. In embodiments, the fourth standard control is the $58^{th}$ percentile of the expression level of RNA transcripts from the endocrine signaling positive gene set of a population of metastatic ER+ breast cancer patients. In embodiments, the fourth standard control is the $59^{th}$ percentile of the expression level of RNA transcripts from the endocrine signaling positive gene set of a population of metastatic ER+ breast cancer patients. In embodiments, the fourth standard control is the $60^{th}$ percentile of the expression level of RNA transcripts from the endocrine signaling positive gene set of a population of metastatic ER+ breast cancer patients. In embodiments, the fourth standard control is the $61^{st}$ percentile of the expression level of RNA transcripts from the endocrine signaling positive gene set of a population of metastatic ER+ breast cancer patients. In embodiments, the fourth standard control is the $62^{nd}$ percentile of the expression level of RNA transcripts from the endocrine signaling positive gene set of a population of metastatic ER+ breast cancer patients. In embodiments, the fourth standard control is the $63^{rd}$ percentile of the expression level of RNA transcripts from the endocrine signaling positive gene set of a population of metastatic ER+ breast cancer patients. In embodiments, the fourth standard control is the $64^{th}$ percentile of the expression level of RNA transcripts from the endocrine signaling positive gene set of a population of metastatic ER+ breast cancer patients. In embodiments, the fourth standard control is the $65^{th}$ percentile of the expression level of RNA transcripts from the endocrine signaling positive gene set of a population of metastatic ER+ breast cancer patients. In embodiments, the fourth standard control is the $66^{th}$ percentile of the expression level of RNA transcripts from the endocrine signaling positive gene set of a population of metastatic ER+ breast cancer patients. In embodiments, the fourth standard control is the $67^{th}$ percentile of the expression level of RNA transcripts from the endocrine signaling positive gene set of a population of metastatic ER+ breast cancer patients. In embodiments, the fourth standard control is the $68^{th}$ percentile of the expression level of RNA transcripts from the endocrine signaling positive gene set of a population of metastatic ER+ breast cancer patients. In embodiments, the fourth standard control is the $69^{th}$ percentile of the expression level of RNA transcripts from the endocrine signaling positive gene set of a population of metastatic ER+ breast cancer patients. In embodiments, the fourth standard control is the $70^{th}$ percentile of the expression level of RNA transcripts from the endocrine signaling positive gene set of a population of metastatic ER+ breast cancer patients. In embodiments, the fourth standard control is the $71^{st}$ percentile of the expression level of RNA transcripts from the endocrine signaling positive gene set of a population of metastatic ER+ breast cancer patients. In embodiments, the fourth standard control is the $72^{nd}$ percentile of the expression level of RNA transcripts from the endocrine signaling positive gene set of a population of metastatic ER+ breast cancer patients. In embodiments, the fourth standard control is the $73^{rd}$ percentile of the expression level of RNA transcripts from the endocrine signaling positive gene set of a population of metastatic ER+ breast cancer patients. In embodiments, the fourth standard control is the $74^{th}$ percentile of the expression level of RNA transcripts from the endocrine signaling positive gene set of a population of metastatic ER+ breast cancer patients. In embodiments, the fourth standard control is the $75^{th}$ percentile of the expression level of RNA transcripts from the endocrine signaling positive gene set of a population of metastatic ER+ breast cancer patients. In embodiments, the fourth standard control is the $76^{th}$ percentile of the expression level of RNA transcripts from the endocrine signaling positive gene set of a population of metastatic ER+ breast cancer patients. In embodiments, the fourth standard control is the $77^{th}$ percentile of the expression level of RNA transcripts from the endocrine signaling positive gene set of a population of metastatic ER+ breast cancer patients. In embodiments, the fourth standard control is the $78^{th}$ percentile of the expression level of RNA transcripts from the endocrine signaling positive gene set of a population of metastatic ER+ breast cancer patients. In embodiments, the fourth standard control is the $79^{th}$ percentile of the expression level of RNA transcripts from the endocrine signaling positive gene set of a population of metastatic ER+ breast cancer patients. In embodiments, the fourth standard control is the $80^{th}$ percentile of the expression level of RNA transcripts from the endocrine signaling positive gene set of a population of metastatic ER+ breast cancer patients.

In embodiments, the high level of expression is higher than the $30^{th}$ percentile of the expression level of RNA transcripts from the endocrine signaling positive gene set of a population of metastatic ER+ breast cancer patients. In embodiments, the high level of expression is higher than the $31^{st}$ percentile of the expression level of RNA transcripts from the endocrine signaling positive gene set of a population of metastatic ER+ breast cancer patients. In embodiments, the high level of expression is higher than the $32^{nd}$ percentile of the expression level of RNA transcripts from the endocrine signaling positive gene set of a population of metastatic ER+ breast cancer patients. In embodiments, the high level of expression is higher than the $33^{rd}$ percentile of the expression level of RNA transcripts from the endocrine signaling positive gene set of a population of metastatic ER+ breast cancer patients. In embodiments, the high level of expression is higher than the $34^{th}$ percentile of the expression level of RNA transcripts from the endocrine signaling positive gene set of a population of metastatic ER+ breast cancer patients. In embodiments, the high level of expression is higher than the $35^{th}$ percentile of the expression level of RNA transcripts from the endocrine signaling positive gene set of a population of metastatic ER+ breast cancer patients. In embodiments, the high level of expression is higher than the $36^{th}$ percentile of the expression level of RNA transcripts from the endocrine signaling positive gene set of a population of metastatic ER+ breast cancer patients. In embodiments, the high level of expression is higher than the $37^{th}$ percentile of the expression level of RNA transcripts from the endocrine signaling positive gene set of a population of metastatic ER+ breast cancer patients. In embodiments, the high level of expression is higher than the $38^{th}$ percentile of the expression level of RNA transcripts from the endocrine signaling positive gene set of a population of metastatic ER+ breast cancer patients. In embodiments, the high level of expression is higher than the $39^{th}$ percentile of the expression level of RNA transcripts from the endocrine signaling positive gene set of a population of metastatic ER+ breast cancer patients. In embodiments, the high level of expression is higher than the $40^{th}$ percentile of the expression level of RNA transcripts from the endocrine signaling positive gene set of a population of metastatic ER+ breast cancer patients. In embodiments, the high level of expression is higher than the $41^{st}$ percentile of the expression level of RNA transcripts from the endocrine signaling positive gene set of a population of metastatic ER+ breast cancer patients. In embodiments, the high level of expression is higher than the $42^{nd}$ percentile of the expression level of RNA transcripts from the endocrine signaling positive gene set of a population of metastatic ER+ breast cancer patients. In embodiments, the high level of expression is higher than the $43^{rd}$ percentile of the expression level of RNA transcripts from the endocrine signaling positive gene set of a population of metastatic ER+ breast cancer patients. In embodiments, the high level of expression is higher than the $44^{th}$ percentile of the expression level of RNA transcripts from the endocrine signaling positive gene set of a population of metastatic ER+ breast cancer patients. In embodiments, the high level of expression is higher than the $45^{th}$ percentile of the expression level of RNA transcripts from the endocrine signaling positive gene set of a population of metastatic ER+ breast cancer patients. In embodiments, the high level of expression is higher than the $46^{th}$ percentile of the expression level of RNA transcripts from the endocrine signaling positive gene set of a population of metastatic ER+ breast cancer patients. In embodiments, the high level of expression is higher than the $47^{th}$ percentile of the expression level of RNA transcripts from the endocrine signaling positive gene set of a population of metastatic ER+ breast cancer patients. In embodiments, the high level of expression is higher than the $48^{th}$ percentile of the expression level of RNA transcripts from the endocrine signaling positive gene set of a population of metastatic ER+ breast cancer patients. In embodiments, the high level of expression is higher than the $49^{th}$ percentile of the expression level of RNA transcripts from the endocrine signaling positive gene set of a population of metastatic ER+ breast cancer patients. In embodiments, the high level of expression is higher than the $50^{th}$ percentile of the expression level of RNA transcripts from the endocrine signaling positive gene set of a population of metastatic ER+ breast cancer patients In embodiments, the high level of expression is higher than the $50^{th}$ percentile of the expression level of RNA transcripts from the endocrine signaling positive gene set of a population of metastatic ER+ breast cancer patients. In embodiments, the high level of expression is higher than the $51^{st}$ percentile of the expression level of RNA transcripts from the endocrine signaling positive gene set of a population of metastatic ER+ breast cancer patients. In embodiments, the high level of expression is higher than the $52^{nd}$ percentile of the expression level of RNA transcripts from the endocrine signaling positive gene set of a population of metastatic ER+ breast cancer patients. In embodiments, the high level of expression is higher than the $53^{rd}$ percentile of the expression level of RNA transcripts from the endocrine signaling positive gene set of a population of metastatic ER+ breast cancer patients. In embodiments, the high level of expression is higher than the $54^{th}$ percentile of the expression level of RNA transcripts from the endocrine signaling positive gene set of a population of metastatic ER+ breast cancer patients. In embodiments, the high level of expression is higher than the $55^{th}$ percentile of the expression level of RNA transcripts from the endocrine signaling positive gene set of a population of metastatic ER+ breast cancer patients. In embodiments, the high level of expression is higher than the $56^{th}$ percentile of the expression level of RNA transcripts from the endocrine signaling positive gene set of a population of metastatic ER+ breast cancer patients. In embodiments, the high level of expression is higher than the $57^{th}$ percentile of the expression level of RNA transcripts from the endocrine signaling positive gene set of a population of metastatic ER+ breast cancer patients. In embodiments, the high level of expression is higher than the $58^{th}$ percentile of the expression level of RNA transcripts from the endocrine signaling positive gene set of a population of metastatic ER+ breast cancer patients. In embodiments, the high level of expression is higher than the $59^{th}$ percentile of the expression level of RNA transcripts from the endocrine signaling positive gene set of a population of metastatic ER+ breast cancer patients. In embodiments, the high level of expression is higher than the $60^{th}$ percentile of the expression level of RNA transcripts from the endocrine signaling positive gene set of a population of metastatic ER+ breast cancer patients. In embodiments, the high level of expression is higher than the $61^{st}$ percentile of the expression level of RNA transcripts from the endocrine signaling positive gene set of a population of metastatic ER+ breast cancer patients. In embodiments, the high level of expression is higher than the $62^{nd}$ percentile of the expression level of RNA transcripts from the endocrine signaling positive gene set of a population of metastatic ER+ breast cancer patients. In embodiments, the high level of expression is higher than the $63^{d}$ percentile of the expression level of RNA transcripts from the endocrine signaling positive gene set of a population of metastatic ER+ breast cancer patients. In embodiments, the high level of expression is higher than the $64^{th}$ percentile of the expression level of RNA transcripts from the endocrine signaling positive gene set of a population of metastatic ER+ breast cancer patients. In embodiments, the high level of expression is higher than the $65^{th}$ percentile of the expression level of RNA transcripts from the endocrine signaling positive gene set of a population of metastatic ER+ breast cancer patients. In embodiments, the high level of expression is higher than the $66^{th}$ percentile of the expression level of RNA transcripts from the endocrine signaling positive gene set of a population of metastatic ER+ breast cancer patients. In embodiments, the high level of expression is higher than the $67^{th}$ percentile of the expression level of RNA transcripts from the endocrine signaling positive gene set of a population of metastatic ER+ breast cancer patients. In embodiments, the high level of expression is higher than the $68^{th}$ percentile of the expression level of RNA transcripts from the endocrine signaling positive gene set of a population of metastatic ER+ breast cancer patients. In embodiments, the high level of expression is higher than the $69^{th}$ percentile of the expression level of RNA transcripts from the endocrine signaling positive gene set of a population of metastatic ER+ breast cancer patients. In embodiments, the high level of expression is higher than the $70^{th}$ percentile of the expression level of RNA transcripts from the endocrine signaling positive gene set of a population of metastatic ER+ breast cancer patients. In embodiments, the high level of expression is higher than the $71^{st}$ percentile of the expression level of RNA transcripts from the endocrine signaling positive gene set of a population of metastatic ER+ breast cancer patients. In embodiments, the high level of expression is higher than the $72^{nd}$ percentile of the expression level of RNA transcripts from the endocrine signaling positive gene set of a population of metastatic ER+ breast cancer patients. In embodiments, the high level of expression is higher than the $73^{d}$ percentile of the expression level of RNA transcripts from the endocrine signaling positive gene set of a population of metastatic ER+ breast cancer patients. In embodiments, the high level of expression is higher than the $74^{th}$ percentile of the expression level of RNA transcripts from the endocrine signaling positive gene set of a population of metastatic ER+ breast cancer patients. In embodiments, the high level of expression is higher than the $75^{th}$ percentile of the expression level of RNA transcripts from the endocrine signaling positive gene set of a population of metastatic ER+ breast cancer patients. In embodiments, the high level of expression is higher than the $76^{th}$ percentile of the expression level of RNA transcripts from the endocrine signaling positive gene set of a population of metastatic ER+ breast cancer patients. In embodiments, the high level of expression is higher than the $77^{th}$ percentile of the expression level of RNA transcripts from the endocrine signaling positive gene set of a population of metastatic ER+ breast cancer patients. In embodiments, the high level of expression is higher than the $78^{th}$ percentile of the expression level of RNA transcripts from the endocrine signaling positive gene set of a population of metastatic ER+ breast cancer patients. In embodiments, the high level of expression is higher than the $79^{th}$ percentile of the expression level of RNA transcripts from the endocrine signaling positive gene set of a population of metastatic ER+ breast cancer patients. In embodiments, the high level of expression is higher than the $80^{th}$ percentile of the expression level of RNA transcripts from the endocrine signaling positive gene set of a population of metastatic ER+ breast cancer patients.

In embodiments, (a) the determining a low level of expression of the endocrine signaling negative gene set relative to a third standard control includes determining a first aggregate rank of the expression level of RNA transcripts from the endocrine signaling negative gene set relative to the expression level of RNA transcripts from the remainder gene set, wherein the first aggregate rank is low relative to the third standard control; and (b) determining a high level of expression of the endocrine signaling positive gene set relative to a fourth standard control includes determining a second aggregate rank of the expression level of RNA transcripts from the endocrine signaling positive gene set relative to the expression level of RNA transcripts from the remainder gene set, wherein the second aggregate rank is high relative to the fourth standard control.

For the methods provided herein, in embodiments, the third standard control is the average aggregate rank of the expression level of RNA transcripts from the endocrine signaling negative gene set of a population of metastatic ER+ breast cancer patients. In embodiments, the third standard control is the average aggregate rank of the expression level of RNA transcripts from the endocrine signaling negative gene set of a population of metastatic ER+ breast cancer patients that are responsive to endocrine therapy.

In embodiments, the third standard control is the $30^{th}$ percentile of the aggregate rank of RNA transcripts from the endocrine signaling negative gene set of a population of metastatic ER+ breast cancer patients. In embodiments, the third standard control is the $40^{th}$ percentile of the aggregate rank of RNA transcripts from the endocrine signaling negative gene set of a population of metastatic ER+ breast cancer patients. In embodiments, the third standard control is the $50^{th}$ percentile of the aggregate rank of RNA transcripts from the endocrine signaling negative gene set of a population of metastatic ER+ breast cancer patients. In embodiments, the third standard control is the $60^{th}$ percentile of the aggregate rank of RNA transcripts from the endocrine signaling negative gene set of a population of metastatic ER+ breast cancer patients. In embodiments, the third standard control is the $61^{st}$ percentile of the aggregate rank of RNA transcripts from the endocrine signaling negative gene set of a population of metastatic ER+ breast cancer patients. In embodiments, the third standard control is the $62^{nd}$ percentile of the aggregate rank of RNA transcripts from the endocrine signaling negative gene set of a population of metastatic ER+ breast cancer patients. In embodiments, the third standard control is the $63^{rd}$ percentile of the aggregate rank of RNA transcripts from the endocrine signaling negative gene set of a population of metastatic ER+ breast cancer patients. In embodiments, the third standard control is the $64^{th}$ percentile of the aggregate rank of RNA transcripts from the endocrine signaling negative gene set of a population of metastatic ER+ breast cancer patients. In embodiments, the third standard control is the $65^{th}$ percentile of the aggregate rank of RNA transcripts from the endocrine signaling negative gene set of a population of metastatic ER+ breast cancer patients. In embodiments, the third standard control is the $66^{th}$ percentile of the aggregate rank of RNA transcripts from the endocrine signaling negative gene set of a population of metastatic ER+ breast cancer patients. In embodiments, the third standard control is the $67^{th}$ percentile of the aggregate rank of RNA transcripts from the endocrine signaling negative gene set of a population of metastatic ER+ breast cancer patients. In embodiments, the third standard control is the $68^{th}$ percentile of the aggregate rank of RNA transcripts from the endocrine signaling negative gene set of a population of metastatic ER+ breast cancer patients. In embodiments, the third standard control is the $69^{th}$ percentile of the aggregate rank of RNA transcripts from the endocrine signaling negative gene set of a population of metastatic ER+ breast cancer patients. In embodiments, the third standard control is the $70^{th}$ percentile of the aggregate rank of RNA transcripts from the endocrine signaling negative gene set of a population of metastatic ER+ breast cancer patients. In embodiments, the third standard control is the $70^{th}$ percentile of the aggregate rank of RNA transcripts from the endocrine signaling negative gene set of a population of metastatic ER+ breast cancer patients. In embodiments, the third standard control is the $71^{st}$ percentile of the aggregate rank of RNA transcripts from the endocrine signaling negative gene set of a population of metastatic ER+ breast cancer patients. In embodiments, the third standard control is the $72^{nd}$ percentile of the aggregate rank of RNA transcripts from the endocrine signaling negative gene set of a population of metastatic ER+ breast cancer patients. In embodiments, the third standard control is the $73^{d}$ percentile of the aggregate rank of RNA transcripts from the endocrine signaling negative gene set of a population of metastatic ER+ breast cancer patients. In embodiments, the third standard control is the $74^{th}$ percentile of the aggregate rank of RNA transcripts from the endocrine signaling negative gene set of a population of metastatic ER+ breast cancer patients. In embodiments, the third standard control is the $75^{th}$ percentile of the aggregate rank of RNA transcripts from the endocrine signaling negative gene set of a population of metastatic ER+ breast cancer patients. In embodiments, the third standard control is the $76^{th}$ percentile of the aggregate rank of RNA transcripts from the endocrine signaling negative gene set of a population of metastatic ER+ breast cancer patients. In embodiments, the third standard control is the $77^{th}$ percentile of the aggregate rank of RNA transcripts from the endocrine signaling negative gene set of a population of metastatic ER+ breast cancer patients. In embodiments, the third standard control is the 78$^{th}$ percentile of the aggregate rank of RNA transcripts from the endocrine signaling negative gene set of a population of metastatic ER+ breast cancer patients. In embodiments, the third standard control is the 79$^{th}$ percentile of the aggregate rank of RNA transcripts from the endocrine signaling negative gene set of a population of metastatic ER+ breast cancer patients. In embodiments, the third standard control is the 80$^{th}$ percentile of the aggregate rank of RNA transcripts from the endocrine signaling negative gene set of a population of metastatic ER+ breast cancer patients. In embodiments, the third standard control is the 81$^{st}$ percentile of the aggregate rank of the expression level of RNA transcripts from the endocrine signaling negative gene set of a population of metastatic ER+ breast cancer patients. In embodiments, the third standard control is the 82$^{nd}$ percentile of the aggregate rank of RNA transcripts from the endocrine signaling negative gene set of a population of metastatic ER+ breast cancer patients. In embodiments, the third standard control is the 83$^{rd}$ percentile of the aggregate rank of RNA transcripts from the endocrine signaling negative gene set of a population of metastatic ER+ breast cancer patients. In embodiments, the third standard control is the 84$^{th}$ percentile of the aggregate rank of RNA transcripts from the endocrine signaling negative gene set of a population of metastatic ER+ breast cancer patients. In embodiments, the third standard control is the 85$^{th}$ percentile of the aggregate rank of RNA transcripts from the endocrine signaling negative gene set of a population of metastatic ER+ breast cancer patients. In embodiments, the third standard control is the 86$^{th}$ percentile of the aggregate rank of RNA transcripts from the endocrine signaling negative gene set of a population of metastatic ER+ breast cancer patients. In embodiments, the third standard control is the 87$^{th}$ percentile of the aggregate rank of RNA transcripts from the endocrine signaling negative gene set of a population of metastatic ER+ breast cancer patients. In embodiments, the third standard control is the 88$^{th}$ percentile of the aggregate rank of RNA transcripts from the endocrine signaling negative gene set of a population of metastatic ER+ breast cancer patients. In embodiments, the third standard control is the 89$^{th}$ percentile of the aggregate rank of RNA transcripts from the endocrine signaling negative gene set of a population of metastatic ER+ breast cancer patients. In embodiments, the third standard control is the 90$^{th}$ percentile of the aggregate rank of RNA transcripts from the endocrine signaling negative gene set of a population of metastatic ER+ breast cancer patients. In embodiments, the third standard control is the 91$^{st}$ percentile of the aggregate rank of the expression level of RNA transcripts from the endocrine signaling negative gene set of a population of metastatic ER+ breast cancer patients. In embodiments, the third standard control is the 92$^{nd}$ percentile of the aggregate rank of RNA transcripts from the endocrine signaling negative gene set of a population of metastatic ER+ breast cancer patients. In embodiments, the third standard control is the 93$^{rd}$ percentile of the aggregate rank of RNA transcripts from the endocrine signaling negative gene set of a population of metastatic ER+ breast cancer patients. In embodiments, the third standard control is the 94$^{th}$ percentile of the aggregate rank of RNA transcripts from the endocrine signaling negative gene set of a population of metastatic ER+ breast cancer patients. In embodiments, the third standard control is the 95$^{th}$ percentile of the aggregate rank of RNA transcripts from the endocrine signaling negative gene set of a population of metastatic ER+ breast cancer patients.

In embodiments, the first aggregate rank is lower than the 30$^{th}$ percentile of the aggregate rank of RNA transcripts from the endocrine signaling negative gene set of a population of metastatic ER+ breast cancer patients. In embodiments, the first aggregate rank is lower than the 40$^{th}$ percentile of the aggregate rank of RNA transcripts from the endocrine signaling negative gene set of a population of metastatic ER+ breast cancer patients. In embodiments, the first aggregate rank is lower than the 50$^{th}$ percentile of the aggregate rank of RNA transcripts from the endocrine signaling negative gene set of a population of metastatic ER+ breast cancer patients. In embodiments, the first aggregate rank is lower than the 60$^{th}$ percentile of the aggregate rank of RNA transcripts from the endocrine signaling negative gene set of a population of metastatic ER+ breast cancer patients. In embodiments, the first aggregate rank is lower than the 61$^{st}$ percentile of the aggregate rank of RNA transcripts from the endocrine signaling negative gene set of a population of metastatic ER+ breast cancer patients. In embodiments, the first aggregate rank is lower than the 62$^{nd}$ percentile of the aggregate rank of RNA transcripts from the endocrine signaling negative gene set of a population of metastatic ER+ breast cancer patients. In embodiments, the first aggregate rank is lower than the 63, percentile of the aggregate rank of RNA transcripts from the endocrine signaling negative gene set of a population of metastatic ER+ breast cancer patients. In embodiments, the first aggregate rank is lower than the 64$^{th}$ percentile of the aggregate rank of RNA transcripts from the endocrine signaling negative gene set of a population of metastatic ER+ breast cancer patients. In embodiments, the first aggregate rank is lower than the 65$^{th}$ percentile of the aggregate rank of RNA transcripts from the endocrine signaling negative gene set of a population of metastatic ER+ breast cancer patients. In embodiments, the first aggregate rank is lower than the 66$^{th}$ percentile of the aggregate rank of RNA transcripts from the endocrine signaling negative gene set of a population of metastatic ER+ breast cancer patients. In embodiments, the first aggregate rank is lower than the 67$^{th}$ percentile of the aggregate rank of RNA transcripts from the endocrine signaling negative gene set of a population of metastatic ER+ breast cancer patients. In embodiments, the first aggregate rank is lower than the 68$^{th}$ percentile of the aggregate rank of RNA transcripts from the endocrine signaling negative gene set of a population of metastatic ER+ breast cancer patients. In embodiments, the first aggregate rank is lower than the 69$^{th}$ percentile of the aggregate rank of RNA transcripts from the endocrine signaling negative gene set of a population of metastatic ER+ breast cancer patients. In embodiments, the first aggregate rank is lower than the 70$^{th}$ percentile of the aggregate rank of RNA transcripts from the endocrine signaling negative gene set of a population of metastatic ER+ breast cancer patients. In embodiments, the first aggregate rank is lower than the 71$^{st}$ percentile of the aggregate rank of RNA transcripts from the endocrine signaling negative gene set of a population of metastatic ER+ breast cancer patients. In embodiments, the first aggregate rank is lower than the 72$^{nd}$ percentile of the aggregate rank of RNA transcripts from the endocrine signaling negative gene set of a population of metastatic ER+ breast cancer patients. In embodiments, the first aggregate rank is lower than the 73$^{rd}$ percentile of the aggregate rank of RNA transcripts from the endocrine signaling negative gene set of a population of metastatic ER+ breast cancer patients. In embodiments, the first aggregate rank is lower than the 74$^{th}$ percentile of the aggregate rank of RNA transcripts from the endocrine signaling negative gene set of a population of metastatic ER+ breast cancer patients. In embodiments, the first aggregate rank is lower than the $75^{th}$ percentile of the aggregate rank of RNA transcripts from the endocrine signaling negative gene set of a population of metastatic ER+ breast cancer patients. In embodiments, the first aggregate rank is lower than the $76^{th}$ percentile of the aggregate rank of RNA transcripts from the endocrine signaling negative gene set of a population of metastatic ER+ breast cancer patients. In embodiments, the first aggregate rank is lower than the $77^{th}$ percentile of the aggregate rank of RNA transcripts from the endocrine signaling negative gene set of a population of metastatic ER+ breast cancer patients. In embodiments, the first aggregate rank is lower than the $78^{th}$ percentile of the aggregate rank of RNA transcripts from the endocrine signaling negative gene set of a population of metastatic ER+ breast cancer patients. In embodiments, the first aggregate rank is lower than the $79^{th}$ percentile of the aggregate rank of RNA transcripts from the endocrine signaling negative gene set of a population of metastatic ER+ breast cancer patients. In embodiments, the first aggregate rank is lower than the $80^{th}$ percentile of the aggregate rank of RNA transcripts from the endocrine signaling negative gene set of a population of metastatic ER+ breast cancer patients. In embodiments, the first aggregate rank is lower than the $81^{st}$ percentile of the aggregate rank of the expression level of RNA transcripts from the endocrine signaling negative gene set of a population of metastatic ER+ breast cancer patients. In embodiments, the first aggregate rank is lower than the $82^{nd}$ percentile of the aggregate rank of RNA transcripts from the endocrine signaling negative gene set of a population of metastatic ER+ breast cancer patients. In embodiments, the first aggregate rank is lower than the $83^{rd}$ percentile of the aggregate rank of RNA transcripts from the endocrine signaling negative gene set of a population of metastatic ER+ breast cancer patients. In embodiments, the first aggregate rank is lower than the $84^{th}$ percentile of the aggregate rank of RNA transcripts from the endocrine signaling negative gene set of a population of metastatic ER+ breast cancer patients. In embodiments, the first aggregate rank is lower than the $85^{th}$ percentile of the aggregate rank of RNA transcripts from the endocrine signaling negative gene set of a population of metastatic ER+ breast cancer patients. In embodiments, the first aggregate rank is lower than the $86^{th}$ percentile of the aggregate rank of RNA transcripts from the endocrine signaling negative gene set of a population of metastatic ER+ breast cancer patients. In embodiments, the first aggregate rank is lower than the $87^{th}$ percentile of the aggregate rank of RNA transcripts from the endocrine signaling negative gene set of a population of metastatic ER+ breast cancer patients. In embodiments, the first aggregate rank is lower than the $88^{th}$ percentile of the aggregate rank of RNA transcripts from the endocrine signaling negative gene set of a population of metastatic ER+ breast cancer patients. In embodiments, the first aggregate rank is lower than the $89^{th}$ percentile of the aggregate rank of RNA transcripts from the endocrine signaling negative gene set of a population of metastatic ER+ breast cancer patients. In embodiments, the first aggregate rank is lower than the $90^{th}$ percentile of the aggregate rank of RNA transcripts from the endocrine signaling negative gene set of a population of metastatic ER+ breast cancer patients. In embodiments, the first aggregate rank is lower than the $91^{st}$ percentile of the aggregate rank of the expression level of RNA transcripts from the endocrine signaling negative gene set of a population of metastatic ER+ breast cancer patients. In embodiments, the first aggregate rank is lower than the $92^{nd}$ percentile of the aggregate rank of RNA transcripts from the endocrine signaling negative gene set of a population of metastatic ER+ breast cancer patients. In embodiments, the first aggregate rank is lower than the $93^{rd}$ percentile of the aggregate rank of RNA transcripts from the endocrine signaling negative gene set of a population of metastatic ER+ breast cancer patients. In embodiments, the first aggregate rank is lower than the $94^{th}$ percentile of the aggregate rank of RNA transcripts from the endocrine signaling negative gene set of a population of metastatic ER+ breast cancer patients. In embodiments, the first aggregate rank is lower than the $95^{th}$ percentile of the aggregate rank of RNA transcripts from the endocrine signaling negative gene set of a population of metastatic ER+ breast cancer patients.

In embodiments, the fourth standard control is the average aggregate rank of the expression level of RNA transcripts from the endocrine signaling positive gene set of a population of metastatic ER+ breast cancer patients. In embodiments, the fourth standard control is the average aggregate rank of the expression level of RNA transcripts from the endocrine signaling positive gene set of a population of metastatic ER+ breast cancer patients that are responsive to endocrine therapy.

In embodiments, the fourth standard control is the $30^{th}$ percentile of the aggregate rank of RNA transcripts from the endocrine signaling positive gene set of a population of metastatic ER+ breast cancer patients. In embodiments, the fourth standard control is the $31^{st}$ percentile of the aggregate rank of RNA transcripts from the endocrine signaling positive gene set of a population of metastatic ER+ breast cancer patients. In embodiments, the fourth standard control is the $32^{nd}$ percentile of the aggregate rank of RNA transcripts from the endocrine signaling positive gene set of a population of metastatic ER+ breast cancer patients. In embodiments, the fourth standard control is the $33^{rd}$ percentile of the aggregate rank of RNA transcripts from the endocrine signaling positive gene set of a population of metastatic ER+ breast cancer patients. In embodiments, the fourth standard control is the $34^{th}$ percentile of the aggregate rank of RNA transcripts from the endocrine signaling positive gene set of a population of metastatic ER+ breast cancer patients. In embodiments, the fourth standard control is the $35^{th}$ percentile of the aggregate rank of RNA transcripts from the endocrine signaling positive gene set of a population of metastatic ER+ breast cancer patients. In embodiments, the fourth standard control is the $36^{th}$ percentile of the aggregate rank of RNA transcripts from the endocrine signaling positive gene set of a population of metastatic ER+ breast cancer patients. In embodiments, the fourth standard control is the $37^{th}$ percentile of the aggregate rank of RNA transcripts from the endocrine signaling positive gene set of a population of metastatic ER+ breast cancer patients. In embodiments, the fourth standard control is the $38^{th}$ percentile of the aggregate rank of RNA transcripts from the endocrine signaling positive gene set of a population of metastatic ER+ breast cancer patients. In embodiments, the fourth standard control is the $39^{th}$ percentile of the aggregate rank of RNA transcripts from the endocrine signaling positive gene set of a population of metastatic ER+ breast cancer patients. In embodiments, the fourth standard control is the $40^{th}$ percentile of the aggregate rank of RNA transcripts from the endocrine signaling positive gene set of a population of metastatic ER+ breast cancer patients. In embodiments, the fourth standard control is the $41^{st}$ percentile of the aggregate rank of RNA transcripts from the endocrine signaling positive gene set of a population of metastatic ER+ breast cancer patients. In embodiments, the fourth standard control is the $42^{nd}$ percentile of the aggregate rank of RNA transcripts from the endocrine signaling positive gene set of a population of metastatic ER+ breast cancer patients. In embodiments, the fourth standard control is the $43^{rd}$ percentile of the aggregate rank of RNA transcripts from the endocrine signaling positive gene set of a population of metastatic ER+ breast cancer patients. In embodiments, the fourth standard control is the $44^{th}$ percentile of the aggregate rank of RNA transcripts from the endocrine signaling positive gene set of a population of metastatic ER+ breast cancer patients. In embodiments, the fourth standard control is the $45^{th}$ percentile of the aggregate rank of RNA transcripts from the endocrine signaling positive gene set of a population of metastatic ER+ breast cancer patients. In embodiments, the fourth standard control is the $46^{th}$ percentile of the aggregate rank of RNA transcripts from the endocrine signaling positive gene set of a population of metastatic ER+ breast cancer patients. In embodiments, the fourth standard control is the $47^{th}$ percentile of the aggregate rank of RNA transcripts from the endocrine signaling positive gene set of a population of metastatic ER+ breast cancer patients. In embodiments, the fourth standard control is the $48^{th}$ percentile of the aggregate rank of RNA transcripts from the endocrine signaling positive gene set of a population of metastatic ER+ breast cancer patients. In embodiments, the fourth standard control is the $49^{th}$ percentile of the aggregate rank of RNA transcripts from the endocrine signaling positive gene set of a population of metastatic ER+ breast cancer patients. In embodiments, the fourth standard control is the $50^{th}$ percentile of the aggregate rank of RNA transcripts from the endocrine signaling positive gene set of a population of metastatic ER+ breast cancer patients In embodiments, the fourth standard control is the $50^{th}$ percentile of the aggregate rank of RNA transcripts from the endocrine signaling positive gene set of a population of metastatic ER+ breast cancer patients. In embodiments, the fourth standard control is the $51^{st}$ percentile of the aggregate rank of RNA transcripts from the endocrine signaling positive gene set of a population of metastatic ER+ breast cancer patients. In embodiments, the fourth standard control is the $52^{nd}$ percentile of the aggregate rank of RNA transcripts from the endocrine signaling positive gene set of a population of metastatic ER+ breast cancer patients. In embodiments, the fourth standard control is the $53^{rd}$ percentile of the aggregate rank of RNA transcripts from the endocrine signaling positive gene set of a population of metastatic ER+ breast cancer patients. In embodiments, the fourth standard control is the $54^{th}$ percentile of the aggregate rank of RNA transcripts from the endocrine signaling positive gene set of a population of metastatic ER+ breast cancer patients. In embodiments, the fourth standard control is the $55^{th}$ percentile of the aggregate rank of RNA transcripts from the endocrine signaling positive gene set of a population of metastatic ER+ breast cancer patients. In embodiments, the fourth standard control is the $56^{th}$ percentile of the aggregate rank of RNA transcripts from the endocrine signaling positive gene set of a population of metastatic ER+ breast cancer patients. In embodiments, the fourth standard control is the $57^{th}$ percentile of the aggregate rank of RNA transcripts from the endocrine signaling positive gene set of a population of metastatic ER+ breast cancer patients. In embodiments, the fourth standard control is the $58^{th}$ percentile of the aggregate rank of RNA transcripts from the endocrine signaling positive gene set of a population of metastatic ER+ breast cancer patients. In embodiments, the fourth standard control is the $59^{th}$ percentile of the aggregate rank of RNA transcripts from the endocrine signaling positive gene set of a population of metastatic ER+ breast cancer patients. In embodiments, the fourth standard control is the $60^{th}$ percentile of the aggregate rank of RNA transcripts from the endocrine signaling positive gene set of a population of metastatic ER+ breast cancer patients. In embodiments, the fourth standard control is the $61^{st}$ percentile of the aggregate rank of RNA transcripts from the endocrine signaling positive gene set of a population of metastatic ER+ breast cancer patients. In embodiments, the fourth standard control is the $62^{nd}$ percentile of the aggregate rank of RNA transcripts from the endocrine signaling positive gene set of a population of metastatic ER+ breast cancer patients. In embodiments, the fourth standard control is the $63^{rd}$ percentile of the aggregate rank of RNA transcripts from the endocrine signaling positive gene set of a population of metastatic ER+ breast cancer patients. In embodiments, the fourth standard control is the $64^{th}$ percentile of the aggregate rank of RNA transcripts from the endocrine signaling positive gene set of a population of metastatic ER+ breast cancer patients. In embodiments, the fourth standard control is the $65^{th}$ percentile of the aggregate rank of RNA transcripts from the endocrine signaling positive gene set of a population of metastatic ER+ breast cancer patients. In embodiments, the fourth standard control is the $66^{th}$ percentile of the aggregate rank of RNA transcripts from the endocrine signaling positive gene set of a population of metastatic ER+ breast cancer patients. In embodiments, the fourth standard control is the $67^{th}$ percentile of the aggregate rank of RNA transcripts from the endocrine signaling positive gene set of a population of metastatic ER+ breast cancer patients. In embodiments, the fourth standard control is the $68^{th}$ percentile of the aggregate rank of RNA transcripts from the endocrine signaling positive gene set of a population of metastatic ER+ breast cancer patients. In embodiments, the fourth standard control is the $69^{th}$ percentile of the aggregate rank of RNA transcripts from the endocrine signaling positive gene set of a population of metastatic ER+ breast cancer patients. In embodiments, the fourth standard control is the $70^{th}$ percentile of the aggregate rank of RNA transcripts from the endocrine signaling positive gene set of a population of metastatic ER+ breast cancer patients. In embodiments, the fourth standard control is the $71^{st}$ percentile of the aggregate rank of RNA transcripts from the endocrine signaling positive gene set of a population of metastatic ER+ breast cancer patients. In embodiments, the fourth standard control is the $72^{nd}$ percentile of the aggregate rank of RNA transcripts from the endocrine signaling positive gene set of a population of metastatic ER+ breast cancer patients. In embodiments, the fourth standard control is the $73^{rd}$ percentile of the aggregate rank of RNA transcripts from the endocrine signaling positive gene set of a population of metastatic ER+ breast cancer patients. In embodiments, the fourth standard control is the $74^{th}$ percentile of the aggregate rank of RNA transcripts from the endocrine signaling positive gene set of a population of metastatic ER+ breast cancer patients. In embodiments, the fourth standard control is the $75^{th}$ percentile of the aggregate rank of RNA transcripts from the endocrine signaling positive gene set of a population of metastatic ER+ breast cancer patients. In embodiments, the fourth standard control is the $76^{th}$ percentile of the aggregate rank of RNA transcripts from the endocrine signaling positive gene set of a population of metastatic ER+ breast cancer patients. In embodiments, the fourth standard control is the $77^{th}$ percentile of the aggregate rank of RNA transcripts from the endocrine signaling positive gene set of a population of metastatic ER+ breast cancer patients. In embodiments, the fourth standard control is the $78^{th}$ percentile of the aggregate rank of RNA transcripts from the endocrine signaling positive gene set of a population of metastatic ER+ breast cancer patients. In embodiments, the fourth standard control is the $79^{th}$ percentile of the aggregate rank of RNA transcripts from the endocrine signaling positive gene set of a population of metastatic ER+ breast cancer patients. In embodiments, the fourth standard control is the $80^{th}$ percentile of the aggregate rank of RNA transcripts from the endocrine signaling positive gene set of a population of metastatic ER+ breast cancer patients.

In embodiments, the second aggregate rank is higher than the $30^{th}$ percentile of the aggregate rank of RNA transcripts from the endocrine signaling positive gene set of a population of metastatic ER+ breast cancer patients. In embodiments, the second aggregate rank is higher than the $31^{st}$ percentile of the aggregate rank of RNA transcripts from the endocrine signaling positive gene set of a population of metastatic ER+ breast cancer patients. In embodiments, the second aggregate rank is higher than the $32^{nd}$ percentile of the aggregate rank of RNA transcripts from the endocrine signaling positive gene set of a population of metastatic ER+ breast cancer patients. In embodiments, the second aggregate rank is higher than the $33^{rd}$ percentile of the aggregate rank of RNA transcripts from the endocrine signaling positive gene set of a population of metastatic ER+ breast cancer patients. In embodiments, the second aggregate rank is higher than the $34^{th}$ percentile of the aggregate rank of RNA transcripts from the endocrine signaling positive gene set of a population of metastatic ER+ breast cancer patients. In embodiments, the second aggregate rank is higher than the $35^{th}$ percentile of the aggregate rank of RNA transcripts from the endocrine signaling positive gene set of a population of metastatic ER+ breast cancer patients. In embodiments, the second aggregate rank is higher than the $36^{th}$ percentile of the aggregate rank of RNA transcripts from the endocrine signaling positive gene set of a population of metastatic ER+ breast cancer patients. In embodiments, the second aggregate rank is higher than the $37^{th}$ percentile of the aggregate rank of RNA transcripts from the endocrine signaling positive gene set of a population of metastatic ER+ breast cancer patients. In embodiments, the second aggregate rank is higher than the $38^{th}$ percentile of the aggregate rank of RNA transcripts from the endocrine signaling positive gene set of a population of metastatic ER+ breast cancer patients. In embodiments, the second aggregate rank is higher than the $39^{th}$ percentile of the aggregate rank of RNA transcripts from the endocrine signaling positive gene set of a population of metastatic ER+ breast cancer patients. In embodiments, the second aggregate rank is higher than the $40^{th}$ percentile of the aggregate rank of RNA transcripts from the endocrine signaling positive gene set of a population of metastatic ER+ breast cancer patients. In embodiments, the second aggregate rank is higher than the $41^{st}$ percentile of the aggregate rank of RNA transcripts from the endocrine signaling positive gene set of a population of metastatic ER+ breast cancer patients. In embodiments, the second aggregate rank is higher than the $42^{nd}$ percentile of the aggregate rank of RNA transcripts from the endocrine signaling positive gene set of a population of metastatic ER+ breast cancer patients. In embodiments, the second aggregate rank is higher than the $43^{rd}$ percentile of the aggregate rank of RNA transcripts from the endocrine signaling positive gene set of a population of metastatic ER+ breast cancer patients. In embodiments, the second aggregate rank is higher than the $44^{th}$ percentile of the aggregate rank of RNA transcripts from the endocrine signaling positive gene set of a population of metastatic ER+ breast cancer patients. In embodiments, the second aggregate rank is higher than the $45^{th}$ percentile of the aggregate rank of RNA transcripts from the endocrine signaling positive gene set of a population of metastatic ER+ breast cancer patients. In embodiments, the second aggregate rank is higher than the $46^{th}$ percentile of the aggregate rank of RNA transcripts from the endocrine signaling positive gene set of a population of metastatic ER+ breast cancer patients. In embodiments, the second aggregate rank is higher than the $47^{th}$ percentile of the aggregate rank of RNA transcripts from the endocrine signaling positive gene set of a population of metastatic ER+ breast cancer patients. In embodiments, the second aggregate rank is higher than the $48^{th}$ percentile of the aggregate rank of RNA transcripts from the endocrine signaling positive gene set of a population of metastatic ER+ breast cancer patients. In embodiments, the second aggregate rank is higher than the $49^{th}$ percentile of the aggregate rank of RNA transcripts from the endocrine signaling positive gene set of a population of metastatic ER+ breast cancer patients. In embodiments, the second aggregate rank is higher than the $50^{th}$ percentile of the aggregate rank of RNA transcripts from the endocrine signaling positive gene set of a population of metastatic ER+ breast cancer patients In embodiments, the second aggregate rank is higher than the 50n percentile of the aggregate rank of RNA transcripts from the endocrine signaling positive gene set of a population of metastatic ER+ breast cancer patients. In embodiments, the second aggregate rank is higher than the $51^{st}$ percentile of the aggregate rank of RNA transcripts from the endocrine signaling positive gene set of a population of metastatic ER+ breast cancer patients. In embodiments, the second aggregate rank is higher than the $52^{nd}$ percentile of the aggregate rank of RNA transcripts from the endocrine signaling positive gene set of a population of metastatic ER+ breast cancer patients. In embodiments, the second aggregate rank is higher than the $53^{rd}$ percentile of the aggregate rank of RNA transcripts from the endocrine signaling positive gene set of a population of metastatic ER+ breast cancer patients. In embodiments, the second aggregate rank is higher than the $54^{th}$ percentile of the aggregate rank of RNA transcripts from the endocrine signaling positive gene set of a population of metastatic ER+ breast cancer patients. In embodiments, the second aggregate rank is higher than the $55^{th}$ percentile of the aggregate rank of RNA transcripts from the endocrine signaling positive gene set of a population of metastatic ER+ breast cancer patients. In embodiments, the second aggregate rank is higher than the $56^{th}$ percentile of the aggregate rank of RNA transcripts from the endocrine signaling positive gene set of a population of metastatic ER+ breast cancer patients. In embodiments, the second aggregate rank is higher than the $57^{th}$ percentile of the aggregate rank of RNA transcripts from the endocrine signaling positive gene set of a population of metastatic ER+ breast cancer patients. In embodiments, the second aggregate rank is higher than the $58^{th}$ percentile of the aggregate rank of RNA transcripts from the endocrine signaling positive gene set of a population of metastatic ER+ breast cancer patients. In embodiments, the second aggregate rank is higher than the $59^{th}$ percentile of the aggregate rank of RNA transcripts from the endocrine signaling positive gene set of a population of metastatic ER+ breast cancer patients. In embodiments, the second aggregate rank is higher than the $60^{th}$ percentile of the aggregate rank of RNA transcripts from the endocrine signaling positive gene set of a population of metastatic ER+ breast cancer patients. In embodiments, the second aggregate rank is higher than the $61^{st}$ percentile of the aggregate rank of RNA transcripts from the endocrine signaling positive gene set of a population of metastatic ER+ breast cancer patients. In embodiments, the second aggregate rank is higher than the $62^{nd}$ percentile of the aggregate rank of RNA transcripts from the endocrine signaling positive gene set of a population of metastatic ER+ breast cancer patients. In embodiments, the second aggregate rank is higher than the $63^{rd}$ percentile of the aggregate rank of RNA transcripts from the endocrine signaling positive gene set of a population of metastatic ER+ breast cancer patients. In embodiments, the second aggregate rank is higher than the $64^{th}$ percentile of the aggregate rank of RNA transcripts from the endocrine signaling positive gene set of a population of metastatic ER+ breast cancer patients. In embodiments, the second aggregate rank is higher than the $65^{th}$ percentile of the aggregate rank of RNA transcripts from the endocrine signaling positive gene set of a population of metastatic ER+ breast cancer patients. In embodiments, the second aggregate rank is higher than the $66^{th}$ percentile of the aggregate rank of RNA transcripts from the endocrine signaling positive gene set of a population of metastatic ER+ breast cancer patients. In embodiments, the second aggregate rank is higher than the $67^{th}$ percentile of the aggregate rank of RNA transcripts from the endocrine signaling positive gene set of a population of metastatic ER+ breast cancer patients. In embodiments, the second aggregate rank is higher than the $68^{th}$ percentile of the aggregate rank of RNA transcripts from the endocrine signaling positive gene set of a population of metastatic ER+ breast cancer patients. In embodiments, the second aggregate rank is higher than the $69^{th}$ percentile of the aggregate rank of RNA transcripts from the endocrine signaling positive gene set of a population of metastatic ER+ breast cancer patients. In embodiments, the second aggregate rank is higher than the $70^{th}$ percentile of the aggregate rank of RNA transcripts from the endocrine signaling positive gene set of a population of metastatic ER+ breast cancer patients. In embodiments, the second aggregate rank is higher than the $71^{st}$ percentile of the aggregate rank of RNA transcripts from the endocrine signaling positive gene set of a population of metastatic ER+ breast cancer patients. In embodiments, the second aggregate rank is higher than the $72^{nd}$ percentile of the aggregate rank of RNA transcripts from the endocrine signaling positive gene set of a population of metastatic ER+ breast cancer patients. In embodiments, the second aggregate rank is higher than the $73^{d}$ percentile of the aggregate rank of RNA transcripts from the endocrine signaling positive gene set of a population of metastatic ER+ breast cancer patients. In embodiments, the second aggregate rank is higher than the $74^{th}$ percentile of the aggregate rank of RNA transcripts from the endocrine signaling positive gene set of a population of metastatic ER+ breast cancer patients. In embodiments, the second aggregate rank is higher than the $75^{th}$ percentile of the aggregate rank of RNA transcripts from the endocrine signaling positive gene set of a population of metastatic ER+ breast cancer patients. In embodiments, the second aggregate rank is higher than the $76^{th}$ percentile of the aggregate rank of RNA transcripts from the endocrine signaling positive gene set of a population of metastatic ER+ breast cancer patients. In embodiments, the second aggregate rank is higher than the $77^{th}$ percentile of the aggregate rank of RNA transcripts from the endocrine signaling positive gene set of a population of metastatic ER+ breast cancer patients. In embodiments, the second aggregate rank is higher than the $78^{th}$ percentile of the aggregate rank of RNA transcripts from the endocrine signaling positive gene set of a population of metastatic ER+ breast cancer patients. In embodiments, the second aggregate rank is higher than the $79^{th}$ percentile of the aggregate rank of RNA transcripts from the endocrine signaling positive gene set of a population of metastatic ER+ breast cancer patients. In embodiments, the second aggregate rank is higher than the $80^{th}$ percentile of the aggregate rank of RNA transcripts from the endocrine signaling positive gene set of a population of metastatic ER+ breast cancer patients.

In embodiments, the endocrine signaling negative gene set includes at least 10, at least 15, or at least 20 of the following genes: ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, and SPC25.

In embodiments, the endocrine signaling positive gene set includes at least 10 genes, at least 15 genes, or at least 20 of the following genes: GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, and LAD1.

In embodiments, the endocrine signaling negative gene set includes at least one gene selected from KIF20A, ZC3H11A, RABGAP1, HARS, LARP1, TROAP, PPARGC1B, COL4A1, CKAP2L, GSK3B, DBN1, ENC1, APLN, and NKX2-2. In embodiments, the endocrine signaling negative gene set includes at least five or at least ten genes selected from KIF20A, ZC3H11A, RABGAP1, HARS, LARP1, TROAP, PPARGC1B, COL4A1, CKAP2L, GSK3B, DBN1, ENC1, APLN, and NKX2-2.

In embodiments, measuring an expression level includes sequencing, microarray, PCR, or a combination thereof. In embodiments, measuring levels includes hybridizing one or more oligonucleotide probes to one or more of the RNA transcripts, wherein each oligonucleotide probe includes a sequence specific to the RNA transcript.

In embodiments, the endocrine therapy includes a selective estrogen receptor modulator (SERM), a selective estrogen receptor down-regulator (SERD), an aromatase inhibitor, or a combination thereof. In embodiments, the endocrine therapy includes a SERM. In embodiments, the endocrine therapy includes a SERD. In embodiments, the endocrine therapy includes an aromatase inhibitor. In embodiments, the endocrine therapy is an aromatase inhibitor. In embodiments, the aromatase inhibitor is exemestane, anastrozole, or letrozole. In embodiments, the aromatase inhibitor is exemestane. In embodiments, the aromatase inhibitor is anastrozole. In embodiments, the aromatase inhibitor is letrozole. In embodiments, the SERD is fulvestrant. In embodiments, the SERM is tamoxifen, raloxifene arzoxiphene, lasofoxifene, or toremifene. In embodiments, the SERM is tamoxifen. In embodiments, the SERM is raloxifene arzoxiphene. In embodiments, the SERM is lasofoxifene. In embodiments, the SERM is toremifene.

In embodiments, the methods include administering to a subject having a PI3K mutation a PI3K inhibitor. In embodiments, administration of the PI3K inhibitor is particularly effective for treating metastatic ER+ breast cancer subjects who are sensitive to anticancer endocrine therapy and/or are receiving anticancer endocrine therapy. Thus, in embodiments, the method further includes, (a) detecting a PI3 Kinase (PI3K) mutation in the plurality of cells, wherein the PI3K mutation is associated with a PI3K inhibitor sensitivity; and (b) administering a PI3K inhibitor to the subject. In embodiments, the PI3K mutation is a C420R mutation, a E542K mutation, a E545A mutation, a E545D mutation, a E545G mutation, a E545K mutation, a H1047L mutation, a H1047R mutation, a H1047Y mutation, a H1047Y mutation, a Q546E mutation, or a Q546R mutation corresponding to the sequence of SEQ ID NO:1. In embodiments, the PI3K mutation is a C420R mutation corresponding to the sequence of SEQ ID NO:1. In embodiments, the PI3K mutation is a E542K mutation corresponding to the sequence of SEQ ID NO: 1. In embodiments, the PI3K mutation is a E545A mutation corresponding to the sequence of SEQ ID NO:1. In embodiments, the PI3K mutation is a E545D mutation corresponding to the sequence of SEQ ID NO:1. In embodiments, the PI3K mutation is a E545G mutation corresponding to the sequence of SEQ ID NO:1. In embodiments, the PI3K mutation is a E545K mutation corresponding to the sequence of SEQ ID NO:1. In embodiments, the PI3K mutation is a H1047L mutation corresponding to the sequence of SEQ ID NO:1. In embodiments, the PI3K mutation is a H1047R mutation corresponding to the sequence of SEQ ID NO:1. In embodiments, the PI3K mutation is a H1047Y mutation corresponding to the sequence of SEQ ID NO:1. In embodiments, the PI3K mutation is a Q546E mutation corresponding to the sequence of SEQ ID NO:1. In embodiments, the PI3K mutation is a or a Q546R mutation corresponding to the sequence of SEQ ID NO:1.

For the methods provided herein, in embodiments, the breast cancer is a human epidermal growth factor receptor 2 negative (HER2−) breast cancer. In embodiments, the metastatic estrogen receptor positive breast cancer subject previously received anticancer endocrine therapy.

In embodiments, the first aggregate rank and said second aggregate rank are aggregated to form a combined aggregate score. In embodiments, the first aggregate rank is weighted more than the second aggregate rank when aggregating to form the combined aggregate score.

In embodiments, the ratio of the weighting of the first aggregate rank to the second aggregate rank is 1.20-1.80 to 2.4-3.0. In embodiments, the weighting of the first aggregate rank is 1.30-1.80. In embodiments, the weighting of the first aggregate rank is 1.40-1.80. In embodiments, the weighting of the first aggregate rank is 1.50-1.80. In embodiments, the weighting of the first aggregate rank is 1.60-1.80. In embodiments, the weighting of the first aggregate rank is 1.70-1.80.

In embodiments, the weighting of the first aggregate rank is 1.2-1.6. In embodiments, the weighting of the first aggregate rank is 1.2-1.5. In embodiments, the weighting of the first aggregate rank is 1.2-1.4. In embodiments, the weighting of the first aggregate rank is 1.2-1.3. In embodiments, the weighting of the first aggregate rank is 1.2-1.7. In embodiments, the weighting of the first aggregate rank is 1.2, 1.3, 1.4, 1.5, 1.6, 1.8 or 1.8.

In embodiments, the weighting of the second aggregate rank is 2.5-3.0. In embodiments, the weighting of the second aggregate rank is 2.6-3.0. In embodiments, the weighting of the second aggregate rank is 2.7-3.0. In embodiments, the weighting of the second aggregate rank is 2.8-3.0. In embodiments, the weighting of the second aggregate rank is 2.9-3.0.

In embodiments, the weighting of the second aggregate rank is 2.4-2.9. In embodiments, the weighting of the second aggregate rank is 2.4-2.8. In embodiments, the weighting of the second aggregate rank is 2.4-2.7. In embodiments, the weighting of the second aggregate rank is 2.4-2.6. In embodiments, the weighting of the second aggregate rank is 2.4-2.5. In embodiments, the weighting of the second aggregate rank is 2.4, 2.5, 2.6, 2.7, 2.8, 2.9, or 3.0.

In embodiments, the ratio of the weighting of the first aggregate rank to the second aggregate rank is 1.4-1.6 to 2.6-2.8. In embodiments, the weighting of the first aggregate rank is 1.4-1.6. In embodiments, the weighting of the first aggregate rank 1.42-1.6. In embodiments, the weighting of the first aggregate rank is 1.44-1.6. In embodiments, the weighting of the first aggregate rank is 1.48-1.6. In embodiments, the weighting of the first aggregate rank is 1.5-1.6. In embodiments, the weighting of the first aggregate rank 1.52-1.6. In embodiments, the weighting of the first aggregate rank is 1.54-1.6. In embodiments, the weighting of the first aggregate rank is 1.58-1.6.

In embodiments, the weighting of the first aggregate rank is 1.4-1.58. In embodiments, the weighting of the first aggregate rank is 1.4-1.56. In embodiments, the weighting of the first aggregate rank is 1.4-1.54. In embodiments, the weighting of the first aggregate rank is 1.4-1.52. In embodiments, the weighting of the first aggregate rank is 1.4-1.50. In embodiments, the weighting of the first aggregate rank is 1.4-1.48. In embodiments, the weighting of the first aggregate rank is 1.4-1.46. In embodiments, the weighting of the first aggregate rank is 1.4-1.44. In embodiments, the weighting of the first aggregate rank is 1.4-1.42. In embodiments, the weighting of the first aggregate rank is 1.4, 1.42, 1.44, 1.46, 1.48, 1.5, 1.52, 1.54, 1.56, 1.58, or 1.6.

In embodiments, the weighting of the second aggregate rank is 2.6-2.8. In embodiments, the weighting of the second aggregate rank is 2.62-2.8. In embodiments, the weighting of the second aggregate rank is 2.64-2.8. In embodiments, the weighting of the second aggregate rank is 2.66-2.8. In embodiments, the weighting of the second aggregate rank is 2.68-2.8. In embodiments, the weighting of the second aggregate rank is 2.7-2.8. In embodiments, the weighting of the second aggregate rank is 2.72-2.8. In embodiments, the weighting of the second aggregate rank is 2.74-2.8. In embodiments, the weighting of the second aggregate rank is 2.76-2.8. In embodiments, the weighting of the second aggregate rank is 2.78-2.8.

In embodiments, the ratio of the weighting of the second aggregate rank is 2.6-2.78. In embodiments, the ratio of the weighting of the second aggregate rank is 2.6-2.76. In embodiments, the ratio of the weighting of the second aggregate rank is 2.6-2.74. In embodiments, the ratio of the weighting of the second aggregate rank is 2.6-2.72. In embodiments, the ratio of the weighting of the second aggregate rank is 2.6-2.7. In embodiments, the ratio of the weighting of the second aggregate rank is 2.6-2.68. In embodiments, the ratio of the weighting of the second aggregate rank is 2.6-2.66. In embodiments, the ratio of the weighting of the second aggregate rank is 2.6-2.64. In embodiments, the ratio of the weighting of the second aggregate rank is 2.6-2.62. In embodiments, the ratio of the weighting of the second aggregate rank is 2.6, 2.62, 2.64, 2.66, 2.68, 2.7, 2.72, 2.74, 2.76, 2.78, or 2.8. In embodiments, the ratio of the weighting of the first aggregate rank to the second aggregate rank is about 1.5 to about 2.7. In embodiments, the ratio of the weighting of the first aggregate rank to the second aggregate rank is 1.5 to 2.7. In embodiments, the ratio of the weighting of the first aggregate rank to the second aggregate rank is about 1.54 to about 2.72. In embodiments, the ratio of the weighting of the first aggregate rank to the second aggregate rank is 1.54 to 2.72.

In embodiments, the methods provided herein include administration of an mTOR inhibitor to a subject having metastatic ER+ breast cancer, wherein the subject is not being administered a PI3K inhibitor and/or is not sensitive to a PI3K inhibitor. Thus, for the methods provided herein, in embodiments, the metastatic estrogen receptor positive breast cancer subject is a PI3K mutation negative subject, wherein the method further includes measuring the expression level of an mTor sensitivity gene. As used herein, "PI3K mutation negative subject" refers to a subject who does not have a PI3K mutation in the plurality of cells obtained from a tumor from the metastatic estrogen receptor positive breast cancer, wherein the PI3K mutation is a C420R mutation, a E542K mutation, a E545A mutation, a E545D mutation, a E545G mutation, a E545K mutation, a H1047L mutation, a H1047R mutation, a H1047Y mutation, a Q546E mutation, or a Q546R mutation corresponding to the sequence of SEQ ID NO:1.

In embodiments, an mTor sensitivity gene includes one or more of the following genes: CYP1A1, METTL1, DHX37, LTV1, NUBP1, SLC19A1, UTP20, GPATCH4, TEF, LANCL2, HEATR3, ZNF414, PER2, MARS2, DTWD2, CCDC58, MON1A, SCFD2, ZNF668, MMACHC, U2AF2, SP2, NCOA5, MRPL54, MAT2A, AMIGO3, UTP15, SRFBP1, HMOX1, SLC7A11, GCLM, TXNRD1, SRXN1, GCLC, PIM1, ABHD4, GADD45G, MAFG, SQSTM1, HBP1, BBC3, KLHL24, ULK1, FECH, IRS2, RIT1, BSDC1, JUND, NUMBL, SYF2, ZFAND5, ANKZF1, HECA, TP53INP1, PNRC1, FRAT1, NBR1, CAMLG, FRAT2, OTUD5, JMY, DGCR8, WBP2, CLDND1, STK40, ZNF222, TNKS, SLC35D2, RFFL, TMEM50A, MYB, CRIPT, PJA2, ZNF160, ZXDB, PLP2, MTX3, RETNLB, DISC1, FOLR3, PHKB, SERPINA3, SIAH1, C14orf39, FAM86A, GPR162, RASL11B, MS4A2, PTS, RASSF1, SEC14L1, TCF25, ATP11B, IL15RA, KLHL15, NOL10, and UBE2J1.

In embodiments, an mTor sensitivity gene includes one or more of the following genes: CYP1A1, METTL1, DHX37, LTV1, NUBP1, SLC19A1, UTP20, GPATCH4, TEF, LANCL2, HEATR3, ZNF414, PER2, MARS2, DTWD2, CCDC58, MON1A, SCFD2, ZNF668, MMACHC, U2AF2, SP2, NCOA5, MRPL54, MAT2A, AMIGO3, UTP15, SRFBP1, HMOX1, SLC7A11, GCLM, TXNRD1, SRXN1, GCLC, PIM1, ABHD4, GADD45G, MAFG, SQSTM1, HBP1, BBC3, KLHL24, ULK1, FECH, IRS2, RIT1, BSDC1, JUND, NUMBL, SYF2, ZFAND5, ANKZF1, HECA, TP53INP1, PNRC1, FRAT1, NBR1, CAMLG, FRAT2, OTUD5, JMY, DGCR8, WBP2, CLDND1, STK40, ZNF222, TNKS, SLC35D2, RFFL, TMEM50A, MYB, CRIPT, PJA2, ZNF160, ZXDB, PLP2, MTX3, RETNLB, DISC1, FOLR3, PHKB, SERPINA3, SIAH1, C14orf39, FAM86A, GPR162, RASL11B, MS4A2, PTS, RASSF1, SEC14L1, TCF25, ATP11B, IL15RA, KLHL15, NOL10, and UBE2J1 and no other genes.

In embodiments, an mTor sensitivity gene includes five or more of the following genes: CYP1A1, METTL1, DHX37, LTV1, NUBP1, SLC19A1, UTP20, GPATCH4, TEF, LANCL2, HEATR3, ZNF414, PER2, MARS2, DTWD2, CCDC58, MON1A, SCFD2, ZNF668, MMACHC, U2AF2, SP2, NCOA5, MRPL54, MAT2A, AMIGO3, UTP15, SRFBP1, HMOX1, SLC7A11, GCLM, TXNRD1, SRXN1, GCLC, PIM1, ABHD4, GADD45G, MAFG, SQSTM1, HBP1, BBC3, KLHL24, ULK1, FECH, IRS2, RIT1, BSDC1, JUND, NUMBL, SYF2, ZFAND5, ANKZF1, HECA, TP53INP1, PNRC1, FRAT1, NBR1, CAMLG, FRAT2, OTUD5, JMY, DGCR8, WBP2, CLDND1, STK40, ZNF222, TNKS, SLC35D2, RFFL, TMEM50A, MYB, CRIPT, PJA2, ZNF160, ZXDB, PLP2, MTX3, RETNLB, DISC1, FOLR3, PHKB, SERPINA3, SIAH1, C14orf39, FAM86A, GPR162, RASL11B, MS4A2, PTS, RASSF1, SEC14L1, TCF25, ATP11B, IL15RA, KLHL15, NOL10, and UBE2J1.

In embodiments, an mTor sensitivity gene includes ten or more of the following genes: CYP1A1, METTL1, DHX37, LTV1, NUBP1, SLC19A1, UTP20, GPATCH4, TEF, LANCL2, HEATR3, ZNF414, PER2, MARS2, DTWD2, CCDC58, MON1A, SCFD2, ZNF668, MMACHC, U2AF2, SP2, NCOA5, MRPL54, MAT2A, AMIGO3, UTP15, SRFBP1, HMOX1, SLC7A11, GCLM, TXNRD1, SRXN1, GCLC, PIM1, ABHD4, GADD45G, MAFG, SQSTM1, HBP1, BBC3, KLHL24, ULK1, FECH, IRS2, RIT1, BSDC1, JUND, NUMBL, SYF2, ZFAND5, ANKZF1, HECA, TP53INP1, PNRC1, FRAT1, NBR1, CAMLG, FRAT2, OTUD5, JMY, DGCR8, WBP2, CLDND1, STK40, ZNF222, TNKS, SLC35D2, RFFL, TMEM50A, MYB, CRIPT, PJA2, ZNF160, ZXDB, PLP2, MTX3, RETNLB, DISC1, FOLR3, PHKB, SERPINA3, SIAH1, C14orf39, FAM86A, GPR162, RASL11B, MS4A2, PTS, RASSF1, SEC14L1, TCF25, ATP11B, IL15RA, KLHL15, NOL10, and UBE2J1.

In embodiments, an mTor sensitivity gene includes twenty or more of the following genes: CYP1A1, METTL1, DHX37, LTV1, NUBP1, SLC19A1, UTP20, GPATCH4, TEF, LANCL2, HEATR3, ZNF414, PER2, MARS2, DTWD2, CCDC58, MON1A, SCFD2, ZNF668, MMACHC, U2AF2, SP2, NCOA5, MRPL54, MAT2A, AMIGO3, UTP15, SRFBP1, HMOX1, SLC7A11, GCLM, TXNRD1, SRXN1, GCLC, PIM1, ABHD4, GADD45G, MAFG, SQSTM1, HBP1, BBC3, KLHL24, ULK1, FECH, IRS2, RIT1, BSDC1, JUND, NUMBL, SYF2, ZFAND5, ANKZF1, HECA, TP53INP1, PNRC1, FRAT1, NBR1, CAMLG, FRAT2, OTUD5, JMY, DGCR8, WBP2, CLDND1, STK40, ZNF222, TNKS, SLC35D2, RFFL, TMEM50A, MYB, CRIPT, PJA2, ZNF160, ZXDB, PLP2, MTX3, RETNLB, DISC1, FOLR3, PHKB, SERPINA3, SIAH1, C14orf39, FAM86A, GPR162, RASL11B, MS4A2, PTS, RASSF1, SEC14L1, TCF25, ATP11B, IL15RA, KLHL15, NOL10, and UBE2J1.

In embodiments, an mTor sensitivity gene includes each of CYP1A1, METTL1, DHX37, LTV1, NUBP1, SLC19A1, UTP20, GPATCH4, TEF, LANCL2, HEATR3, ZNF414, PER2, MARS2, DTWD2, CCDC58, MON1A, SCFD2, ZNF668, MMACHC, U2AF2, SP2, NCOA5, MRPL54, MAT2A, AMIGO3, UTP15, SRFBP1, HMOX1, SLC7A11, GCLM, TXNRD1, SRXN1, GCLC, PIM1, ABHD4, GADD45G, MAFG, SQSTM1, HBP1, BBC3, KLHL24, ULK1, FECH, IRS2, RIT1, BSDC1, JUND, NUMBL, SYF2, ZFAND5, ANKZF1, HECA, TP53INP1, PNRC1, FRAT1, NBR1, CAMLG, FRAT2, OTUD5, JMY, DGCR8, WBP2, CLDND1, STK40, ZNF222, TNKS, SLC35D2, RFFL, TMEM50A, MYB, CRIPT, PJA2, ZNF160, ZXDB, PLP2, MTX3, RETNLB, DISC1, FOLR3, PHKB, SERPINA3, SIAH1, C14orf39, FAM86A, GPR162, RASL11B, MS4A2, PTS, RASSF1, SEC14L1, TCF25, ATP11B, IL15RA, KLHL15, NOL10, and UBE2J1.

In embodiments, an mTor sensitivity gene includes one or more of the genes set forth in Table 24. In embodiments, an mTor sensitivity gene includes five or more of the genes set forth in Table 24. In embodiments, an mTor sensitivity gene includes ten or more of the genes set forth in Table 24. In embodiments, an mTor sensitivity gene includes fifteen or more of the genes set forth in Table 24. In embodiments, an mTor sensitivity gene includes twenty or more of the genes set forth in Table 24. In embodiments, an mTor sensitivity gene includes the genes set forth in Table 24 and no other genes.

In embodiments, measuring the expression level of an mTor sensitivity gene includes applying a machine learning model to the expression values of the one or more mTor sensitivity genes associated with the subject. For example, the machine learning model may be a decision tree or random forest (of multiple randomly generated decision trees). The machine learning model may be trained to determine, based on the expression values of the mTor sensitivity genes associated with the subject, a first probability of subject being responsive to an mTor inhibitor and/or a second probability of the subject being non-responsive to an mTor inhibitor. Accordingly, the subject may be classified as a responder to an mTor inhibitor, and subsequently be treated with an mTor inhibitor, if the first probability and/or the second probability satisfy a threshold value. For instance, the subject may be classified as a responder to an mTor inhibitor if the probability of the subject being responsive to an mTor inhibitor is at least 0.7 (or 70%). The subject may be treated with an mTor inhibitor (e.g., everolimus) if the subject is classified as a responder to an mTor inhibitor. In embodiments, the subject may be treated with an mTor inhibitor if the subject is classified as a responder to an mTor inhibitor, has an ENDORSE score less than 2, and is negative for the PIK3CA biomarker. Furthermore, in some cases, in addition to the mTor inhibitor, the subject may also be treated with an aromatase inhibitor (e.g., exemestane), if the subject is classified as a responder to an mTor inhibitor. Alternatively, in the event the subject is classified as a non-responder to an mTor inhibitor, the subject may instead be treated with an aromatase inhibitor, such as fulvestrant, but not an mTor inhibitor.

In embodiments, the machine learning model may be trained based on a training dataset that includes the expression values of the mTor sensitivity genes observed in subjects who respond to an mTor inhibitor. Alternatively and/or additionally, the machine learning model may be trained based on a training dataset that includes the expression values of the mTor sensitivity genes observed in subjects who do not respond to an mTor inhibitor. In the case of a random forest model, the training may include performing a leave-one-out cross-validation (LOOCV) to tune the 'mtry' parameter of the random forest model. The random forest model may include an ensemble of decision trees, which are generated as a part of training the random forest model. Each split point in a decision tree at which a single node is split into sub-nodes may correspond to an input variable. For a random forest model predicting responsiveness to an mTor inhibitor, the input variable at each split point may correspond to an mTor sensivity gene. The tuning the "mtry" parameter may therefore include varying the quantity of input variables (or mTor sensivity genes) sampled as candidates at each split point during the construction of the decision trees in the random forest model. In one embodiment, an ensemble of 500 decision trees are constructed in each iteration of leave-one-out cross-validation.

The random forest model with the highest accuracy (lowest error rate) corresponding to a specific 'mtry' parameter may be selected as the final machine learning model for predicating responsiveness to an mTor inhibitor. The output of a single decision tree within the random forest model may be generated by traversing the decision tree, for example, from a root node to a leaf node, based on the subject's expression level for each corresponding mTor sensitivity gene. Moreover, the output of the random forest model, for example, the probability of the subject being responsive (or non-responsive) to an mTor inhibitor, may correspond to an average (or mean) of the outputs of the individual decision trees within the random forest model. Although individual mTor sensivity genes are not assigned coefficients and there is no concept of control genes or relative ranking of mTor sensitivity genes within the random forest model, each mTor sensivity gene is associated with a calculable relative importance in determining whether the subject is responsive (or non-responsive) to an mTor inhibitor.

In embodiments, the method further includes administering to the metastatic estrogen receptor positive breast cancer subject an mTor inhibitor. In embodiments, the mTor inhibitor is everolimus. In embodiments, the method includes administering to the metastatic estrogen receptor positive breast cancer subject an aromatase inhibitor. In embodiments, the aromatase inhibitor is exemestane.

In embodiments, the method includes administering to the metastatic estrogen receptor positive breast cancer subject an aromatase inhibitor and not administering to the metastatic estrogen receptor positive breast cancer subject an mTor inhibitor. In embodiments, the aromatase inhibitor is fulvestrant.

Thus, in embodiments, the method provided herein includes applying a machine learning model to identify the metastatic estrogen receptor positive breast cancer subject as responsive to the mTor inhibitor or non-responsive to the mTor inhibitor. In embodiments, the machine learning model is trained to determine, based on an expression value of a plurality of mTor sensitivity genes, a first probability of the metastatic estrogen receptor positive breast cancer subject being responsive to the mTor inhibitor and/or a second probability of the metastatic estrogen receptor positive breast cancer subject being non-responsive to the mTor inhibitor. In embodiments, wherein the metastatic estrogen receptor positive breast cancer subject is classified as a responder to the mTor inhibitor based at least on the first probability of said metastatic estrogen receptor positive breast cancer subject being responsive to the mTor inhibitor and/or a second probability of said metastatic estrogen receptor positive breast cancer subject being non-responsive to the mTor inhibitor satisfying one or more thresholds. In embodiments, the metastatic estrogen receptor positive breast cancer subject is classified as a responder to the mTor inhibitor based at least on the first probability of the metastatic estrogen receptor positive breast cancer subject being responsive to the mTor inhibitor being at least 0.7.

In an aspect is provided a method of treating cancer in a metastatic estrogen receptor positive breast cancer subject, the method including: (a) measuring an expression level of a transcriptome set of RNA transcripts in a plurality of cells obtained from a tumor from the metastatic estrogen receptor positive breast cancer subject, wherein the transcriptome set of RNA transcripts includes RNA transcripts expressed from: (i) an endocrine signaling negative gene set, wherein the endocrine signaling negative gene set includes at least 5 genes selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25; (ii) an endocrine signaling positive gene set, wherein the endocrine signaling positive gene set includes at least 5 genes selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1; and (iii) a remainder gene set, wherein the remainder gene set consists of all genes expressing the transcriptome set of RNA transcripts except the endocrine signaling positive gene set and the endocrine signaling negative gene set; (b) determining a first aggregate rank of the expression level of RNA transcripts from the endocrine signaling negative gene set relative to the expression level of RNA transcripts from the remainder gene set and calculating an empirical gene set enrichment score ($GES_{emp}$); (c) determining a second aggregate rank of the expression level of RNA transcripts from an endocrine signaling positive gene set relative to the expression level of RNA transcripts from said remainder gene set and calculating an estrogen response gene set enrichment score ($GES_{er}$); (d) calculating a risk score according to according to the function:

$$\exp(1.54 \times GES_{emp} + -2.72 \times GES_{er})$$

when the risk score is greater than or equal to 2, administering chemotherapy to the metastatic estrogen receptor positive breast cancer subject and not administering anticancer endocrine therapy to the metastatic estrogen receptor positive breast cancer subject, and when the risk score is less than 2, administering anticancer endocrine therapy to the metastatic estrogen receptor positive breast cancer subject and not administering chemotherapy to the metastatic estrogen receptor positive breast cancer subject.

For the function provided herein, "exp" is Euler's number raised to a power, wherein the power is $$(1.54 \times GES_{emp} + -2.72 \times GES_{er}).$$

"exp" may also be written as e^x, wherein e is Euler's number and x is $$(1.54 \times GES_{emp} + -2.72 \times GES_{er}).$$

The value of Euler's number, also referred to as "e", to 10 decimal places is 2.7182818284.

In embodiments, the "endocrine signaling negative gene set enrichment score", also referred to as "empirical gene set enrichment score" ($GES_{emp}$) may be determined by measuring gene expression in a set of genes in a plurality of cells obtained from a tumor from the metastatic estrogen receptor positive breast cancer subject. In embodiments, the set of genes includes the endocrine signaling negative gene set and genes which do not include any of the genes in the endocrine signaling negative gene set. Gene expression may be measured using any method known in the art, and described herein (e.g. microarray (e.g. Illumina HT-12 v3 microarray platform), etc.). For example, in embodiments, genes in the endocrine signaling negative gene set are ranked by their expression levels to quantify the degree to which the genes in the endocrine signaling negative gene set are ranked within the set of genes. For example, the ranking may be used to quantify whether the expression level of the set of genes is overrepresented at the top or at the bottom of the list of genes. Thus, in embodiments, the list is ordered from the highest rank of all measured genes to the lowest rank. In embodiments, the $GES_{emp}$ is calculated by obtaining a sum (e.g. integration) of the difference between a weighted empirical cumulative distribution function (ECDF) of the genes in the endocrine signaling negative gene set and the ECDF of the remaining genes.

Similarly, in embodiments, the "endocrine signaling positive gene set enrichment score", also referred to as "estrogen response gene set enrichment score" ($GES_{er}$) may be determined by measuring gene expression in a set of genes in a plurality of cells obtained from a tumor from the metastatic estrogen receptor positive breast cancer subject. In embodiments, genes in the endocrine signaling positive gene set are ranked by their expression levels to quantify the degree to which genes in the endocrine signaling positive gene set are ranked within the set of genes. In embodiments, the list is ordered from the highest rank of all measured genes to the lowest rank. In embodiments, the $GES_{er}$ is calculated by obtaining a sum (e.g. integration) of the difference between a weighted empirical cumulative distribution function (ECDF) of the genes in the endocrine signaling positive gene set and the ECDF of the remaining genes. Methods for obtaining gene set enrichment scores (e.g. $GES_{emp}$ and $GES_{er}$) are well-known in the art and are described in more detail in: Barbie, D. A. Systematic RNA interference reveals that oncogenic KRAS-driven cancers require TBK1.; *Nature*. 2009 Nov. 5; 462(7269): 108-112. doi:10.1038/nature08460.; which is incorporated by reference herein in its entirety and for all purposes.

In embodiments, the endocrine signaling negative gene set includes at least 10, at least 15, or at least 20 of the following genes: ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, and SPC25.

In embodiments, the endocrine signaling positive gene set includes at least 10 genes, at least 15 genes, or at least 20 of the following genes: GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, and LAD1.

In embodiments, measuring an expression level includes sequencing, microarray, PCR, or a combination thereof. In embodiments, measuring an expression level includes hybridizing one or more oligonucleotide probes to one or more of the RNA transcripts, wherein each oligonucleotide probe comprises a sequence specific to said RNA transcript.

In embodiments, the chemotherapy includes capecitabine, gemicitabine, vinorelbine, doxorubicin, epirubicin, paclitaxel, docetaxel, eribulin, cyclophosphamide, carboplatin, docetaxel, cisplatin, ixabepilone, fluorouracil, methotrexate, or a combination thereof.

In embodiments, the endocrine therapy includes a selective estrogen receptor modulator (SERM), a selective estrogen receptor down-regulator (SERD), an aromatase inhibitor, or a combination thereof.

In embodiments, the method further includes: (a) detecting a PI3 Kinase (PI3K) mutation in the plurality of cells, wherein the PI3K mutation is associated with a PI3K inhibitor sensitivity; and (b) administering a PI3K inhibitor to the subject.

In embodiments, the breast cancer is a human epidermal growth factor receptor 2 negative breast cancer. In embodiments, the metastatic estrogen receptor positive breast cancer subject previously received anticancer endocrine therapy.

In an aspect, provided herein is a method of detecting a breast cancer of a subject, the method including (a) measuring levels of a plurality of target RNA molecules of a tumor of the subject, wherein the tumor is a breast cancer tumor, and further wherein the plurality of target RNA molecules are selected from transcripts of Table 1 genes; (b) aggregating the levels to produce an aggregate measure; and (c) detecting endocrine therapy responsive cancer cells or endocrine therapy resistant cancer cells of the tumor, where (i) endocrine therapy resistant cancer cells are detected when the aggregate measure is equal to or greater than a threshold, or (ii) endocrine therapy responsive cancer cells are detected when the aggregate measure is below the threshold.

In embodiments, the breast cancer is an estrogen receptor positive (ER+) breast cancer. In embodiments, the breast cancer includes a tumor. In embodiments, the tumor is a breast cancer tumor.

In embodiments, the plurality of target genes represent a signature (e.g., an ENDORSE signature) and include at least 5, at least 10, at least 15, at least 20, at least 25, at least 30, at least 35, at least 40, at least 45, at least 50, at least 55, at least 60, or at least 63 genes selected from Table 1. In embodiments, the plurality of target genes include 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63 genes selected from Table 1. In embodiments, the plurality of target genes includes at least 10 genes from Table 1. In embodiments, the plurality of target genes includes at least 25 genes from Table 1. In embodiments, the plurality of target genes includes at least 50 genes from Table 1. In embodiments, the plurality of target genes includes all of the genes from Table 1.

In embodiments, the plurality of target genes represent an ENDORSE signature and are selected from ASF1B, ASPM, AURKA, AURKB, BIRC5, BUB1, CCNA2, CCNB2, CDC20, CDC25C, CDC45, CDCA3, CDCA5, CDCA8, CENPA, CENPE, CENPF, CEP55, CKAP2L, DLGAP5, E2F2, ESPL1, EXO1, FAM64A, FOXM1, GSK3B, HJURP, hNp95, KIF14, KIF15, KIF20A, KIF23, KIF2C, KIF4A, KIFC1, MCM10, MCM2, MELK, MKI67, NCAPG, NUSAP1, OIP5, PKMYT1, PLK1, PLK4, POLQ, PRC1, PTTG1, PTTG3, RACGAP1, RECQL4, SPC25, STIL, TACC3, TIMELESS, TOP2A, TPX2, TRIP13, TROAP, TTK, UBE2C, UBE2S, and ZWINT.

In embodiments, the plurality of target RNA molecules include transcripts of one or more of KIF20A, ZC3H11A, RABGAP1, HARS, LARP1, TROAP, PPARGC1B, COL4A1, CKAP2L, GSK3B, DBN1, ENC1, APLN, and NKX2-2.

In embodiments, the plurality of target RNA molecules include transcripts of at least 5 or at least 10 of KIF20A, ZC3H11A, RABGAP1, HARS, LARP1, TROAP, PPARGC1B, COL4A1, CKAP2L, GSK3B, DBN1, ENC1, APLN, and NKX2-2.

In embodiments, the plurality of target RNA molecules include transcripts of KIF20A, ZC3H11A, RABGAP1, HARS, LARP1, TROAP, PPARGC1B, COL4A1, CKAP2L, GSK3B, DBN1, ENC1, APLN, and NKX2-2.

In embodiments, the plurality of target genes include 1-14 genes listed in Table 2. In embodiments, the plurality of target genes include at least 1, at least 2, at least 3, at least 4, at least 5, at least 6, at least 7, at least 8, at least 9, at least 10, at least 11, at least 12, at least 13, or at least 14 genes selected from Table 2. In embodiments, the plurality of target genes include 1, 2, 3, 4, 5, 6, 7, 8, 9, 10, 11, 12, 13, or 14 genes selected from Table 2. In embodiments, the plurality of target genes include at least 3 of the genes in Table 2. In embodiments, the plurality of target genes include at least 5 of the genes in Table 2. In embodiments, the plurality of target genes include at least 10 of the genes in Table 2. In embodiments, the plurality of target genes include all of the genes in Table 2.

In embodiments, methods described herein include aggregating levels of a plurality of target RNA molecules of a tumor of the subject includes measuring enrichment of the plurality of target RNA molecules relative to other RNA molecules of the tumor, as compared to a control. In embodiments, aggregating includes calculating a risk score. In embodiments, the risk score is a scaled value for the risk of an adverse event with endocrine therapy. In embodiments, the aggregating is performed by a processor executing program code.

In embodiments, the threshold corresponds to an increased risk of adverse event with endocrine therapy of about or more than about 50%, 100%, 200%, 300%, or more. In embodiments, the threshold corresponds to about or more than about a two-fold greater risk of adverse event with endocrine therapy.

In embodiments, methods described herein include selecting a cancer therapy to treat the tumor. In embodiments, selection of the cancer therapy is based on the aggregate measure.

In embodiments, methods described herein include detecting endocrine therapy responsive cancer cells, and selecting a cancer therapy that is an endocrine therapy. In embodiments, the endocrine therapy includes selective estrogen receptor modulator (SERM), selective estrogen receptor down-regulator (SERD), or an aromatase inhibitor. In embodiments, the endocrine therapy includes selective estrogen receptor modulator (SERM). In embodiments, the endocrine therapy includes selective estrogen receptor down-regulator (SERD). In embodiments, the endocrine therapy includes an aromatase inhibitor.

In embodiments, the endocrine therapy includes fulvestrant, tamoxifen, anastrozole, exemestane, letrozole, raloxifene, GW5638, clomiphene, toremifene, arzoxiphene, lasofoxifene, or an analogue or derivative thereof. In embodiments, the endocrine therapy includes fulvestrant. In embodiments, the endocrine therapy includes tamoxifen. In embodiments, the endocrine therapy includes anastrozole. In embodiments, the endocrine therapy includes exemestane. In embodiments, the endocrine therapy includes letrozole. In embodiments, the endocrine therapy includes raloxifene. In embodiments, the endocrine therapy includes GW5638. In embodiments, the endocrine therapy includes clomiphene. In embodiments, the endocrine therapy includes toremifene. In embodiments, the endocrine therapy includes arzoxiphene. In embodiments, the endocrine therapy includes lasofoxifene In embodiments, the methods described herein include detecting endocrine therapy resistant cancer cells are detected, and selecting a cancer therapy that is not endocrine therapy. In embodiments, the methods described herein include where endocrine therapy resistant cancer cells are detected, and the cancer therapy is selected from chemotherapy, immunotherapy, radiation therapy, surgery, or a combination thereof. In embodiments, the methods described herein include where endocrine therapy resistant cancer cells are detected, and the cancer therapy is chemotherapy. In embodiments, the methods described herein include where endocrine therapy resistant cancer cells are detected, and the cancer therapy is immunotherapy. In embodiments, the methods described herein include where endocrine therapy resistant cancer cells are detected, and the cancer therapy is radiation therapy. In embodiments, the methods described herein include where endocrine therapy resistant cancer cells are detected, and the cancer therapy is surgery. In embodiments, the methods described herein include where endocrine therapy resistant cancer cells are detected, and the cancer therapy is a combination of one or more of chemotherapy, immunotherapy, radiation therapy, and surgery.

In embodiments, methods of treating a cancer described herein includes administering the cancer therapy.

In embodiments, methods described herein further includes detecting presence of a PI3K mutation. A variety of suitable methods for detecting mutations are available. Non-limiting examples include microarray hybridization and sequencing. In embodiments, the PI3K mutation is a mutation in PI3KA (e.g., with respect to the sequence of GenBank entry NG_012113.2, or an amino acid encoded thereby). In embodiments, the PI3K mutation is a mutation in PI3 KB (e.g., with respect to the sequence of positions 138652698 to 138834928 of GenBank entry NC_000003.12, or an amino acid encoded thereby). In embodiments, the PI3K mutation is a mutation in PI3KCD (e.g., with respect to the sequence of GenBank entry NG_023434.1, or an amino acid encoded thereby). In embodiments, methods described herein include administering a PI3K inhibitor, such as when a PI3K mutation is detected. In embodiments, the PI3K inhibitor is selected from apelisib, idelalisib, copanlisib, and duvelisib. In embodiments, the PI3K inhibitor is apelisib. In embodiments, the PI3K inhibitor is idelalisib. In embodiments, the PI3K inhibitor is copanlisib. In embodiments, the PI3K inhibitor is duvelisib.

In embodiments, provided herein are methods where the subject previously received endocrine therapy.

In an aspect, provided herein are methods of treating breast cancer in a subject, including detecting a breast cancer of the subject, where detecting includes (a) measuring levels of a plurality of target RNA molecules of a tumor of the subject, wherein the tumor is a breast cancer tumor, and further wherein the plurality of target RNA molecules are selected from transcripts of Table 1; (b) aggregating the levels to produce an aggregate measure; and (c) administering a cancer therapy to the subject, where (i) the cancer therapy is not endocrine therapy when the aggregate measure is equal to or greater than a threshold, or (ii) the cancer therapy is endocrine therapy when the aggregate measure is below the threshold.

In an aspect, provided herein are methods of treating an estrogen receptor positive (ER+) breast cancer in a female subject, the method including (a) detecting an increased level of a plurality of target RNA molecules of a breast cancer tumor of the subject, wherein the plurality of target RNA molecules are selected from transcripts of Table 1, and where the increased level is increased relative to a control; and (b) administering a cancer therapy to the subject, wherein the cancer therapy is not an endocrine therapy.

In embodiments, the methods described herein include cancer therapy that is not endocrine therapy includes surgery, immunotherapy, chemotherapy and/or radiation therapy.

In embodiments, the methods of treatment described herein include where the plurality of target RNA molecules comprises transcripts of at least 5, at least 10, at least 15, or at least 20 genes of Table 1, where the plurality of target RNA molecules comprises transcripts of at least 1, 5, or 10 of KIF20A, ZC3H11A, RABGAP1, HARS, LARP1, TROAP, PPARGC1B, COL4A1, CKAP2L, GSK3B, DBN1, ENC1, APLN, and NKX2-2, or where the plurality of target RNA molecules comprises transcripts of all of KIF20A, ZC3H11A, RABGAP1, HARS, LARP1, TROAP, PPARGC1B, COL4A1, CKAP2L, GSK3B, DBN1, ENC1, APLN, and NKX2-2. In embodiments, the methods of treatment described herein include where the plurality of target RNA molecules comprises transcripts of at least 5, at least 10, at least 15, or at least 20 genes of Table 1. In embodiments, the methods of treatment described herein include where the plurality of target RNA molecules comprises transcripts of at least 1, 5, or 10 of KIF20A, ZC3H11A, RABGAP1, HARS, LARP1, TROAP, PPARGC1B, COL4A1, CKAP2L, GSK3B, DBN1, ENC1, APLN, and NKX2-2. In embodiments, the methods of treatment described herein include where the plurality of target RNA molecules comprises transcripts of all of KIF20A, ZC3H11A, RABGAP1, HARS, LARP1, TROAP, PPARGC1B, COL4A1, CKAP2L, GSK3B, DBN1, ENC1, APLN, and NKX2-2.

In embodiments, the methods of treatment described herein further include detecting presence of a PI3K mutation. A variety of suitable methods for detecting mutations are available. Non-limiting examples include microarray hybridization and sequencing. In embodiments, the PI3K mutation is a mutation in PI3KA (e.g., with respect to the sequence of GenBank entry NG_012113.2, or an amino acid encoded thereby). In embodiments, the PI3K mutation is a mutation in PI3 KB (e.g., with respect to the sequence of positions 138652698 to 138834928 of GenBank entry NC_000003.12, or an amino acid encoded thereby). In embodiments, the PI3K mutation is a mutation in PI3KCD (e.g., with respect to the sequence of GenBank entry NG_023434.1, or an amino acid encoded thereby). In embodiments, the methods of treatment described herein further include administering a PI3K inhibitor, such as when a PI3K mutation is detected. In embodiments, the PI3K inhibitor is selected from apelisib, idelalisib, copanlisib, and duvelisib. In embodiments, the PI3K inhibitor is apelisib. In embodiments, the PI3K inhibitor is idelalisib. In embodiments, the PI3K inhibitor is copanlisib. In embodiments, the PI3K inhibitor is duvelisib.

Methods for Preparing Samples

In an aspect, provided herein are methods of preparing a sample from a female subject with estrogen receptor positive (ER+) breast cancer, the method including: (a) extracting RNA from a breast cancer tumor of the subject; (b) hybridizing oligonucleotides to a plurality of target RNA molecules in the extracted RNA, where the plurality of target RNA molecules are selected from transcripts of Table 1 genes; and (c) measuring levels of the target RNA molecules.

In embodiments, the methods of preparing a sample described herein include where each of the oligonucleotides includes a target-specific sequence that is complementary to a sequence of the target RNA molecule to which it hybridizes.

In embodiments, the methods of preparing a sample described herein include where the oligonucleotides include oligonucleotide probes on a solid surface. A variety of suitable solid surfaces are available. In embodiments, the solid surface is an array. In embodiments, the solid surface is a bead.

In embodiments, the methods of preparing a sample described herein include where each of the oligonucleotides include a common sequence that is complementary to an adapter sequence joined to the target RNA molecules or a complement thereof. For example, prior to the hybridizing, adapters may be ligated to the target RNA molecules by an RNA ligase, the adapters including a known sequence to which the common sequence may hybridize. In embodiments, each of the oligonucleotides include an amplification primer or sequencing primer. In embodiments, the primers are a collection of primers each of which is specific to a target RNA molecule. In embodiments, the primers hybridize to an adapter sequence joined to the target RNA molecules by virtue of a common sequence. In embodiments, target RNA molecules are enriched from a starting sample prior to the measuring step, such as through the use of surface-bound enrichment probes.

In embodiments, the methods of preparing a sample described herein include where the step of measuring includes a nucleic acid amplification reaction.

In embodiments, the methods of preparing a sample described herein include measuring levels of the target RNA molecules which includes sequencing.

In embodiments of methods of preparing a sample described herein, the plurality of target RNA molecules include transcripts of at least 5, at least 10, at least 15, or at least 20 genes of Table 1, where the plurality of target RNA molecules comprises transcripts of at least 1, 5, or 10 of KIF20A, ZC3H11A, RABGAP1, HARS, LARP1, TROAP, PPARGC1B, COL4A1, CKAP2L, GSK3B, DBN1, ENC1, APLN, and NKX2-2, or where the plurality of target RNA molecules comprises transcripts of all of KIF20A, ZC3H11A, RABGAP1, HARS, LARP1, TROAP, PPARGC1B, COL4A1, CKAP2L, GSK3B, DBN1, ENC1, APLN, and NKX2-2. In embodiments of methods of preparing a sample described herein, the plurality of target RNA molecules include transcripts of at least 5, at least 10, at least 15, or at least 20 genes of Table 1. In embodiments of methods of preparing a sample described herein, the plurality of target RNA molecules comprises transcripts of at least 1, 5, or 10 of KIF20A, ZC3H11A, RABGAP1, HARS, LARP1, TROAP, PPARGC1B, COL4A1, CKAP2L, GSK3B, DBN1, ENC1, APLN, and NKX2-2. In embodiments of methods of preparing a sample described herein, the plurality of target RNA molecules comprises transcripts of all of KIF20A, ZC3H11A, RABGAP1, HARS, LARP1, TROAP, PPARGC1B, COL4A1, CKAP2L, GSK3B, DBN1, ENC1, APLN, and NKX2-2.

In embodiments of methods of preparing a sample described herein, the methods include aggregating levels to produce an aggregate measure. In embodiments, aggregating includes calculating a risk score. In embodiments, the risk score is a scaled value for the a risk of an adverse event with endocrine therapy. In embodiments, the aggregating is performed by a processor executing program code.

In embodiments of methods of preparing a sample described herein, the methods further include detecting endocrine therapy responsive cancer cells or endocrine therapy resistant cancer cells of the tumor, where (i) endocrine therapy resistant cancer cells are detected when the aggregate measure is equal to or greater than a threshold, or (ii) endocrine therapy responsive cancer cells are detected when the aggregate measure is below the threshold. In embodiments of methods of preparing a sample described herein, the methods further include detecting endocrine therapy responsive cancer cells or endocrine therapy resistant cancer cells of the tumor, where endocrine therapy resistant cancer cells are detected when the aggregate measure is equal to or greater than a threshold. In embodiments of methods of preparing a sample described herein, the methods further include detecting endocrine therapy responsive cancer cells or endocrine therapy resistant cancer cells of the tumor, where endocrine therapy responsive cancer cells are detected when the aggregate measure is below the threshold.

In embodiments, the methods of preparing a sample described herein, further include selecting a cancer therapy to treat the tumor, and optionally administering the therapy. In embodiments, selection of the cancer therapy is based on the aggregate risk score. In embodiments, the risk score is a scaled value for the a risk of an adverse event with endocrine therapy. In embodiments, the aggregating is performed by a processor executing program code.

Compositions

In an aspect, provided herein are compositions including a plurality of oligonucleotide probes. The plurality of oligonucleotide probes include probes that specifically hybridize to RNA transcripts of at least 5 genes from Table 1, 2 or Table 13. In embodiments, each oligonucleotide probe includes a target-specific sequence attached to a detectable molecule.

In embodiments, the plurality of oligonucleotide probes include probes that specifically hybridize to RNA transcripts of at least 5, at least 10, at least 15, at least 20, at least 25, at least 30, at least 35, at least 40, at least 45, at least 50, at least 55, or at least 60 genes selected from Table 1, 2 or Table 13. In embodiments, the plurality of oligonucleotide probes include probes that specifically hybridize to RNA transcripts of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63 genes selected from Table 1, 2 or Table 13. In embodiments, the plurality of oligonucleotide probes include probes that specifically hybridize to RNA transcripts of at least 10 genes from Table 1. In embodiments, the plurality of oligonucleotide probes include probes that specifically hybridize to RNA transcripts of all of the genes from Table 1, 2 or Table 13.

In embodiments, the plurality of oligonucleotide probes include probes that specifically hybridize to RNA transcripts of genes selected from ASF1B, ASPM, AURKA, AURKB, BIRC5, BUB1, CCNA2, CCNB2, CDC20, CDC25C, CDC45, CDCA3, CDCA5, CDCA8, CENPA, CENPE, CENPF, CEP55, CKAP2L, DLGAP5, E2F2, ESPL1, EXO1, FAM64A, FOXM1, GSK3B, HJURP, hNp95, KIF14, KIF15, KIF20A, KIF23, KIF2C, KIF4A, KIFC1, MCM10, MCM2, MELK, MKI67, NCAPG, NUSAP1, OIP5, PKMYT1, PLK1, PLK4, POLQ, PRC1, PTTG1, PTTG3, RACGAP1, RECQL4, SPC25, STIL, TACC3, TIMELESS, TOP2A, TPX2, TRIP13, TROAP, TTK, UBE2C, UBE2S, and ZWINT.

In embodiments, the plurality of oligonucleotide probes include probes that specifically hybridize to RNA transcripts of genes selected from KIF20A, ZC3H11A, RABGAP1, HARS, LARP1, TROAP, PPARGC1B, COL4A1, CKAP2L, GSK3B, DBN1, ENC1, APLN, and NKX2-2.

In embodiments, the plurality of oligonucleotide probes include probes that specifically hybridize to RNA transcripts of genes selected from at least 5 or at least 10 of KIF20A, ZC3H11A, RABGAP1, HARS, LARP1, TROAP, PPARGC1B, COL4A1, CKAP2L, GSK3B, DBN1, ENC1, APLN, and NKX2-2.

In embodiments, the plurality of oligonucleotide probes include probes that specifically hybridize to RNA transcripts of genes selected from KIF20A, ZC3H11A, RABGAP1, HARS, LARP1, TROAP, PPARGC1B, COL4A1, CKAP2L, GSK3B, DBN1, ENC1, APLN, and NKX2-2.

In embodiments, the plurality of oligonucleotide probes include probes that specifically hybridize to RNA transcripts of at least 5-14 genes from Table 2. In embodiments, each oligonucleotide probe includes a target-specific sequence attached to a detectable molecule.

In embodiments, the plurality of oligonucleotide probes include probes that specifically hybridize to RNA transcripts of at least 1, at least 2, at least 3, at least 4, at least 5, at least 6, at least 7, at least 8, at least 9, at least 10, at least 11, at least 12, at least 13, or at least 14 genes selected from Table 2. The plurality of oligonucleotide probes include probes that specifically hybridize to RNA transcripts of 1, 2, 3, 4, 5, 6, 7, 8, 9, 10, 11, 12, 13, or 14 genes selected from Table 2. In embodiments, the plurality of oligonucleotide probes include probes that specifically hybridize to RNA transcripts of at least 5 of the genes in Table 2. In embodiments, the plurality of oligonucleotide probes include probes that specifically hybridize to RNA transcripts of at least 10 of the genes in Table 2.

In embodiments, the plurality of oligonucleotide probes include probes that specifically hybridize to RNA transcripts of genes selected from KIF20A, ZC3H11A, RABGAP1, HARS, LARP1, TROAP, PPARGC1B, COL4A1, CKAP2L, GSK3B, DBN1, ENC1, APLN, and NKX2-2.

Systems

In an aspect, provided herein is a system including (a) at least one processor; and (b) at least one memory including program code which when executed by the at least one processor provides operations for performing one or more steps in the method of any one of the methods described herein.

A computer for use in the system can comprise one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. A client-server, relational database architecture can be used in embodiments of the system. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments, the server computer handles all of the database functionality. The client computer can have software that handles all the front-end data management and can also receive data input/instructions from users.

TABLE 1

| Empirical Response gene set (also referred to herein as the endocrine signaling negative gene set) | | | | |
|---|---|---|---|---|
| ASF1B | CDCA8 | HJURP | NCAPG | STIL |
| ASPM | CENPA | hNp95 | NUSAP1 | TACC3 |
| AURKA | CENPE | KIF14 | OIP5 | TIMELESS |
| AURKB | CENPF | KIF15 | PKMYT1 | TOP2A |
| BIRC5 | CEP55 | KIF20A | PLK1 | TPX2 |
| BUB1 | CKAP2L | KIF23 | PLK4 | TRIP13 |
| CCNA2 | DLGAP5 | KIF2C | POLQ | TROAP |
| CCNB2 | E2F2 | KIF4A | PRC1 | TTK |
| CDC20 | ESPL1 | KIFC1 | PTTG1 | UBE2C |
| CDC25C | EXO1 | MCM10 | PTTG3 | UBE2S |
| CDC45 | FAM64A | MCM2 | RACGAP1 | ZWINT |
| CDCA3 | FOXM1 | MELK | RECQL4 | |
| CDCA5 | GSK3B | MKI67 | SPC25 | |

TABLE 2

| Example subset of target RNA molecules | | | |
|---|---|---|---|
| KIF20A | LARP1 | CKAP2L | APLN |
| ZC3H11A | TROAP | GSK3B | NKX2-2 |
| RABGAP1 | PPARGC1B | DBN1 | |
| HARS | COL4A1 | ENC1 | |

TABLE 13

| Estrogen Response Gene Set (also referred to herein as endocrine signaling positive gene set) | | | | | |
|---|---|---|---|---|---|
| GREB1 | SLC27A2 | PLAAT3 | TUBB2B | ZNF185 | IL6ST |
| CA12 | FKBP4 | SLC7A5 | TBC1D30 | SLC19A2 | SYNGR1 |
| SLC9A3R1 | CXCL12 | MPPED2 | SEC14L2 | SLC1A4 | SH3BP5 |
| MYB | TMPRSS3 | TIAM1 | ENDOD1 | FHL2 | ALDH3B1 |
| ANXA9 | RARA | CLDN7 | HR | BCL2 | THSD4 |
| IGFBP4 | IL17RB | MYOF | SCARB1 | PMAIP1 | CLIC3 |
| SYBU | CBFA2T3 | RBBP8 | NCOR2 | AREG | NXT1 |
| NPY1R | TFF3 | OLFML3 | RHOD | OVOL2 | NAV2 |
| PDZK1 | UGCG | GFRA1 | INPP5F | TSKU | RRP12 |
| NRIP1 | CCND1 | FARP1 | PPIF | ADCY9 | ADCY1 |
| MLPH | SLC22A5 | SVIL | DHRS3 | RASGRP1 | DHCR7 |
| HSPB8 | WFS1 | TGM2 | FDFT1 | MUC1 | MICB |
| EGR3 | PTGES | DEPTOR | GAB2 | KAZN | AKAP1 |
| KRT19 | WWC1 | CYP26B1 | UNC119 | FRK | SLC7A2 |
| LRIG1 | CCN5 | PAPSS2 | KLF10 | DHRS2 | LAD1 |
| KDM4B | MYC | SLC1A1 | HES1 | AQP3 | |
| PGR | ITPK1 | DLC1 | FKBP5 | KCNK15 | |
| RHOBTB3 | TMEM164 | JAK2 | SLC2A1 | TGIF2 | |
| TPD52L1 | ARL3 | AFF1 | AMFR | FOXC1 | |
| ELOVL2 | MED13L | KLK10 | NADSYN1 | ELF3 | |
| RET | SEMA3B | P2RY2 | INHBB | REEP1 | |
| TPBG | KRT18 | BLVRB | BHLHE40 | PEX11A | |
| TFF1 | SLC16A1 | CISH | CALB2 | PODXL | |
| MAPT | TJP3 | GLA | FASN | KLF4 | |
| SCNN1A | SLC26A2 | ADD3 | CHPT1 | BAG1 | |
| ABAT | FCMR | PDLIM3 | MYBBP1A | CELSR1 | |
| FLNB | SULT2B1 | MINDY1 | ELOVL5 | ABHD2 | |
| XBP1 | SNX24 | FOS | DYNLT3 | AR | |
| CELSR2 | TFAP2C | KRT8 | ABLIM1 | SLC39A6 | |
| RAB31 | TTC39A | SLC37A1 | SOX3 | SYT12 | |
| MYBL1 | GJA1 | B4GALT1 | SLC24A3 | CD44 | |
| MREG | PRSS23 | CALCR | RAB17 | MED24 | |
| FAM102A | OLFM1 | ESRP2 | MAST4 | BCL11B | |
| MSMB | RAPGEFL1 | IGF1R | KCNK5 | CANT1 | |
| STC2 | ASB13 | NBL1 | ELF1 | KRT13 | |
| RETREG1 | TIPARP | SFN | RPS6KA2 | KRT15 | |
| SIAH2 | ABCA3 | OPN3 | ISG20L2 | TOB 1 | |

TABLE 24

| mTOR inhibitor response gene set | | | |
|---|---|---|---|
| CYP1A1 | GCLM | JMY | SEC14L1 |
| METTL1 | TXNRD1 | DGCR8 | TCF25 |
| DHX37 | SRXN1 | WBP2 | ATP11B |
| LTV1 | GCLC | CLDND1 | IL15RA |
| NUBP1 | PIM1 | STK40 | KLHL15 |
| SLC19A1 | ABHD4 | ZNF222 | NOL10 |
| UTP20 | GADD45G | TNKS | UBE2J1 |
| GPATCH4 | MAFG | SLC35D2 | |
| TEF | SQSTM1 | RFFL | |
| LANCL2 | HBP1 | TMEM50A | |
| HEATR3 | BBC3 | MYB | |
| ZNF414 | KLHL24 | CRIPT | |
| PER2 | ULK1 | PJA2 | |
| MARS2 | FECH | ZNF160 | |
| DTWD2 | IRS2 | ZXDB | |
| CCDC58 | RIT1 | PLP2 | |
| MON1A | BSDC1 | MTX3 | |
| SCFD2 | JUND | RETNLB | |
| ZNF668 | NUMBL | DISC1 | |
| MMACHC | SYF2 | FOLR3 | |
| U2AF2 | ZFAND5 | PHKB | |
| SP2 | ANKZF1 | SERPINA3 | |
| NCOA5 | HECA | SIAH1 | |
| MRPL54 | TP53INP1 | C14orf39 | |
| MAT2A | PNRC1 | FAM86A | |
| AMIGO3 | FRAT1 | GPR162 | |
| UTP15 | NBR1 | RASL11B | |
| SRFBP1 | CAMLG | MS4A2 | |
| HMOX1 | FRAT2 | PTS | |
| SLC7A11 | OTUD5 | RASSF1 | |

P EMBODIMENTS

Embodiment P1. A method of detecting a breast cancer of a subject, the method comprising: (a) measuring levels of a plurality of target RNA molecules of a tumor of the subject, wherein the tumor is a breast cancer tumor, and further wherein the plurality of target RNA molecules are selected from transcripts of Table 1 genes; (b) aggregating the levels to produce an aggregate measure; (c) detecting endocrine therapy responsive cancer cells or endocrine therapy resistant cancer cells of the tumor, wherein (i) endocrine therapy resistant cancer cells are detected when the aggregate measure is equal to or greater than a threshold, or (ii) endocrine therapy responsive cancer cells are detected when the aggregate measure is below the threshold Embodiment P2. A method of detecting endocrine therapy resistant cancer cells in a breast cancer tumor of a subject, the method comprising measuring levels of a plurality of target RNA molecules of a tumor of the subject, wherein (a) the plurality of target RNA molecules are selected from transcripts of Table 1 genes; and (b) the plurality of target RNA molecules are detected at a level above a threshold level, thereby detecting the endocrine therapy resistant cancer cells.

Embodiment P3. The method of embodiment P1 or P2, wherein the breast cancer is an estrogen receptor positive (ER+) breast cancer.

Embodiment P4. The method of any one of embodiments P1-P3, wherein the plurality of target RNA molecules comprises transcripts of at least 5, at least 10, at least 15, or at least 20 genes of Table 1.

Embodiment P5. The method of any one of embodiments P1-P4, wherein the plurality of target RNA molecules comprises transcripts of one or more of KIF20A, ZC3H11A, RABGAP1, HARS, LARP1, TROAP, PPARGC1B, COL4A1, CKAP2L, GSK3B, DBN1, ENC1, APLN, and NKX2-2.

Embodiment P6. The method of any one of embodiments P1-P5, wherein the plurality of target RNA molecules comprises transcripts of at least 5 or at least 10 of KIF20A, ZC3H11A, RABGAP1, HARS, LARP1, TROAP, PPARGC1B, COL4A1, CKAP2L, GSK3B, DBN1, ENC1, APLN, and NKX2-2.

Embodiment P7. The method of any one of embodiments P1-P6, wherein the plurality of target RNA molecules comprises transcripts of KIF20A, ZC3H11A, RABGAP1, HARS, LARP1, TROAP, PPARGC1B, COL4A1, CKAP2L, GSK3B, DBN1, ENC1, APLN, and NKX2-2.

Embodiment P8. The method of any one of embodiments P1-P7, wherein the plurality of target RNA molecules comprises transcripts of ASF1B, ASPM, AURKA, AURKB, BIRC5, BUB1, CCNA2, CCNB2, CDC20, CDC25C, CDC45, CDCA3, CDCA5, CDCA8, CENPA, CENPE, CENPF, CEP55, CKAP2L, DLGAP5, E2F2, ESPL1, EXO1, FAM64A, FOXM1, GSK3B, HJURP, hNp95, KIF14, KIF15, KIF20A, KIF23, KIF2C, KIF4A, KIFC1, MCM10, MCM2, MELK, MKI67, NCAPG, NUSAP1, OIP5, PKMYT1, PLK1, PLK4, POLQ, PRC1, PTTG1, PTTG3, RACGAP1, RECQL4, SPC25, STIL, TACC3, TIMELESS, TOP2A, TPX2, TRIP13, TROAP, TTK, UBE2C, UBE2S, and ZWINT.

Embodiment P9. The method of any one of embodiments P1-P8, wherein measuring levels comprises sequencing, microarray, PCR, or a combination thereof.

Embodiment P10. The method of any one of embodiments P1-P9, wherein measuring levels comprises hybridizing a plurality of oligonucleotide probes to one or more of the plurality of target RNA molecules, wherein each oligonucleotide probe comprises a target-specific sequence.

Embodiment P11. The method of any one of embodiments P1 or P3-P7, wherein aggregating the levels comprises measuring enrichment of the plurality of target RNA molecules relative to other RNA molecules of the tumor, as compared to a control.

Embodiment P12. The method of embodiment P11, wherein the aggregating comprises calculating a risk score.

Embodiment P13. The method of embodiment P12, wherein the risk score is a risk of an adverse event with endocrine therapy.

Embodiment P14. The method of embodiment P12 or P13, wherein the threshold corresponds to a two-fold greater risk of adverse event with endocrine therapy.

Embodiment P15. The method of any one of embodiments P1-P14, further comprising selecting a cancer therapy to treat the tumor.

Embodiment P16. The method of embodiment P15, wherein endocrine therapy responsive cancer cells are detected, and the cancer therapy is endocrine therapy.

Embodiment P17. The method of embodiment P16, wherein the endocrine therapy comprises selective estrogen receptor modulator (SERM), selective estrogen receptor down-regulator (SERD), or an aromatase inhibitor.

Embodiment P18. The method of embodiment P17, wherein the endocrine therapy comprises an aromatase inhibitor.

Embodiment P19. The method of embodiment P17, wherein the endocrine therapy comprises fulvestrant, tamoxifen, anastrozole, exemestane, letrozole, raloxifene, GW5638, clomiphene, toremifene, arzoxiphene, lasofoxifene, or an analogue or derivative thereof.

Embodiment P20. The method of embodiment P15, wherein endocrine therapy resistant cancer cells are detected, and the cancer therapy is not endocrine therapy.

Embodiment P21. The method of embodiment P20, wherein the cancer therapy is selected from chemotherapy, immunotherapy, radiation therapy, surgery, or a combination thereof.

Embodiment P22. The method of any one of embodiments P15-P21, further comprising administering the cancer therapy.

Embodiment P23. The method of any one of embodiment P1-P22, further comprising detecting presence of a PI3K mutation.

Embodiment P24. The method of embodiment P23, further comprising administering a PI3K inhibitor.

Embodiment P25. The method of embodiment P24, wherein the PI3K inhibitor is selected from apelisib, idelalisib, copanlisib, and duvelisib.

Embodiment P26. The method of any one of embodiments P1-P25, wherein the subject previously received endocrine therapy Embodiment P27. A method of preparing a sample from a female subject with estrogen receptor positive (ER+) breast cancer, the method comprising: (a) extracting RNA from a breast cancer tumor of the subject; (b) hybridizing oligonucleotides to a plurality of target RNA molecules in the extracted RNA, wherein the plurality of target RNA molecules are selected from transcripts of Table 1 genes; and (c) measuring levels of the target RNA molecules.

Embodiment P28. The method of embodiment P27, wherein each of the oligonucleotides comprises a target-specific sequence that is complementary to a sequence of the target RNA molecule to which it hybridizes.

Embodiment P29. The method of embodiment P28, wherein the oligonucleotides comprise oligonucleotide probes on a solid surface.

Embodiment P30. The method of embodiment P27, wherein each of the oligonucleotides comprises a common sequence that is complementary to an adapter sequence joined to the target RNA molecules or a complement thereof.

Embodiment P31. The method of embodiment P30, wherein each of the oligonucleotides comprise an amplification primer or sequencing primer.

Embodiment P32. The method of embodiments P30 or P31, wherein the step of measuring comprises a nucleic acid amplification reaction.

Embodiment P33. The method of any one of embodiments P31-P32, wherein the measuring comprises sequencing.

Embodiment P34. The method of any one of embodiments P27-P33, wherein: (a) the plurality of target RNA molecules comprises transcripts of at least 5, at least 10, at least 15, or at least 20 genes of Table 1; (b) the plurality of target RNA molecules comprises transcripts of at least 1, 5, or 10 of KIF20A, ZC3H11A, RABGAP1, HARS, LARP1, TROAP, PPARGC1B, COL4A1, CKAP2L, GSK3B, DBN1, ENC1, APLN, and NKX2-2; or (c) the plurality of target RNA molecules comprises transcripts of all of KIF20A, ZC3H11A, RABGAP1, HARS, LARP1, TROAP, PPARGC1B, COL4A1, CKAP2L, GSK3B, DBN1, ENC1, APLN, and NKX2-2.

Embodiment P35. The method of any one of embodiments P27-P34, further comprising aggregating the levels to produce an aggregate measure Embodiment P36. The method of embodiment P35, wherein the aggregating comprises calculating a risk score.

Embodiment P37. The method of embodiment P36 or P37, further comprising detecting endocrine therapy responsive cancer cells or endocrine therapy resistant cancer cells of the tumor, wherein (i) endocrine therapy resistant cancer cells are detected when the aggregate measure is equal to or greater than a threshold, or (ii) endocrine therapy responsive cancer cells are detected when the aggregate measure is below the threshold.

Embodiment P38. The method of embodiment P37, further comprising selecting a cancer therapy to treat the tumor, and optionally administering said therapy.

Embodiment P39. A method of treating breast cancer in a subject, comprising: (a) detecting a breast cancer of the subject, wherein detecting comprises: (i) measuring levels of a plurality of target RNA molecules of a tumor of the subject, wherein the tumor is a breast cancer tumor, and further wherein the plurality of target RNA molecules are selected from transcripts of Table 1; and (ii) aggregating the levels to produce an aggregate measure; and (c) administering a cancer therapy to the subject, wherein (i) the cancer therapy is not endocrine therapy when the aggregate measure is equal to or greater than a threshold, or (ii) the cancer therapy is endocrine therapy when the aggregate measure is below the threshold.

Embodiment P40. A method of treating an estrogen receptor positive (ER+) breast cancer in a female subject, the method comprising: (a) detecting an increased level of a plurality of target RNA molecules of a breast cancer tumor of the subject, wherein the plurality of target RNA molecules are selected from transcripts of Table 1, and wherein the increased level is increased relative to a control; and (b) administering a cancer therapy to the subject, wherein the cancer therapy is not an endocrine therapy.

Embodiment P41. The method of embodiment P39 or P40, wherein the cancer therapy that is not endocrine therapy comprises surgery, immunotherapy, chemotherapy and/or radiation therapy.

Embodiment P42. The method of any one of embodiments P39-P41, wherein: (a) the plurality of target RNA molecules comprises transcripts of at least 5, at least 10, at least 15, or at least 20 genes of Table 1; (b) the plurality of target RNA molecules comprises transcripts of at least 1, 5, or 10 of KIF20A, ZC3H11A, RABGAP1, HARS, LARP1, TROAP, PPARGC1B, COL4A1, CKAP2L, GSK3B, DBN1, ENC1, APLN, and NKX2-2; or (c) the plurality of target RNA molecules comprises transcripts of all of KIF20A, ZC3H11A, RABGAP1, HARS, LARP1, TROAP, PPARGC1B, COL4A1, CKAP2L, GSK3B, DBN1, ENC1, APLN, and NKX2-2.

Embodiment P43. The method of any one of embodiments P39-P42, further comprising detecting presence of a PI3K mutation.

Embodiment P44. The method of embodiment P43, further comprising administering a PI3K inhibitor.

Embodiment P45. A system comprising (a) at least one processor; and (b) at least one memory including program code which when executed by the at least one processor provides operations for performing one or more steps in the method of any one of embodiments P1-P44.

EMBODIMENTS

Embodiment 1. A method of treating cancer in a metastatic estrogen receptor positive breast cancer subject, the method comprising: (a) measuring an expression level of a transcriptome set of RNA transcripts in a plurality of cells obtained from a tumor from said metastatic estrogen receptor positive breast cancer subject, wherein the transcriptome set of RNA transcripts comprises RNA transcripts expressed from (i) an endocrine signaling negative gene set, wherein said endocrine signaling negative gene set comprises at least 5 genes selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25; (ii) an endocrine signaling positive gene set, wherein said endocrine signaling positive gene set comprises at least 5 genes selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1; and (iii) a remainder gene set, wherein said remainder gene set consists of all genes expressing said transcriptome set of RNA transcripts except said endocrine signaling positive gene set and said endocrine signaling negative gene set; (b) determining a high level of expression of the endocrine signaling negative gene set relative to a first standard control; (c) determining a low level of expression of the endocrine signaling positive gene set relative to a second standard control; and (d) administering a chemotherapy to said metastatic estrogen receptor positive breast cancer subject and not administering anticancer endocrine therapy to said metastatic estrogen receptor positive breast cancer subject.

Embodiment 2. The method of embodiment 1, wherein, (a) said determining a high level of expression of the endocrine signaling negative gene set relative to said first standard control comprises determining a first aggregate rank of the expression level of RNA transcripts from the endocrine signaling negative gene set relative to the expression level of RNA transcripts from said remainder gene set, wherein the first aggregate rank is high relative to said first standard control; and (b) said determining a low level of expression of the endocrine signaling positive gene set relative to said second standard control comprises determining a second aggregate rank of the expression level of RNA transcripts from an endocrine signaling positive gene set relative to the expression level of RNA transcripts from said remainder gene set, wherein the second aggregate rank is low relative to said second standard control.

Embodiment 3. The method of embodiment 1 or 2, wherein said endocrine signaling negative gene set comprises at least 10, at least 15, or at least 20 genes selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25.

Embodiment 4. The method of any one of embodiments 1-3, wherein said endocrine signaling positive gene set comprises at least 10 genes, at least 15 genes, or at least 20 genes selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1.

Embodiment 5. The method of any one of embodiments 1-4, wherein the endocrine signaling negative gene set comprises at least one gene selected from KIF20A, ZC3H11A, RABGAP1, HARS, LARP1, TROAP, PPARGC1B, COL4A1, CKAP2L, GSK3B, DBN1, ENC1, APLN, or NKX2-2.

Embodiment 6. The method of embodiment 5, wherein the endocrine signaling negative gene set comprises at least five or at least ten genes selected from KIF20A, ZC3H11A, RABGAP1, HARS, LARP1, TROAP, PPARGC1B, COL4A1, CKAP2L, GSK3B, DBN1, ENC1, APLN, or NKX2-2.

Embodiment 7. The method of any one of embodiments 1-6, wherein measuring an expression level comprises sequencing, microarray, PCR, or a combination thereof.

Embodiment 8. The method of any one of embodiments 1-7, wherein measuring an expression level comprises hybridizing one or more oligonucleotide probes to one or more of the RNA transcripts, wherein each oligonucleotide probe comprises a sequence specific to said RNA transcript.

Embodiment 9. The method of any one of embodiments 1-8, wherein said chemotherapy comprises capecitabine, gemicitabine, vinorelbine, doxorubicin, epirubicin, paclitaxel, docetaxel, eribulin, cyclophosphamide, carboplatin, cisplatin, ixabepilone, fluorouracil, methotrexate, or a combination thereof.

Embodiment 10. The method of embodiment 9, wherein said chemotherapy is capecitabine.

Embodiment 11. The method of any one of embodiments 1-10, wherein said breast cancer is a human epidermal growth factor receptor 2 negative breast cancer.

Embodiment 12. A method of treating cancer in a metastatic estrogen receptor positive breast cancer subject, the method comprising: (a) measuring an expression level of a transcriptome set of RNA transcripts in a plurality of cells obtained from a tumor from said metastatic estrogen receptor positive breast cancer subject, wherein the transcriptome set of RNA transcripts comprises RNA transcripts expressed from: (i) an endocrine signaling negative gene set, wherein said endocrine signaling negative gene set comprises at least 5 genes selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25; (ii) an endocrine signaling positive gene set, wherein said endocrine signaling negative gene set comprises at least 5 genes selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1; and (iii) a remainder gene set, wherein said remainder gene set consists of all genes expressing said transcriptome set of RNA transcripts except said endocrine signaling positive gene set and said endocrine signaling negative gene set; (b) determining a low level of expression of the endocrine signaling negative gene set relative to a third standard control; (c) determining a high level of expression of the endocrine signaling positive gene set relative to a fourth standard control; and; and (d) administering anticancer endocrine therapy to said metastatic estrogen receptor positive breast cancer subject and not administering chemotherapy to said metastatic estrogen receptor positive breast cancer subject.

Embodiment 13. The method of embodiment 12, wherein (a) said determining a low level of expression of the endocrine signaling negative gene set relative to said third standard control comprises determining a first aggregate rank of the expression level of RNA transcripts from the endocrine signaling negative gene set relative to the expression level of RNA transcripts from said remainder gene set, wherein the first aggregate rank is low relative to said third standard control; and (b) said determining a high level of expression of the endocrine signaling positive gene set relative to said fourth standard control comprises determining a second aggregate rank of the expression level of RNA transcripts from the endocrine signaling positive gene set relative to the expression level of RNA transcripts from said remainder gene set, wherein the second aggregate rank is high relative to said fourth standard control.

Embodiment 14. The method of embodiment 12 or 13, wherein said endocrine signaling negative gene set comprises at least 10, at least 15, or at least 20 genes selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25.

Embodiment 15. The method of any one of embodiments 12-14, wherein said endocrine signaling positive gene set comprises at least 10 genes, at least 15 genes, or at least 20 genes selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1.

Embodiment 16. The method of any one of embodiments 12-15, wherein the endocrine signaling negative gene set comprises at least one gene selected from KIF20A, ZC3H11A, RABGAP1, HARS, LARP1, TROAP, PPARGC1B, COL4A1, CKAP2L, GSK3B, DBN1, ENC1, APLN, or NKX2-2.

Embodiment 17. The method of any one of embodiments 12-16, wherein the endocrine signaling negative gene set comprises at least five or at least ten genes selected from KIF20A, ZC3H11A, RABGAP1, HARS, LARP1, TROAP, PPARGC1B, COL4A1, CKAP2L, GSK3B, DBN1, ENC1, APLN, or NKX2-2.

Embodiment 18. The method of any one of embodiments 12-17, wherein measuring an expression level comprises sequencing, microarray, PCR, or a combination thereof.

Embodiment 19. The method of any one of embodiments 12-18, wherein measuring levels comprises hybridizing one or more oligonucleotide probes to one or more of the RNA transcripts, wherein each oligonucleotide probe comprises a sequence specific to said RNA transcript.

Embodiment 20. The method of any one of embodiments 12-19, wherein said endocrine therapy comprises a selective estrogen receptor modulator (SERM), a selective estrogen receptor down-regulator (SERD), an aromatase inhibitor, or a combination thereof.

Embodiment 21. The method of embodiment 20, wherein said endocrine therapy is an aromatase inhibitor.

Embodiment 22. The method of embodiment 21, wherein said aromatase inhibitor is exemestane, anastrozole, or letrozole.

Embodiment 23. The method of embodiment 20, wherein said SERD is fulvestrant.

Embodiment 24. The method of embodiment 20, wherein said SERM is tamoxifen, raloxifene arzoxiphene, lasofoxifene, or toremifene.

Embodiment 25. The method of any one of embodiments 12-24, further comprising: (a) detecting a PI3 Kinase (PI3K) mutation in said plurality of cells, wherein said PI3K mutation is associated with a PI3K inhibitor sensitivity; and (b) administering a PI3K inhibitor to said subject.

Embodiment 26. The method of embodiment 25, wherein said PI3K mutation is a C420R mutation, a E542K mutation, a E545A mutation, a E545D mutation, a E545G mutation, a E545K mutation, a H1047L mutation, a H1047R mutation, a H1047Y mutation, a Q546E mutation, or a Q546R mutation corresponding to the sequence of SEQ ID NO:1.

Embodiment 27. The method of embodiment 25, wherein said PI3K inhibitor is apelisib, idelalisib, copanlisib, or duvelisib.

Embodiment 28. The method of any one of embodiments 12-27, wherein said breast cancer is a human epidermal growth factor receptor 2 negative breast cancer.

Embodiment 29. The method of one of embodiments 1-28, wherein said first aggregate rank and said second aggregate rank are aggregated to form a combined aggregate score.

Embodiment 30. The method of embodiment 29, wherein said first aggregate rank is weighted more than said second aggregate rank when aggregating to form said combined aggregate score.

Embodiment 31. The method of embodiment 30, wherein the ratio of the weighting of said first aggregate rank to said second aggregate rank is 1.4-1.6 to 2.6-2.8.

Embodiment 32. The method of embodiment 31, wherein the ratio of the weighting of said first aggregate rank to said second aggregate rank is 1.5 to 2.7.

Embodiment 33. The method of any one of embodiments 12-19, wherein the metastatic estrogen receptor positive breast cancer subject is a PI3K mutation negative subject, the method further comprising measuring the expression level of an mTor sensitivity gene.

Embodiment 34. The method of embodiment 33, further comprising administering to said metastatic estrogen receptor positive breast cancer subject an mTor inhibitor.

Embodiment 35. The method of embodiment 34, wherein said mTor inhibitor is everolimus.

Embodiment 36. The method of embodiment 34 or 35, further comprising administering to said metastatic estrogen receptor positive breast cancer subject an aromatase inhibitor.

Embodiment 37. The method of embodiment 36, wherein said aromatase inhibitor is exemestane.

Embodiment 38. The method of embodiment 33, further comprising administering to said metastatic estrogen receptor positive breast cancer subject an aromatase inhibitor and not administering to said metastatic estrogen receptor positive breast cancer subject the mTor inhibitor.

Embodiment 39. The method of embodiment 38, wherein said aromatase inhibitor is fulvestrant.

Embodiment 40. The method of any one of embodiments 33-39, further comprising applying a machine learning model to identify said metastatic estrogen receptor positive breast cancer subject as responsive to the mTor inhibitor or non-responsive to the mTor inhibitor.

Embodiment 41. The method of embodiment 40, wherein the machine learning model is trained to determine, based on an expression value of a plurality of mTor sensitivity genes, a first probability of said metastatic estrogen receptor positive breast cancer subject being responsive to the mTor inhibitor and/or a second probability of said metastatic estrogen receptor positive breast cancer subject being non-responsive to the mTor inhibitor.

Embodiment 42. The method of embodiment 41, wherein said metastatic estrogen receptor positive breast cancer subject is classified as a responder to the mTor inhibitor based at least on the first probability of said metastatic estrogen receptor positive breast cancer subject being responsive to the mTor inhibitor and/or a second probability of said metastatic estrogen receptor positive breast cancer subject being non-responsive to the mTor inhibitor satisfying one or more thresholds.

Embodiment 43. The method of embodiment 42, wherein said metastatic estrogen receptor positive breast cancer subject is classified as a responder to the mTor inhibitor based at least on the first probability of said metastatic estrogen receptor positive breast cancer subject being responsive to the mTor inhibitor being at least 0.7.

Embodiment 44. The method of any one of embodiments 33-43, wherein the plurality of mTor sensitivity genes include one or more of CYP1A1, METTL1, DHX37, LTV1, NUBP1, SLC19A1, UTP20, GPATCH4, TEF, LANCL2, HEATR3, ZNF414, PER2, MARS2, DTWD2, CCDC58, MON1A, SCFD2, ZNF668, MMACHC, U2AF2, SP2, NCOA5, MRPL54, MAT2A, AMIGO3, UTP15, SRFBP1, HMOX1, SLC7A11, GCLM, TXNRD1, SRXN1, GCLC, PIM1, ABHD4, GADD45G, MAFG, SQSTM1, HBP1, BBC3, KLHL24, ULK1, FECH, IRS2, RIT1, BSDC1, JUND, NUMBL, SYF2, ZFAND5, ANKZF1, HECA, TP53INP1, PNRC1, FRAT1, NBR1, CAMLG, FRAT2, OTUD5, JMY, DGCR8, WBP2, CLDND1, STK40, ZNF222, TNKS, SLC35D2, RFFL, TMEM50A, MYB, CRIPT, PJA2, ZNF160, ZXDB, PLP2, MTX3, RETNLB, DISC1, FOLR3, PHKB, SERPINA3, SIAH1, C14orf39, FAM86A, GPR162, RASL11B, MS4A2, PTS, RASSF1, SEC14L1, TCF25, ATP11B, IL15RA, KLHL15, NOL10, or UBE2J1

Embodiment 45. The method of any one of embodiments 41-44, wherein the machine learning model comprises a decision tree.

Embodiment 46. The method of any one of embodiments 41-45, wherein the machine learning model comprises a random forest model.

Embodiment 47. The method of any one of embodiments 41-46, further comprising training, based at least on a training dataset, the machine learning model, the training dataset including the expression value of the plurality of mTor sensitivity genes associated with one or more responders to the mTor inhibitor and/or non-responders to the mTor inhibitor.

Embodiment 48. A method of treating cancer in a metastatic estrogen receptor positive breast cancer subject, the method comprising: (a) measuring an expression level of a transcriptome set of RNA transcripts in a plurality of cells obtained from a tumor from said metastatic estrogen receptor positive breast cancer subject, wherein the transcriptome set of RNA transcripts comprises RNA transcripts expressed from: (i) an endocrine signaling negative gene set, wherein said endocrine signaling negative gene set comprises at least 5 genes selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25; (ii) an endocrine signaling positive gene set, wherein said endocrine signaling negative gene set comprises at least 5 genes selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1; and (iii) a remainder gene set, wherein said remainder gene set consists of all genes expressing said transcriptome set of RNA transcripts except said endocrine signaling positive gene set and said endocrine signaling negative gene set; (b) determining a first aggregate rank of the expression level of RNA transcripts from the endocrine signaling negative gene set relative to the expression level of RNA transcripts from said remainder gene set and calculating an empirical gene set enrichment score ($GES_{emp}$); (c) determining a second aggregate rank of the expression level of RNA transcripts from an endocrine signaling positive gene set relative to the expression level of RNA transcripts from said remainder gene set and calculating an estrogen response gene set enrichment score ($GES_{er}$); (d) calculating a risk score according to according to the function:

$$\exp(1.54\times GES_{emp}+-2.72\times GES_{er})$$

when said risk score is greater than or equal to 2, administering chemotherapy to said metastatic estrogen receptor positive breast cancer subject and not administering anticancer endocrine therapy to said metastatic estrogen receptor positive breast cancer subject, and when said risk score is less than 2, administering anticancer endocrine therapy to said metastatic estrogen receptor positive breast cancer subject and not administering chemotherapy to said metastatic estrogen receptor positive breast cancer subject.

Embodiment 49. The method of embodiment 48, wherein said endocrine signaling negative gene set comprises at least 10, at least 15, or at least 20 genes selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25.

Embodiment 50. The method of embodiment 48 or 49, wherein said endocrine signaling positive gene set comprises at least 10 genes, at least 15 genes, or at least 20 genes selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1.

Embodiment 51. The method of any one of embodiments 48-50, wherein measuring an expression level comprises sequencing, microarray, PCR, or a combination thereof.

Embodiment 52. The method of any one of embodiments 48-51, wherein measuring an expression level comprises hybridizing one or more oligonucleotide probes to one or more of the RNA transcripts, wherein each oligonucleotide probe comprises a sequence specific to said RNA transcript.

Embodiment 53. The method of any one of embodiments 48-52, wherein said chemotherapy comprises capecitabine, gemicitabine, vinorelbine, doxorubicin, epirubicin, paclitaxel, docetaxel, eribulin, cyclophosphamide, carboplatin, docetaxel, cisplatin, ixabepilone, fluorouracil, methotrexate, or a combination thereof.

Embodiment 54. The method of any one of embodiments 48-52, wherein said endocrine therapy comprises a selective estrogen receptor modulator (SERM), a selective estrogen receptor down-regulator (SERD), an aromatase inhibitor, or a combination thereof.

Embodiment 55. The method of any one of embodiments 48-52 or 54, further comprising: (a) detecting a PI3 Kinase (PI3K) mutation in said plurality of cells, wherein said PI3K mutation is associated with a PI3K inhibitor sensitivity; and (b) administering a PI3K inhibitor to said subject.

Embodiment 56. The method of any one of embodiments 48-55, wherein said breast cancer is a human epidermal growth factor receptor 2 negative breast cancer.

EXAMPLES

Example 1: Development of Custom Gene Signature

Experiments described herein sought to develop a framework based on a custom gene signature as a prognostic biomarker for ER+ breast cancers. As the number of candidate genes are much greater than the number of available samples (p>>n), the statistical method for selecting candidate biomarkers were carefully considered. Complex expression-based models based on a large number of variables can be difficult to interpret, are easy to overfit and often overperform in training datasets (See, for example, Ref 10). To mitigate these issues, supervised feature selection based on a LASSO regularized Cox proportional hazards model was combined with a pathway signature approach to derive a univariate biomarker of endocrine response (See, for example, Refs. 11,12). The robustness and reproducibility of the endocrine response signature (ENDORSE) biomarker was demonstrated through cross-validation analyses, simulations and validation in multiple independent clinical datasets, including metastatic ER+ breast cancers. Analyses demonstrated that the ENDORSE biomarker is a reliable prognostic biomarker for endocrine response in ER+ breast cancers.

Results

Framework for Developing and Validating Endocrine Response Signature

The endocrine response biomarker was developed using the METABRIC ER+ breast cancer cohort as the training dataset (See, for example, Refs. 13,14). The selection criteria for inclusion in the training data were hormone receptor status (ER+/HER2−), no treatment with chemotherapy and, in case of death, cancer listed as the cause of death. Clinical details of the METABRIC training cohort are listed in Table 3.

TABLE 3

ER+ METABRIC patient characteristics

| Variable | Mean | 95% C.I. | N available |
|---|---|---|---|
| Time to event (in months) | 135 | 130-140 | 833 |
| Events | 0.409 | 0.376-0.443 | 833 |
| Age at diagnosis | 61.5 | 60.7-62.3 | 833 |
| Tumor size | 24.3 | 23.4-25.1 | 828 |
| Tumor stage | 1.64 | 1.59-1.69 | 634 |
| Stage 0-1 (n = 270) | | | |
| Stage 2 (n = 324) | | | |
| Stage >3 (n = 40) | | | |
| Mutation count | 5.55 | 5.31-5.79 | 809 |
| Number of positive lymph nodes detected | 1.56 | 1.32-1.79 | 833 |
| 0 (n = 491) | | | |
| 1-3 (n = 228) | | | |
| 4-9 (n = 85) | | | |
| >10 (n = 29) | | | |

To construct the biomarker, curated and hallmark molecular signatures, or all available genes as candidate features were considered (FIG. 1) (See, for example, Refs. 15, 16). Enrichment scores for the molecular signatures were calculated using single sample gene set enrichment analysis (See, for example, Refs. 17,18). Next, a LASSO-regularized Cox regression model was used to perform feature selection on the enrichment scores or gene expression profiles. The fit and predictive ability of the selected features were evaluated in a 10-fold cross validation repeated 50 times. In addition, a custom signature composed of genes with non-zero positive coefficients from the gene expression model was defined. This gene signature was further expanded to include genes that were positively correlated with the selected genes in the previous step. Each instance of the cross-validation analysis yielded a custom signature. Then, a consensus endocrine response signature comprised of features selected in more than half of the cross-validations. Finally, the coefficients associated with the consensus endocrine response (ENDORSE) signature were calculated in an age-adjusted Cox proportional hazards model. To validate the ability of the ENDORSE to stratify patients, the estimated risk of event was predicted using the coefficients determined from the METABRIC model and applied to independent clinical datasets.

Comparing Performance of Endocrine Response Prediction Models

Figure 2A:
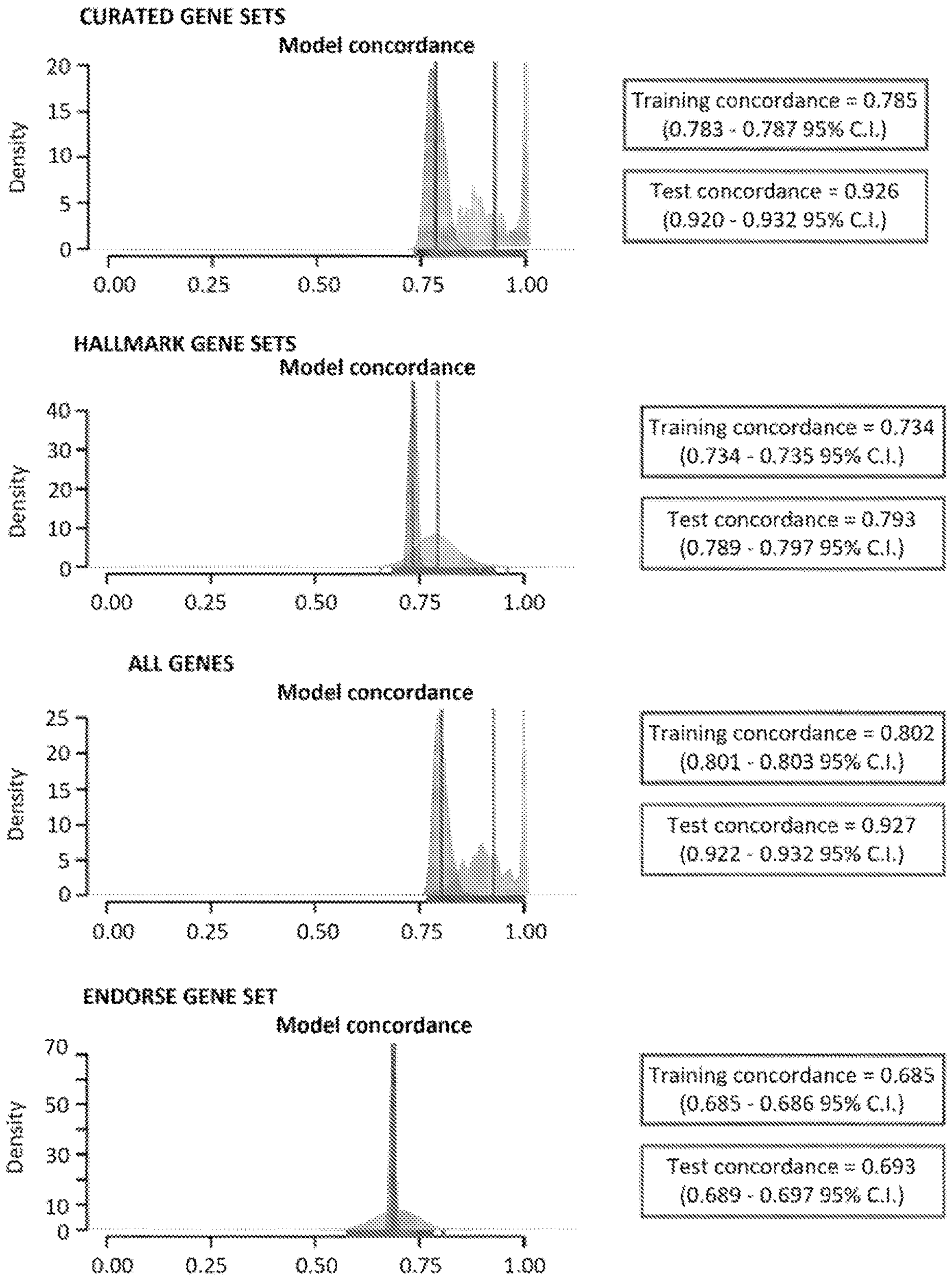
FIGS. 2A-2B show comparison of various features as candidate predictors of endocrine response.
Figure 2B:
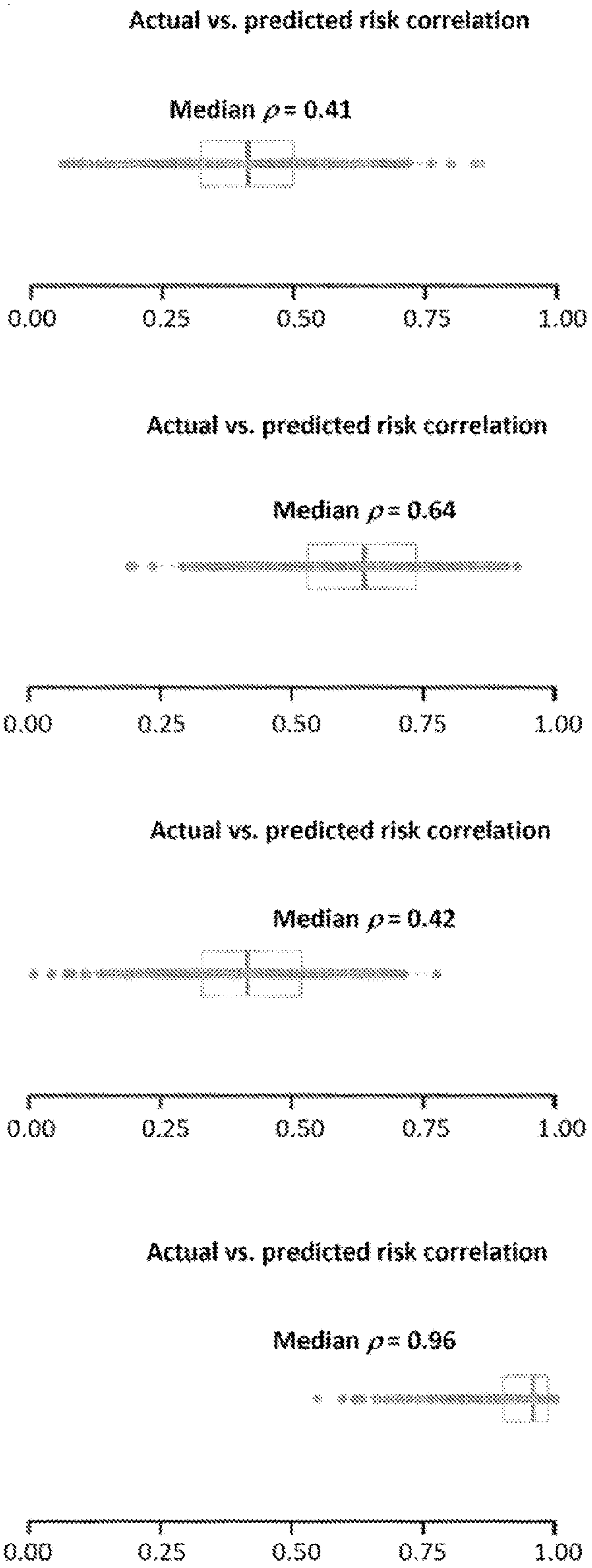
Figure 6A:
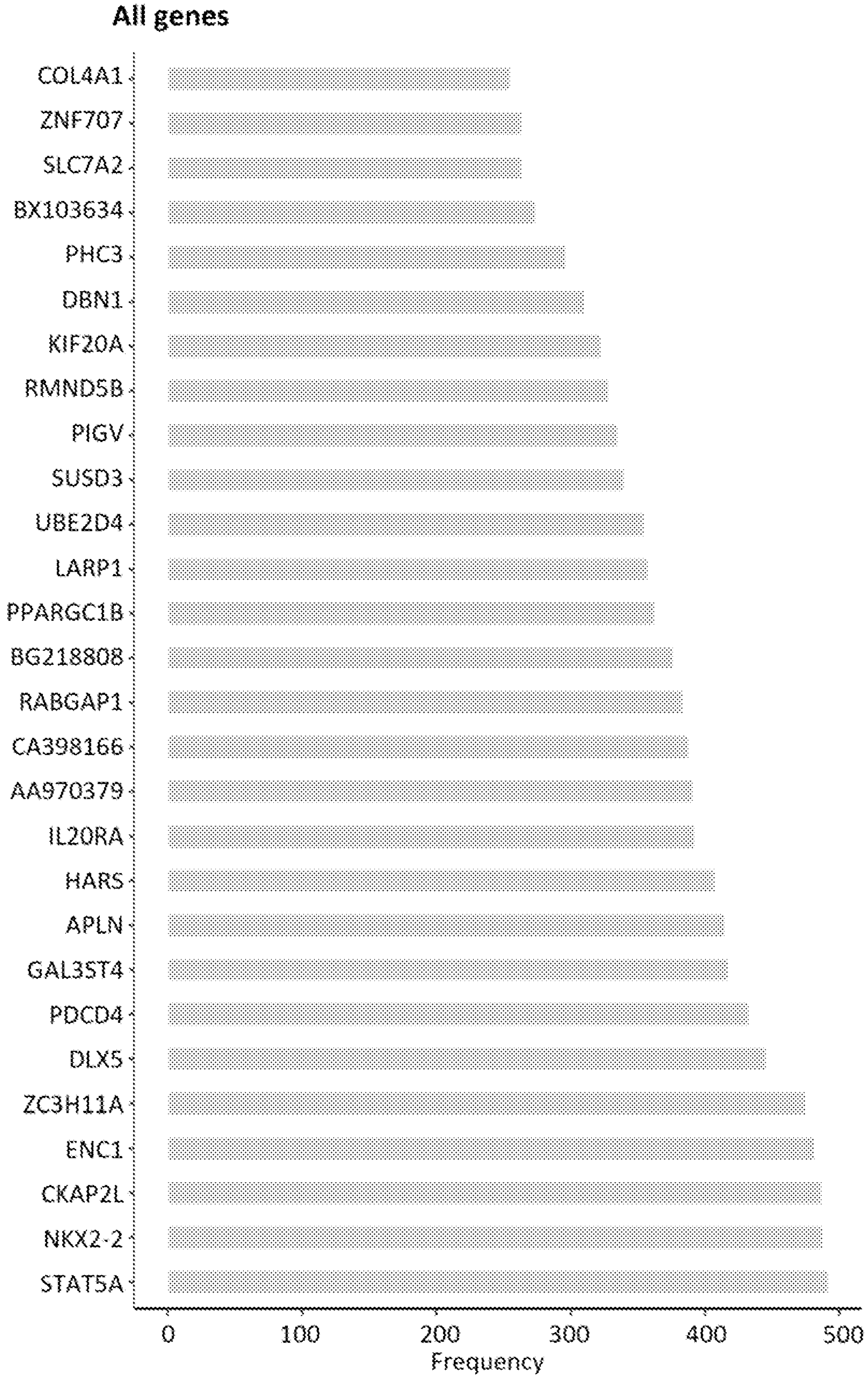
FIGS. 6A-6B are graphs showing features picked in over 50% of the models based on either all genes (FIG. 6A), or ENDORSE genes in accordance with an embodiment (FIG. 6B).
Figure 6B:
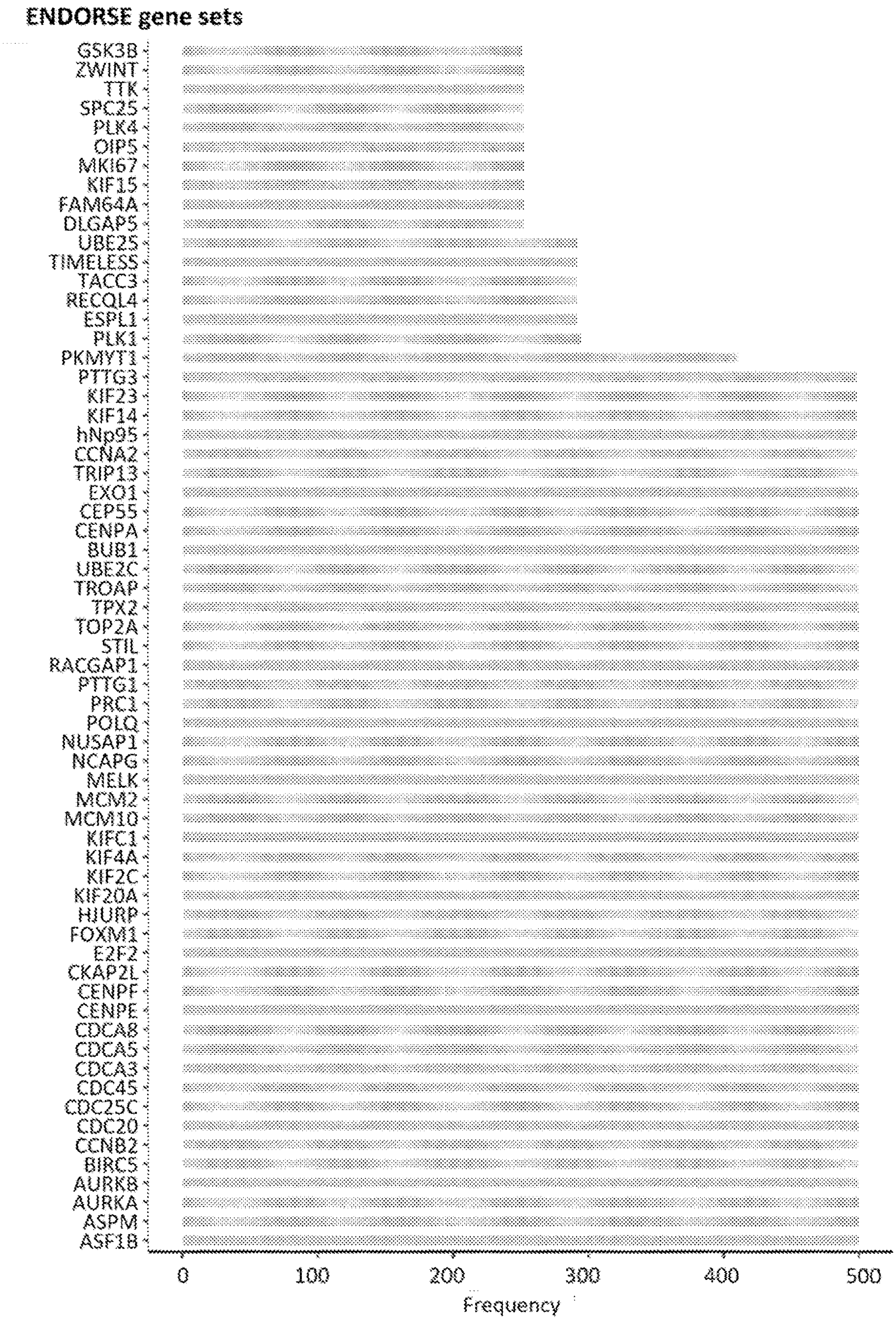

The performance of endocrine response prediction models was evaluated based on curated or hallmark gene signatures, all genes or the custom ENDORSE score. The curated gene set and all-gene models resulted in selection of a unique set of predictors in each cross-validation fold (see, e.g., FIGS. 6A-6B and Tables 5-8). In contrast, hallmark gene sets and ENDORSE models selected a consistent set of predictive features (see, e.g., FIGS. 6A-6B and Tables 4-7). To evaluate the predictive performance of each set of predictors, the concordance index of the univariate Cox models was first compared (FIG. 2A). Here, the median concordances of both the training models and test models based were higher in models with large number of available features. For example, curated gene sets test concordance (0.927) were greater than hallmark test concordance (0.793), while the single feature ENDORSE models had the lowest median concordance. In contrast, the correlation between actual and predicted risk of event showed an opposite trend (FIG. 2B). Here, the median correlation for the ENDORSE models (ρ=0.96) suggest that the single-feature model clearly outperformed multi-feature models (curated gene set ρ=0.41, hallmark ρ=0.64, all genes ρ=0.42). Moreover, the performance evaluation suggested that it was easy to overfit multi-feature models that conformed well to the training data but may not be particularly robust for predictions in independent data.

TABLE 4

Cox model coefficients for various clinical and predictive features

| | H.R. | 95% C.I. | P-value |
|---|---|---|---|
| Clinical variables | | | |
| Age | 1.04 | 1.02-1.05 | $6.1 \times 10^{-9}$ |
| Tumor Size | 1.02 | 1.01-1.02 | $8.3 \times 10^{-5}$ |
| Tumor Stage | 1.38 | 1.1-1.74 | 0.0061 |
| Mutation Count | 1.02 | 0.985-1.05 | 0.3 |
| Lymph Node | 1.05 | 1.01-1.09 | 0.01 |
| PAM50 subtypes | | | |
| PAM50 claudin-low | 0.545 | 0.259-1.15 | 0.11 |
| PAM50 Her2 | 1.34 | 0.655-2.76 | 0.42 |
| PAM50 LumA | 0.427 | 0.228-0.799 | 0.0077 |
| PAM50 LumB | 0.85 | 0.456-1.59 | 0.61 |
| PAM50 NC | 1.35 | 0.374-4.86 | 0.65 |
| PAM50 Normal | 0.593 | 0.294-1.2 | 0.14 |
| IntClust classes | | | |
| IntClust10 | 0.532 | 0.221-1.28 | 0.16 |
| IntClust2 | 1.44 | 0.846-2.46 | 0.18 |
| IntClust3 | 0.547 | 0.345-0.866 | 0.01 |
| IntClust4ER− | NA | | |
| IntClust4ER+ | 0.804 | 0.518-1.25 | 0.33 |
| IntClust5 | 1.55 | 0.474-5.08 | 0.47 |
| IntClust6 | 1.53 | 0.935-2.51 | 0.09 |
| IntClust7 | 0.841 | 0.527-1.34 | 0.47 |
| IntClust8 | 0.783 | 0.511-1.2 | 0.26 |
| IntClust9 | 1.41 | 0.876-2.28 | 0.16 |

TABLE 4-continued

Cox model coefficients for various clinical and predictive features

| | H.R. | 95% C.I. | P-value |
|---|---|---|---|
| Hormone receptors | | | |
| ESR1 expression | 1.07 | 0.979-1.17 | 0.13 |
| PGR expression | 0.748 | 0.665-0.842 | $1.4 \times 10^{-6}$ |
| ENDORSE enrichment scores | | | |
| ENDORSE | 4.89 | 3.24-7.38 | $4.4 \times 10^{-14}$ |
| ENDORSE risk groups | | | |
| Medium Risk | 2.44 | 1.89-3.15 | $8.2 \times 10^{-12}$ |
| High Risk | 4.1 | 3.07-5.48 | $1.2 \times 10^{-21}$ |

TABLE 5

Multivariate ENDORSE Cox Models with PAM50 subtypes

| Variable | HR | 95% C.I. | P-value |
|---|---|---|---|
| PAM50 claudin-low | 1.13 | 0.515-2.46 | 0.77 |
| PAM50 Her2 | 1.48 | 0.712-3.08 | 0.29 |
| PAM50 LumA | 0.864 | 0.444-1.68 | 0.67 |
| PAM50 LumB | 0.984 | 0.518-1.87 | 0.96 |
| PAM50 NC | 1.68 | 0.456-6.17 | 0.44 |
| PAM50 Normal | 1.38 | 0.652-2.92 | 0.4 |
| ENDORSE Risk Groups: Medium Risk | 2.37 | 1.79-3.13 | 1.4E−09 |
| ENDORSE Risk Groups: High Risk | 3.93 | 2.77-5.58 | 1.8E−14 |

TABLE 6

Multivariate ENDORSE Cox Models with IntClust classes

| Variable | HR | 95% C.I. | P-value |
|---|---|---|---|
| IntClust 10 | 0.421 | 0.175-1.02 | 0.054 |
| IntClust 2 | 1.33 | 0.782-2.27 | 0.29 |
| IntClust 3 | 0.875 | 0.546-1.4 | 0.58 |
| IntClust 4 ER− | | NA | |
| IntClust 4 ER+ | 1.38 | 0.872-2.17 | 0.17 |
| IntClust 5 | 0.982 | 0.297-3.25 | 0.98 |
| IntClust 6 | 1.61 | 0.98-2.64 | 0.06 |
| IntClust 7 | 1.09 | 0.679-1.74 | 0.73 |
| IntClust 8 | 1.03 | 0.668-1.58 | 0.9 |
| IntClust 9 | 1.41 | 0.875-2.28 | 0.16 |
| ENDORSE Risk Groups: Medium Risk | 2.4 | 1.84-3.14 | 1.4E−10 |
| ENDORSE Risk Groups: High Risk | 4.19 | 3.05-5.77 | 1.1E−18 |

TABLE 7

Multivariate ENDORSE Cox Models with HR gene expression

| Variable | HR | 95% C.I. | P-value |
|---|---|---|---|
| ESR1 expression | 0.953 | 0.874-1.04 | 0.28 |
| PGR expression | 0.854 | 0.757-0.964 | 0.01 |
| ENDORSE Risk Groups: Medium Risk | 2.39 | 1.83-3.12 | 1.9E−10 |
| ENDORSE Risk Groups: High Risk | 3.94 | 2.92-5.32 | 4.2E−19 |

Stratifying METABRIC Breast Cancers Based on ENDORSE Scores

Figure 3A:
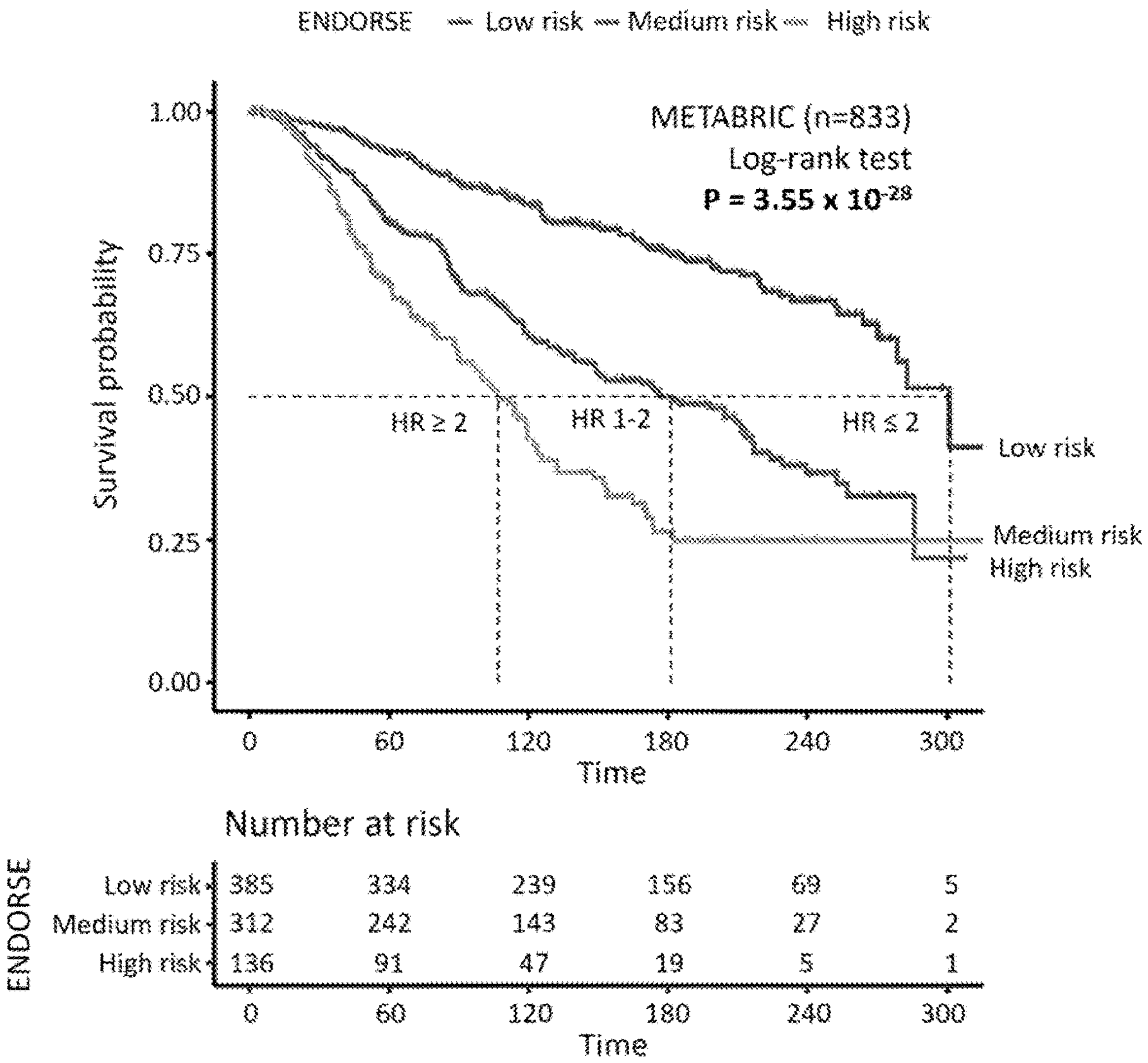
FIGS. 3A-3D illustrate stratification of METABRIC ER+ breast cancers based on a gene signature in accordance with embodiments, designated "ENDORSE.
Figure 3B:
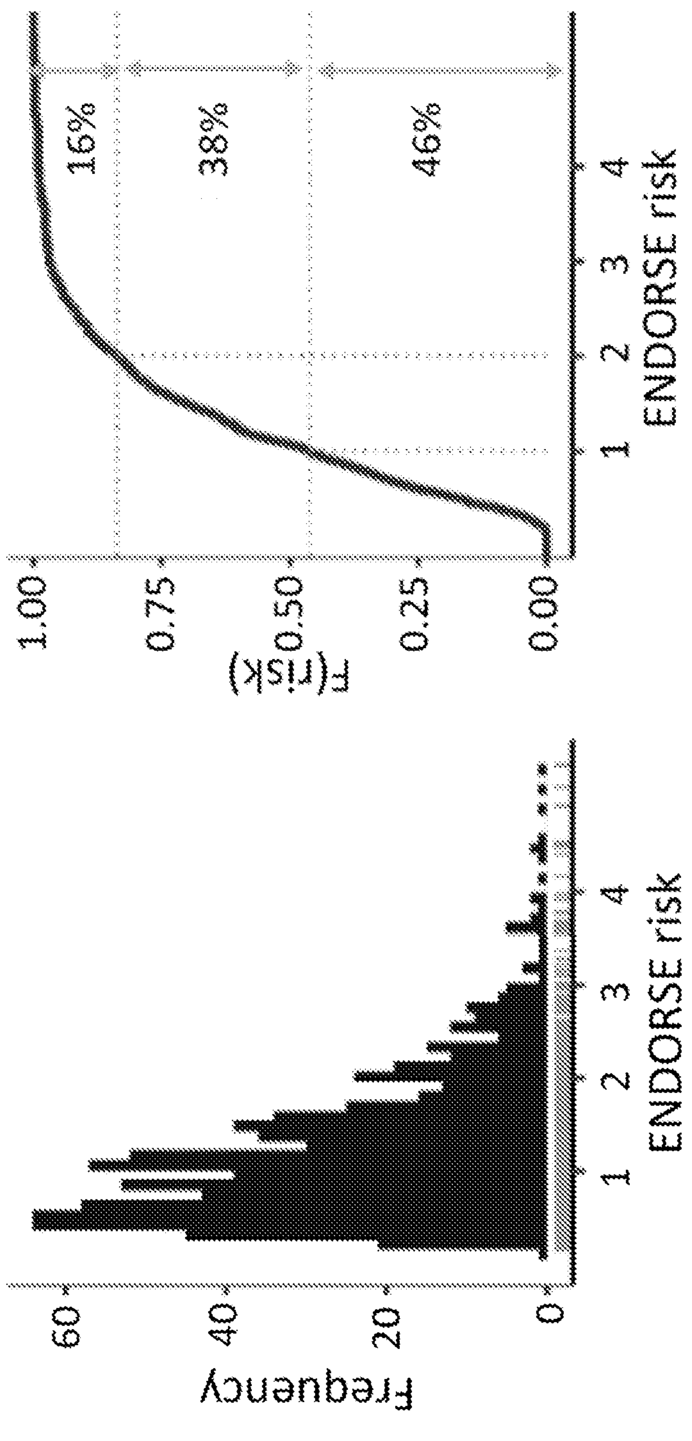

To demonstrate the ability of the ENDOSE scores to stratify all ER+ breast cancers, the METABRIC ER+ cancers were grouped based on estimated event risk. Cancers were classified with an ENDORSE score estimated hazard ratio of ≥2 as high risk, ≤1 as low risk and all cancers with intermediate hazard ratios as medium risk (FIG. 3B). Kaplan-Meier plots show significant differences in the survival curves $$(P = 3.55 \times 10^{-24})$$

of cancers stratified based on ENDORSE risk estimates. In the METABRIC cohort, the majority of cancers were classified in the low or medium risk class, while only 16% of the patients were classified in high-risk class (FIG. 3B).

Figure 3C:
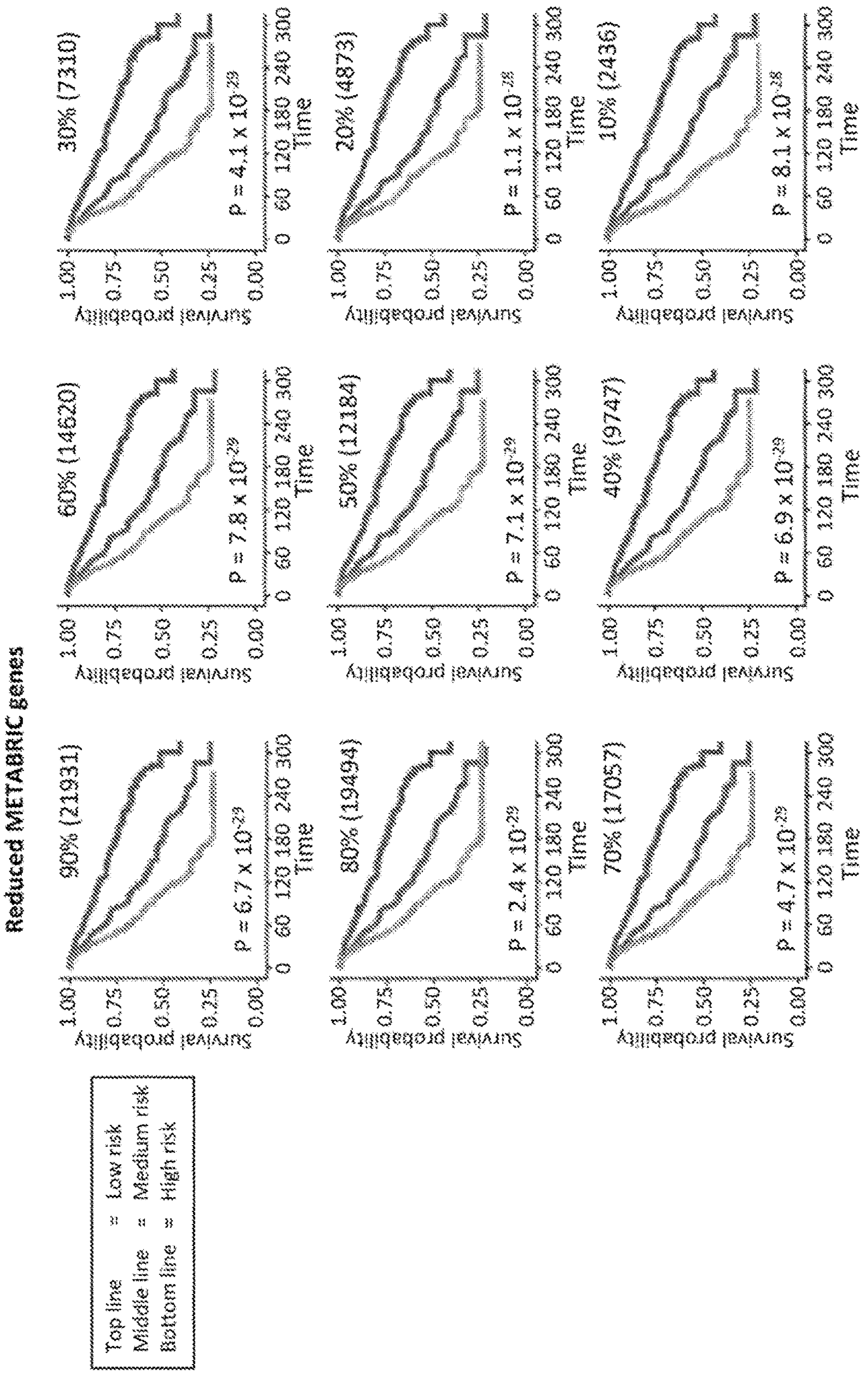
Figure 3D:
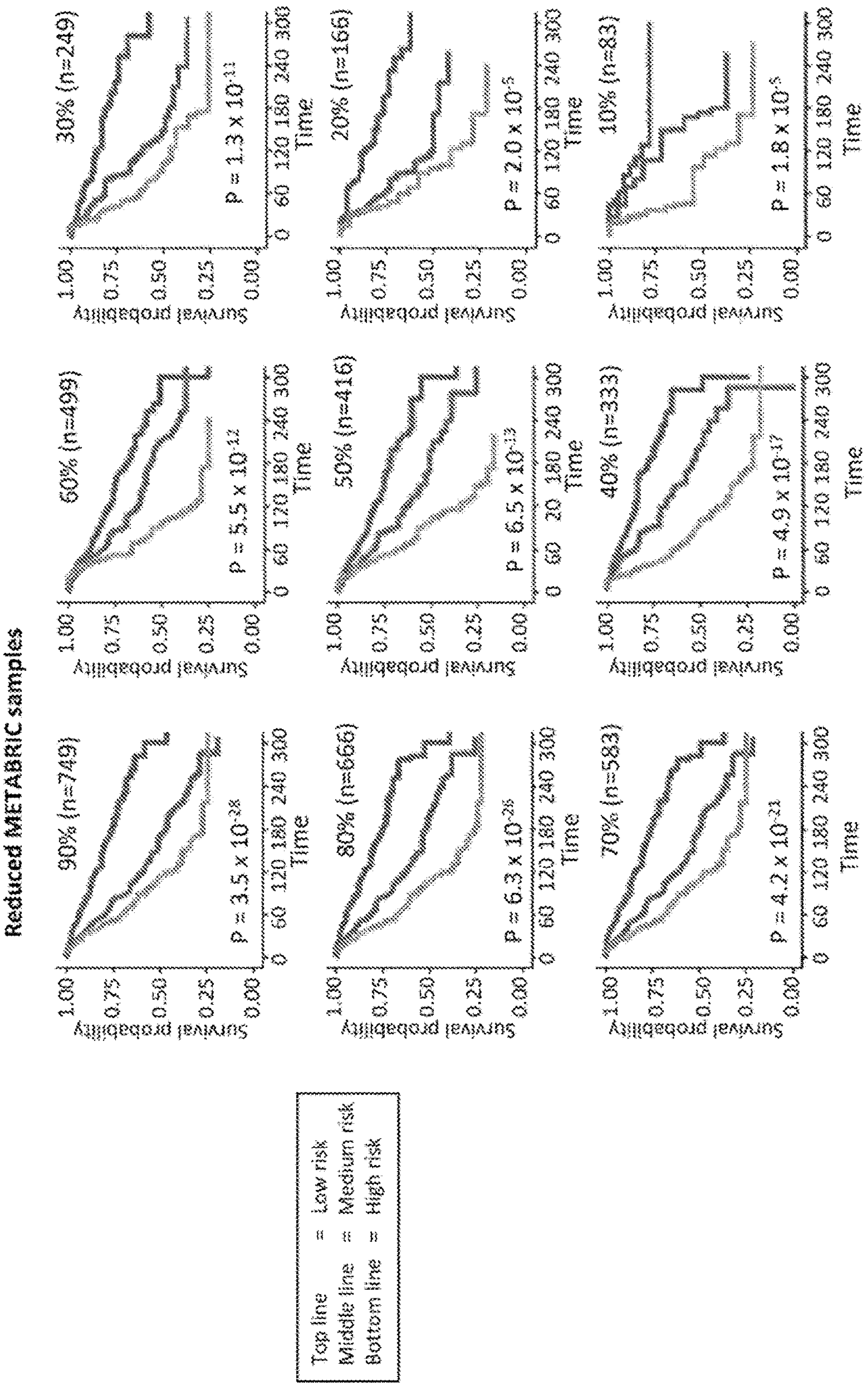

To demonstrate the robustness of the ENDORSE scores and risk estimates, the Kaplan-Meier survival curves of METABRIC patients were reanalyzed by either reducing the number of genes that were available to recalculate the ENDORSE scores (FIG. 3C) or by reducing the number of samples available to stratify based on risk estimates (FIG. 3D). It was observed that even after reducing the number of genes down to 10%, the log-rank test P-values were within the same order of magnitude as the original stratification. Upon reduction of the sample size, the stratification yielded significant P-values even when sub-sampled down to 10% of the original dataset.

The performance of the ENDORSE scores were further compared with clinical covariates, hormone receptor gene expression and other established breast cancer stratification models including PAM50 intrinsic subtypes (see, for example, Ref. 6) and IntClust classes (See, for example, Ref. 19) (Table 4). Univariate Cox models based on the ENDORSE scores and risk estimates outperform all other variables evaluated. Additionally, multivariate Cox-analysis with the ENDORSE signature along with hormone receptor expression, PAM50 subtypes and IntClust classes demonstrates that ENDORSE captures unique and significant proportion of the model variance over these predictors (See Tables 8-10). Thus, the ENDORSE scores are non-redundant from existing molecular classifications and augment risk stratification of ER+ breast cancers.

TABLE 8

Multivariate ENDORSE Cox Models with meta-PCNA

| Variable | HR | 95% C.I. | P-value |
|---|---|---|---|
| meta-PCNA (Proliferation Index) | 1.04 | 0.75-1.45 | 0.8 |
| ENDORSE Risk Groups: Medium Risk | 2.4 | 1.8-3.19 | 2.3E−09 |
| ENDORSE Risk Groups: High Risk | 3.99 | 2.78-5.74 | 7.2E−14 |

TABLE 9

Multivariate ENDORSE Cox Models with meta-PCNA

| Variable | HR | 95% C.I. | P-value |
|---|---|---|---|
| meta-PCNA (Proliferation Index) | 0.978 | 0.703-1.36 | 0.89 |
| ENDORSE Risk | 1.88 | 1.64-2.16 | 5.7E−19 |

TABLE 10

| METABRIC Mutation Analysis | | | | | |
|---|---|---|---|---|---|
| | Number of samples with mutation | | | | |
| Gene | Low Risk | Medium Risk | High Risk | Chi-square P-value | FDR |
| TP53 | 48 | 71 | 44 | 6.59E−05 | 0.001847 |
| AKAP9 | 17 | 16 | 18 | 3.35E−04 | 0.009033 |
| GATA3 | 74 | 59 | 11 | 2.91E−03 | 0.075576 |
| CDH1 | 37 | 30 | 25 | 4.58E−03 | 0.114529 |
| PIK3CA | 255 | 152 | 65 | 2.87E−02 | 0.689714 |
| AHNAK | 35 | 32 | 15 | 7.26E−01 | 1 |
| AHNAK2 | 90 | 66 | 26 | 4.66E−01 | 1 |
| AKT1 | 13 | 22 | 8 | 8.39E−01 | 1 |
| ARID1A | 15 | 27 | 15 | 5.38E−02 | 1 |
| BIRC6 | 12 | 26 | 10 | 5.03E−01 | 1 |
| CBFB | 44 | 15 | 10 | 7.95E−01 | 1 |
| COL22A1 | 18 | 19 | 5 | 5.61E−01 | 1 |
| DNAH11 | 25 | 38 | 14 | 7.64E−01 | 1 |
| DNAH2 | 30 | 27 | 11 | 1.00E+00 | 1 |
| DNAH5 | 30 | 20 | 10 | 1.00E+00 | 1 |
| HERC2 | 19 | 29 | 12 | 5.37E−01 | 1 |
| KMT2C | 50 | 44 | 24 | 2.55E−01 | 1 |
| LAMA2 | 19 | 19 | 8 | 1.00E+00 | 1 |
| MAP3K1 | 80 | 44 | 18 | 2.43E−01 | 1 |
| MLL2 | 30 | 23 | 9 | 8.24E−01 | 1 |
| MUC16 | 63 | 60 | 31 | 1.96E−01 | 1 |
| PDE4DIP | 21 | 23 | 5 | 3.19E−01 | 1 |
| RYR2 | 19 | 28 | 8 | 8.56E−01 | 1 |
| SYNE1 | 50 | 34 | 22 | 2.38E−01 | 1 |
| TBX3 | 28 | 22 | 6 | 3.22E−01 | 1 |
| TG | 20 | 15 | 11 | 2.20E−01 | 1 |
| THADA | 20 | 17 | 6 | 8.25E−01 | 1 |
| USH2A | 24 | 25 | 14 | 2.54E−01 | 1 |

Validating ENDORSE Risk Estimates in Independent Datasets

Figure 4A:
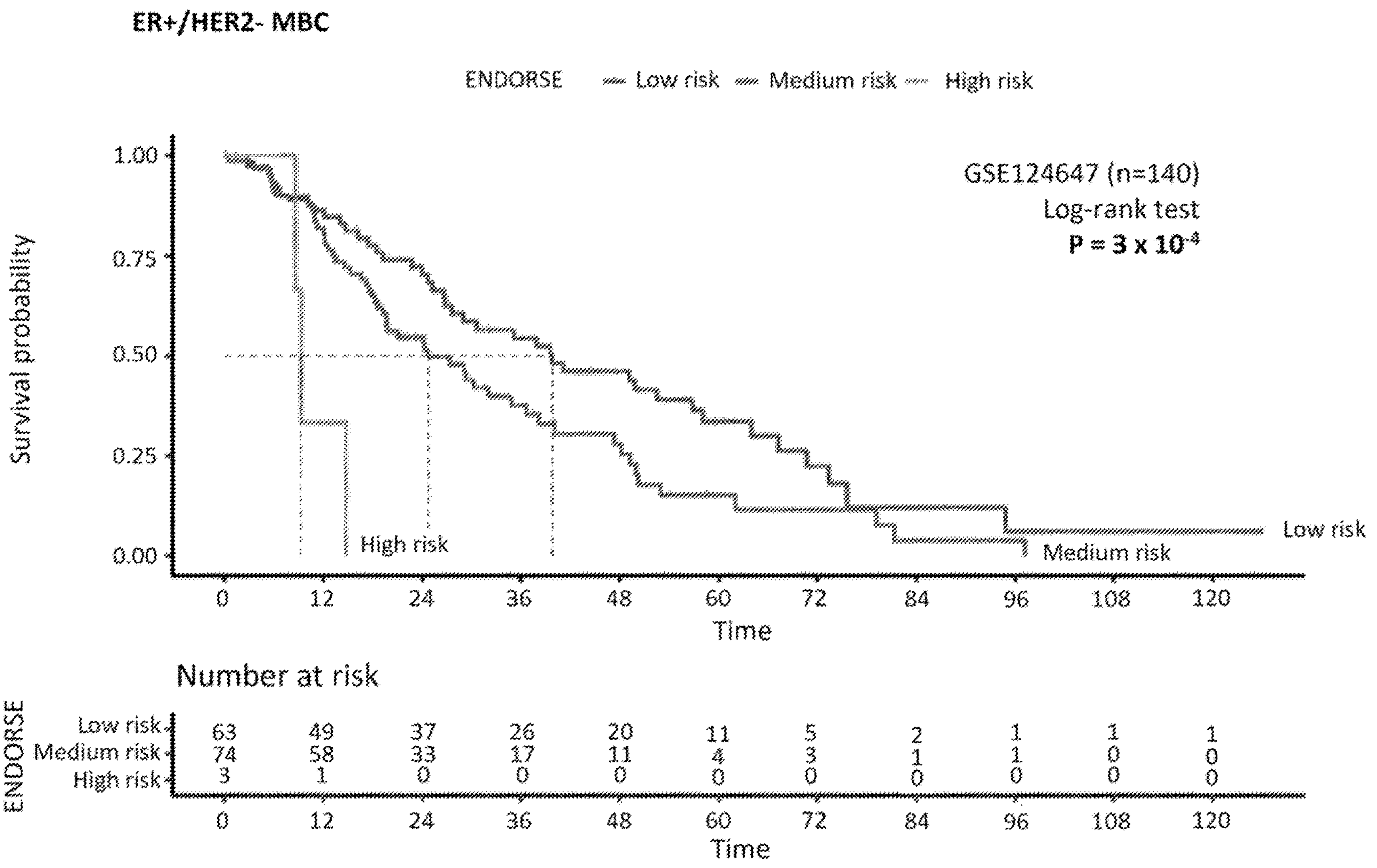
FIGS. 4A-4E illustrate validation of ENDORSE score and risk estimates, in accordance with embodiments.

The reliability and reproducibility of the ENDORSE score-based risk stratification was demonstrated by applying the Cox model coefficients obtained from the METABRIC model to ER+ breast cancers in independent datasets. The first independent clinical trial reported endocrine therapy treatment outcomes of 140 stage IV ER+ metastatic breast cancers (See, for example, Ref. 20). The ENDORSE gene set enrichment scores were calculated from the transcriptomic data obtained from the metastases and the cancers stratified based on METABRIC-derived ENDORSE coefficients (FIG. 4A). Only four cancers were predicted to be high-risk based on the ENDORSE risk estimates. Nevertheless, analysis of the survival curves shows indicates accurate stratification of the cancers based on the risk estimates $$(P = 3\times10^{-4}).$$

Next, data from the NCT00265759 clinical trial was examined, which evaluated neoadjuvant AI treatment in Stage II or III ER+ breast cancers (See, for example, Ref. 21). This study used 10% Ki67 staining at the end of treatment (2-4 weeks) as the threshold for sensitive or resistant cancers. It was found that the ENDORSE risk estimates successfully stratified the cancers in agreement with reported Ki67% at both baseline $$(P = 2.7\times10^{-8})$$

and end of treatment $$(P = 5.6\times10^{-3})$$

Figure 4B:
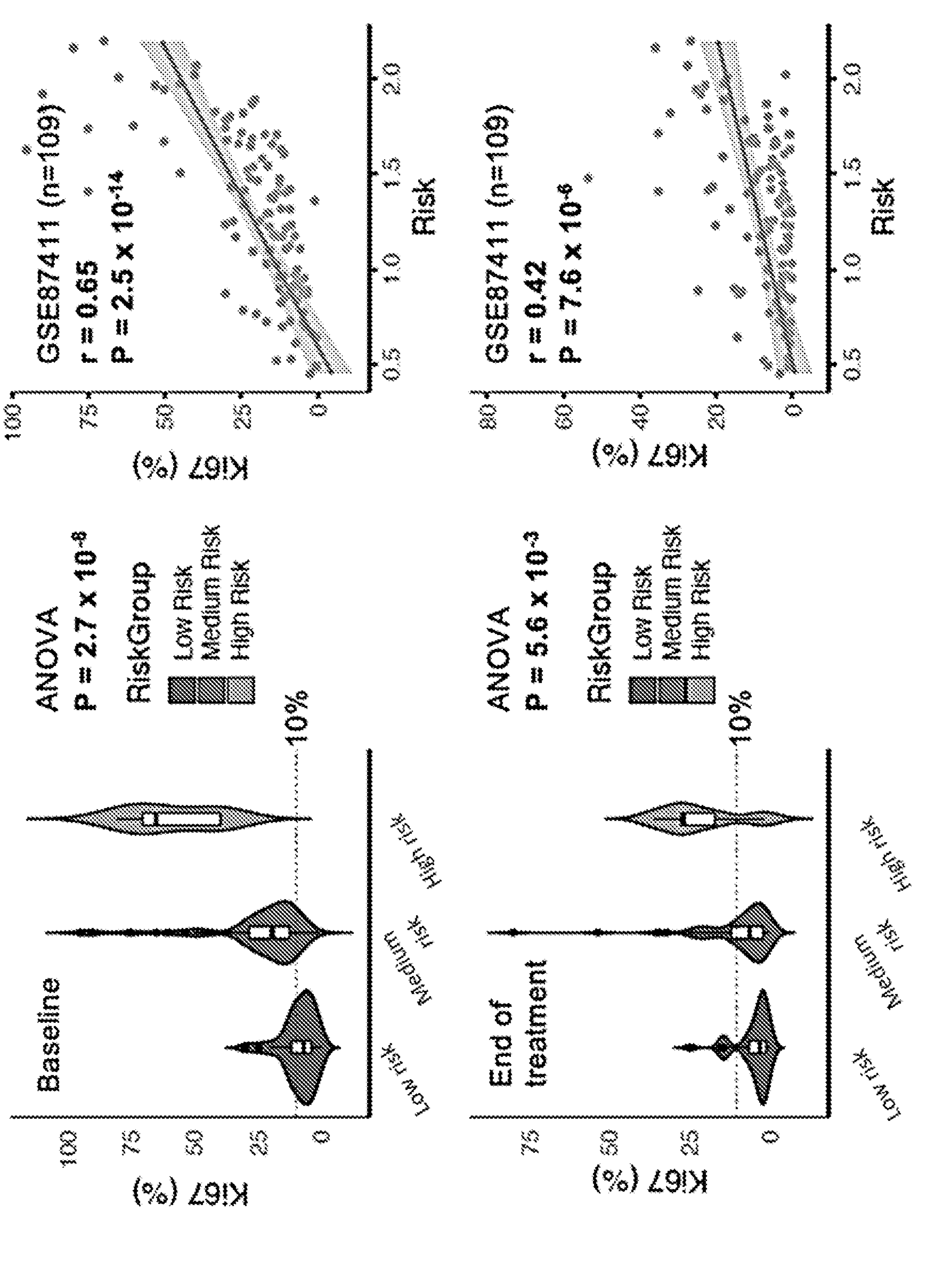

(FIG. 4B). The third independent clinical trial evaluated fulvestrant response in advanced metastatic ER+ breast cancers (CONFIRM study) (See for example, Ref. 22). This study classified tumors as resistant or sensitive based on a 10% Ki67 staining threshold. Again, the stratification of these cancers based on ENDORSE risk estimates showed clear differences in Ki67% across the risk groups $$(P = 1.6\times10^{-9}),$$

in addition to significant correlation with the continuous risk score $$(P = 2.5\times10^{-11})$$

Figure 4C:
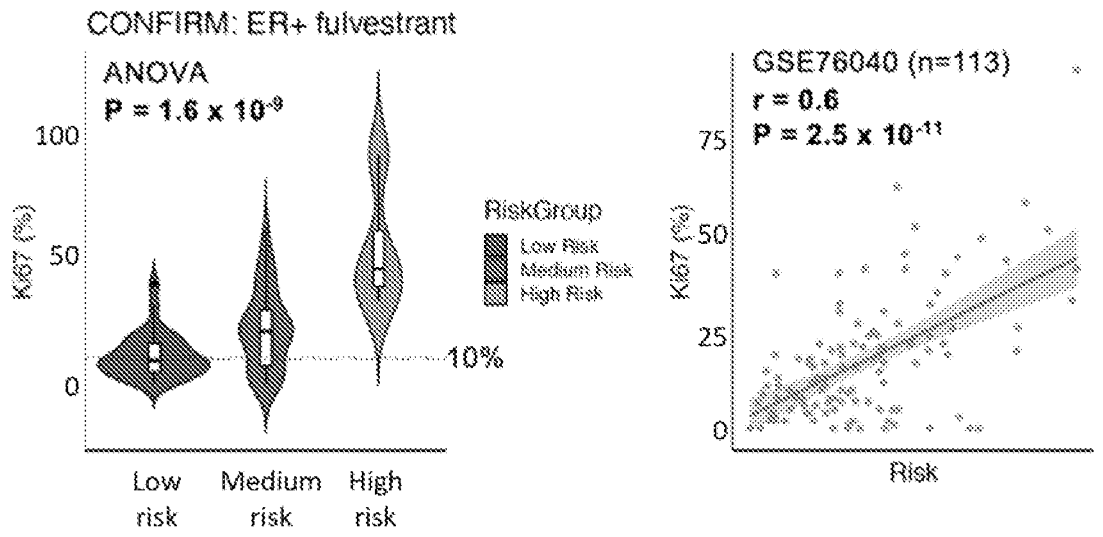

(FIG. 4*c*). Similar consistent patterns were observed with the continuous risk scores. In both the CONFIRM and NCT00265759 trial, patients stratified in low risk groups were consistently classified as sensitive based on the trial outcome data, while high risk tumors were classified as resistant (FIGS. 4B, C).

In addition to the endocrine therapy trials in ER+ breast cancer, the ENDORSE risk estimates were applied to stratify ER− breast cancers or ER+ breast cancers on non-endocrine therapy as negative controls. First, ENDORSE risk estimates were compared in a trial for neoadjuvant trastuzumab and lapatinib in ER+/HER2+ or ER−/HER2+ breast cancers. In both molecular subtypes, there was no significant difference in endorse risk estimates between the partial clinical response and residual disease groups $$(ER + P = 0.465,\ ER - P = 0.824)$$

Figure 4D:
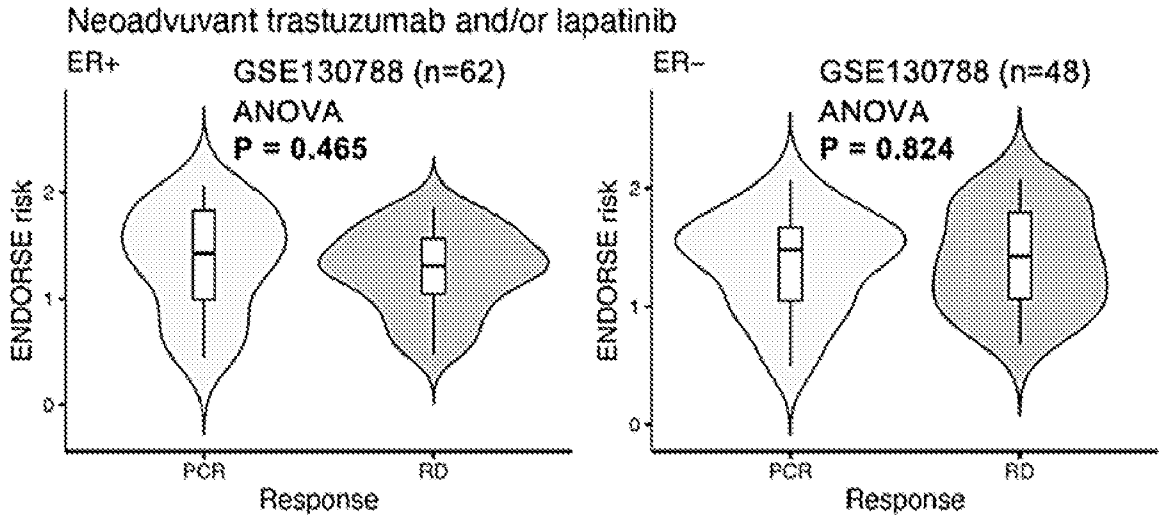
Figure 4E:
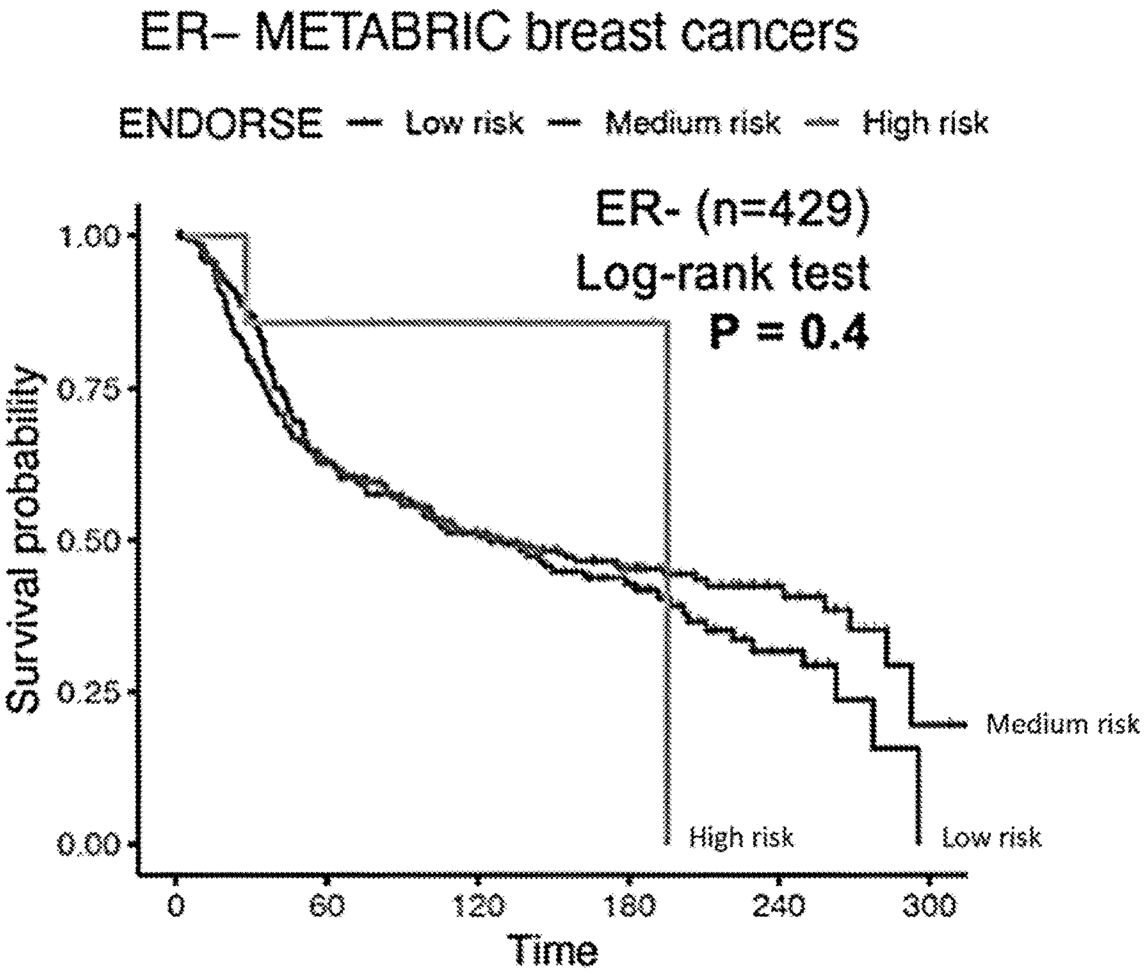

(FIG. 4D). Similarly, stratification of the ER− cancers based on the estimated ENDORSE risk resulted in no significant differences between the survival curves (P=0.4) (FIG. 4E). These results suggest the ENDORSE risk estimate is not a general biomarker for aggressive breast cancers, but specific to ER+ breast cancers on endocrine therapy.

Understanding the Biology of High-Risk Cancers

Figure 5A:
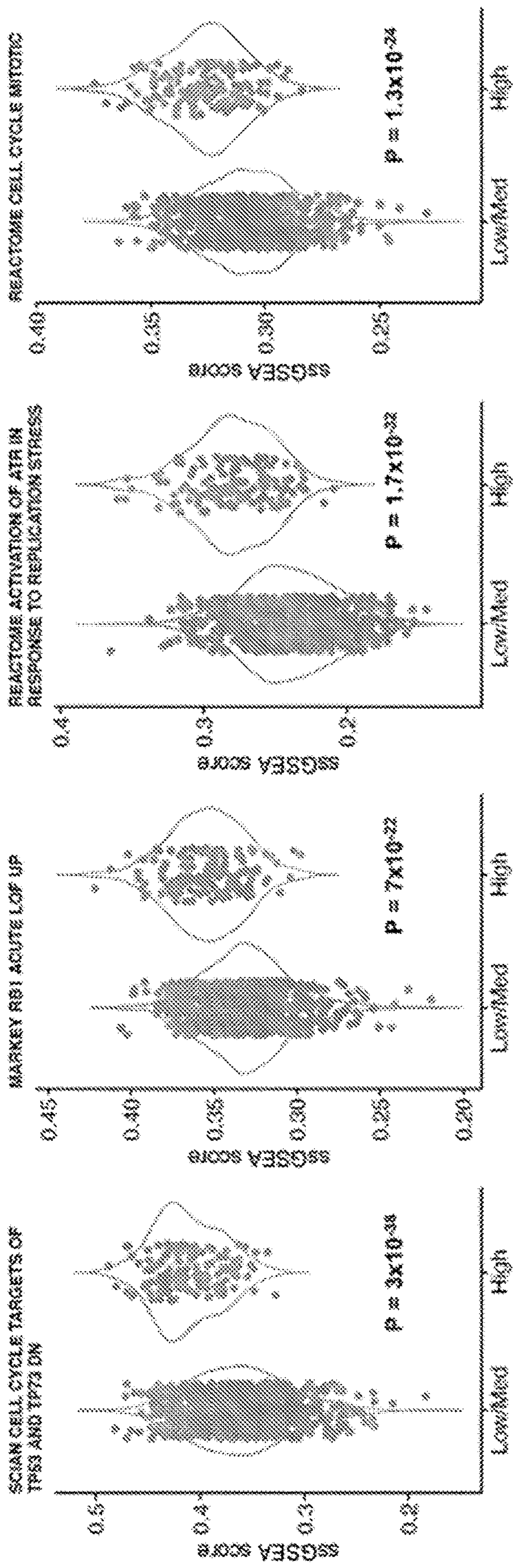
FIGS. 5A-5D illustrate the biology of high-risk tumors.
Figure 5B:
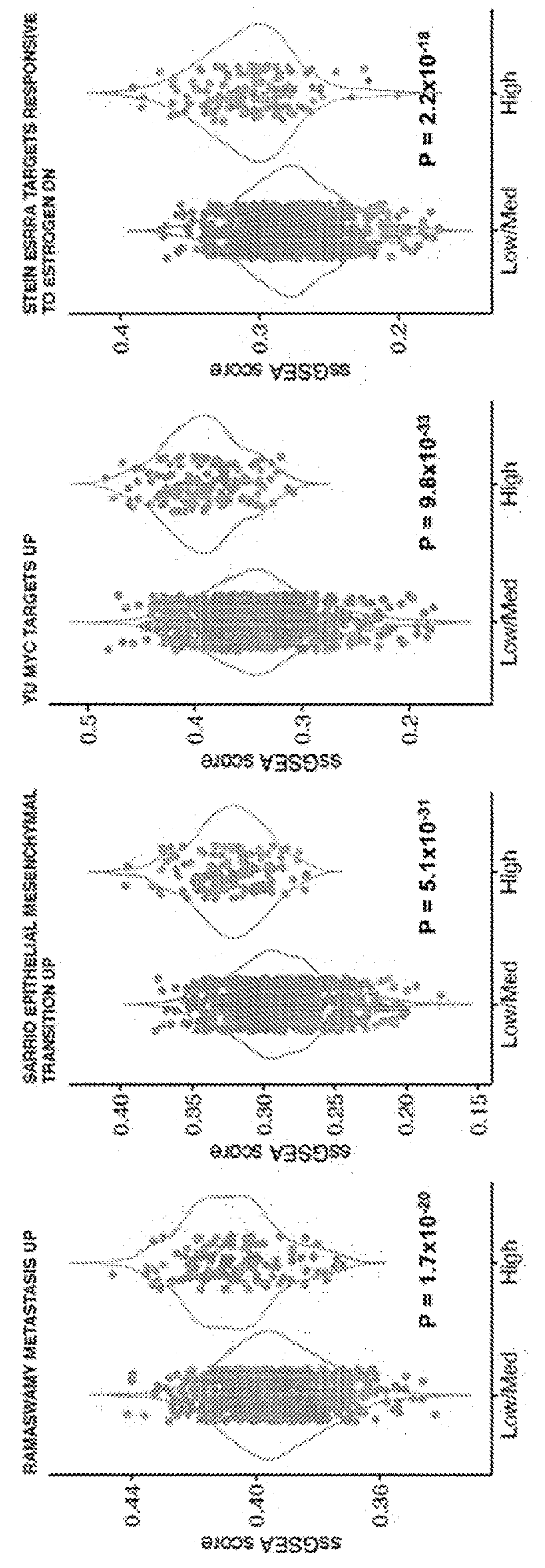
Figure 5C:
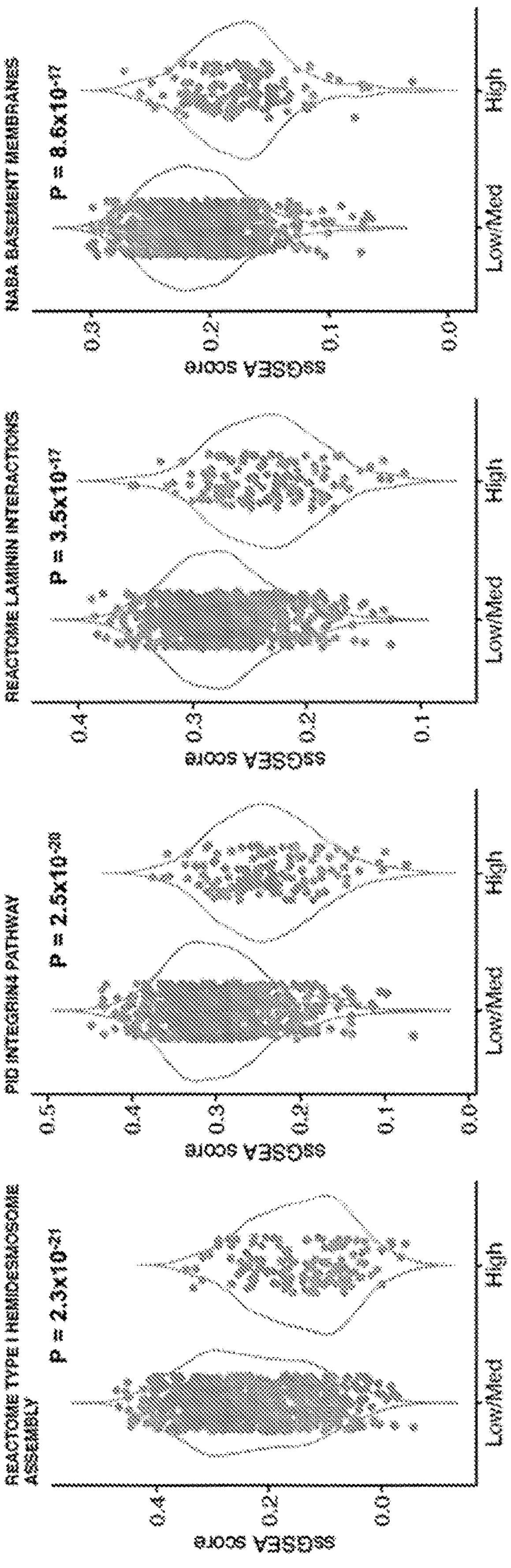

To gain insights into the biology of high-risk cancers, the gene set enrichment scores, gene-level mutation and copy number alteration frequencies across the METABRIC ENDORSE risk strata were compared. It was determined that multiple pathways linked with functional loss of P53 and RB were elevated in the high-risk cancers (FIG. 5A, and data not shown). Concurrently, DNA-damage repair and cell cycle pathways that are closely associated with p53 and Rb loss were also enriched (FIG. 5A). As a related consequence of aggressive tumors, metastasis and epithelial to mesenchymal transition signatures were elevated in the high-risk tumors, along with elevated expression of MYC targets and reduced expression of estrogen targets (FIG. 5B). Among gene signatures that were enriched in the low/medium risk strata, we predominantly found pathways and complexes associated with extracellular matrix interaction, including integrin, laminin, hemidesmosome and basement membranes (FIG. 5C). To demonstrate that the ENDORSE risk strata were not solely driven by a proliferative signal (See, for example, Ref 23), the meta-PCNA proliferation index was calculated and the multivariate Cox models containing the proliferation index and the ENDORSE scores or risk groups as covariates were analyzed. This analysis reinforces the notion that the ENDORSE scores capture information beyond mere proliferation.

Figure 5D:
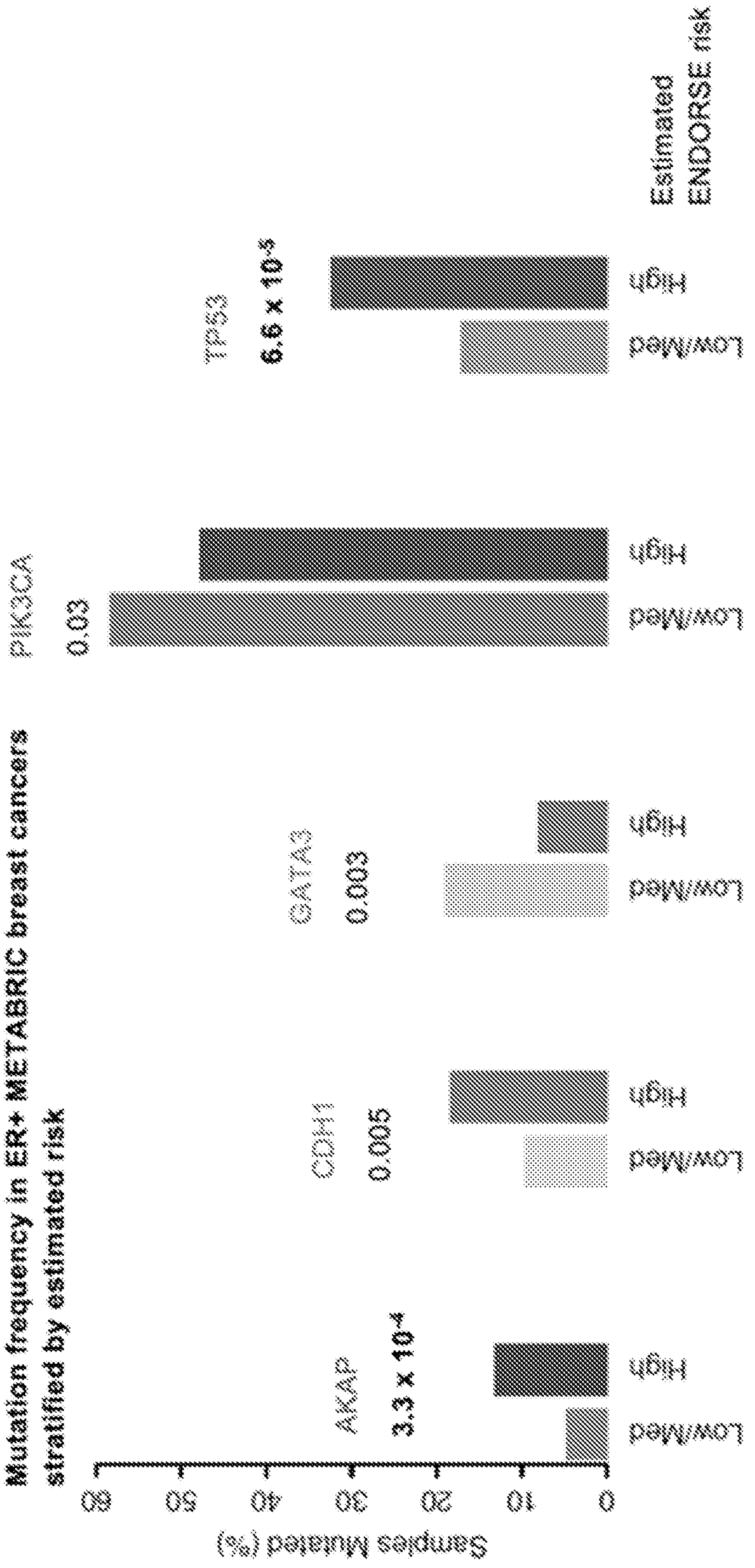

Next, the somatic mutation and copy number profiles of the METABRIC cancers were analyzed. None of the copy number gain or losses were enriched in the high-risk tumors compared to low/medium risk tumors, but the somatic mutation frequencies for few cancer-associated genes were significant at the nominal threshold (FIG. 5D). However, only two genes, $$TP53\ (P = 6.6\times10^{-5})\ \text{and}\ AKAP\ (P = 3.3\times10^{-4})$$

were significant at an FDR<0.05 threshold. The functional impact of p53 mutation frequency in high-risk tumors was corroborated by the enrichment of p53 loss of function-linked gene signatures (FIG. 5A). Tumor sequencing efforts have shown high frequency of AKAP mutations in metastatic lesions compared to primary tumors (See, for example, Ref. 24), corroborating the observed enrichment in high-risk tumors.

Discussion

In this study, a biomarker for the prognosis of ER+ breast cancers was developed using METABRIC data. A LASSO regularized Cox model for feature selection was used, effectively reducing the dimensionality of the gene expression data. In addition, a pathway signature approach was adapted in this framework, which further reduced the number of predictors down to a single integrated variable as the final biomarker.

The reliability and robustness of our biomarker through cross-validation analyses and simulations in the METABRIC ER+ cohort was evaluated. The analyses revealed that the univariate ENDORSE biomarker consistently outperformed multivariate models based on gene expression or literature-derived gene signatures (FIGS. 2A-2B). Furthermore, it was found that reducing the number of available genes to calculate the ENDORSE risk estimates had a minimal impact on the ability of the biomarker to stratify METABRIC ER+ cancers. This distinct advantage of using the gene set enrichment scores (GES) over individual genes or pathway predictors can be explained by the algorithm for GES calculation. The ssGSEA method proposed by Barbie et al. replaces gene expression by their ranks, followed by calculating the differences in the empirical distribution functions of the signature genes vs. all other genes (See, for example, Ref 18). The rank-based method helps mitigate issues encountered due to batch effects and differences in methods for transcriptome profiling, while the redundancy in the signature ensures the scores remain consistent even in the case some genes are missing in the data. The ENDORSE biomarker was successful in stratifying ER+ breast cancers in multiple independent validation datasets from diverse gene expression profiling platforms.

The ENDORSE biomarker stratified cancers based on estimated risk of death due to the disease while on endocrine therapy. In addition to testing its potential to serve as a robust biomarker, we explored the biology of the high-risk tumors for possible hints into their mechanism. We found that high-risk tumors showed a consistent enrichment of pathways associated with loss of p53 and Rb, along with DNA damage repair and cell cycle progression. Mutations in the TP53 have long been associated with aggressiveness and chemotherapeutic resistance in hormone-receptor negative breast cancers (See, for example, Refs. 28, 29). However, recent studies show that even though TP53 are infrequent in ER+ breast cancers, they have similar negative impact on patient outcome as hormone-receptor negative breast cancers (See, for example, Ref. 30). Similarly, inactivation of the tumor suppressor Rb has been associated with therapeutic resistance in ER+ breast cancers (See, for example, Refs. 31, 32). Concurrently, data showed a gain in metastasis and epithelial to mesenchymal transition signatures, both features of aggressive and invasive tumors (See, for example, Ref. 33). Interestingly, the signature for estrogen-like receptor alpha targets were down in the high-risk tumors. While this receptor shares structural homology with ER, its activity is currently believed to be independent of estrogen ligand binding and regulates metabolism instead of proliferation and growth (See, for example, Refs. 34,35). Finally, data showed signatures for tumor-ECM interactions are reduced in the high-risk tumors, a feature associated with aggressive tumors and therapeutic resistance (See, for example, Refs. 36,37). A previous meta-analysis of gene signatures by Venet et al. associated with breast cancer outcomes showed that most signatures were redundant with proliferation (See, for example, Ref. 23). While proliferation is indeed an important feature of aggressive tumors, our analyses showed that proliferation signature did not encompass the entirety of the signal from the ENDORSE biomarker.

Example 2: Methods

Data Retrieval, Pre-Processing and Analysis

METABRIC gene expression, phenotypic and survival data were retrieved using cBioPortal for cancer genomics (See, for example, Ref. 38). Independent validation datasets used in this study were retrieved from the NCBI GEO portal under the following accession IDs: GSE124647, GSE87411, GSE76040 and GSE130788 (See, for example, Refs. 20-22). For each gene expression dataset, genes with zero variance were removed and summarized genes with multiple probes by mean expression. Each dataset was scaled, such that the mean of each gene across the samples was zero with standard deviation equal to 1.

The analyses were performed in R 3.6.1, RStudio 1.2.1335.

Selecting Samples for Training Models

The METABRIC cohort contained a total of 2509 samples. We constructed the training models for ER+ cancers and endocrine therapy response by filtering the samples on the following criteria: 1. The tumors were positive for estrogen receptor and negative for human epidermal growth factor receptor 2 (ER+ and HER2−) in their immunohistochemistry profile, 2. If the patient died, then disease was listed as cause of death, and 3. The patient did not receive chemotherapy alone or in combination with endocrine therapy. After filtering based on these criteria, we retained 833 samples with both gene expression and complete clinical data available.

Training Features and Model Construction

Four sets of features were derived and compared as potential predictors of long-term outcome of ER+ METABRIC tumors, including curated gene set and hallmark gene set enrichment scores, expression profiles of all genes and the ENDORSE gene signature (FIG. 1). The curated gene sets and hallmark gene sets (v7.0) were retrieved from MSigDb (See, for example, Refs. 15, 16). For each gene signature, the gene set enrichment scores were calculated using the GSVA package for R using the ssGSEA method (See, for example, Refs. 17, 18). Next, the gene set enrichment scores (GES) or expression profiles of all genes, along with age at diagnosis, were used as input features in LASSO-regularized Cox regression models, with overall survival as the outcome variable (See, for example, Ref. 39). The hazard function in the Cox model is defined as:

$$h_i(t) = h_0(t)\exp(\beta x_i^T)$$

where, X is a set of predictive features and $h_0$ is an arbitrary baseline hazard function. Curated GES, hallmark GES and all genes were considered each as individual sets of predictive features in separate analyses. The coefficient (β) for each predictor in the model can be estimated by maximizing the partial likelihood function L(β), defined as:

$$L(\beta) = \prod_i \frac{\exp(\beta x_{j(i)}^T)}{\sum_{l \in R_i} \exp(\beta x_j^T)}$$

where $R_i$ is the set of indices of observations failing (events) at time $t_i$. In the LASSO Cox model, In the LASSO Cox model, the regularized coefficient is obtained by adding a penalty parameter λ to the log of the likelihood function.

$$\hat{\beta} = \min - \frac{1}{N} l(\beta) + \lambda \|\beta\|_1$$

where, l(β)=log L(β). The λ penalty parameter was determined using 10-fold cross-validation implemented in R package glmnet (See, for example, Refs. 40-41). The optimal λ for the curated or hallmark GES and gene expression feature sets were defined as the λ that minimized model deviance for each feature set. We defined the preliminary endocrine resistance gene set (ENDORSE) using the features with positive coefficients in the LASSO model for all genes, with optimal λ within one standard error from the minimum model deviance. The signature was further expanded by including genes that were positively correlated (Pearson's correlation >0.75) with the selected features in the ER+ METABRIC samples. Next, the GES was calculated for each sample using GSVA and use the GES as a predictive feature.

Repeated Cross-Validation, Consensus ENDORSE Signature and Performance Evaluation To evaluate the performance of each set of predictive features and derive a consensus ENDORSE model, 10-fold cross-validation analysis was performed and repeated 50 times. In this analysis, the features selected in the LASSO model from each set of predictors were evaluated in multivariate Cox model. In each of the 50 repeats, the samples were split into 10 equal parts, with one part serving as the test set and the remaining parts serving as the training set in each fold of cross-validation. In each fold, the feature selection was performed for curated, hallmark or ENDORSE GES and gene expression only using the training set. Then, the Cox model coefficients were derived for each set of selected features using only the training set. To evaluate performance, we applied the coefficients from the training model to the GES or gene expression data from the test data. The concordance indices of the Cox model fit in the training and test data were reported. In addition, the correlation between the actual risk of event in the test data and the predict risk of event based on the coefficients derived from the training data and applied to the test data were reported.

The consensus ENDORSE set was defined as the set of predictive features that were selected in more 50% of the repeated cross-validations. This resulted in the selection of 63 genes (see Table 1) that comprised the consensus ENDORSE set for subsequent analysis involving risk or hazard ratio (HR) estimation and predictions in independent datasets. After the consensus ENDORSE set was defined, ENDORSE GES and Cox model coefficient for the complete ER+ METABRIC cohort were obtained. Then, the tumors were stratified based on estimated risk, defining cancers with HR 1 as low-risk, HR≥2 as high-risk, and those with HR between 1 and 2 as medium risk.

METABRIC Survival Models and Simulations

The ENDORSE model was evaluated in the METABRIC cohort by stratifying the ER+ cancers based on estimated risk in the low, medium or high-risk categories. For comparisons with clinical variables and other breast cancer classification approaches, including PAM50 and IntClust, the HR and p-values of the Cox model coefficients were reported for these predictors in univariate analyses. In addition, the results of multivariate analyses that included the PAM50 or IntClust classes along with the ENDORSE risk estimates were reported.

The survival curves of METABRIC ER+ tumors stratified based on ENDORSE risk estimates using the log-rank test were calculated. To simulate the effects of random dropouts or missing data, the total number of available genes was sequentially reduced to calculate the ENDORSE GES and the risk estimate recalculated. Here, 10% of the genes in each iteration were randomly sampled and removed until 90% of the genes were removed. In each iteration, the ability of the recalculated risk estimate to stratify the cancers based on the difference in survival curves using the log-rank test was calculated. Similarly, the impact of reduced sample set was simulated by sequentially reducing the number of samples available for recalculating the ENDORSE scores by 10% in each iteration and analyzed the difference in survival curves using the log-rank test.

Validation in Independent Clinical Trial Datasets

The performance and ability of ENDORSE to predict treatment response in a set of three independent clinical trials was analyzed. These trials were selected based on criteria that the trial cohort included any stage of ER+/HER2− breast cancers receiving endocrine therapy but did not receive chemotherapy. In addition, the trials should have reported a clinical assessment of treatment response or over survival outcomes, in addition to providing gene expression datasets. Three datasets were found that met the above criteria (GSE12647, GSE87411 and GSE76040). The first trial (GSE12647) reported survival outcomes of 140 metastatic breast cancers on endocrine therapy. For this dataset, the estimated risk of event was predicted based on the ENDORSE coefficients derived from the METABRIC ER+ model. First, the ENDORSE GES for the test samples was calculated using the baseline expression of the tumors. Next, the estimate risk of event was predicted using the META- BRIC-derived coefficients. Then, the difference in survival curves for the different strata was analyzed using the log-rank test.

For the two subsequent datasets (GSE87411 and GSE76040), the estimated risk was predicted based on ENDORSE GES from the baseline gene expression data. The NCT00265759 trial evaluated neoadjuvant aromatase inhibitor response in a cohort of 109 stage II-III ER+ breast cancers. This trial provided Ki67 data at both baseline and end of treatment and classified tumor with Ki67>10% at end of treatment as non-responders. The CONFIRM trial evaluated 113 metastatic ER+ cancers on fulvestrant, and also reported Ki6 staining data at end of treatment. Since both trials reported Ki67 as a determinant for treatment response, the Ki67% across the ENDORSE risk strata or continuous risk scores as measure of performance evaluation was compared.

In addition, the ENDORSE risk estimates was also evaluated in two negative control datasets. The first negative control dataset (GSE130788) evaluated trastuzumab and lapatinib response in 62 ER+/HER+ or 48 ER−/HER+ breast cancers. The trial reported clinical response (partial clinical response or residual disease) at the end of treatment. The estimated ENDORSE risk scores was predicted using baseline gene expression and compared across the clinical response classes. As an additional negative control, the 429 ER− breast cancers in METABRIC were predicted and stratified based on ENDORSE estimates. Then, the difference in survival curves using log-rank test was compared.

Biological Features Associated with High-Risk Cancers

The features that may be important in explaining the biological difference between high-risk cancers compared to low/medium risk cancers were assessed by comparing the curated and hallmark enrichment scores, somatic mutation and copy number frequencies across the ER+ METABRIC. For the comparison of GES, t-tests were performed for each signature and adjusted the p-values using false discovery rate (FDR) or Benjamini-Hochberg method. In addition, the effect size of the difference in means was calculated using Cohen's D method. An absolute Cohen's D>0.8 was considered as large effect.

The somatic mutations for the METABRIC ER+ cohort were summarized at the gene-level by first removing all synonymous variants as non-consequential, then binarizing the gene by mutation matrix based on presence of a mutation. Next, genes with a sample mutation frequency <0.05 were filtered out. Then, a 2×2 contingency matrix was constructed for each gene and the METABRIC ER+ tumor stratified based on low/medium risk or high risk. The p-values for enrichment was calculated using the Chi-square test, followed by FDR adjustment. Similar to the mutation analysis, the Chi-square test was performed on binary matrices of tumor gain or loss across all genes, followed by FDR adjustment.

To compare the information captured by the ENDORSE scores with the proliferative meta-PCNA signature (See, for example, Ref. 23), the proliferation index of the METABRIC ER+ tumors was calculated using the R-package Proliferation Index (See, for example, Ref 42). The package calculates the median expression of the meta-PCNA genes, as described by Venet et al. (See, for example, Ref 23). Next, a multivariate Cox analysis of the ER+ tumors was performed with the proliferation index and either ENDORSE risk groups or continuous risk estimates as covariates.

Example 3: Calculating the ENDORSE GES (Gene Set Enrichment Score)

Retrieved METABRIC gene expression data was obtained using the Illumina HT-12 v3 microarray platform, and reported as normalized values presented on a log 2 scale for 24,368 genes (see Curtis et al.; Ref. 13). The data set is publicly available at www.cbioportal.org/study/summary?id=brca_metabric.

The tumor transcriptome of the patient sample was pre-processed by:

1) Removing all genes with zero variance across the samples.
2) Imputing missing data using K-nearest neighbor regression.
3) Standardizing the data by scaling the expression of each gene to a mean of zero and standard deviation of one (by subtracting the mean and dividing by the standard deviation of the expression of a gene across all samples)

The ENDORSE GES was calculated from the transcriptome of a tumor biopsy using the single-sample gene set enrichment method proposed by Barbie et al. (See, for example Ref. 43) using the R-package GSVA (See, for example Ref. 44).

Briefly, the expression values of the sample are ranked (instead of absolute values), and the GES (also represented as ES(G, S) was calculated by integration of the difference between empirical cumulative distribution function (ECDF) of the genes in the ENDORSE gene set (Table 1) and the empirical cumulative distribution function of all remaining genes in the tumor transcriptome. The formula for calculating the ES(G, S) is given by:

$$ES(G, S) = \sum_{i=1}^{N}\left[P_G^w(G, S, i) - P_{NG}(G, S, i)\right] \text{ where}$$

$$P_G^w(G, S, i) = \sum_{r_j \in G, j \le i} \frac{|r_j|^\alpha}{\sum_{r_j \in G} |r_j|^\alpha} \text{ and}$$

$$P_{NG}(G, S, i) = \sum_{r_j \notin G, j \le i} \frac{1}{(N - N_G)}.$$

Example 4: Calculating the ENDORSE Risk Estimate to Stratify Estrogen-Receptor Positive Patients Based on Risk of Death on Endocrine-Therapy The ENDORSE risk estimate was calculated using the Cox model coefficients derived from the age-adjusted model fit using METABRIC data described in the manuscript. Thus, the $$\text{ENDORSE risk estimate} = 4.8864 \times \text{ENDORSE } GES.$$

The risk categories were defined as follows:

1. Low risk: an ENDORSE risk estimate less than or equal to 1.

This suggests the patient has an equal or lesser chance of death while on endocrine therapy as compared to other patients in the METABRIC cohort
2. Medium risk: an ENDORSE risk estimate greater than 1 but less than 2.
3. High risk: an ENDORSE risk estimate greater or equal to 2.

This suggests the patient is twice-as likely to die on endocrine-therapy while on endocrine therapy as compared to other patients in the METABRIC cohort.

These groups represented 385, 312, and 136 samples from the METABRIC study classified as low risk, medium risk, and high risk, respectively. Based on the risk categories so defined, the average hazard ratio of adverse event on endocrine therapy for samples from the METABRIC study were 0.6, 1.4, and 2.67 for low risk, medium risk, and high risk, respectively. The average ENDORSE GES for each group was 0.45, 0.6, and 0.7, for low risk, medium risk, and high risk, respectively. In embodiments, the average hazard ratio or the average GES is used as a threshold for classifying a cancer as endocrine therapy responsive (below the threshold) or endocrine therapy resistant (at or above the threshold).

Mean expression values for individual genes in the signature among samples classified as low, medium or high risk are provided in Table 11. In embodiments, the mean expression level for a given gene is used as a threshold for the gene.

TABLE 11

Normalized Expression Values of ENDORSE Genes by Risk Category

| Gene | Mean Level (Low Risk) | Mean Level (Medium Risk) | Mean Level (High Risk) |
|---|---|---|---|
| ASF1B | 6.25 | 6.71 | 7.08 |
| ASPM | 6.78 | 7.44 | 7.83 |
| AURKA | 6.89 | 7.49 | 7.95 |
| AURKB | 6.4 | 6.95 | 7.42 |
| BIRC5 | 6.46 | 7.09 | 7.62 |
| BUB1 | 6.13 | 6.62 | 6.91 |
| CCNA2 | 6.48 | 6.93 | 7.27 |
| CCNB2 | 7.3 | 7.99 | 8.5 |
| CDC20 | 8 | 8.76 | 9.29 |
| CDC25C | 5.84 | 6.22 | 6.49 |
| CDC45 | 6.57 | 7.2 | 7.56 |
| CDCA3 | 6.12 | 6.59 | 6.92 |
| CDCA5 | 7.64 | 8.32 | 8.9 |
| CDCA8 | 6.36 | 6.76 | 7.1 |
| CENPA | 6.21 | 6.67 | 6.98 |
| CENPE | 6.43 | 6.85 | 7.15 |
| CENPF | 6.81 | 7.34 | 7.81 |
| CEP55 | 6.6 | 7.09 | 7.5 |
| CKAP2L | 6.14 | 6.65 | 6.98 |
| DLGAP5 | 6.12 | 6.46 | 6.74 |
| E2F2 | 6.74 | 7.27 | 7.73 |
| ESPL1 | 6.36 | 6.59 | 6.76 |
| EXO1 | 6.28 | 6.75 | 7.16 |
| FAM64A | 5.98 | 6.33 | 6.73 |
| FOXM1 | 5.9 | 6.36 | 6.76 |
| GSK3B | 8.12 | 8.33 | 8.5 |
| HJURP | 6.19 | 6.64 | 7.01 |
| hNp95 | 7.48 | 8.12 | 8.58 |
| KIF14 | 5.87 | 6.18 | 6.4 |
| KIF15 | 5.97 | 6.32 | 6.64 |
| KIF20A | 6.6 | 7.21 | 7.64 |
| KIF23 | 6.16 | 6.49 | 6.82 |
| KIF2C | 6.25 | 6.72 | 7.12 |
| KIF4A | 5.87 | 6.26 | 6.6 |
| KIFC1 | 6.38 | 6.85 | 7.31 |
| MCM10 | 6.24 | 6.7 | 7.11 |
| MCM2 | 7.21 | 7.69 | 8.14 |
| MELK | 6.82 | 7.38 | 7.82 |
| MKI67 | 5.66 | 5.86 | 6.04 |
| NCAPG | 6.57 | 7.17 | 7.49 |
| NUSAP1 | 7.62 | 8.36 | 8.81 |
| OIP5 | 6.61 | 7.11 | 7.47 |
| PKMYT1 | 6.12 | 6.56 | 6.99 |
| PLK1 | 6.26 | 6.46 | 6.64 |
| PLK4 | 6.53 | 6.89 | 7.14 |
| POLQ | 6.19 | 6.62 | 6.94 |

TABLE 11-continued

Normalized Expression Values of ENDORSE Genes by Risk Category

| Gene | Mean Level (Low Risk) | Mean Level (Medium Risk) | Mean Level (High Risk) |
|---|---|---|---|
| PRC1 | 7.94 | 8.67 | 9.16 |
| PTTG1 | 8.3 | 9.1 | 9.56 |
| PTTG3 | 7.3 | 8 | 8.35 |
| RACGAP1 | 7.46 | 7.98 | 8.35 |
| RECQL4 | 5.87 | 6.22 | 6.5 |
| SPC25 | 5.92 | 6.19 | 6.39 |
| STIL | 6.94 | 7.34 | 7.62 |
| TACC3 | 6.42 | 6.83 | 7.08 |
| TIMELESS | 7.42 | 7.83 | 8.15 |
| TOP2A | 8.04 | 8.91 | 9.38 |
| TPX2 | 6.3 | 6.85 | 7.35 |
| TRIP13 | 6.51 | 7.04 | 7.51 |
| TROAP | 6.28 | 6.81 | 7.21 |
| TTK | 6.26 | 6.74 | 7.08 |
| UBE2C | 8.15 | 9.17 | 9.82 |
| UBE2S | 8.75 | 9.28 | 9.67 |
| ZWINT | 6.91 | 7.4 | 7.74 |

Example 5: ENDORSE—A Prognostic Model for Endocrine Therapy Response in Advanced Estrogen-Receptor Positive Breast Cancers Endocrine therapy remains the primary treatment for advanced and metastatic estrogen receptor-positive (ER+) breast cancers. Patients who progress on endocrine therapy may benefit from add-on treatment targeting the PI3K/MTOR signaling pathways or by switching to chemotherapy. However, these options are only available after progression on first-line treatment with endocrine therapy. In the absence of reliable prognostic tests for endocrine therapy in advanced ER+ breast cancers, it is currently not possible to stratify patients into alternate treatment arms at the baseline. To address this, we have developed a low-dimensional endocrine response signature (ENDORSE) model for advanced and metastatic ER+ breast cancers. The ENDORSE model was developed using the baseline transcriptomes and long-term survival outcomes of >800 invasive ER+ breast cancers and predicts the relative risk of death on endocrine therapy. ENDORSE was validated in multiple metastatic ER+ clinical trial datasets and demonstrated superior predictive performance over clinical factors, proliferation scores and other published gene signatures. Our results show that ENDORSE is a reproducible and accurate prognostic model for endocrine therapy response in advanced and metastatic ER+ breast cancers.

Introduction

Breast cancer is the most common form of cancer globally, with more than two million cases diagnosed in 2020[1]. Pathogenesis and classification of breast cancer is based on the presence or absence of estrogen receptor alpha (ER), progesterone receptor (PR) and human growth factor-neu receptor (HER2). These subtypes guide the selection of systemic therapy for breast cancer patients. More than 70% of breast cancers express ER and are negative for HER2 (ER+/IER2−)[2,3]. The primary systemic therapy for ER+/HER2− breast cancer is endocrine therapy, which counters the growth of tumors by targeting their dependency on estrogen signaling[4]. This includes selective estrogen receptor modulators (SERMs) such as tamoxifen and selective estrogen receptor degraders (SERDs) such as fulvestrant that directly prevent ER activation, or aromatase inhibitors like exemestane and anastrozole that reduce circulating levels of estrogen in the body[5,6]. Endocrine therapy substantially reduces the risk of recurrence within 5-years, although chemotherapy may be recommended for some patients with high risk of recurrence. While clinicopathological features are not reliable predictors of recurrence risk, gene expression-based genomic tests that predict the risk of recurrence can aid in deciding whether the benefit of adding chemotherapy outweighs its side effects in certain patients[7,8]. These biomarkers are have been validated and recommended for clinical use only in early stage, node-negative cancers based on guidelines from the American Society of Clinical Onoclogy and European Group on Tumor Markers[9,10].

Locally advanced and metastatic ER+ breast cancers often develop resistance to endocrine therapy with significantly higher rates of recurrence and death compared to early-stage disease. Despite these challenges, single-agent endocrine therapy or in combination with CDK4/6 inhibitors remains the primary systemic therapy recommended for locally advanced and metastatic breast cancers$_{11}$. Patients may benefit from the addition of targeted inhibitor against the mTOR or PI3K pathways[12,13] or switching to chemotherapy$_{11}$. However, these treatment options are recommended for consideration only upon progression on endocrine therapy, according to the American Society for Clinical Oncology[14], National Comprehensive Cancer Network[15,16] and European Society for Medical Oncology[17] clinical practice guidelines. Therefore, the ability to predict the potential benefit from first-line endocrine therapy may be crucial for locally advanced and metastatic ER+ breast cancers that may benefit from continued endocrine therapy, a combination treatment or chemotherapy as the primary treatment strategy.

Unlike early stage, node-negative disease, genomic tests for endocrine therapy response are not available for advanced and metastatic ER+ breast cancers. To address this limitation, a few attempts have been made so far to develop a genomic signature of endocrine response in ER+ metastatic breast cancers (ER+ MBC)[18,19]. The TransCONFIRM trial evaluated the transcriptomes of 112 ER+/HER2− MBCs and identified a set of 37 genes that were associated with progression-free survival (PFS) of patients receiving fulvestrant[19]. Another study analyzed the transcriptomes of 140 ER+/HER2− MBC on endocrine therapy to develop $SET_{ER/PR}$, an 18-gene predictive score for endocrine therapy sensitivity[18]. While both the TransCONFIRM and $SET_{ER/PR}$ biomarkers predicted endocrine response in their respective training datasets, neither study performed systematic validation of their predictive signatures to demonstrate the reproducibility and accuracy in independent clinical datasets. This issue highlights a critical flaw in biomarker development pipelines and is one important reason why genomic biomarkers are infrequently translated into clinical practice[20]. Another pervasive issue hindering clinical translation arises from the reliance on a large number of predictive features in complex models that are difficult to interpret and often perform poorly in independent validation due to overfitting[21,22].

Here we developed ENDORSE: a low-dimensional expression-based prognostic model for endocrine therapy and systemically tested its performance and predictive ability in multiple-independent clinical trials against other diagnostic models and genomic signatures. ENDORSE was developed and trained using the tumor transcriptomes and overall survival (OS) of more than 800 ER+ breast cancers on endocrine therapy[23,24]. We validated the ENDORSE model in multiple independent clinical trial datasets, including the TransCONFIRM and $SET_{ER/PR}$ trials for endocrine therapy in metastatic ER+ breast cancer. Our results show that ENDORSE reproducibly predicts endocrine response in independent validation clinical studies, and consistently outperforms all other models of endocrine therapy response in metastatic ER+ breast cancers, clinical factors, and proliferation signatures.

Results

Developing a Low-Dimensional Prognostic Model for Endocrine Therapy

Figure 7A:
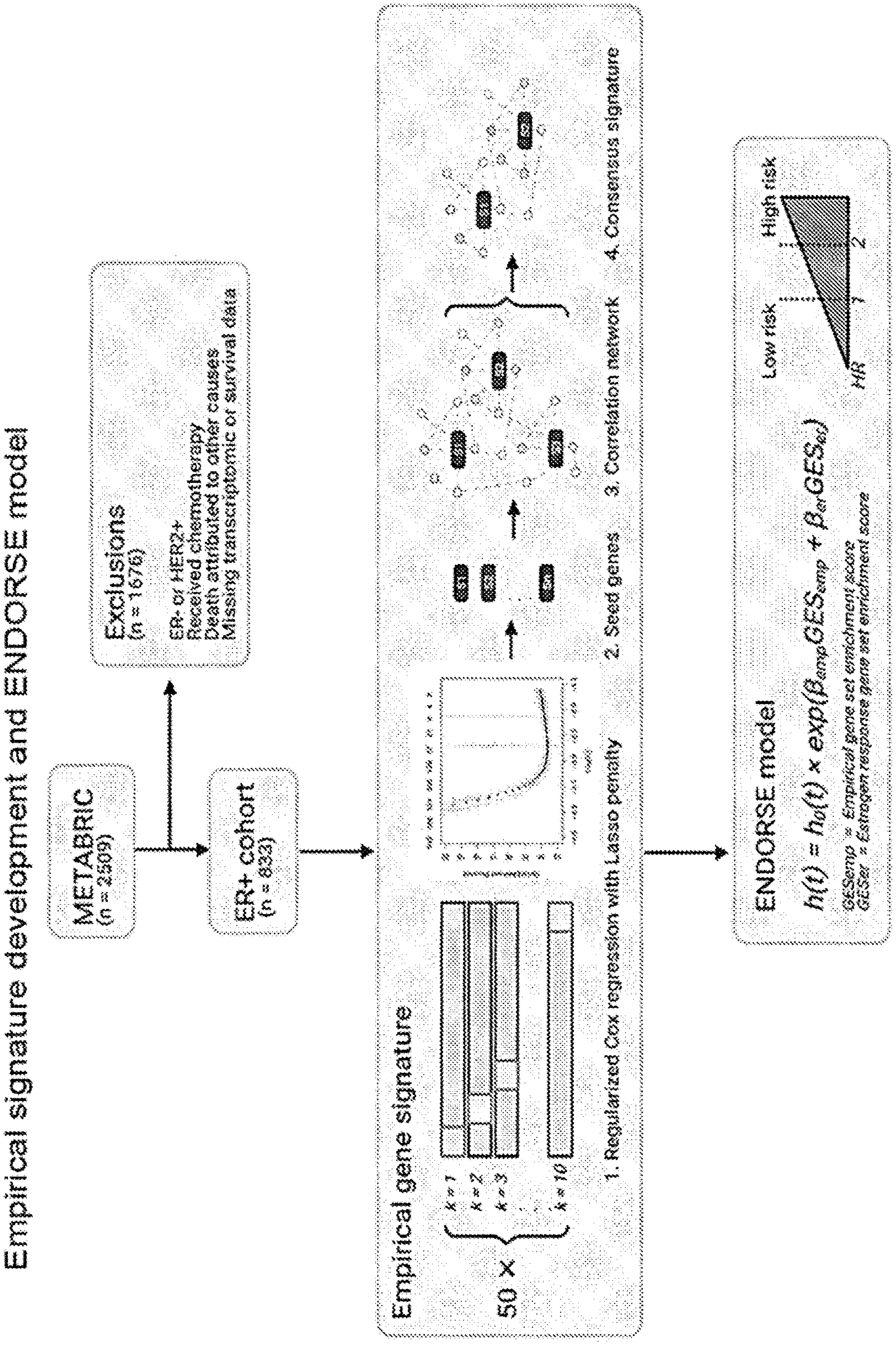
FIGS. 7A-7C. ENDORSE model development in METABRIC.
Figure 7B:
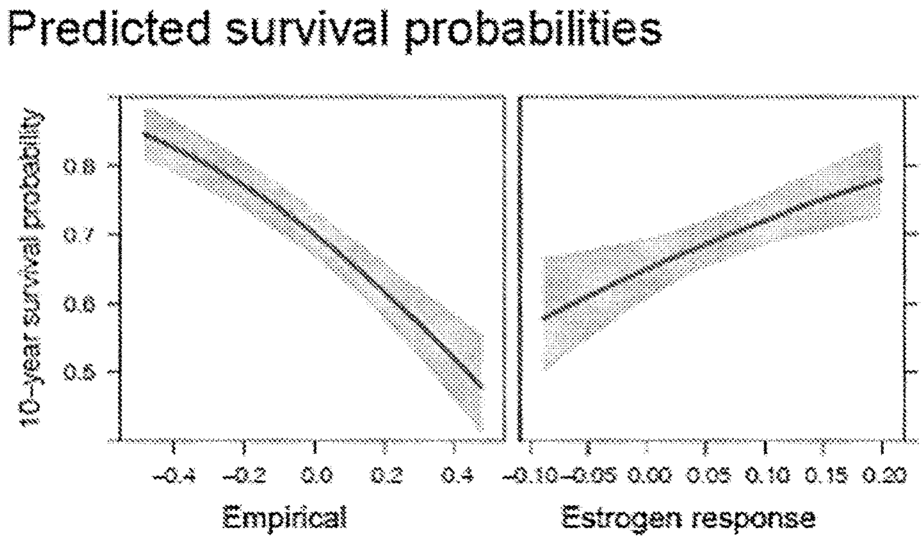
Figure 7C:
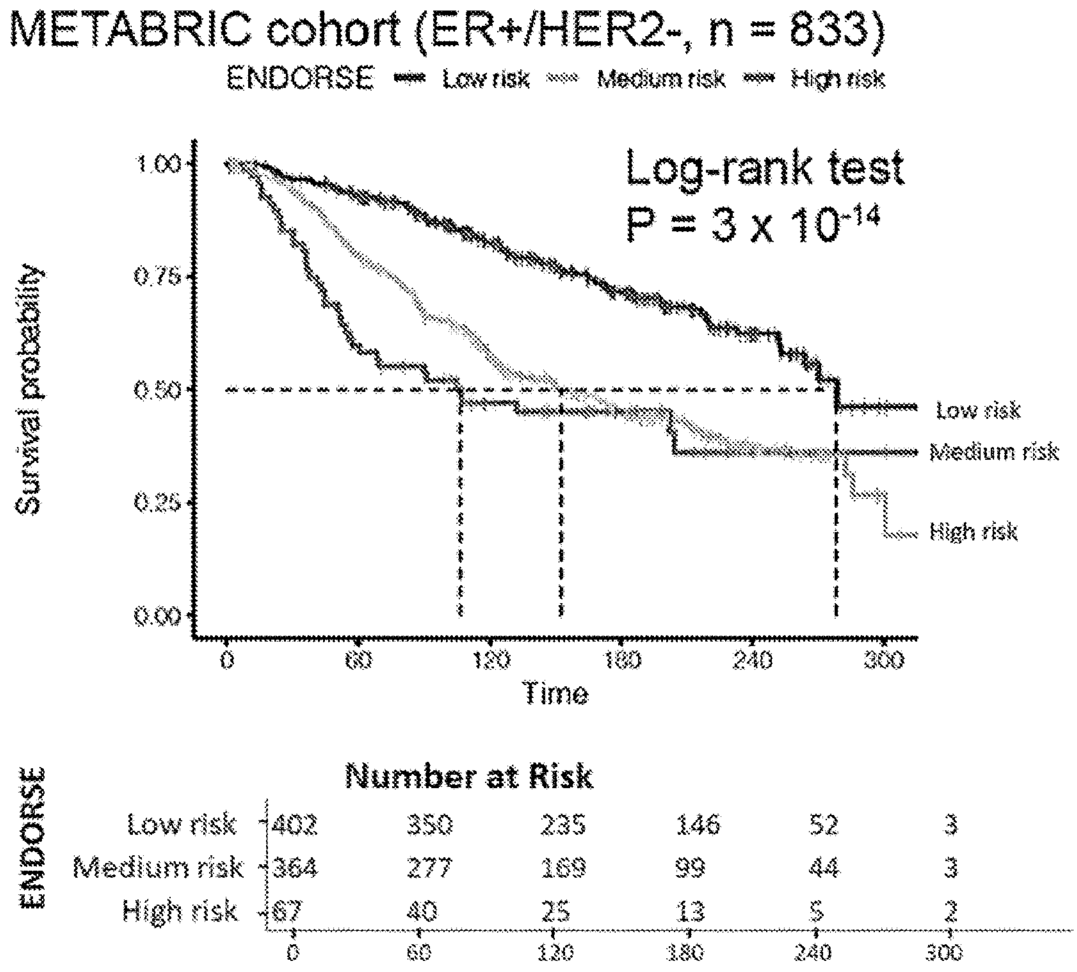

We developed a two-component prognostic model for endocrine therapy response using the tumor transcriptomes and long-term survival outcomes of 833 ER+/HER2− tumors that received endocrine therapy[23,24] (Table 12, FIG. 7A). About 2 in 5 tumors in this training cohort were node-positive, while more than a third of the tumors were poorly differentiated, grade 3 tumors (Table 12). The two components included an empirical gene signature modeled on OS (median=10 years) and a curated gene signature defining response to estrogen[25]. FIG. 7A outlines the inclusion criteria for the training dataset, method for developing the empirical gene signature and the final Cox proportional hazards model based on the gene set enrichments scores (GES) of the two signatures. The empirical signature was developed by first performing a feature selection on the training dataset using a repeated cross-validation analysis of a lasso-regularized proportional hazards model. Each iteration yielded a core set of predictive features that were expanded to a correlation network. The final gene signature was derived from the consensus correlation network, defined as genes appearing in at least 50% of the cross-validation iterations (Table 1). In a bivariate Cox proportional hazards model of the training data, the empirical signature was associated with a reduction in survival probability, while the estrogen response signature was associated with improved survival (FIG. 7B). The coefficients for the endocrine response, or ENDORSE, model was calculated using the training cohort, resulting in $$\text{ENDORSE} = 1.54 \times (\text{empirical signature } GES) - (2.72 \times \text{estrogen response } GES).$$

The ENDORSE model could also be used to stratify the tumors based on predicted risk, for example by setting a threshold of ≥2-fold relative risk of death as "high-risk" and ≤1 risk as "low-risk", resulting in significant differences in the Kaplan-Meier survival curves across the strata $$(P = 3 \times 10^{-14})$$

(FIG. 7C).

TABLE 12

Training data patient characteristics

| Variable | Mean | 95% C.I. | N available |
|---|---|---|---|
| Time to event (in months) | 135 | 130-140 | 833 |
| Events (death due to disease) | 0.409 | 0.376-0.443 | 833 |
| Age at diagnosis | 61.5 | 60.7-62.3 | 833 |

TABLE 12-continued

| Training data patient characteristics | | | |
|---|---|---|---|
| Variable | Mean | 95% C.I. | N available |
| Mutation count | 5.55 | 5.31-5.79 | 809 |
| Tumor size | 24.3 | 23.4-25.1 | 828 |
| Tumor stage | 1.64 | 1.59-1.69 | 634 |
| Stage 0-1 (n = 270) | | | |
| Stage 2 (n = 324) | | | |
| Stage >3 (n = 40) | | | |
| Tumor Grade | 2.29 | 2.18-2.27 | 808 |
| Grade 1 (n = 103) | | | |
| Grade 2 (n = 417) | | | |
| Grade 3 (n = 288) | | | |
| Number of positive lymph nodes detected | 1.56 | 1.32-1.79 | 833 |
| 0 (n = 491) | | | |
| 1-3 (n = 228) | | | |
| 4-9 (n = 85) | | | |
| >10 (n = 29) | | | |

Internal Performance Evaluation, Comparison with Clinical Covariates and Published Breast Cancer Signatures We performed bootstrap resampling analyses to validate the Cox model in the training dataset (FIG. 8A) and performed likelihood ratio tests (FIG. 8B) to compare with other univariate prognostic models including clinical factors, proliferation index and published prognostic signatures for ER+ breast cancers. First, we compared the ENDORSE model to the univariate models based on the individual components of ENDORSE, i.e., the empirical signature and estrogen response signature. The ENDORSE model (Somer's D or $D_{xy}$=0.301) was a better fit than the empirical signature $$(D_{xy} = 0.296,\ P = 1.09 \times 10^{-3})$$

and the estrogen response signature $$(D_{xy} = 0.141,\ P = 3.93 \times 10^{-14})$$

univariate models.

We then compared ENDORSE with clinical factors, such as tumor grade and mutation burden. The ENDORSE model performed better than both tumor grade $$(D_{xy} = 0.141,\ P = 2.08 \times 10^{-3})$$

and mutation count $$(D_{xy} = 0.059,\ P = 9.76 \times 10^{-6}).$$

We also compared the model with a 'meta-PCNA' proliferation index that was reported to capture the prognostic ability of most published signatures of breast cancer[26,27]. Again, the ENDORSE model performed significantly better than the proliferation index $$(D_{xy} = 0.235,\ P = 4.42 \times 10^{-5}),$$

indicating its utility over measures of proliferation as a prognostic tool.

Next, we evaluated published prognostic signatures for breast cancers and compared their performance with ENDORSE. These signatures included PAM50, a 50-gene signature that was previously reported to be a better prognostic tool for ER+ breast cancers on endocrine therapy than clinical factors, such as histopathological classification and tumor grade[28]. A genomic classifier, IntClust, that developed by the METABRIC consortium authors and trained on the same training dataset was also included in this comparison[29]. The PAM50 model ($D_{xy}$=0.220) performed better than IntClust ($D_{xy}$=0.153), however the ENDORSE model outperformed both PAM50 (P=0.033) and IntClust (P=0.02) models.

Two previous clinical trials evaluating endocrine therapy response in metastatic ER+ breast cancers developed prognostic signatures using tumor transcriptomes. The first signature developed in the TransCONFIRM trial included 37 genes that were associated with PFS of advanced ER+ breast cancers on fulvestrant[19]. We replicated the approach described in the study by performing hierarchical clustering of the samples based on the expression levels of the 37 genes and cutting the tree to obtain two clusters. We referred to resultant clusters as the 'TransCONFIRM' score. The TransCONFIRM score applied to the METABRIC dataset performed poorly ($D_{xy}$=−0.002), suggesting that the signature performed no better than a random set of genes and was unsurprisingly outperformed by ENDORSE $$(P = 9.73 \times 10^{-6}).$$

The second signature ($SET_{ER}/P_R$) was developed using tumor transcriptomes of metastatic ER+ breast cancers on endocrine therapy[18]. This signature included 18 predictive genes that were correlated with ESR1 or PGR expression and normalized using 10 reference transcripts. We implemented the methods described in original study and referred to the resultant score as 'SET'. The SET score ($D_{xy}$=0.152) performed better than TransCONFIRM; however, it was also easily outperformed by ENDORSE $$(P = 3.53 \times 10^{-5}).$$

Finally, we calculated a surrogate based on the published formula for the 21-gene prognostic signature approved for early-stage, node-negative ER+ breast cancers[30]. We referred to this score as ODX. We also compared a classifier that stratified samples based on $25^{th}$ percentile of ODX score as a proxy for the latest risk stratification threshold for this signature[8], and referred to this score as ODX25. We found that the ODX model ($D_{xy}$=0.159) was comparable to other published signatures like the SET score but the stratified ODX25 score performed poorly ($D_{xy}$=0.056). Again, the ENDORSE model performed significantly better than both ODX $$(P = 6.15 \times 10^{-5})$$

and ODX25

$$(P = 1.32 \times 10^{-5})$$

models. These results show that ENDORSE is significantly better prognostic model than available gene signatures, clinical factors and proliferation index for endocrine therapy in the METABRIC dataset.

Validation and Performance Evaluation in Independent Clinical Trial Datasets

To test the reproducibility and validate the performance of ENDORSE, we applied the model to the baseline transcriptomes of ER+ tumors from three independent clinical trials and compared the ENDORSE-predicted risk or strata with the outcomes reported in each trial. These independent trials also included the TransCONFIRM and $SET_{ER/PR}$ studies discussed earlier. So, we also compared the performance of TransCONFIRM and SET scores in their respective training datasets and also across other independent datasets.

The TransCONFIRM trial evaluated fulvestrant response in 112 advanced metastatic ER+ breast cancers previously treated with an antiestrogen[19]. While the original study developed and evaluated the performance of their 37-gene signature based on PFS, this survival data was not made available with the publication (the authors did not respond to our requests for this data). However, the study reported the post-therapy resistant or sensitive states of the tumors based on histopathological staining (Ki67 staining). Therefore, we compared the percentage of cells positive for Ki67 staining reported by in study with risk predictions from ENDORSE and other signatures (FIGS. 9A-9D). The percentage of cells positive of Ki67 were significantly correlated with the ENDORSE estimated risk $$(P = 2.5 \times 10^{-5})$$

(FIG. 9A), while stratification of the patients based on the risk thresholds also showed significant difference in Ki67 staining percentage between the strata $$(P = 1.2 \times 10 - 3)$$

Figure 9D:
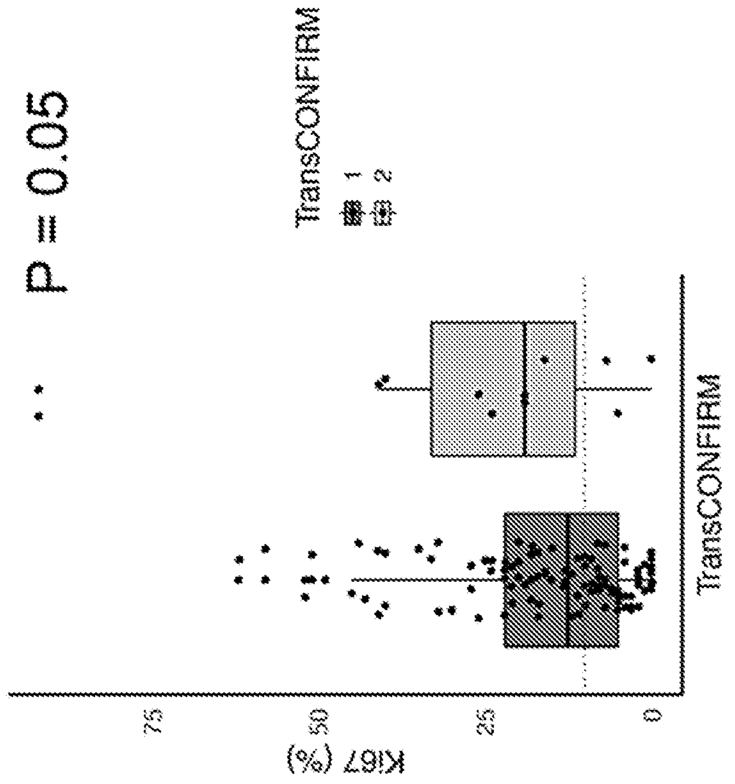
Figure 9C:
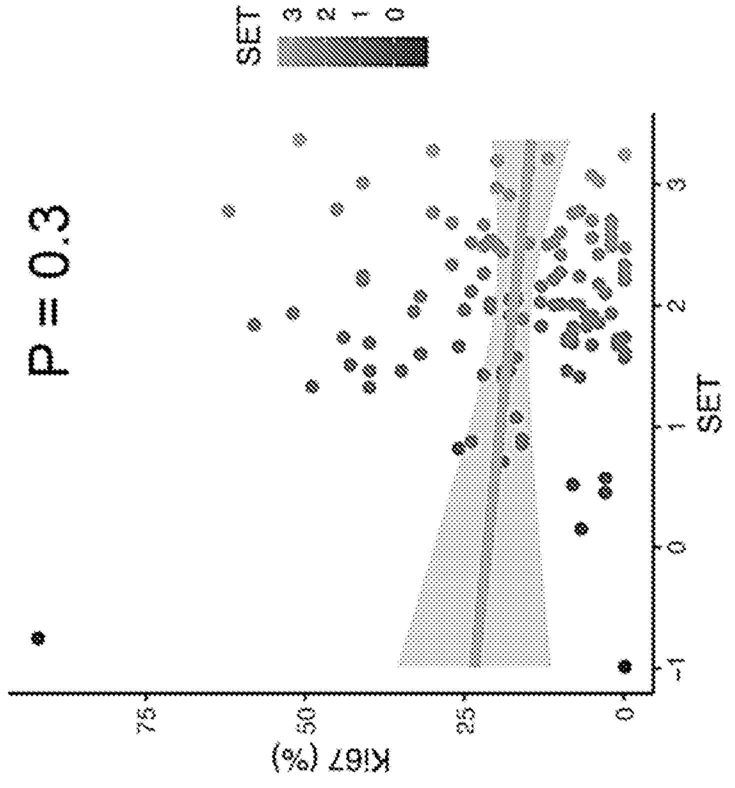

(FIG. 9B). However, the SET score was not correlated with Ki67 staining (P=0.3) (FIG. 9C). The TransCONFIRM score that was developed on this dataset was significant (P=0.05) but performed worse than the ENDORSE score trained on an independent dataset.

Figure 10A:
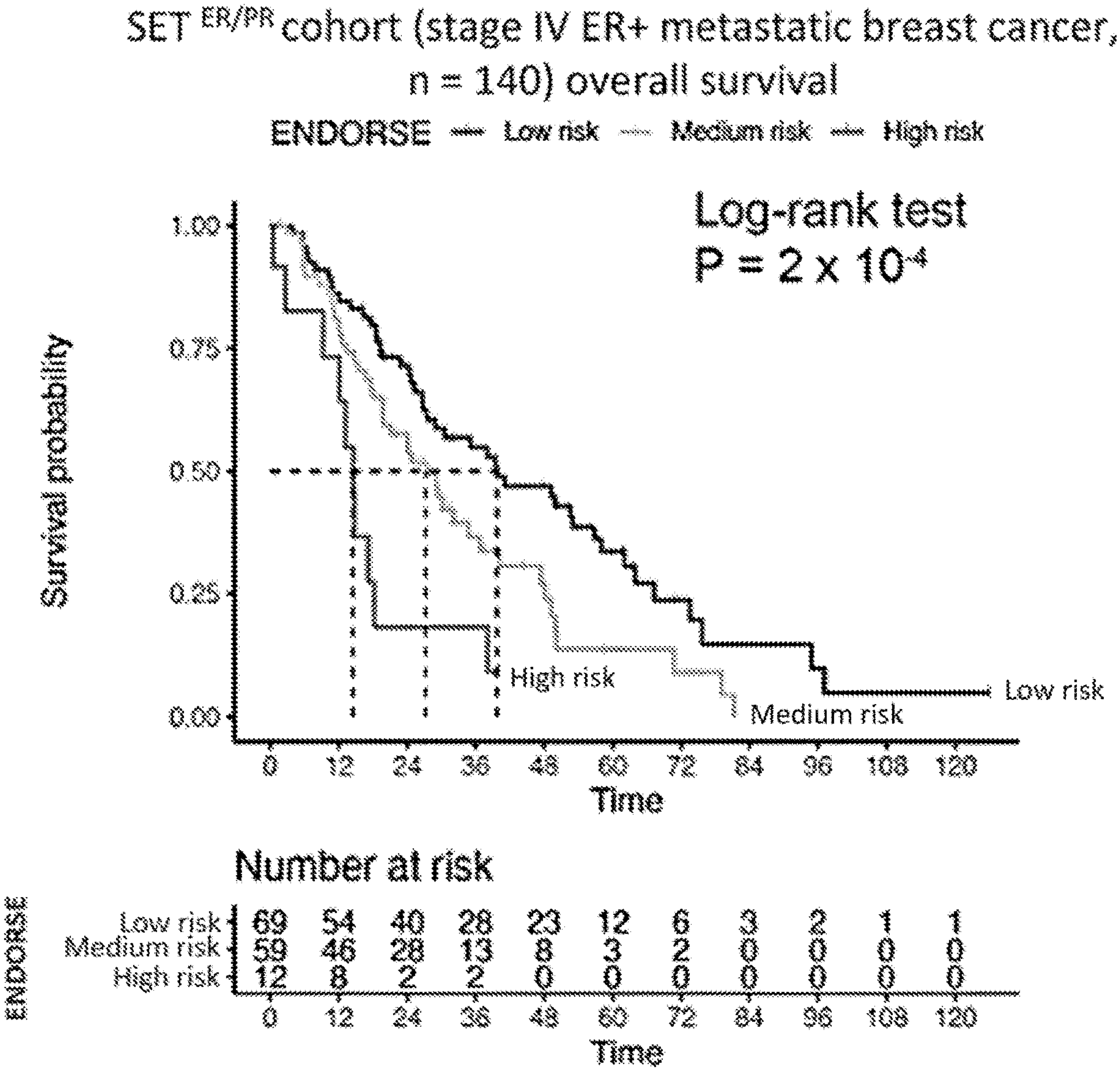
Figure 10B:
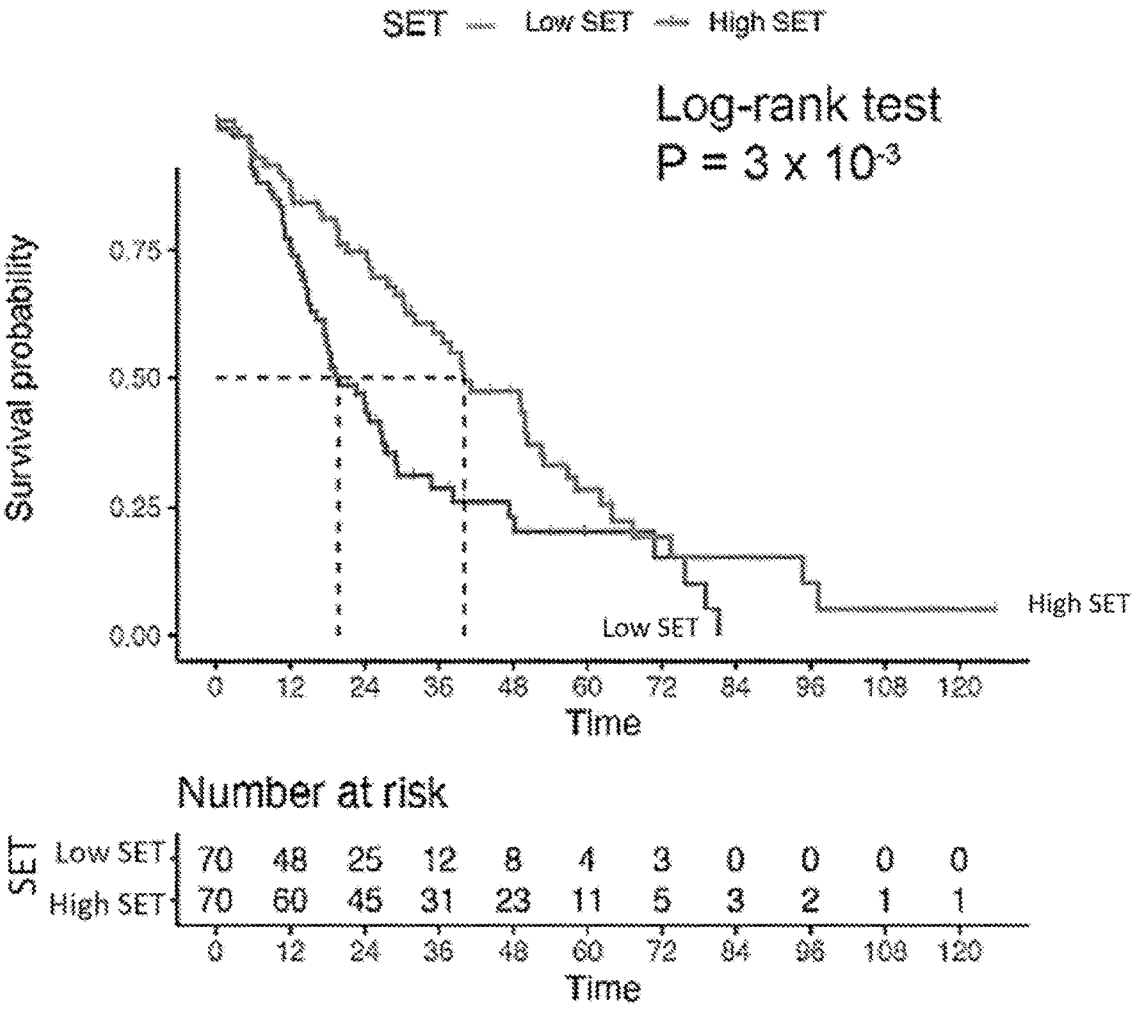

Next, we evaluated the performance of the signatures in the $SET_{ER/PR}$ cohort. This clinical trial reported the PFS and OS of 140 stage IV ER+ metastatic breast cancers on endocrine therapy. We compared the survival curves of the patients by stratifying them based on the ENDORSE predicted risk, median SET scores, as described in the original study, and the TransCONFIRM score. The stratification based on ENDORSE (FIG. 10A) and SET (FIG. 10B) scores both resulted in significant differences in the survival curves $$(\text{ENDORSE } P = 2 \times 10^{-4,} \text{ SET } P = 3 \times 10^{-3}).$$

Figure 10C:
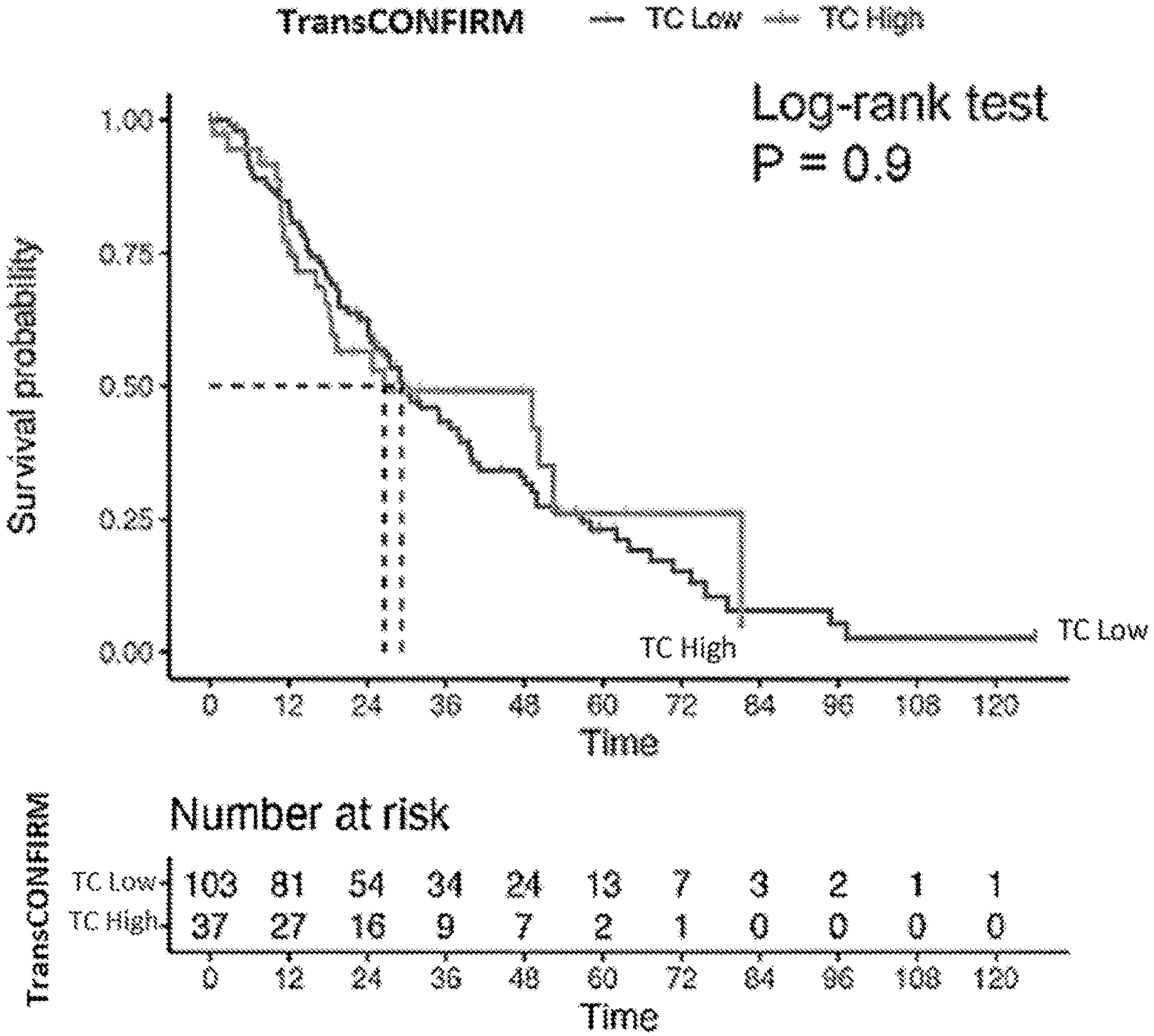
Figure 10D:
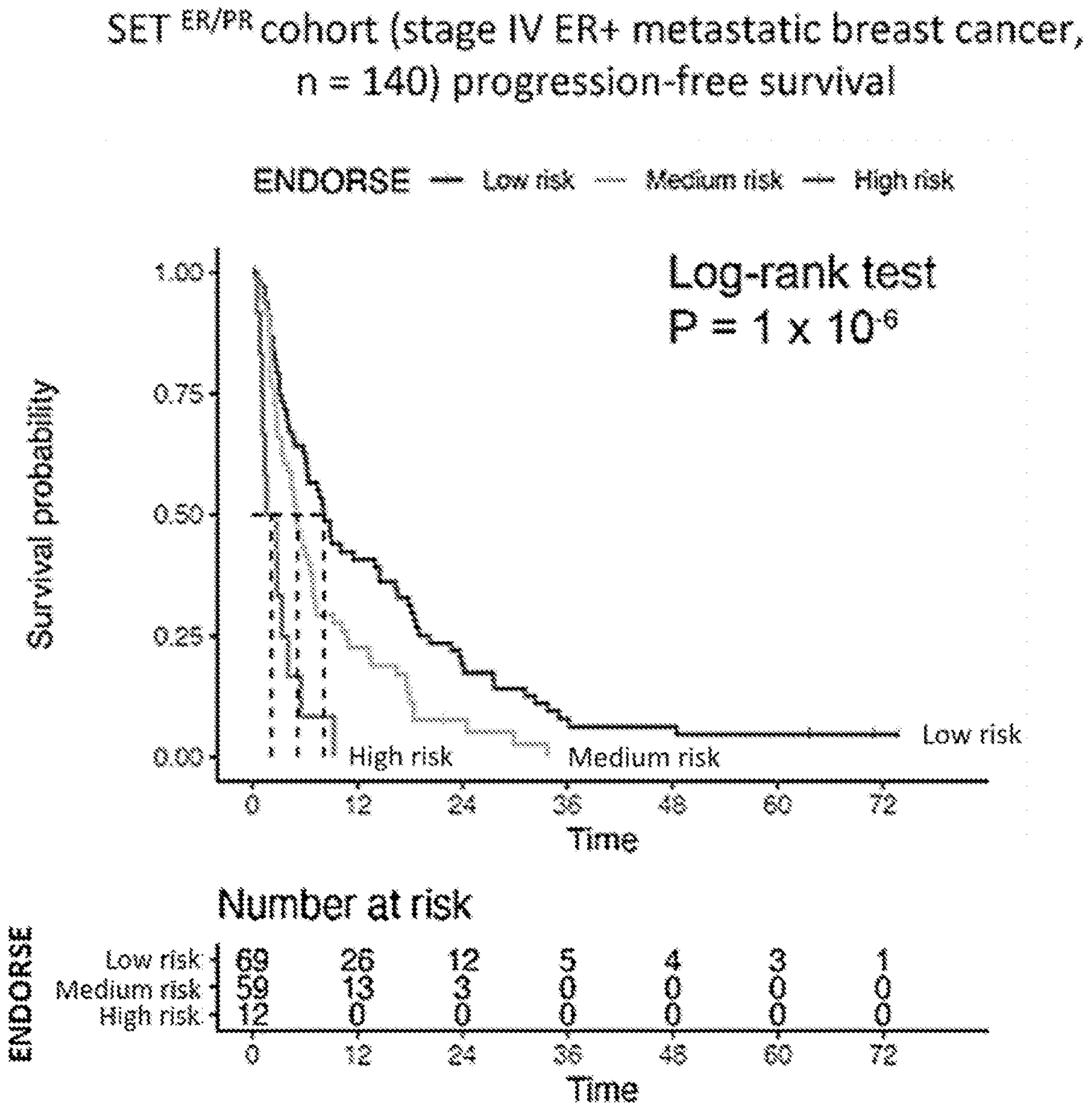
Figure 10E:
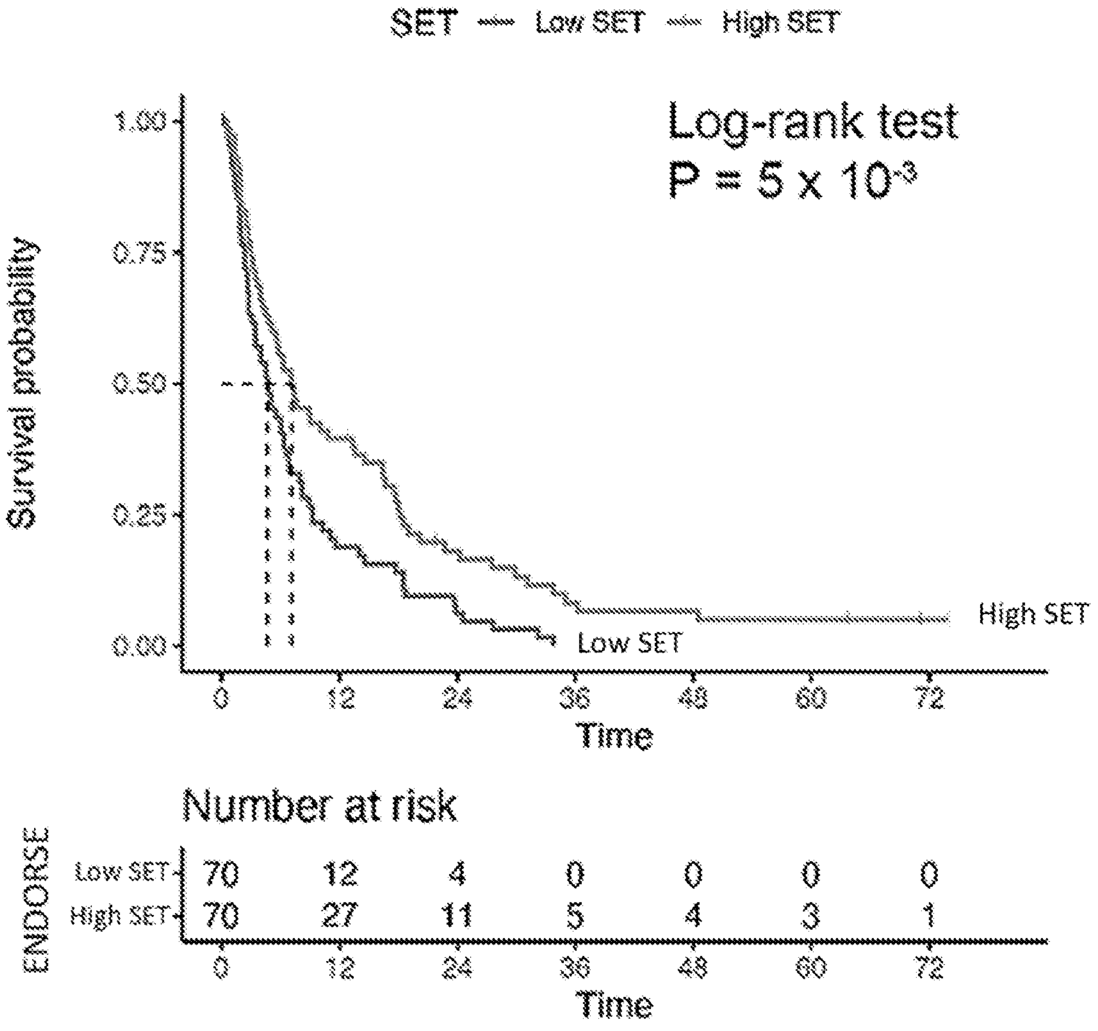
Figure 10F:
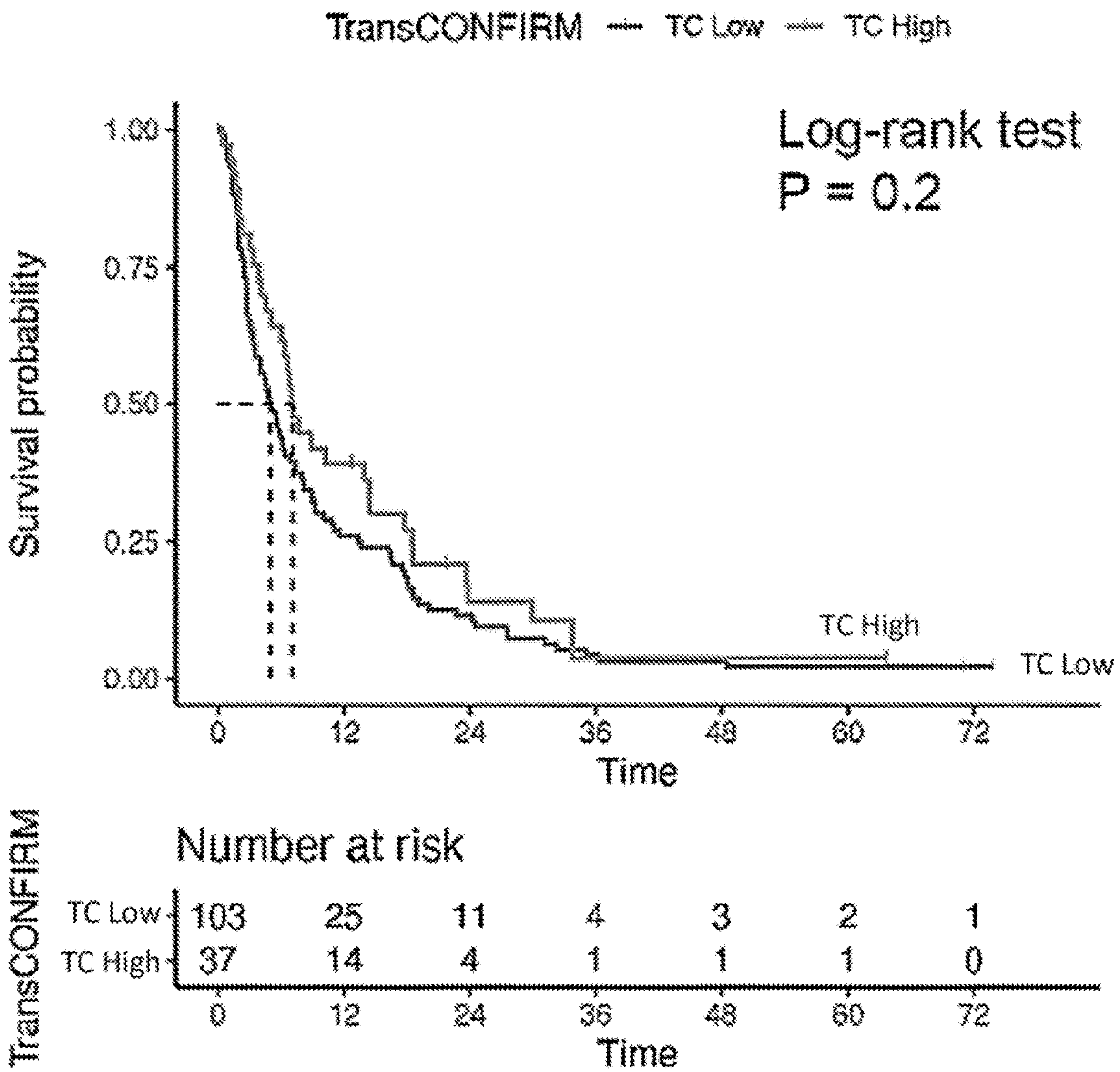

However, the TransCONFIRM score (FIG. 10C) was not significant (P=0.9). Similarly, we observed that ENDORSE (FIG. 10D) and SET (FIG. 10E) scores both resulted in significant differences in the PFS curves $$(\text{ENDORSE } P = 1 \times 10^{-6,} \text{ SET } P = 5 \times 10^{-3}),$$

while TransCONFIRM was not significant (P=0.2). Additionally, we compared the model fits using partial likelihood ratio tests. The SET model that was trained using the same dataset was not a better fit than the ENDORSE mode (OS P=0.667, PFS P=0.258). The ENDORSE model was a better fit than the TransCONFIRM model in each case (OS P=0.046, PFS P=0.038).

In addition to the two metastatic ER+ breast cancer trials, we also evaluated the performance of the signatures examined data from the ACOSOG Z1031B clinical trial which evaluated neoadjuvant aromatase inhibitor (AI) treatment in Stage II or III ER+ breast cancers[31]. This study reported percentage of Ki67 staining both at the study baseline and at the end of treatment (2-4 weeks). We compared the percentage of Ki67 positive cells across cancers stratified by the ENDORSE score and found significant difference across the classes at both the baseline $$(P = 4.9 \times 10^{-9})$$

and at the end of treatment $$(P = 3 \times 10^{-18})$$

Figure 11A:
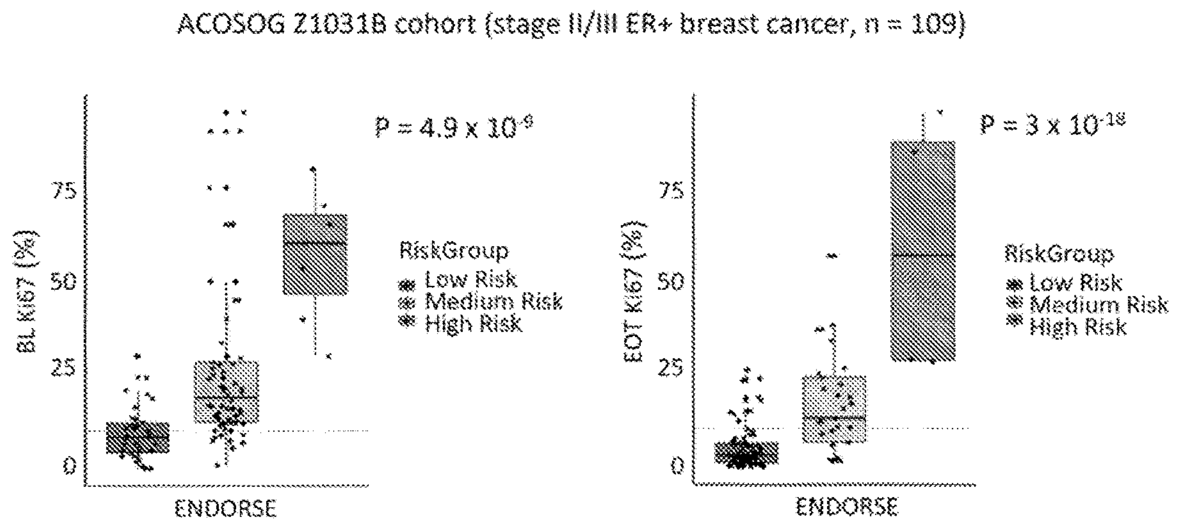
FIGS. 11A-11G. Model validation in ACOSOG Z1031B cohort.

(FIG. 11A). Similarly, the continuous ENDORSE scores were significantly correlated with both the baseline $$(P = 3.3 \times 10^{-15})$$

and end of treatment $$(P = 1.1 \times 10^{-17})$$

Figure 11B:
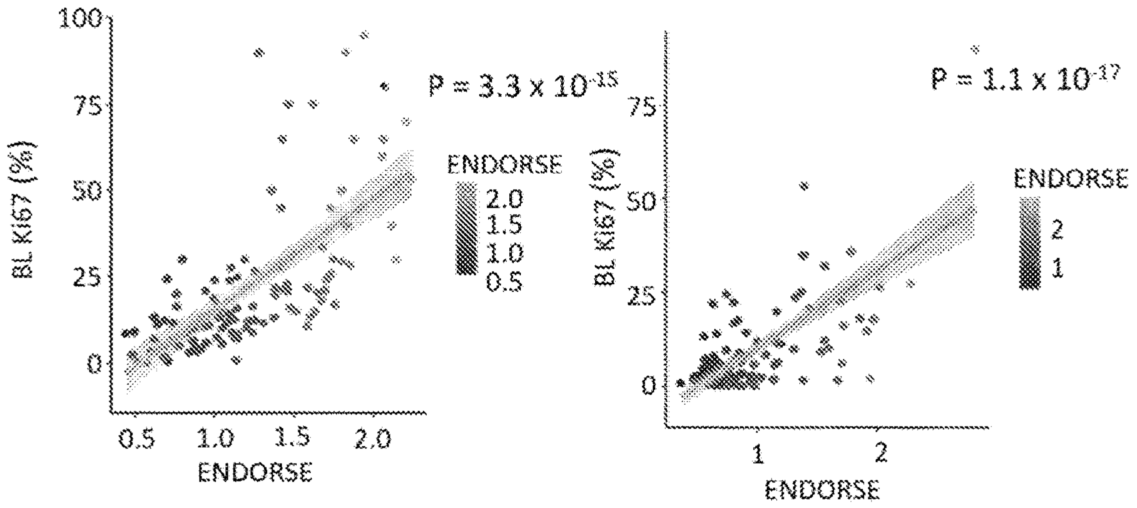

Ki67 percentage (FIG. 11B). The ENDORSE scores were also significantly higher in the tumors that were classified as resistant based on clinical response $$(P = 4.6 \times 10^{-6})$$

Figure 11C:
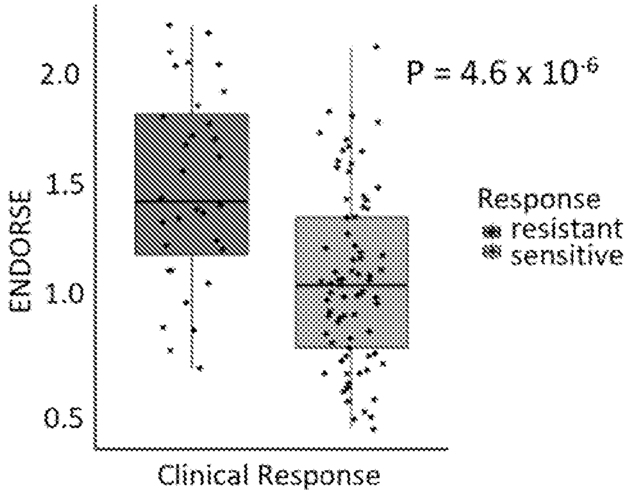

(FIG. 11C). In this cohort, the SET score was also significantly correlated with Ki67 percentage at the baseline $$(P = 2.8 \times 10^{-5})$$

and end of treatment $$(P = 2.2 \times 10^{-4})$$

Figure 11D:
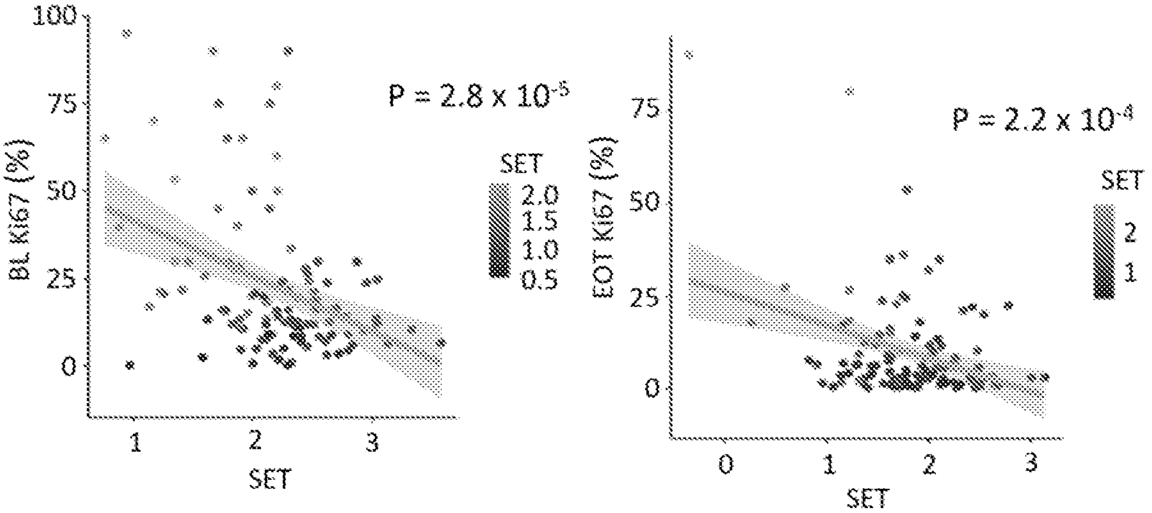
Figure 11E:
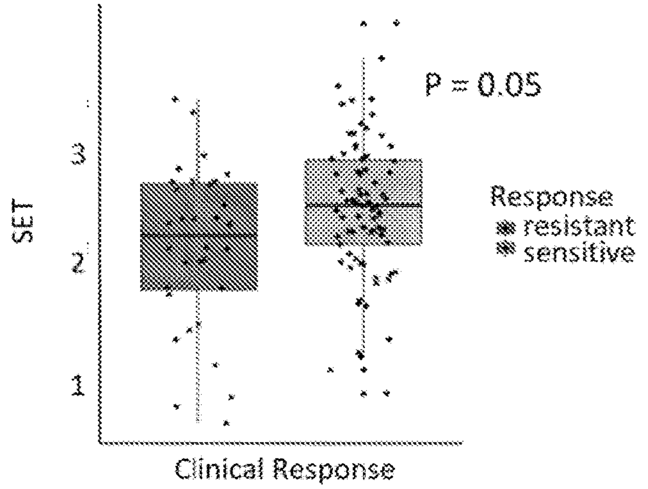
Figure 11F:
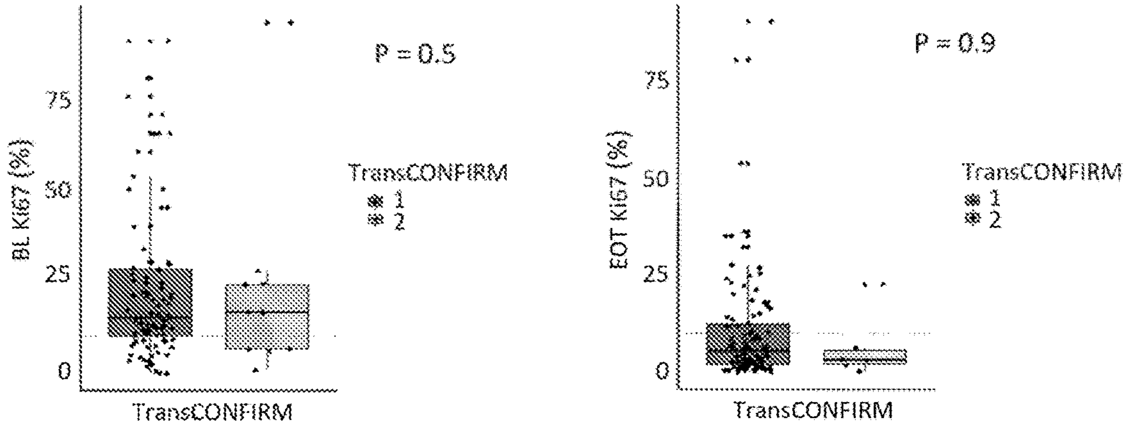
Figure 11G:
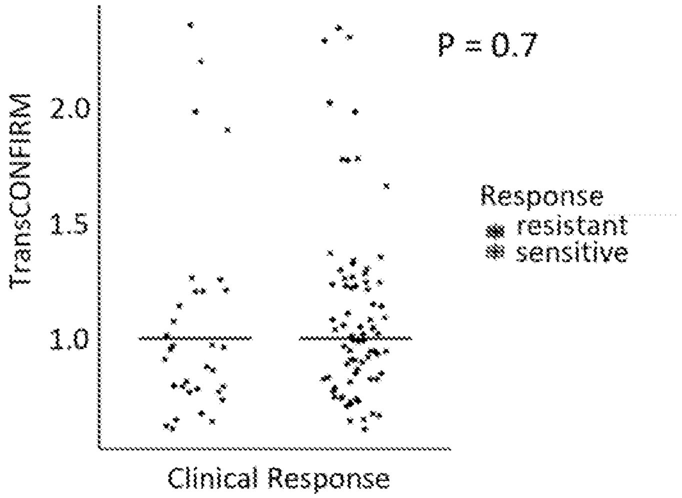

(FIG. 11D), with significant difference in the SET scores between the resistant and sensitive tumors (P=0.05) (FIG. 11E). The transCONFIRM scores were not significant at the baseline (P=0.5) and end of treatment (FIG. 11F) or between resistant and sensitive tumors (P=0.7) (FIG. 11G).

In addition to the endocrine therapy trials in ER+ breast cancer, we also applied the ENDORSE risk estimates to stratify 429 ER-negative METABRIC breast cancers as negative controls. Kaplan-Meier analyses show no significant difference between the strata (P=0.26). This suggests that the ENDORSE model is specific to the ER+ cohort and not a general prognostic model.

We analyzed the pathway phenotypes enriched in each dataset to identify potential mechanisms that defined the high-risk tumors. First, we calculated the GES for 50 hallmark, 4690 curated and 189 oncogenic signatures from the METABRIC transcriptomes and fitted a generalized additive model for ENDORSE scores with each signature as the predictor (Tables 14 and 15).

Figure 12A:
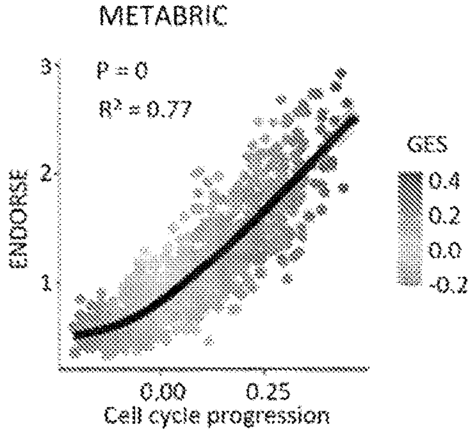
FIGS. 12A-12L. Biology of the high-risk tumors.

We found multiple hallmark signatures and oncogenic pathways to be significantly associated with the ENDORSE scores (Tables 14 and 15). Key enriched hallmark signatures included MTOR signaling ($P=1.03\times10^{-72}$) and MYC targets (v2, $P=2.66\times10^{-83}$), while key oncogenic signatures included gain in E2F1 target expression ($P=8.06\times10^{-302}$) and loss of RB1 activity via p107 and p130 ($P=9.51\times10^{-137}$, $1.31\times10^{-67}$) (Tables 14 and 15). Next, we calculated the GES for the hallmark and oncogenic signatures in the three validation datasets (Tables 16-21). We observed that pathways associated with cell-cycle progression and proliferation, along with signatures for the loss of RB-1 activity and activation of the PI3K/AKT/MTOR signaling pathways were generally enriched across the METABRIC and all the three validation datasets (FIG. 12A). Similar to the training dataset, we also found gain in cell cycle progression along with MTOR signaling and E2F1 target expression to be associated with high ENDORSE scores across all datasets (FIG. 12A, Tables 16-21). The commonality of the signatures enriched across different datasets suggested similar underlying phenotypes were acquired by the high-risk tumors.

Figure 12B:
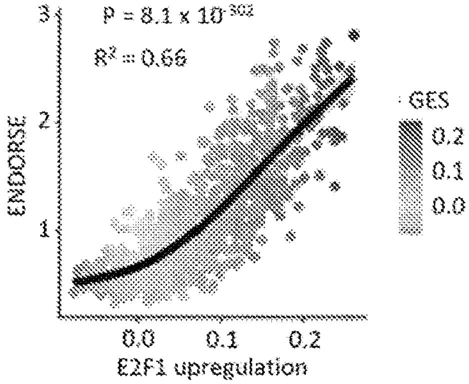

We also analyzed the association between gene-level somatic mutations, including non-synonymous single-nucleotide variants (SNV) and copy number alterations, with the ENDORSE scores of the METABRIC ER+ tumors. We found a statistically significant association (FDR<0.05) between the ENDORSE scores and SNVs of only five genes (FIG. 12B, Table 22). While PIK3CA mutations were found in ~50% of all tumors, we found that ENDORSE scores were not significantly higher in tumors with non-synonymous PIK3CA variants or activating PIK3CA variants that guide the use of PI3K inhibitors. Of the five significant genes, only tumors with TP53 mutations showed a significantly higher ENDORSE score (FIG. 12B). We then performed bootstrap analyses with the univariate Cox models of the significant genes and found that none of the SNV Cox models performed better than the ENDORSE model (FIG. 12B).

Figure 12C:
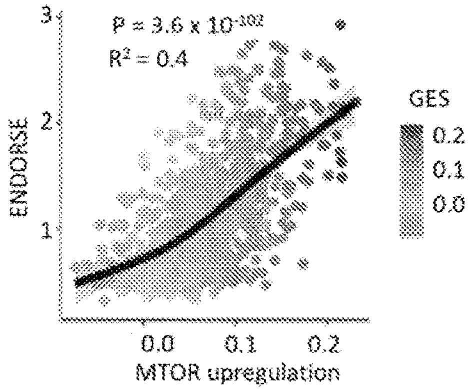
Figure 12D:
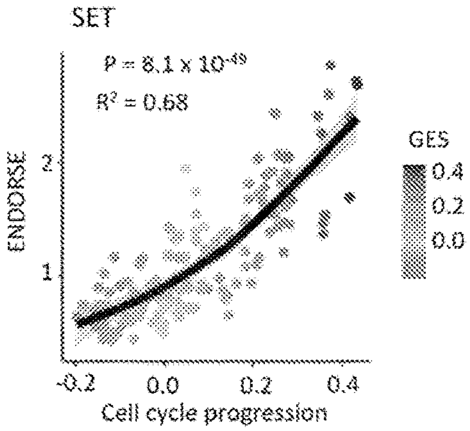
Figure 12E:
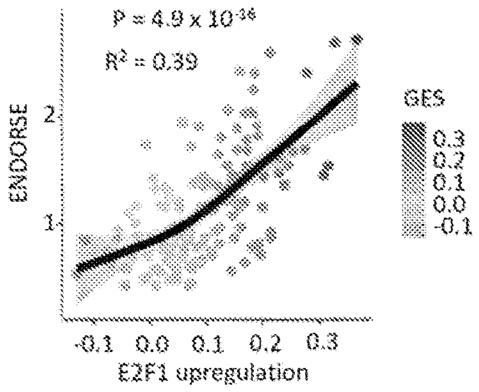
Figure 12F:
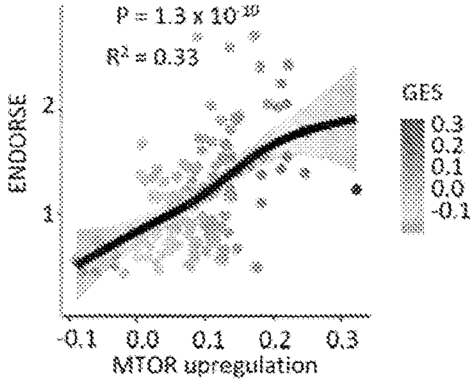
Figure 12G:
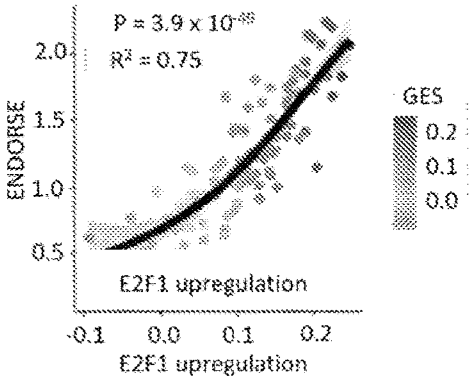
Figure 12H:
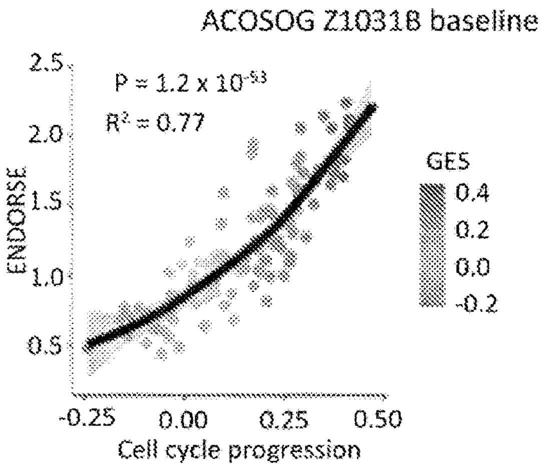
Figure 12I:
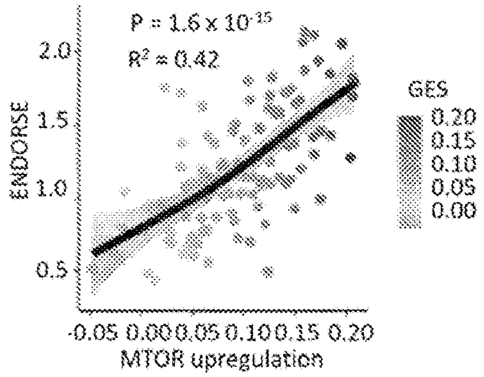
Figure 12J:
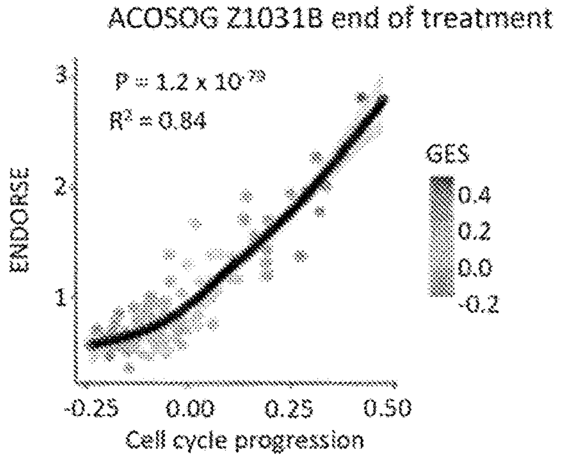
Figure 12K:
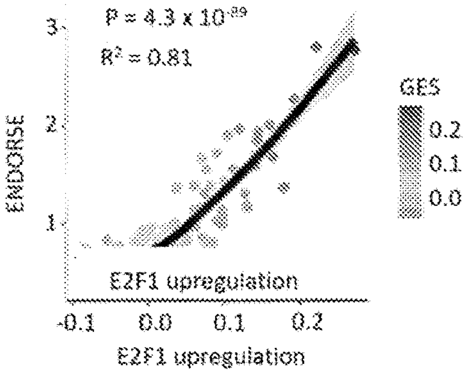
Figure 12L:
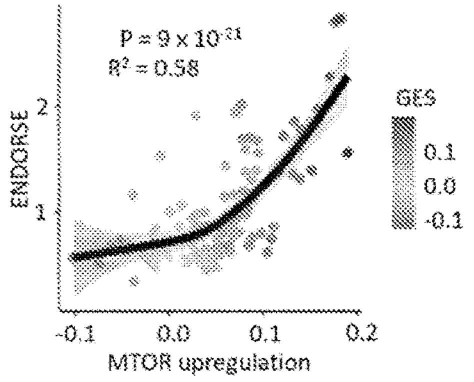
Figure 12M:
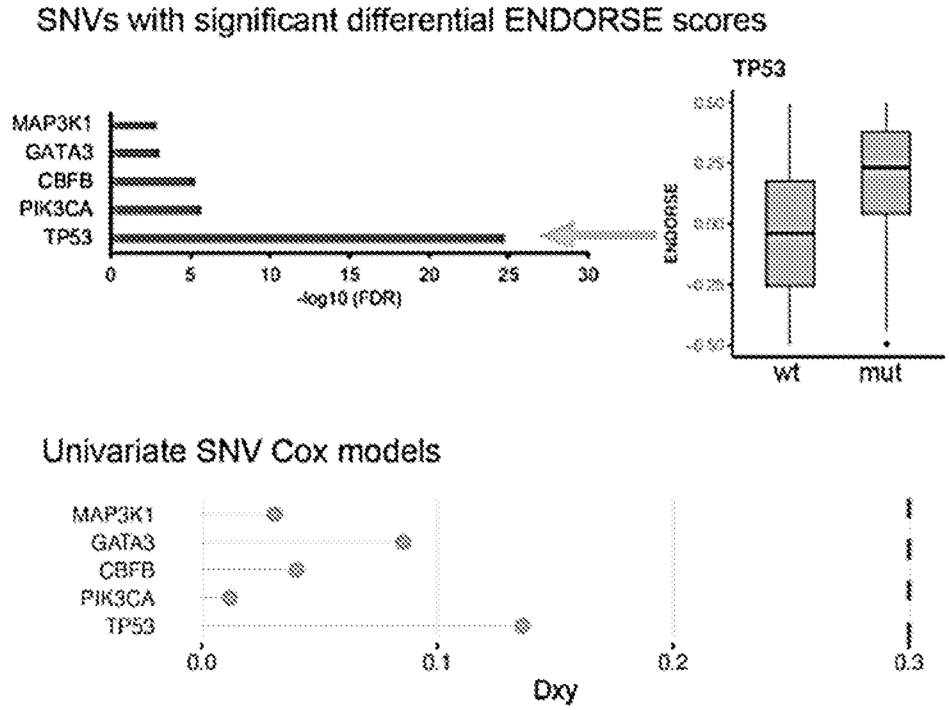
FIG. 12M. Barplots showing p-values from the ANOVA analysis of ENDORSE scores with mutation status as the grouping variable. The boxplot on the right shows difference in the ENDORSE scores between TP53 mutant and wildtype tumors. The lollipop plot below shows Somer's $D_{xy}$ of the univariate Cox models for the SNVs, with the vertical dotted line indicating $D_{xy}$ of the ENDORSE model.
Figure 12N:
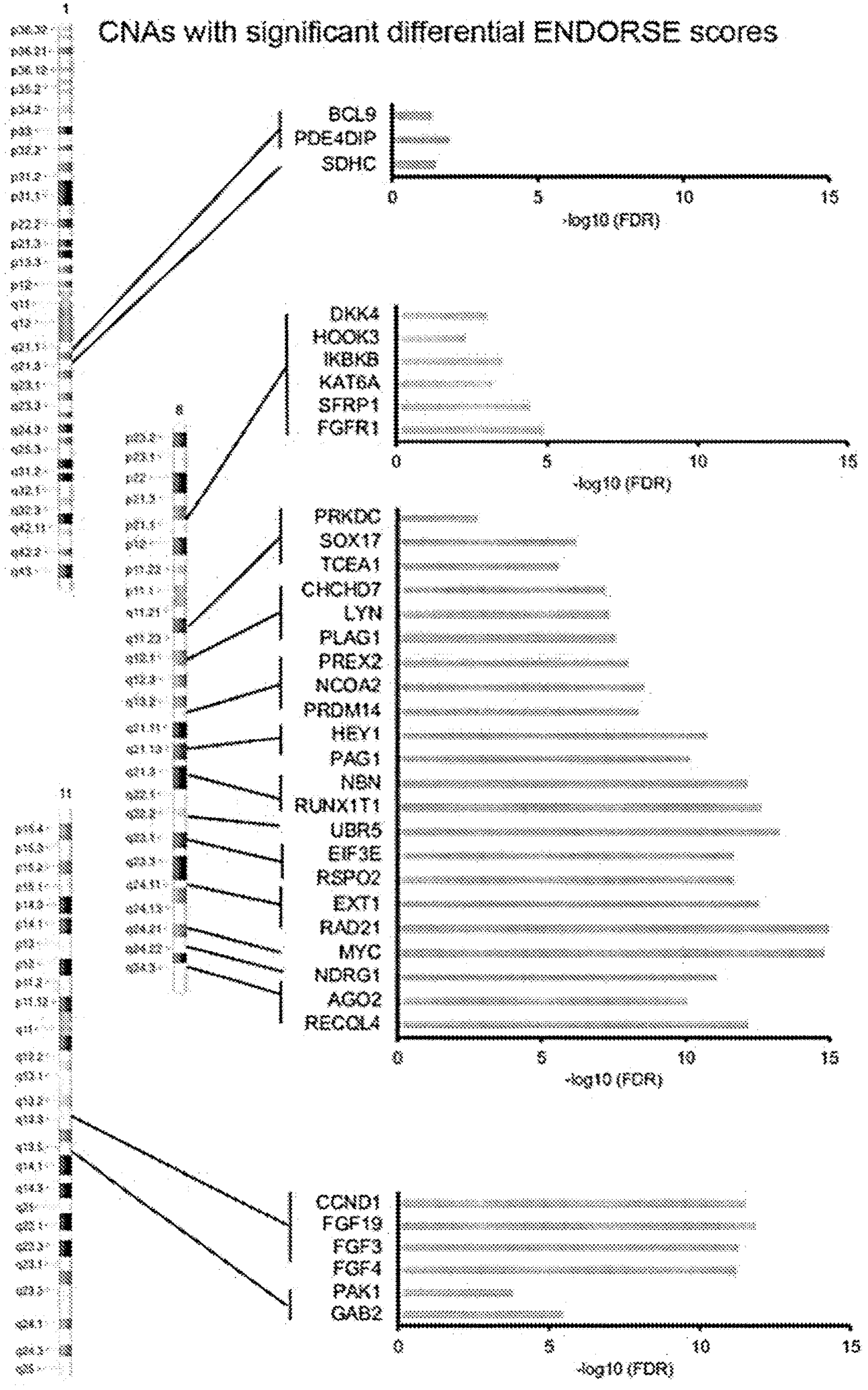
FIG. 12N. Ideograms showing mapped regions with copy number gains that are significant in ANOVA analysis of ENDORSE scores with copy number gain status as the grouping variables. Barplots on the right show p-values from the ANOVA analysis.
Figure 12O:
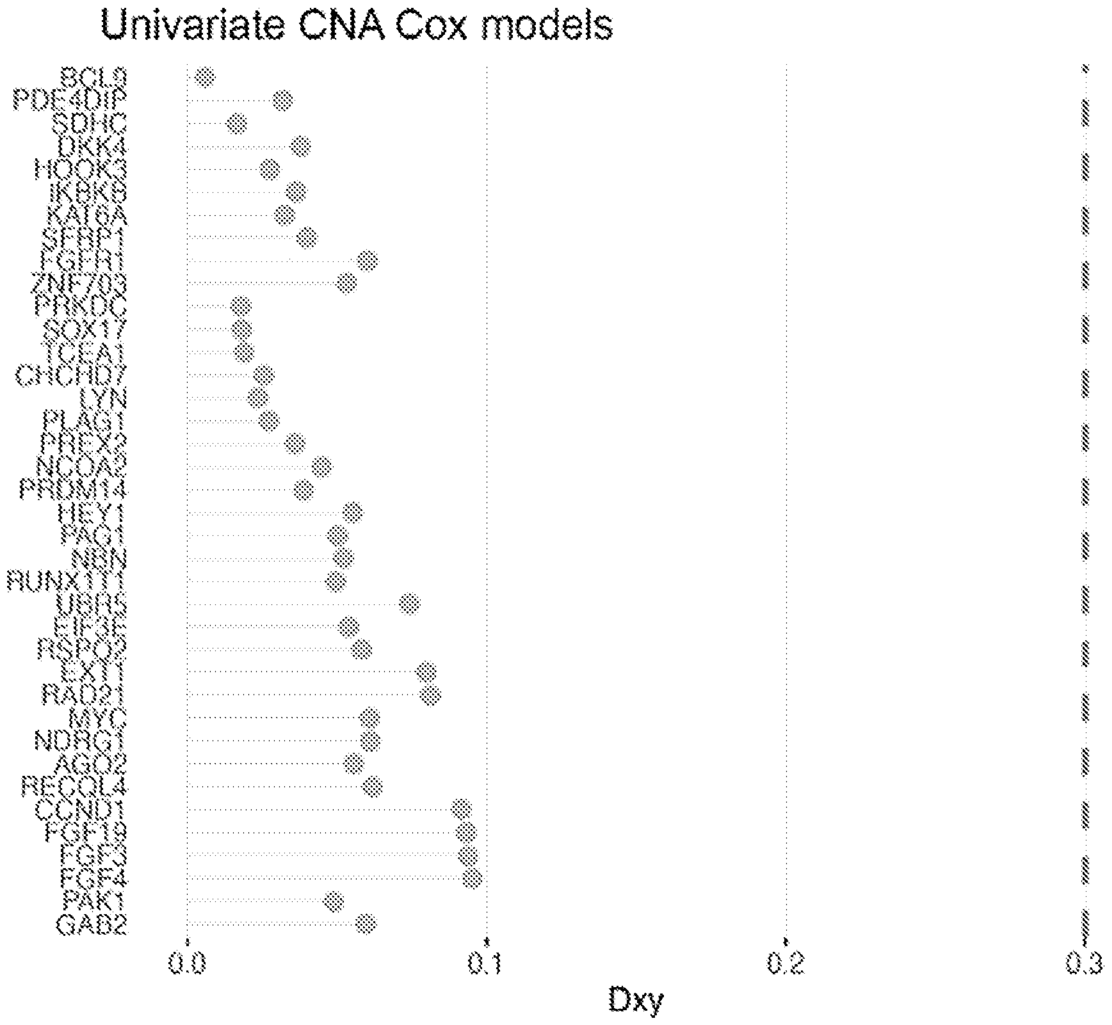
FIG. 12O. Lollipop plot showing Somer's $D_{xy}$ of the univariate Cox models for the copy number gains, with the vertical dotted line indicating $D_{xy}$ of the ENDORSE model.
Figure 13A:
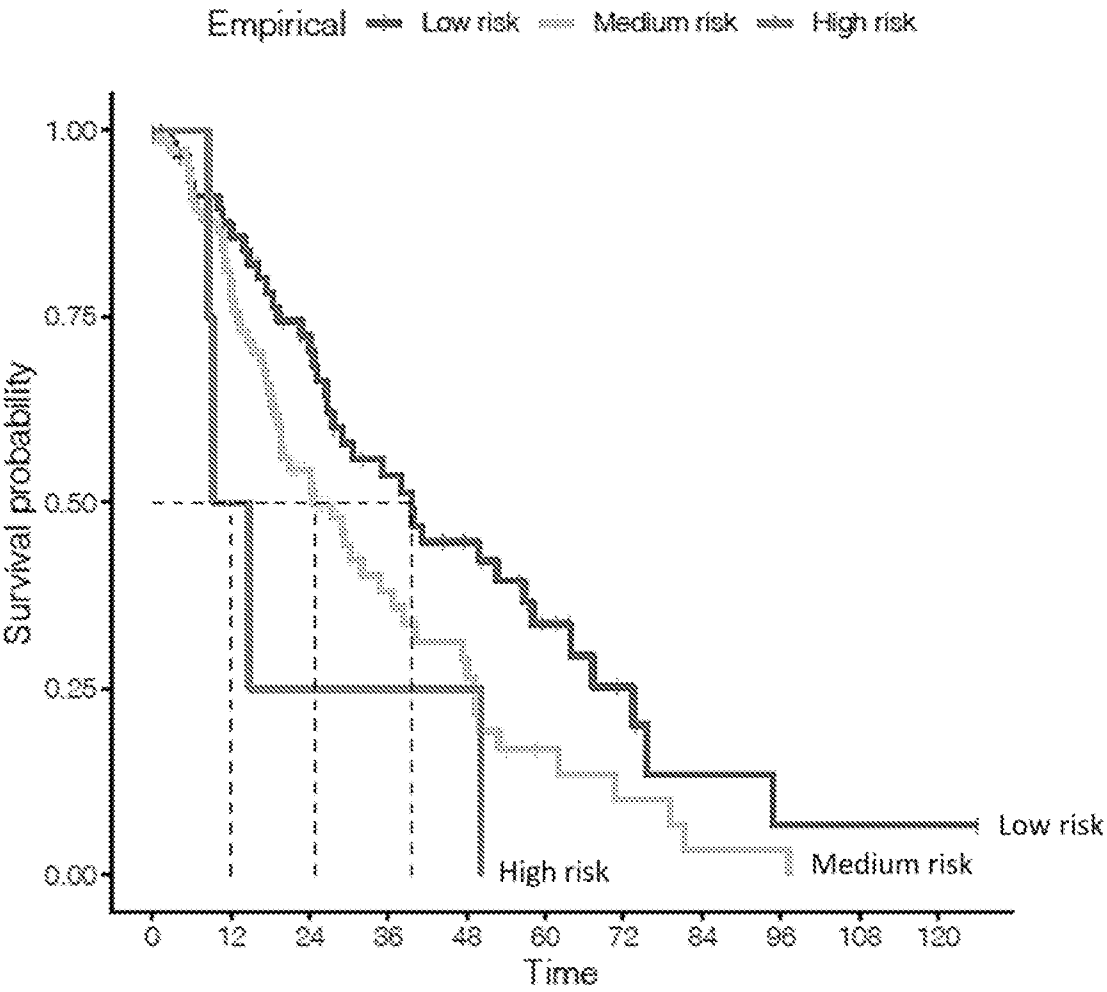
FIGS. 13A-13D. Comparison of the ENDORSE model components in the $SET_{ER/PR}$ cohort.
Figure 13B:
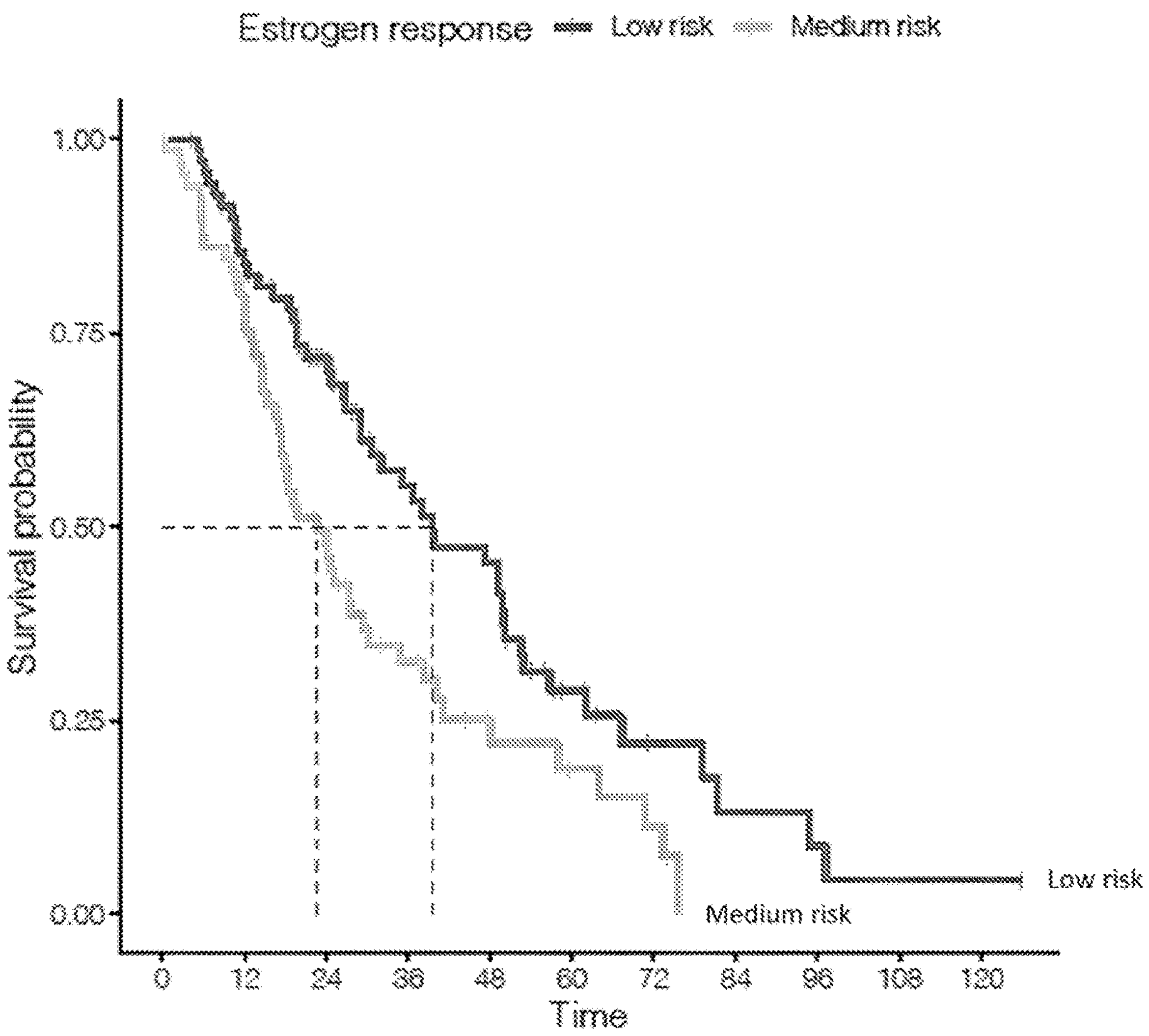
Figure 13C:
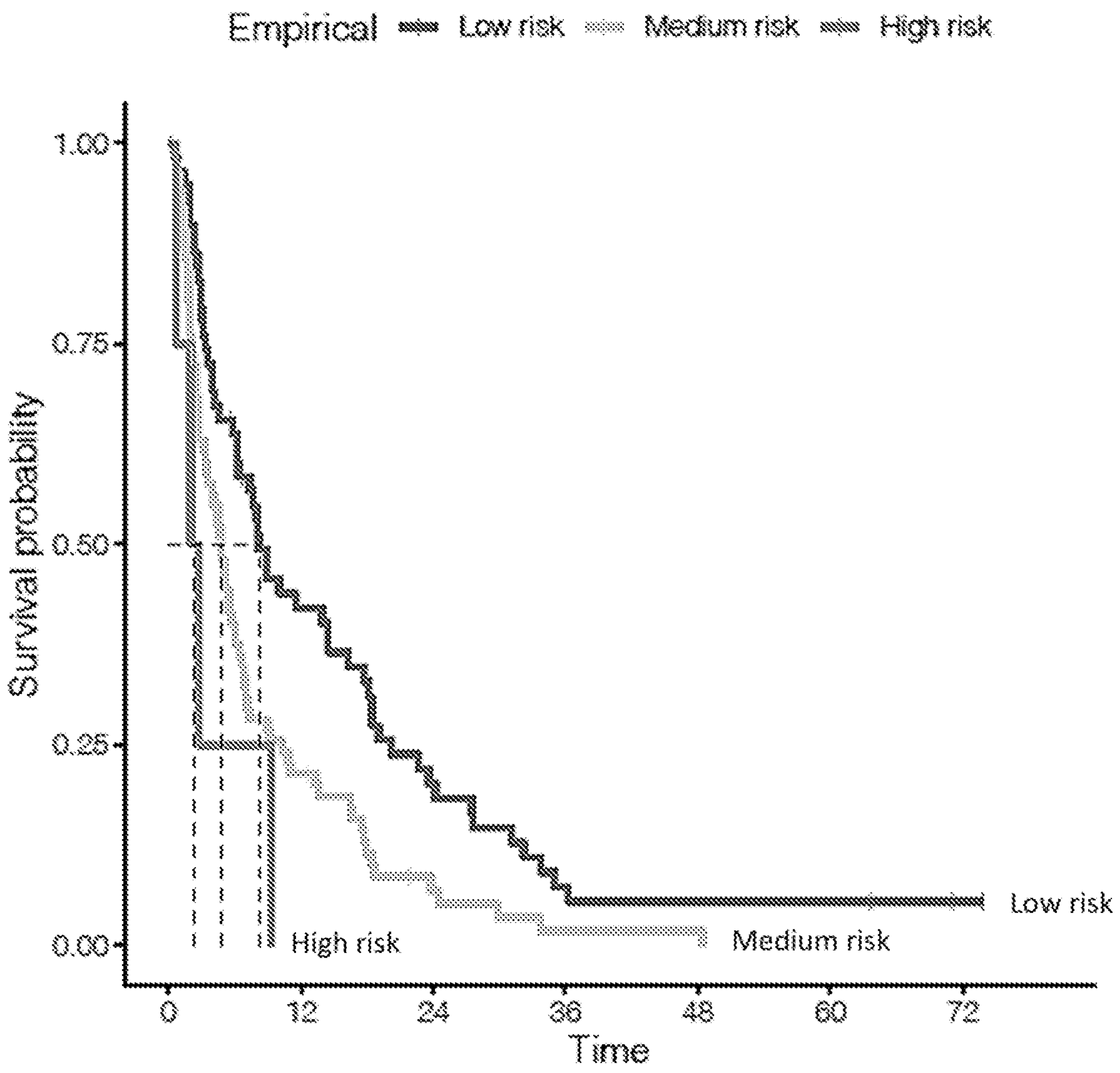
Figure 13D:
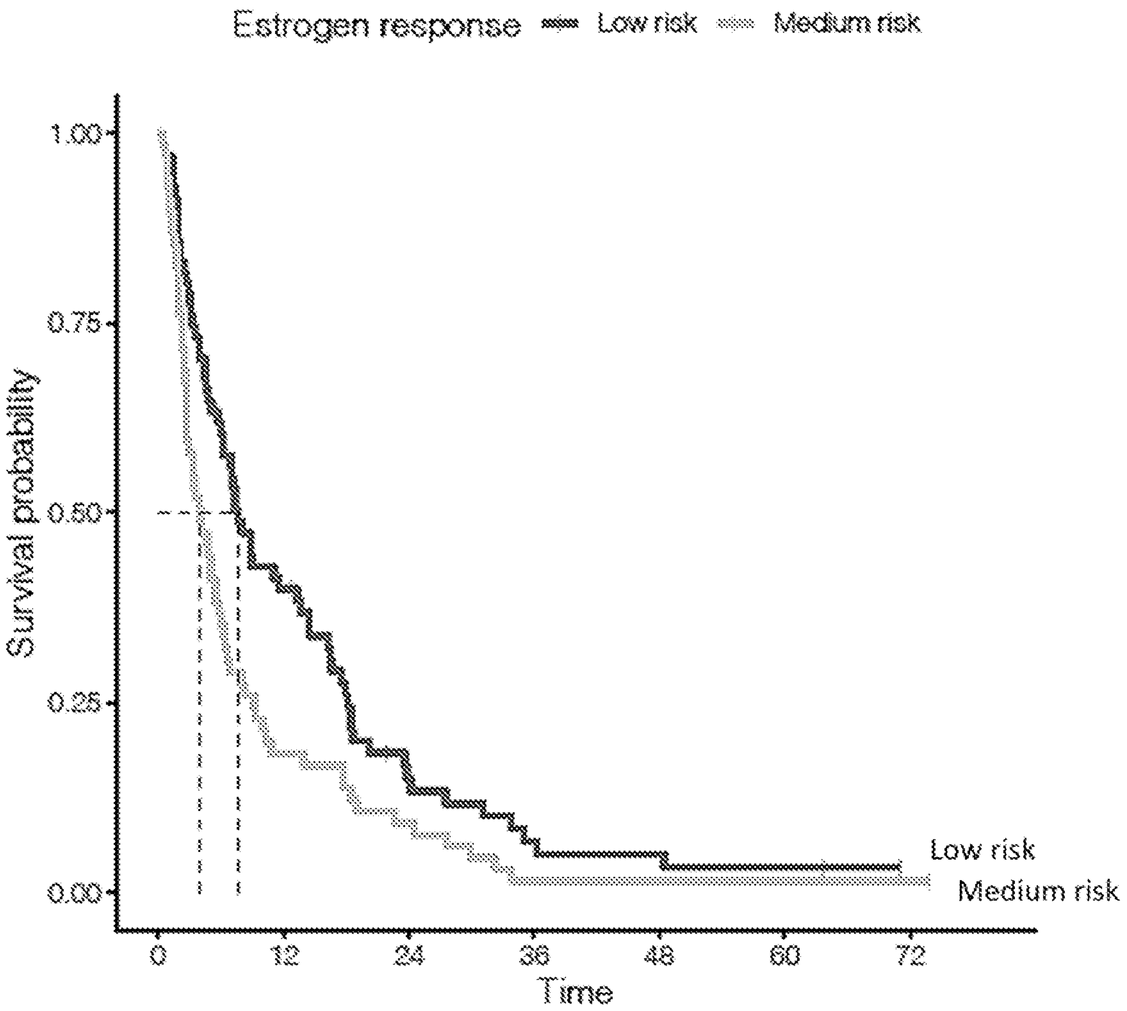
Figure 14A:
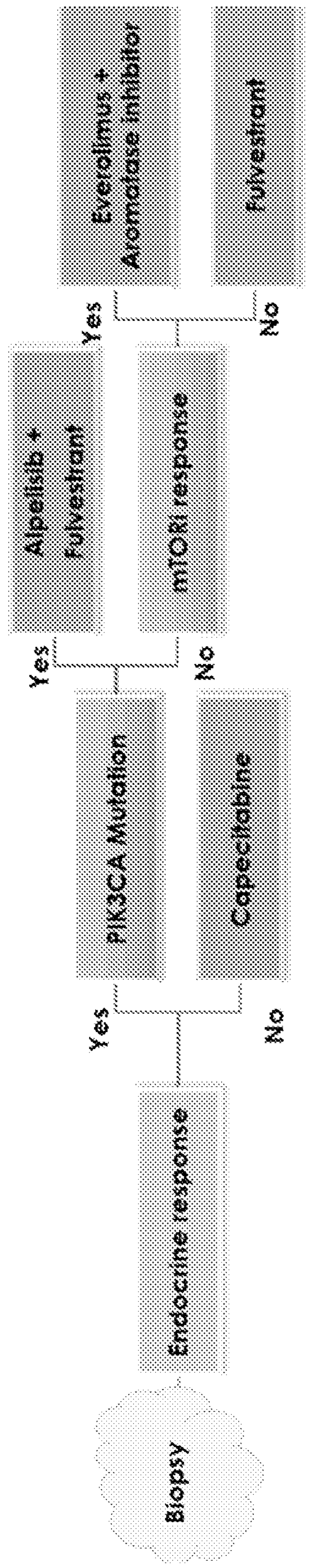
Figure 14B:
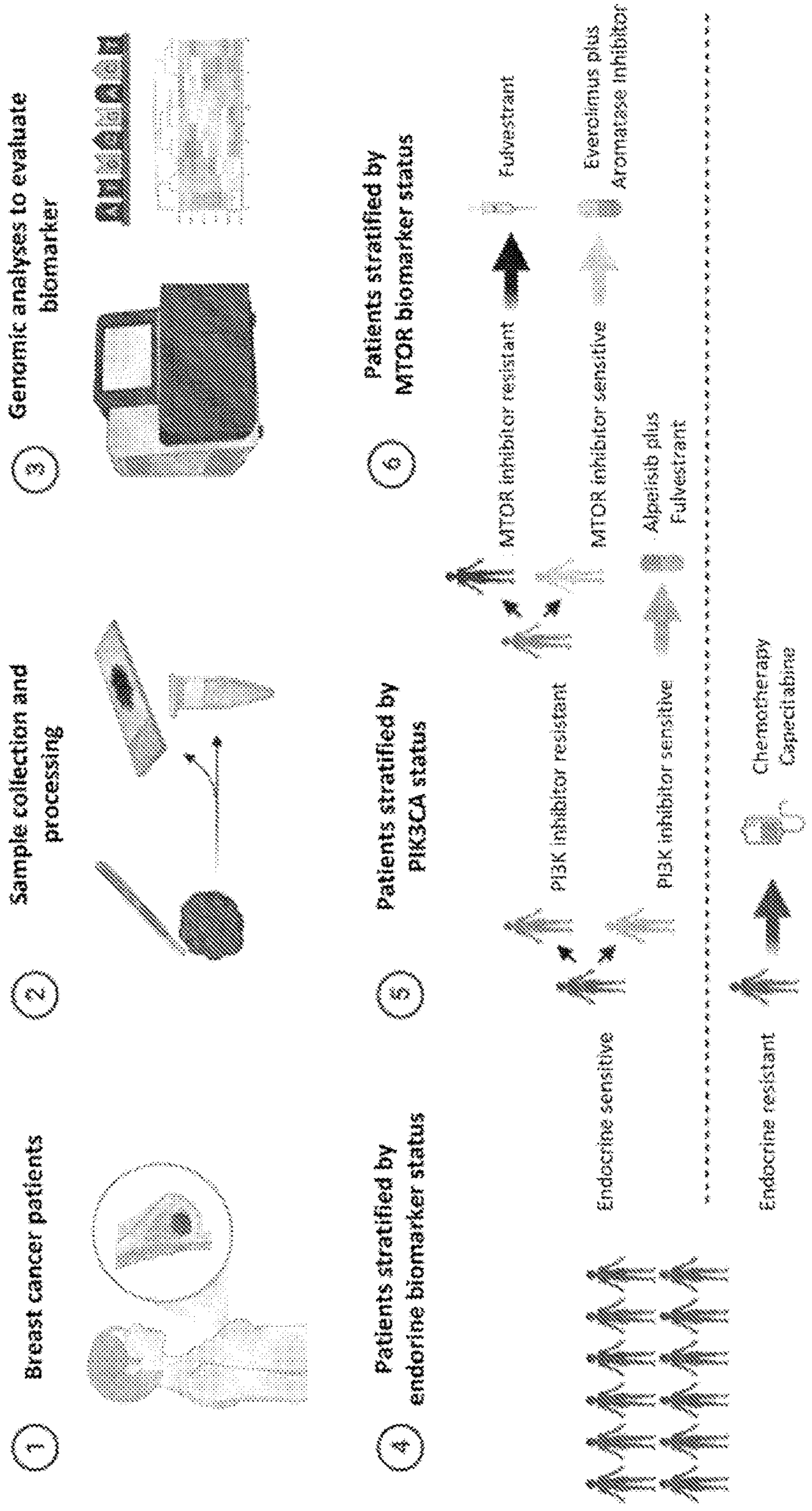
Figure 14C:
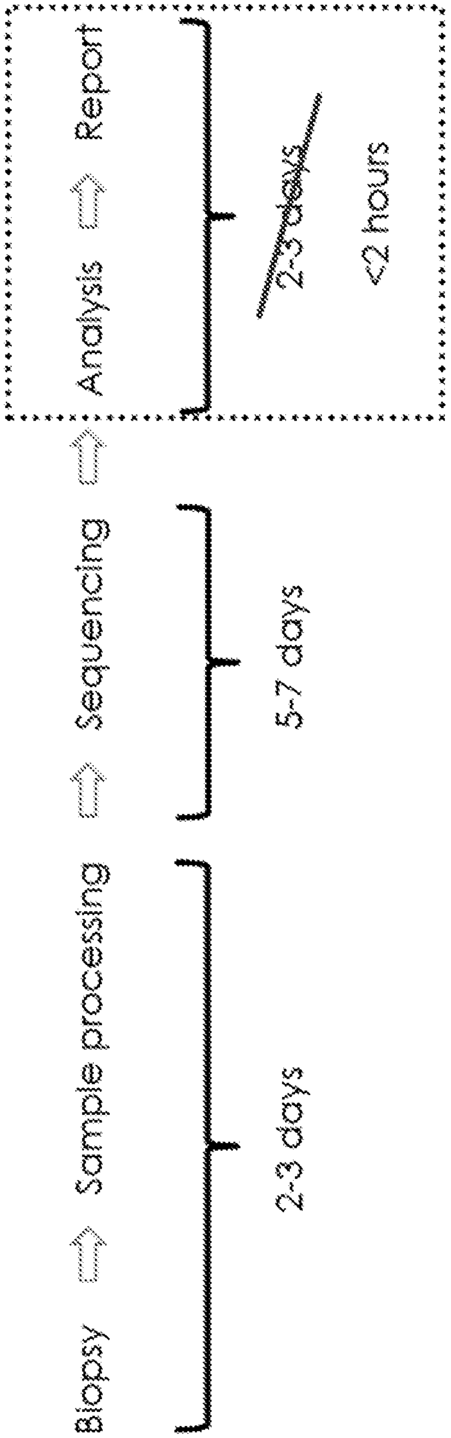
Figure 14D:
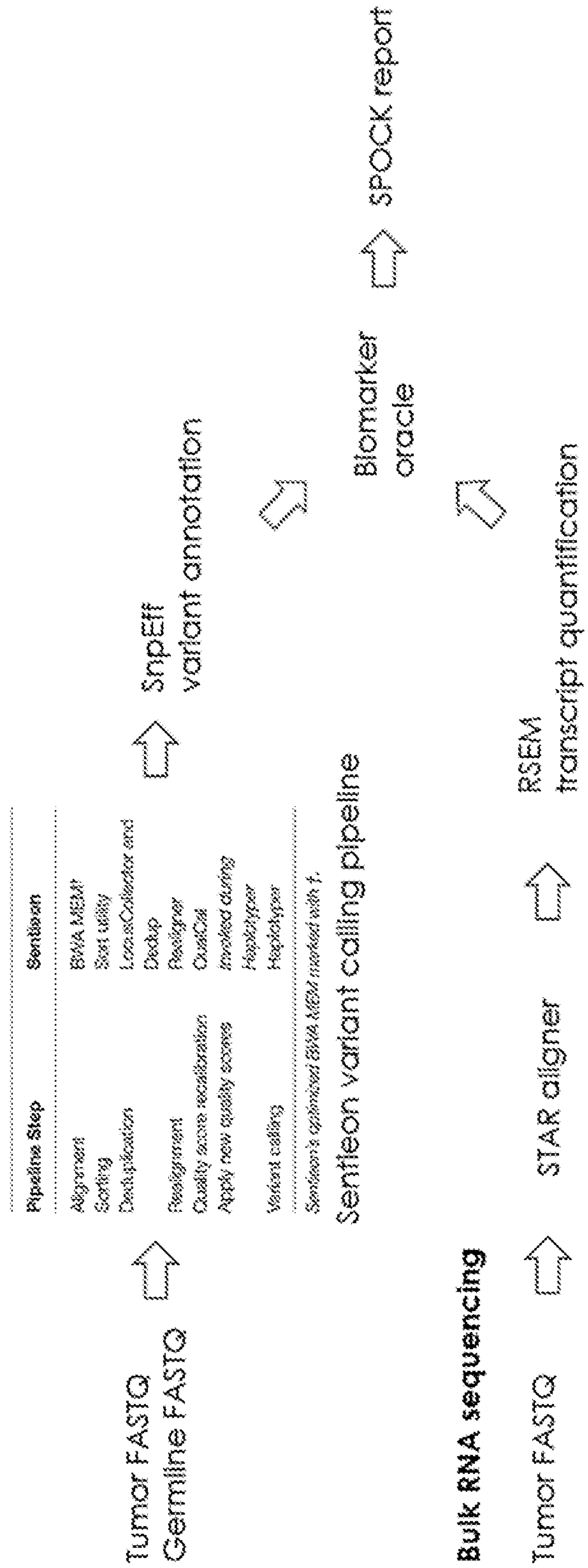
Figure 14E:
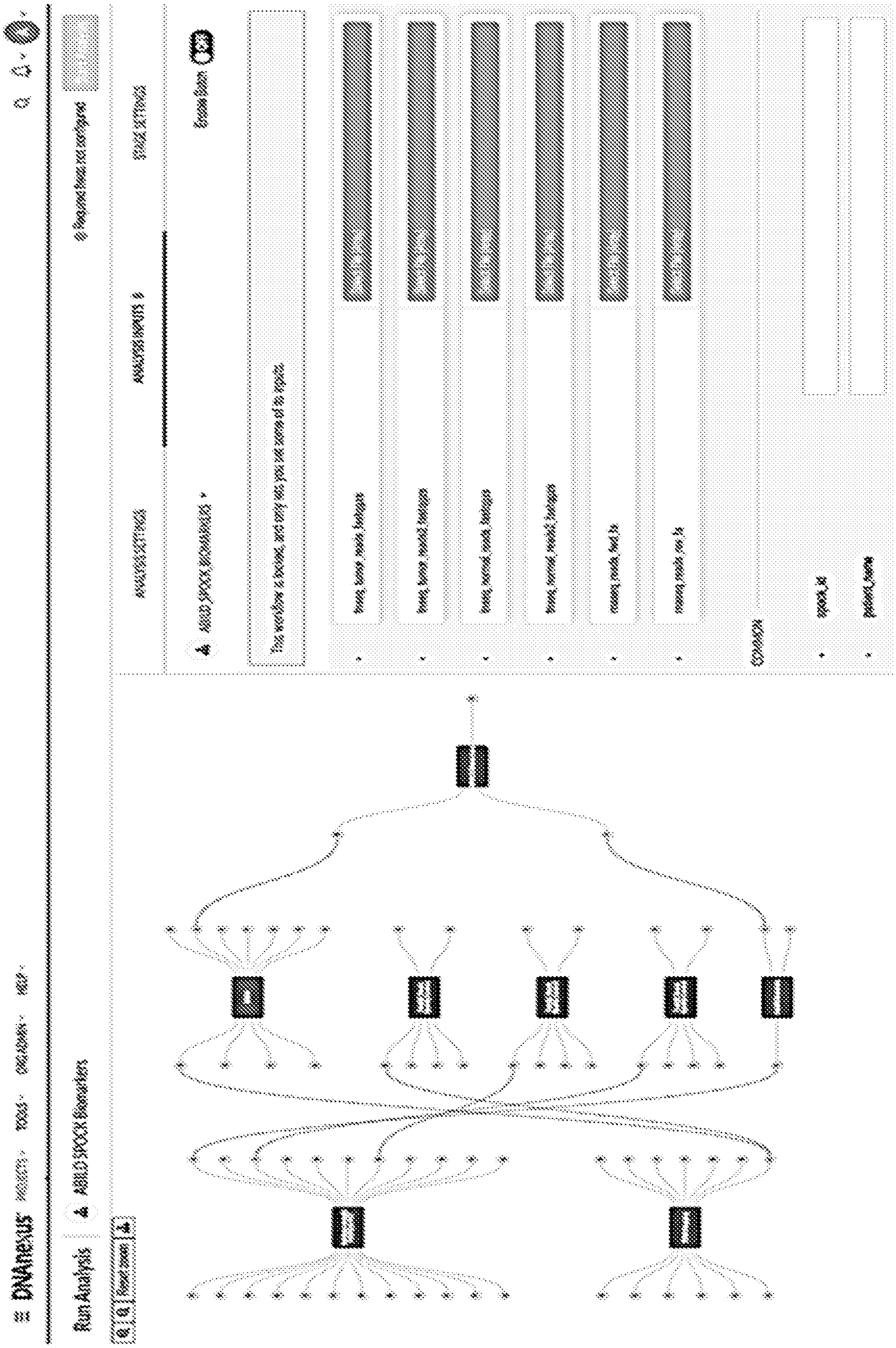
Figures 15A, 15B:
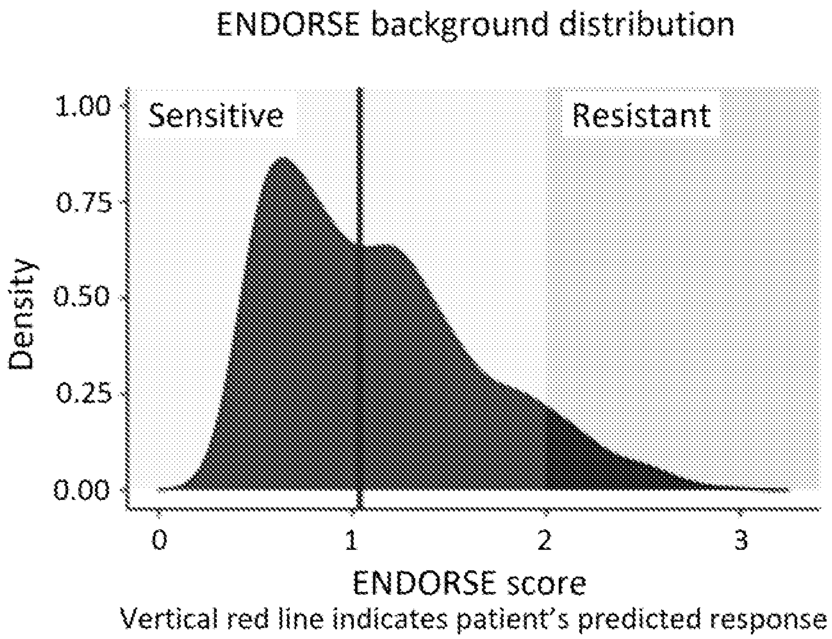
FIGS. 15A-15C. Example report generated using the cloud application, which is used for a clinical trial testing the methods described herein including embodiments thereof.
Figure 15C:
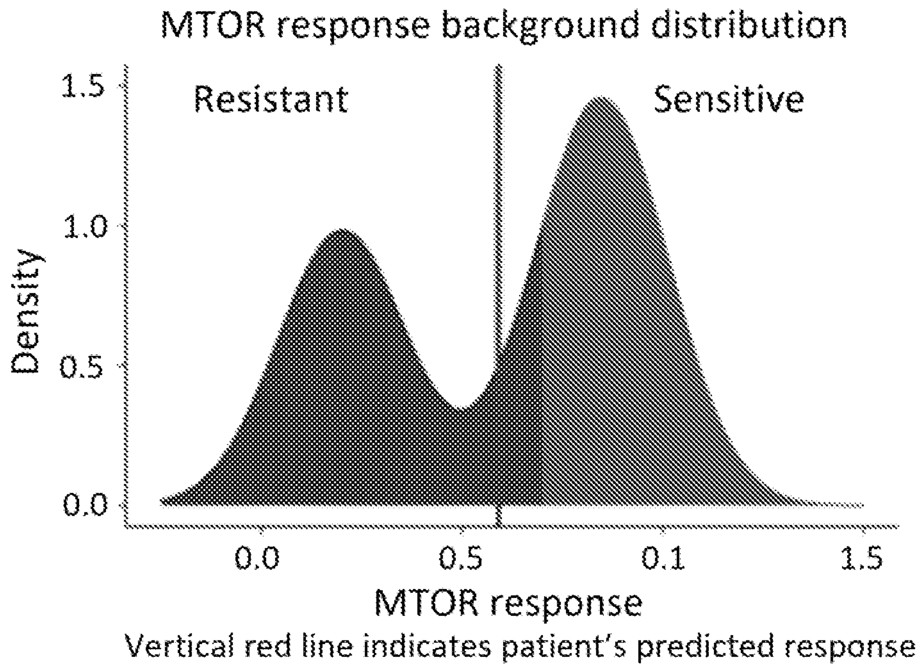

Several gene-level amplifications were also associated with significant differences in ENDORSE scores (FIG. 12C). Interestingly, the significant amplifications were localized at chromosome 1q, 8p, 8q, or 11q, suggesting different genetic alterations affecting a recurring set of loci may be correlated with the emergence of resistance in the high-risk tumors (FIG. 12C, Table 23). Like the univariate SNV models above, the univariate copy number alteration models also performed poorly when compared to the ENDORSE model in bootstrap resampling analyses (FIG. 12D).

Discussion

The criteria for classifying tumor as ER+ is based on a broad criteria of positive immunohistochemical staining of 1-100% of cell nuclei for the estrogen receptor[14,32]. However, ER+ tumors are heterogeneous, both in terms of dependence on estrogen signaling for growth and survival and intrinsic or acquired resistance to endocrine therapy[1,14]. Therefore, optimal clinical management of each ER+ breast cancer depends on accurate prediction of response to endocrine therapy and selection of companions for endocrine therapy. Several genomic tests are available for classifying breast cancers into molecular subtypes 35 or assessing the likelihood of benefit from chemotherapy in early-stage, node-negative ER+ breast cancers[7,30]. Results from the MINDACT and TAILORx studies[7,8] show that it is possible for node-negative, early-stage breast cancers to safely waive additional chemotherapy if they are predicted to be at a low risk of recurrence based on genomic signatures. However, these tests have not proven to be useful in the advanced and metastatic ER+ breast cancer setting. The default primary treatment for advanced ER+ breast cancer remains endocrine therapy, despite proven benefit from add-on targeted therapy or potential switch to chemotherapy. Therefore, the key challenge in advanced ER+ breast cancer is to stratify patients that will likely benefit from continued endocrine therapy and patients that are likely resistant to single-agent endocrine therapy and will benefit from selecting a different treatment strategy[36].

To address this challenge, we have developed a new prognostic model to predict endocrine response in advanced ER+ breast cancers. We developed our model using invasive tumors from the METABRIC study that were ER+ and included node-positive, high-grade tumors. Our model addressed several challenges associated with the development of genomic biomarkers. Since the number of available features to train the genomic models tend to be much larger than the number of available samples (p>>n), it is quite easy to create complex prediction models that contain a large number of predictor variables. Often, such models perform very well in the training datasets, but the performance cannot be replicated in independent test datasets due to overfitting. A number of approaches have been proposed to address this issue. Broadly, these can be classified into unsupervised and supervised approaches. The unsupervised approach typically relies on grouping or clustering the samples into based on similarity of gene expression profiles, followed by analysis of association with survival outcomes[37]. Alternatively, a supervised approach is to perform dimensionality reduction prior to modelling the survival outcome or drug response using univariate or multivariate models[38]. Our model utilized the later strategy by using a regularized Cox model for feature selection, effectively reducing the dimensionality of the gene expression data. We further collapsed the genes into a signature and parameterized the final Cox model on the GES of the signatures. The rank-based approach to calculate GES also helped mitigate issues associated with batch effects and differences in methods for transcriptome profiling. We performed extensive performance evaluation of our model against other published signatures and clinical factors. Consistently, we found that the ENDORSE model was a better predictor than all other models in the training dataset (FIGS. 8A and 8B). Moreover, ENDORSE clearly outperformed all other published signatures when they were applied to external validation datasets (FIGS. 11A-11G, 12A-12D). Our results show that ENDORSE is a highly accurate and reproducible model that outperforms current approaches to predict endocrine response in metastatic ER+ breast cancer.

We also explored the biology of the ER+ tumors to identify possible mechanisms that are commonly shared by high-risk tumor. We found that high-risk tumors showed a consistent enrichment of pathways associated cell cycle progression and gain of PI3K/MTOR signaling pathways (FIG. 12A). In addition, we observed consistent gain of the E2F1 signature, which may be associated with metastatic progression of breast cancers[39,40]. We also observed loss of Rb1 activity, which has been associated with therapeutic resistance in ER+ breast cancers[41,42]

In addition to common pathway phenotypes shared across high-risk tumors, mutations in the TP53 tumor suppressor genes were also significant (FIG. 12B). Loss of function TP53 variants have long been associated with aggressiveness and chemotherapeutic resistance in hormone-receptor negative breast cancers[43,44] However, recent studies show that even though TP53 mutations are infrequent in ER+ breast cancers, they have similar negative impact on patient outcome as hormone-receptor negative breast cancers[45]. We also found recurrent copy number gains at chromosomes 8 and 11 to be associated with high-risk tumors (FIG. 12C). Amplifications at these loci have been previously associated with aggressive and drug resistant cancers, and included several oncogenes such as MYC, CCND1 and multiple fibroblast growth factors[46,47]. The survival models based on genomic alterations were clearly outperformed by ENDORSE; however, the recurrent nature of these alterations in high-risk tumors suggests further studies to investigate their role in promoting endocrine resistance are warranted.

Drugs that target CDK4/6 to inhibit cell cycle activation[48], PI3K-inhibitors that target tumor with activating PIK3CA mutations[12] and mTOR-inhibitors that prevent the activation of mTOR signaling and cell proliferation[13] have been studied and approved for the treatment of advanced ER+ breast cancers in combination with endocrine therapy. However, patients must first advance on primary endocrine therapy, with or without additional CDK4/6 inhibitors, before they can be stratified in a different treatment arm. Therefore, identifying high-risk tumors with the ENDORSE model prior to first-line administration of single-agent endocrine therapy could help identify which cancers may be better suited for an add-on regimen or switching to chemotherapy. Ultimately, early and accurate prediction of endocrine response in advanced, metastatic ER+ breast cancers could help prolong survival for patients by stratifying in more appropriate treatment group.

Methods

Data Retrieval and Pre-Processing

METABRIC gene expression, phenotypic and survival data were retrieved using cBioPortal for cancer genomics[49]. Independent validation datasets used in this study were retrieved from the NCB1 Gene Expression Omnibus database with the following accession IDs: SET ER/PR GSE124647[18], TransCONFIRM GSE76040[19], and ACOSOG Z1031B GSE87411[31]. For each gene expression dataset, we removed genes with zero variance and summarized genes with multiple probes by mean expression, followed by log 2(x+1) transformation, and scaling of the expression levels of each gene to a mean of zero and standard deviation of one.

Inclusion Criteria for METABRIC Training Cohort

The METABRIC cohort contained a total of 2509 samples. Samples that met all of the following criteria were included in the training cohort: patients that were ER-positive and HER2-negative based on immunohistochemistry, patients that received hormone therapy but did not receive additional chemotherapy, patients that were either alive or died due to the disease and not other causes, and patients with complete survival and transcriptomic data. After filtering, 833 samples were retained for model construction.

Empirical Signature and ENDORSE Model Construction

The empirical gene signature was developed using a LASSO-regularized Cox proportional hazards models, with OS as the outcome variable[50]. The hazard function in the Cox model is defined as:

$$h_i(t) = h_0(t)\exp(\beta x_i^T)$$

Where, X is a set of predictive gene expression features and $h_0$ is an arbitrary baseline hazard function. The coefficient ($\beta$) for each predictor in the model can be estimated by maximizing the partial likelihood function $L(\beta)$, defined as:

$$L(\beta) = \prod_i \frac{\exp(\beta x_{j(i)}^T)}{\sum_{l\in R_i}\exp(\beta x_i^T)}$$

Where $R_i$ is the set of indices of observations failing (events) at time $t_i$. In the LASSO Cox model, the regularized coefficient is obtained by adding a penalty parameter $\lambda$ to the log of the likelihood function.

$$\hat{\beta} = \min - \frac{1}{N} l(\beta) + \lambda\|\beta\|_1$$

Where, $l(\beta)=\log L(\beta)$. The $\lambda$ penalty parameter was determined using 10-fold cross-validation implemented in R package glmnet[36,37]. The optimal k minimized model deviance.

We applied the model in a repeated (50×10-fold) cross validation framework. In each iteration, a set of 'seed genes' or features with positive coefficients in the regularized Cox model at a k equal to one standard error from the minimum model deviance were identified. The seed genes were expanded to a redundant correlation network by adding all genes in the training transcriptome dataset that had Pearson's correlation >0.75 with any of the seed genes. Across all iterations, we identified the common set of features that were present in at least 50% of the correlation networks and defined this set of features as the empirical signature.

The ENDORSE model was defined as the hazard's ratio of the Cox proportional hazards model fitted on OS data of the training cohort with two components: GES for the empirical gene signature and GES for the hallmark estrogen early response signature.

$$h(t) = h_0(t)\times\exp(\beta_{emp}GES_{emp} + \beta_{er}GES_{er})$$

where, emp represents the empirical signature and er represents the estrogen response signature. For each signature, the GES were calculated for individual samples using the GSVA package for R[53] using the ssGSEA method[54]. The parameters for the ENDORSE model were obtained by fitting the model to the full training cohort of 833 samples, resulting in $\beta_{emp}$=1.54 and $\beta_{er}$=−2.72.

Models Based on External Signatures and Clinical Factors

Clinical features such as tumor grade and mutation count, along with scores from PAM50 and IntClust analyses were obtained directly from the METABRIC clinical annotations accompanying the transcriptome data and were directly utilized in univariate Cox models. Proliferation index based on the metaPCNA signature was calculated using the R-package ProliferativeIndex[27].

We replicated the signatures and algorithms developed in the TransCONFIRM, SET ER/PR and 21-gene prognostic signature studies by following the methods described in the respective studies. The TransCONFIRM signature composed of 37 genes was implemented by performing hierarchical clustering of the gene expression data using these genes and cutting the tree (k=2) to stratify samples in high or low TransCONFIRM score categories. The SET signature was implemented by calculating (the average expression of the 18-genes in the signature)−(the expression of 10 housekeeping genes)+2. The 21-gene signature (ODX) score was calculated by following the unscaled risk score calculation reported by the study. BAG1 transcript was missing from the METABRIC cohort and was not included in the unscaled score calculation. Since this transcript was uniformly missing on all samples, the relative risk scores could be compared across the samples.

Cox Model Performance Evaluation in Training Data

The predictive ability of ENDORSE and various other models were evaluated in the METABRIC training dataset using a bootstrap resampling analysis of the Cox regression models. The resampling was repeated 150 times for each model and a Somer's $D_{xy}$ rank correlation was calculated in each repeat. A final bias-corrected index of Somer's $D_{xy}$ was obtained as measure of the model's predictive ability. The bootstrap resampling and calculations of the Somer's $D_{xy}$ were performed using the R package 'rms'. Models based on SNVs and CNAs significantly associated with ENDORSE scores were also evaluated by obtaining Somer's $D_{xy}$ rank correlation metric of the univariate Cox model.

To compare each of the external signatures and clinical feature models with the ENDORSE model, we applied Vuong's[55] partial likelihood ratio test for non-nested Cox regression models calculated using the R package 'nonnestcox' (https://github.com/thomashielscher/nonnestcox/). The individual components of the ENDORSE model were compared to the full model using likelihood ratio tests for nested Cox models.

Model Validation in Independent Datasets

We compared the predictive performance of ENDORSE in multiple independent datasets. First, we performed batch correction using the ComBat function of the R package 'sva'[56]. Next, we calculated the GES for the ENDORSE signatures in the training (METABRIC) and test (independent validation) splits of the batch-corrected gene expression dataset. Then, the parameters of the ENDORSE Cox model were calculated on the batch-corrected training split with the OS data as the response variable. Finally, the parameterized Cox model was applied to the test split to obtain a predicted risk score.

In case of the SET ER/PR cohort, we used the predicted ENDORSE risk scores to stratify the patients into risk categories, with an ENDORSE score ≥2 representing the high-risk group, ≤1 representing the low-risk group and other intermediate values representing the medium risk group. We compared the significance of stratification of both OS and PFS curves based on ENDORSE, SET and TransCONFIRM scores using log-rank tests. Further, we compared the models using partial likelihood ratio tests for non-nested Cox models.

For the TransCONFIRM and ACOSOG cohorts, we compared the ENDORSE risk scores, SET and TransCONFIRM predictions with reported clinical variables, such as percentage of cells positive for Ki67 at the end of treatment and clinical outcomes using generalized linear models for continuous outcome variables or one-way ANOVA analysis for categorical outcomes.

Biological Features Associated with ENDORSE Scores

To determine the possible biological mechanisms associated with emergence of endocrine resistance and high ENDORSE risk scores, we evaluated the enrichment scores of various biological pathway and oncogenic signatures across the training and independent validation cohorts. We used the ssGSEA method to obtain GES for hallmark, curated (C2) and oncogenic signature (C6) gene sets from the molecular signatures database[17]. For each signature, we fitted a generalized additive model against the predicted ENDORSE score to obtain significance of the fit, $R^2$ and proportion of variance explained by the model. None of the curated signatures were significant in the METABRIC analyses and were excluded from further consideration in the independent validation datasets.

Gene-level somatic SNV and CNV analyses were performed using data reported by the METABRIC study. SNV's were retained based on a mutation frequency of ≥5 across all samples and limited to genes that are known cancer-related genes. Pathogenic PIK3CA variants associated with PI3K inhibitor sensitivity were obtained from the drug labels for alpelisib based on the SOLAR1 clinical trial[12]. Significant SNVs and CNVs were obtained using a one-way ANOVA analysis of the ENDORSE scores with mutation status as the factor.

Data Availability and Code

All training and validation datasets used in this study are publicly available and listed under "data retrieval, preprocessing and analysis". All analyses were performed in RStudio (1.2.1335, R 3.6.1). The sample code for reproducing the analyses in this study are available at https://osf.io/bd3m7/?view_only=da4f860bd2474745880944fce1d433b1.

TABLE 14

METABRIC ENDORSE: hallmark signature pathway generalized additive model summary

| Pathway | P-value | R-squared | Variance explained |
|---|---|---|---|
| HALLMARK_TNFA_SIGNALING_VIA_NFKB | 1.28E−05 | 0.021473329 | 0.022649443 |
| HALLMARK_HYPOXIA | 1.38E−08 | 0.046074989 | 0.048372651 |
| HALLMARK_CHOLESTEROL_HOMEOSTASIS | 0.04860069 | 0.004218406 | 0.005541077 |

TABLE 14-continued

METABRIC ENDORSE: hallmark signature pathway generalized additive model summary

| Pathway | P-value | R-squared | Variance explained |
|---|---|---|---|
| HALLMARK_MITOTIC_SPINDLE | 1.72E−120 | 0.439342142 | 0.44229128 |
| HALLMARK_WNT_BETA_CATENIN_SIGNALING | 1.34E−08 | 0.036938151 | 0.038095677 |
| HALLMARK_TGF_BETA_SIGNALING | 9.75E−23 | 0.120035611 | 0.122457407 |
| HALLMARK_IL6_JAK_STAT3_SIGNALING | 0.043730189 | 0.009084966 | 0.011727998 |
| HALLMARK_DNA_REPAIR | 5.51E−62 | 0.284468751 | 0.286292658 |
| HALLMARK_G2M_CHECKPOINT | 0 | 0.768344531 | 0.769454918 |
| HALLMARK_APOPTOSIS | 6.45E−05 | 0.024884141 | 0.027220492 |
| HALLMARK_NOTCH_SIGNALING | 2.08E−20 | 0.096447257 | 0.097533258 |
| HALLMARK_ADIPOGENESIS | 1.45E−11 | 0.061187753 | 0.063230068 |
| HALLMARK_ESTROGEN_RESPONSE_EARLY | 3.92E−45 | 0.204642017 | 0.205597976 |
| HALLMARK_ESTROGEN_RESPONSE_LATE | 5.07E−12 | 0.066652338 | 0.069539444 |
| HALLMARK_ANDROGEN_RESPONSE | 0.001526488 | 0.010833191 | 0.012022093 |
| HALLMARK_MYOGENESIS | 1.86E−36 | 0.175445274 | 0.1764813 |
| HALLMARK_PROTEIN_SECRETION | 0.416802372 | −0.000408858 | 0.000793556 |
| HALLMARK_INTERFERON_ALPHA_RESPONSE | 1.09E−11 | 0.07084803 | 0.076144961 |
| HALLMARK_INTERFERON_GAMMA_RESPONSE | 7.33E−11 | 0.069806369 | 0.077510344 |
| HALLMARK_APICAL_JUNCTION | 2.37E−16 | 0.093815918 | 0.097649856 |
| HALLMARK_APICAL_SURFACE | 1.51E−08 | 0.042654474 | 0.044042582 |
| HALLMARK_HEDGEHOG_SIGNALING | 5.10E−09 | 0.039102605 | 0.04025753 |
| HALLMARK_COMPLEMENT | 0.068678101 | 0.006846574 | 0.009230279 |
| HALLMARK_UNFOLDED_PROTEIN_RESPONSE | 5.64E−44 | 0.208388109 | 0.209959046 |
| HALLMARK_PI3K_AKT_MTOR_SIGNALING | 1.25E−57 | 0.263970167 | 0.265983826 |
| HALLMARK_MTORC1_SIGNALING | 1.03E−72 | 0.318059198 | 0.320222685 |
| HALLMARK_E2F_TARGETS | 0 | 0.694437405 | 0.695723074 |
| HALLMARK_MYC_TARGETS_V1 | 3.93E−56 | 0.26625066 | 0.270054809 |
| HALLMARK_MYC_TARGETS_V2 | 2.66E−83 | 0.349700484 | 0.35182306 |
| HALLMARK_EPITHELIAL_MESENCHYMAL_TRANSITION | 2.40E−13 | 0.074705173 | 0.077857971 |
| HALLMARK_INFLAMMATORY_RESPONSE | 0.106999622 | 0.010133487 | 0.016421911 |
| HALLMARK_XENOBIOTIC_METABOLISM | 5.60E−09 | 0.048416915 | 0.050721838 |
| HALLMARK_FATTY_ACID_METABOLISM | 1.16E−08 | 0.045532894 | 0.047677464 |
| HALLMARK_OXIDATIVE_PHOSPHORYLATION | 0.000417176 | 0.018427915 | 0.020139635 |
| HALLMARK_GLYCOLYSIS | 8.85E−10 | 0.053074118 | 0.055436177 |
| HALLMARK_REACTIVE_OXYGEN_SPECIES_PATHWAY | 1.72E−07 | 0.048589875 | 0.05461275 |
| HALLMARK_P53_PATHWAY | 4.45E−14 | 0.072880828 | 0.074779922 |
| HALLMARK_UV_RESPONSE_UP | 2.05E−22 | 0.106117839 | 0.107192217 |
| HALLMARK_UV_RESPONSE_DN | 3.43E−68 | 0.305406551 | 0.307160719 |
| HALLMARK_ANGIOGENESIS | 1.05E−15 | 0.092205477 | 0.096965717 |
| HALLMARK_HEME_METABOLISM | 5.26E−11 | 0.058943406 | 0.06049381 |
| HALLMARK_COAGULATION | 5.02E−25 | 0.118480401 | 0.119539919 |
| HALLMARK_IL2_STAT5_SIGNALING | 0.375183187 | 0.002439665 | 0.004911488 |
| HALLMARK_BILE_ACID_METABOLISM | 1.45E−27 | 0.130249074 | 0.131294448 |
| HALLMARK_PEROXISOME | 0.010955947 | 0.006568396 | 0.007762424 |
| HALLMARK_ALLOGRAFT_REJECTION | 7.42E−08 | 0.05177159 | 0.058227579 |
| HALLMARK_SPERMATOGENESIS | 2.84E−55 | 0.262899625 | 0.26623284 |
| HALLMARK_KRAS_SIGNALING_UP | 8.40E−07 | 0.034158022 | 0.035744131 |
| HALLMARK_KRAS_SIGNALING_DN | 2.65E−08 | 0.035397365 | 0.036556743 |
| HALLMARK_PANCREAS_BETA_CELLS | 6.83E−06 | 0.034140674 | 0.037964144 |

TABLE 15

METABRIC ENDORSE: oncogenic (C6) signature pathway generalized additive model summary

| Pathway | P-value | R-squared | Variance explained |
|---|---|---|---|
| GLI1_UP.V1_DN | 2.32E−05 | 0.02014657 | 0.021324278 |
| GLI1_UP.V1_UP | 1.15E−08 | 0.037272956 | 0.038430079 |
| E2F1_UP.V1_DN | 7.18E−32 | 0.149600991 | 0.150623106 |
| E2F1_UP.V1_UP | 8.06E−302 | 0.659020623 | 0.660401973 |
| EGFRUP.V1_DN | 0.00948663 | 0.010572848 | 0.012550026 |
| EGFR_UP.V1_UP | 0.000112103 | 0.021340099 | 0.023307206 |
| ERBB2_UP.V1_DN | 5.67E−08 | 0.042465734 | 0.045137229 |
| ERBB2_UP.V1_UP | 1.00E−28 | 0.159293238 | 0.164662047 |
| GCNP_SHH_UP_EARLY.V1_DN | 2.95E−19 | 0.090829481 | 0.091922234 |
| GCNP_SHH_UP_EARLY.V1_UP | 5.28E−105 | 0.401219404 | 0.403617434 |
| GCNP_SHH_UP_LATE.V1_DN | 0.074570708 | 0.002622078 | 0.00382085 |
| GCNP_SHH_UP_LATE.V1_UP | 3.22E−165 | 0.517423201 | 0.519138299 |
| RAPA_EARLY_UP.V1_DN | 0.018315078 | 0.010514595 | 0.013098767 |
| RAPA_EARLY_UP.V1_UP | 8.00E−24 | 0.122026107 | 0.123192616 |
| HINATA_NFKB_IMMU_INF | 0.076217111 | 0.002579264 | 0.003778087 |
| HINATA_NFKB_MATRIX | 0.033204736 | 0.010324292 | 0.01305942 |

TABLE 15-continued

METABRIC ENDORSE: oncogenic (C6) signature pathway generalized additive model summary

| Pathway | P-value | R-squared | Variance explained |
|---|---|---|---|
| CYCLIN_D1_KE_.V1_DN | 2.94E−07 | 0.035569228 | 0.037373574 |
| CYCLIN_D1_KE_.V1_UP | 0.470685411 | −0.000264569 | 0.001058411 |
| CYCLIN_D1_UP.V1_DN | 0.009597635 | 0.006850173 | 0.008043862 |
| CYCLIN_D1_UP.V1_UP | 0.003720124 | 0.008889535 | 0.010080774 |
| CSR_EARLY_UP.V1_DN | 1.98E−30 | 0.151052161 | 0.152737493 |
| CSR_EARLY_UP.V1_UP | 8.80E−12 | 0.071901005 | 0.077211325 |
| CSR_LATE_UP.V1_DN | 3.80E−35 | 0.163835965 | 0.16484097 |
| CSR_LATE_UP.V1_UP | 1.02E−251 | 0.611581831 | 0.613072578 |
| AKT_UP_MTOR_DN.V1_DN | 2.85E−19 | 0.090908399 | 0.092001057 |
| AKT_UP_MTOR_DN.V1_UP | 2.02E−22 | 0.120184245 | 0.122441843 |
| AKT_UP.V1_DN | 7.66E−47 | 0.211251044 | 0.21219906 |
| AKT_UP.V1_UP | 0.274257667 | 0.005274398 | 0.009078722 |
| MTOR_UP.V1_DN | 1.62E−35 | 0.182037292 | 0.184106023 |
| MTOR_UP.V1_UP | 7.63E−102 | 0.39777359 | 0.399863689 |
| PGF_UP.V1_DN | 0.103498509 | 0.001987064 | 0.003186599 |
| PGF_UP.V1_UP | 5.57E−06 | 0.031811236 | 0.034382376 |
| VEGF_A_UP.V1_DN | 3.78E−67 | 0.302794198 | 0.305183596 |
| VEGF_A_UP.V1_UP | 5.11E−09 | 0.045794081 | 0.04755595 |
| BCAT_GDS748_DN | 1.03E−10 | 0.047837772 | 0.048982198 |
| BCAT_GDS748_UP | 1.36E−30 | 0.165815322 | 0.170231278 |
| BCAT.100_UP.V1_DN | 3.49E−17 | 0.094267766 | 0.095750824 |
| BCAT.100_UP.V1_UP | 1.03E−34 | 0.161985882 | 0.16299311 |
| ATF2_S_UP.V1_DN | 2.05E−26 | 0.143703993 | 0.147638265 |
| ATF2_S_UP.V1_UP | 2.22E−16 | 0.089255174 | 0.091524912 |
| ATF2_UP.V1_DN | 1.72E−48 | 0.217529082 | 0.218469552 |
| ATF2_UP.V1_UP | 4.25E−35 | 0.180615672 | 0.183218349 |
| WNT_UP.V1_DN | 4.71E−14 | 0.064901641 | 0.066025557 |
| WNT_UP.V1_UP | 3.51E−07 | 0.039025673 | 0.041968351 |
| ATM_DN.V1_DN | 6.54E−08 | 0.044836586 | 0.04816321 |
| ATM_DN.V1_UP | 2.42E−07 | 0.030412706 | 0.031578076 |
| P53_DN.V2_DN | 1.75E−06 | 0.025964294 | 0.02713501 |
| P53_DN.V2_UP | 0.004577069 | 0.008445167 | 0.009637452 |
| RELA_DN.V1_DN | 0.009877701 | 0.017318085 | 0.022182238 |
| RELA_DN.V1_UP | 1.32E−33 | 0.157192428 | 0.158205418 |
| P53_DN.V1_DN | 7.42E−08 | 0.03740186 | 0.038723853 |
| P53_DN.V1_UP | 3.15E−20 | 0.118704154 | 0.124562393 |
| BCAT_BILD_ET_AL_DN | 0.000118334 | 0.016499068 | 0.01768116 |
| BCAT_BILD_ET_AL_UP | 0.002401157 | 0.009842111 | 0.011032205 |
| E2F3_UP.V1_DN | 2.96E−11 | 0.060472643 | 0.063070707 |
| E2F3_UP.V1_UP | 8.87E−37 | 0.187032146 | 0.19024819 |
| MYC_UP.V1_DN | 0.17363691 | 0.003772219 | 0.005915385 |
| MYC_UP.V1_UP | 8.98E−33 | 0.166249516 | 0.168519399 |
| SRC_UP.V1_DN | 3.54E−45 | 0.214579959 | 0.216787187 |
| SRC_UP.V1_UP | 0.002797072 | 0.009509398 | 0.010699892 |
| SNF5_DN.V1_DN | 6.75E−48 | 0.226906644 | 0.228499841 |
| SNF5_DN.V1_UP | 8.33E−10 | 0.063612476 | 0.070678981 |
| CAMP_UP.V1_DN | 4.55E−08 | 0.052641167 | 0.059116203 |
| CAMP_UP.V1_UP | 8.21E−33 | 0.17117551 | 0.174101455 |
| LTE2_UP.V1_DN | 0.003514084 | 0.020322482 | 0.025212596 |
| LTE2_UP.V1_UP | 1.42E−17 | 0.09496621 | 0.097087694 |
| MEK_UP.V1_DN | 0.050540886 | 0.008896167 | 0.011664584 |
| MEK_UP.V1_UP | 1.06E−06 | 0.044607288 | 0.0514546 |
| RAF_UP.V1_DN | 1.58E−72 | 0.319825872 | 0.321492291 |
| RAF_UP.V1_UP | 3.70E−07 | 0.029456522 | 0.030623041 |
| PRC1_BMI_UP.V1_DN | 0.023704098 | 0.00494497 | 0.006140949 |
| PRC1_BMI_UP.V1_UP | 0.42160376 | −0.000425088 | 0.000777346 |
| PRC2_EED_UP.V1_DN | 6.72E−49 | 0.242217777 | 0.246885133 |
| PRC2_EED_UP.V1_UP | 3.51E−17 | 0.092755204 | 0.094870796 |
| PRC2_EZH2_UP.V1_DN | 1.07E−297 | 0.656354446 | 0.657945621 |
| PRC2_EZH2_UP.V1_UP | 1.43E−15 | 0.086783366 | 0.089860287 |
| PRC2_SUZ12_UP.V1_DN | 2.55E−08 | 0.035479137 | 0.036638417 |
| PRC2_SUZ12_UP.V1_UP | 1.58E−20 | 0.09702639 | 0.098111695 |
| JNK_DN.V1_DN | 1.39E−07 | 0.03166867 | 0.032832705 |
| JNK_DN.V1_UP | 0.000247387 | 0.014855733 | 0.016039801 |
| BRCA1_DN.V1_DN | 0.000369547 | 0.019064514 | 0.021132454 |
| BRCA1_DN.V1_UP | 1.04E−13 | 0.079937783 | 0.084496575 |
| CTIP_DN.V1_DN | 6.17E−12 | 0.05411868 | 0.055255556 |
| CTIP_DN.V1_UP | 0.000699967 | 0.019516329 | 0.022100023 |
| PKCA_DN.V1_DN | 0.004732808 | 0.0177345 | 0.021921798 |
| PKCA_DN.V1_UP | 6.80E−15 | 0.090489918 | 0.096847489 |
| MTOR_UP.N4.V1_DN | 7.05E−44 | 0.218035187 | 0.219960282 |
| MTOR_UP.N4.V1_UP | 1.14E−23 | 0.127049763 | 0.129729852 |
| PTEN_DN.V2_DN | 0.103643169 | 0.001984396 | 0.003183934 |
| PTEN_DN.V2_UP | 1.95E−15 | 0.071870045 | 0.072985586 |

TABLE 15-continued

METABRIC ENDORSE: oncogenic (C6) signature pathway generalized additive model summary

| Pathway | P-value | R-squared | Variance explained |
|---|---|---|---|
| DCA_UP.V1_DN | 1.14E−09 | 0.049939049 | 0.051950741 |
| DCA_UP.V1_UP | 1.09E−06 | 0.035436788 | 0.037988142 |
| ESC_J1_UP_EARLY.V1_DN | 3.11E−10 | 0.061262981 | 0.06545143 |
| ESC_J1_UP_EARLY.V1_UP | 1.10E−37 | 0.186374877 | 0.188627663 |
| ESC_J1_UP_LATE.V1_DN | 0.005430676 | 0.008071355 | 0.009263577 |
| ESC_J1_UP_LATE.V1_UP | 3.37E−46 | 0.225562247 | 0.227300925 |
| ESC_V6.5_UP_EARLY.V1_DN | 1.33E−25 | 0.134873605 | 0.137537495 |
| ESC_V6.5_UP_EARLY.V1_UP | 1.11E−06 | 0.026978402 | 0.0281479 |
| ESC_V6.5_UP_LATE.V1_DN | 2.66E−06 | 0.034054119 | 0.037028647 |
| ESC_V6.5_UP_LATE.V1_UP | 8.49E−31 | 0.158221873 | 0.161417709 |
| ALK_DN.V1_DN | 0.302637514 | 0.002392824 | 0.004559579 |
| ALK_DN.V1_UP | 0.099138154 | 0.002069448 | 0.003268884 |
| BMI1_DN_MEL18_DN.V1_DN | 9.55E−34 | 0.170636801 | 0.172410655 |
| BMI1_DN_MEL18_DN.V1_UP | 2.09E−06 | 0.025560379 | 0.02673158 |
| BMI1_DN.V1_DN | 1.52E−38 | 0.178154134 | 0.17914193 |
| BMI1_DN.V1_UP | 1.80E−10 | 0.059731743 | 0.063422393 |
| MEL18_DN.V1_DN | 1.80E−27 | 0.152512058 | 0.158521536 |
| MEL18_DN.V1_UP | 0.010670939 | 0.01203001 | 0.014774093 |
| PTEN_DN.V1_DN | 5.99E−07 | 0.035007556 | 0.03657399 |
| PTEN_DN.V1_UP | 6.04E−19 | 0.103480907 | 0.104998266 |
| NOTCH_DN.V1_DN | 4.41E−05 | 0.022885241 | 0.024754201 |
| NOTCH_DN.V1_UP | 8.55E−06 | 0.040996234 | 0.049407379 |
| EIF4E_DN | 5.65E−19 | 0.089446543 | 0.090540958 |
| EIF4E_UP | 2.83E−20 | 0.095796371 | 0.096883154 |
| CRX_DN.V1_DN | 1.61E−23 | 0.111384559 | 0.112452606 |
| CRX_DN.V1_UP | 0.00238005 | 0.018165688 | 0.021694876 |
| CRX_NRL_DN.V1_DN | 7.39E−16 | 0.073989632 | 0.075102625 |
| CRX_NRL_DN.V1_UP | 0.408119848 | −0.000378796 | 0.000823583 |
| NRL_DN.V1_DN | 0.245824778 | 0.000419008 | 0.001620427 |
| NRL_DN.V1_UP | 0.613334643 | 0.001218041 | 0.00451737 |
| RB_DN.V1_DN | 3.11E−09 | 0.046595777 | 0.048536006 |
| RB_DN.V1_UP | 7.66E−64 | 0.291379089 | 0.293788111 |
| RB_P107_DN.V1_DN | 0.03823268 | 0.003960331 | 0.005157494 |
| RB_P107_DN.V1_UP | 9.51E−137 | 0.468485723 | 0.47210919 |
| RB_P130_DN.V1_DN | 6.90E−11 | 0.056626294 | 0.058320724 |
| RB_P130_DN.V1_UP | 1.31E−67 | 0.303802554 | 0.307342355 |
| CAHOY_ASTROCYTIC | 0.012845617 | 0.009522092 | 0.011382993 |
| CAHOY_ASTROGLIAL | 1.28E−17 | 0.082761899 | 0.083864349 |
| CAHOY_NEURONAL | 7.48E−06 | 0.022688945 | 0.023863598 |
| CAHOY_OLIGODENDROCUTIC | 0.001802314 | 0.025323542 | 0.034933737 |
| RPS14_DN.V1_DN | 1.15E−264 | 0.624740037 | 0.626557513 |
| RPS14_DN.V1_UP | 0.009186238 | 0.020873141 | 0.029312223 |
| IL15_UP.V1_DN | 1.79E−61 | 0.263761089 | 0.264645992 |
| IL15_UP.V1_UP | 0.010747094 | 0.006609314 | 0.007803293 |
| IL2_UP.V1_DN | 6.18E−43 | 0.195987768 | 0.196954129 |
| IL2_UP.V1_UP | 0.060380037 | 0.004832687 | 0.006374328 |
| IL21_UP.V1_DN | 1.56E−29 | 0.139187537 | 0.140222167 |
| IL21_UP.V1_UP | 3.16E−05 | 0.023326351 | 0.024748855 |
| PDGF_ERK_DN.V1_DN | 0.028219127 | 0.004583689 | 0.005780103 |
| PDGF_ERK_DN.V1_UP | 1.12E−11 | 0.052799577 | 0.053938039 |
| PDGF_UP.V1_DN | 1.14E−15 | 0.073054037 | 0.074168155 |
| PDGF_UP.V1_UP | 5.22E−08 | 0.038821636 | 0.040167744 |
| TGFB_UP.V1_DN | 7.10E−33 | 0.176196605 | 0.181895501 |
| TGFB_UP.V1_UP | 3.03E−16 | 0.092848147 | 0.097090394 |
| YAP1_DN | 0.000538605 | 0.021136958 | 0.024197211 |
| YAP1_UP | 0.000265549 | 0.021733116 | 0.024197301 |
| SIRNA_EIF4GI_DN | 0.021531624 | 0.007804271 | 0.009403839 |
| SIRNA_EIF4GI_UP | 0.0402859 | 0.003853793 | 0.005051085 |
| HOXA9_DN.V1_DN | 6.08E−89 | 0.360003068 | 0.363134433 |
| HOXA9_DN.V1_UP | 1.67E−09 | 0.054309107 | 0.057768634 |
| SINGH_KRAS_DEPENDENCY_SIGNATURE | 2.46E−06 | 0.025194765 | 0.026366405 |
| STK33_DN | 1.46E−05 | 0.038356767 | 0.044988267 |
| STK33_NOMO_DN | 0.489230582 | 0.000430894 | 0.002090036 |
| STK33_NOMO_UP | 9.03E−14 | 0.06346875 | 0.064594389 |
| STK33_SKM_DN | 4.55E−43 | 0.196515814 | 0.19748154 |
| STK33_SKM_UP | 3.40E−11 | 0.050319261 | 0.051460704 |
| STK33_UP | 6.14E−14 | 0.064317238 | 0.065441856 |
| KRAS.AMP.LUNG_UP.V1_DN | 0.000256341 | 0.014776657 | 0.01596082 |
| KRAS.AMP.LUNG_UP.V1_UP | 4.50E−07 | 0.029018192 | 0.030185238 |
| KRAS.DF.V1_DN | 2.35E−07 | 0.037673155 | 0.03928521 |
| KRAS.DF.V1_UP | 1.86E−07 | 0.031002676 | 0.032167336 |
| TBK1.DF_DN | 0.000521234 | 0.013201791 | 0.014387847 |
| TBK1.DF_UP | 4.56E−06 | 0.043048875 | 0.052393692 |
| TBK1.DN.48HRS_DN | 0.116285515 | 0.005216575 | 0.007529052 |

TABLE 15-continued

METABRIC ENDORSE: oncogenic (C6) signature pathway generalized additive model summary

| Pathway | P-value | R-squared | Variance explained |
|---|---|---|---|
| TBK1.DN.48HRS_UP | 0.000132299 | 0.026475218 | 0.029830488 |
| NFE2L2.V2 | 0.355766587 | 0.006866364 | 0.014225156 |
| CORDENONSI_YAP_CONSERVED_SIGNATURE | 0.000145796 | 0.023352582 | 0.025839608 |
| JAK2_DN.V1_DN | 0.077405509 | 0.002548972 | 0.003747831 |
| JAK2_DN.V1_UP | 6.07E−24 | 0.120747026 | 0.122483379 |
| KRAS.300_UP.V1_DN | 0.165961629 | 0.003084154 | 0.004824418 |
| KRAS.300_UP.V1_UP | 1.32E−09 | 0.042133397 | 0.043284679 |
| KRAS.50_UP.V1_DN | 0.00325296 | 0.015657637 | 0.018248593 |
| KRAS.50_UP.V1_UP | 1.12E−07 | 0.032152175 | 0.033315454 |
| KRAS.600_UP.V1_DN | 6.47E−12 | 0.054014577 | 0.055151578 |
| KRAS.600_UP.V1_UP | 1.80E−08 | 0.036271781 | 0.037430108 |
| KRAS.600.LUNG.BREAST_UP.V1_DN | 1.16E−15 | 0.073010639 | 0.074124809 |
| KRAS.600.LUNG.BREAST_UP.V1_UP | 0.00083337 | 0.01711211 | 0.01920813 |
| KRAS.BREAST_UP.V1_DN | 1.86E−21 | 0.113269978 | 0.114507769 |
| KRAS.BREAST_UP.V1_UP | 0.004375237 | 0.008538125 | 0.009729786 |
| KRAS.KIDNEY_UP.V1_DN | 0.327020256 | −4.59E−05 | 0.001156047 |
| KRAS.KIDNEY_UP.V1_UP | 3.72E−42 | 0.19287123 | 0.193841337 |
| KRAS.LUNG_UP.V1_DN | 2.08E−13 | 0.072631108 | 0.074809288 |
| KRAS.LUNG_UP.V1_UP | 0.023217973 | 0.004988058 | 0.006183986 |
| KRAS.LUNG.BREAST_UP.V1_DN | 1.39E−13 | 0.067857267 | 0.069634727 |
| KRAS.LUNG.BREAST_UP.V1_UP | 0.041128991 | 0.012616308 | 0.017808474 |
| KRAS.PROSTATE_UP.V1_DN | 1.33E−18 | 0.087619736 | 0.088716347 |
| KRAS.PROSTATE_UP.V1_UP | 2.60E−08 | 0.03544206 | 0.036601385 |
| LEF1_UP.V1_DN | 1.58E−96 | 0.379202199 | 0.380889151 |
| LEF1_UP.V1_UP | 5.00E−11 | 0.059611973 | 0.061850727 |

TABLE 16

GSE76040 ENDORSE: hallmark signature pathway generalized additive model summary

| Pathway | P-value | R-squared | Variance explained |
|---|---|---|---|
| HALLMARK_TNFA_SIGNALING_VIA_NFKB | 0.025078653 | 0.035766751 | 0.044375976 |
| HALLMARK_HYPOXIA | 0.000396533 | 0.134530863 | 0.148558717 |
| HALLMARK_CHOLESTEROL_HOMEOSTASIS | 0.001200377 | 0.109163867 | 0.120286049 |
| HALLMARK_MITOTIC_SPINDLE | 0.000133862 | 0.182009681 | 0.202396721 |
| HALLMARK_WNT_BETA_CATENIN_SIGNALING | 1.76E−05 | 0.198652557 | 0.217163207 |
| HALLMARK_TGF_BETA_SIGNALING | 0.002580102 | 0.096480149 | 0.107861402 |
| HALLMARK_IL6_JAK_STAT3_SIGNALING | 0.08726855 | 0.017333286 | 0.026107096 |
| HALLMARK_DNA_REPAIR | 0.040486561 | 0.10647292 | 0.159946308 |
| HALLMARK_G2M_CHECKPOINT | 9.50E−12 | 0.409068484 | 0.433319747 |
| HALLMARK_APOPTOSIS | 0.000876137 | 0.087056988 | 0.095208265 |
| HALLMARK_NOTCH_SIGNALING | 0.000194148 | 0.14863013 | 0.163077766 |
| HALLMARK_ADIPOGENESIS | 0.007289606 | 0.10102738 | 0.120086491 |
| HALLMARK_ESTROGEN_RESPONSE_EARLY | 4.37E−08 | 0.228269923 | 0.235160371 |
| HALLMARK_ESTROGEN_RESPONSE_LATE | 0.004680144 | 0.061476666 | 0.069866525 |
| HALLMARK_ANDROGEN_RESPONSE | 0.01360743 | 0.12933887 | 0.180237458 |
| HALLMARK_MYOGENESIS | 0.002097587 | 0.073700033 | 0.081970569 |
| HALLMARK_PROTEIN_SECRETION | 0.013915143 | 0.079076814 | 0.095601986 |
| HALLMARK_INTERFERON_ALPHA_RESPONSE | 0.2356378 | 0.036319336 | 0.062608247 |
| HALLMARK_INTERFERON_GAMMA_RESPONSE | 0.219157368 | 0.043167867 | 0.072863777 |
| HALLMARK_APICAL_JUNCTION | 0.000731187 | 0.126465984 | 0.141374089 |
| HALLMARK_APICAL_SURFACE | 0.184494789 | 0.006941382 | 0.015807977 |
| HALLMARK_HEDGEHOG_SIGNALING | 0.649631094 | −0.007126402 | 0.001865798 |
| HALLMARK_COMPLEMENT | 0.79054741 | −0.008365069 | 0.00063819 |
| HALLMARK_UNFOLDED_PROTEIN_RESPONSE | 0.000756814 | 0.150006431 | 0.170610698 |
| HALLMARK_PI3K_AKT_MTOR_SIGNALING | 0.006339889 | 0.104409143 | 0.123110703 |
| HALLMARK_MTORC1_SIGNALING | 5.44E−05 | 0.196278967 | 0.215759914 |
| HALLMARK_E2F_TARGETS | 1.08E−11 | 0.429265094 | 0.469290249 |
| HALLMARK_MYC_TARGETS_V1 | 1.33E−09 | 0.361264375 | 0.38813874 |
| HALLMARK_MYC_TARGETS_V2 | 0.138212055 | 0.048167139 | 0.07395351 |
| HALLMARK_EPITHELIAL_MESENCHYMAL_TRANSITION | 1.80E−05 | 0.20657573 | 0.228305201 |
| HALLMARK_INFLAMMATORY_RESPONSE | 0.09002864 | 0.016887137 | 0.025664931 |
| HALLMARK_XENOBIOTIC_METABOLISM | 0.142357433 | 0.040814984 | 0.059693815 |
| HALLMARK_FATTY_ACID_METABOLISM | 0.152994532 | 0.009463363 | 0.01830744 |
| HALLMARK_OXIDATIVE_PHOSPHORYLATION | 0.033987497 | 0.072303544 | 0.092145885 |
| HALLMARK_GLYCOLYSIS | 0.108600819 | 0.031541896 | 0.04536138 |
| HALLMARK_REACTIVE_OXYGEN_SPECIES_PATHWAY | 0.143578015 | 0.040673212 | 0.061361658 |
| HALLMARK_P53_PATHWAY | 0.000232203 | 0.126971903 | 0.136338737 |
| HALLMARK_UV_RESPONSE_UP | 0.101687197 | 0.047454133 | 0.067869252 |

TABLE 16-continued

| GSE76040 ENDORSE: hallmark signature pathway generalized additive model summary | | | |
|---|---|---|---|
| Pathway | P-value | R-squared | Variance explained |
| HALLMARK_UV_RESPONSE_DN | 0.017706963 | 0.08069475 | 0.101842071 |
| HALLMARK_ANGIOGENESIS | 0.000589825 | 0.179538193 | 0.217498344 |
| HALLMARK_HEME_METABOLISM | 0.258473399 | 0.002582411 | 0.011487925 |
| HALLMARK_COAGULATION | 0.073568744 | 0.019796273 | 0.028548092 |
| HALLMARK_IL2_STAT5_SIGNALING | 0.100131784 | 0.015370687 | 0.02416202 |
| HALLMARK_BILE_ACID_METABOLISM | 0.685591133 | −0.007513515 | 0.001482141 |
| HALLMARK_PEROXISOME | 0.018429127 | 0.067301045 | 0.082021816 |
| HALLMARK_ALLOGRAFT_REJECTION | 0.018539198 | 0.040340213 | 0.048908603 |
| HALLMARK_SPERMATOGENESIS | 2.36E−13 | 0.446230837 | 0.472749144 |
| HALLMARK_KRAS_SIGNALING_UP | 0.617741995 | −0.006737408 | 0.002251319 |
| HALLMARK_KRAS_SIGNALING_DN | 0.073666562 | 0.052127112 | 0.070160385 |
| HALLMARK_PANCREAS_BETA_CELLS | 0.162921781 | 0.008609595 | 0.017461295 |

TABLE 17

| GSE76040 ENDORSE: oncogenic (C6) signature pathway generalized additive model summary | | | |
|---|---|---|---|
| Pathway | P-value | R-squared | Variance explained |
| GLI1_UP.V1_DN | 0.05128775 | 0.04120057 | 0.05280285 |
| GLI1_UP.V1_UP | 0.38787597 | −0.0022241 | 0.00672432 |
| E2F1_UP.V1_DN | 0.00038191 | 0.10916259 | 0.11783516 |
| E2F1_UP.V1_UP | 8.76E−07 | 0.26262916 | 0.28324073 |
| EGFR_UP.V1_DN | 0.09351604 | 0.04344142 | 0.06032626 |
| EGFR_UP.V1_UP | 0.15303604 | 0.03887308 | 0.05832319 |
| ERBB2_UP.V1_DN | 0.00081461 | 0.15324135 | 0.17793059 |
| ERBB2_UP.V1_UP | 4.83E−05 | 0.19348636 | 0.21464952 |
| GCNP_SHH_UP_EARLY.V1_DN | 0.10905722 | 0.01416223 | 0.02296436 |
| GCNP_SHH_UP_EARLY.V1_UP | 0.0056442 | 0.112396 | 0.13321677 |
| GCNP_SHH_UP_LATE.V1_DN | 0.02181396 | 0.07854416 | 0.10020046 |
| GCNP_SHH_UP_LATE.V1_UP | 0.00029315 | 0.17955065 | 0.20744176 |
| RAPA_EARLY_UP.V1_DN | 0.75092303 | −0.0050984 | 0.00572727 |
| RAPA_EARLY_UP.V1_UP | 4.48E−06 | 0.2701639 | 0.31211551 |
| HINATA_NFKB_IMMU_INF | 0.00375572 | 0.06476324 | 0.07311357 |
| HINATA_NFKB_MATRIX | 0.01574803 | 0.06648157 | 0.0803593 |
| CYCLIN_D1_KE_.V1_DN | 0.01468734 | 0.09284537 | 0.11681667 |
| CYCLIN_D1_KE_.V1_UP | 0.00453576 | 0.0618669 | 0.07024309 |
| CYCLIN_D1_UP.V1_DN | 0.00030676 | 0.10300224 | 0.11101115 |
| CYCLIN_D1_UP.V1_UP | 0.12567779 | 0.0755043 | 0.13508071 |
| CSR_EARLY_UP.V1_DN | 0.00597996 | 0.05762582 | 0.06603988 |
| CSR_EARLY_UP.V1_UP | 0.00374737 | 0.14786165 | 0.18811099 |
| CSR_LATE_UP.V1_DN | 0.01103835 | 0.04823936 | 0.05673722 |
| CSR_LATE_UP.V1_UP | 7.70E−07 | 0.29157227 | 0.32945702 |
| AKT_UP_MTOR_DN.V1_DN | 0.09614119 | 0.03536708 | 0.04973428 |
| AKT_UP_MTOR_DN.V1_UP | 0.00202444 | 0.12760172 | 0.15039153 |
| AKT_UP.V1_DN | 0.00629857 | 0.14726172 | 0.19500743 |
| AKT_UP.V1_UP | 0.06672397 | 0.05444415 | 0.0731437 |
| MTOR_UP.V1_DN | 0.00768281 | 0.05378465 | 0.062233 |
| MTOR_UP.V1_UP | 0.182693 | 0.00707199 | 0.01593742 |
| PGF_UP.V1_DN | 0.98555441 | −0.009006 | 2.97E−06 |
| PGF_UP.V1_UP | 0.54597339 | 0.00444456 | 0.01944372 |
| VEGF_A_UP.V1_DN | 0.00180991 | 0.14011271 | 0.16518809 |
| VEGF_A_UP.V1_UP | 0.03470874 | 0.03088189 | 0.03953473 |
| BCAT_GDS748_DN | 0.49730693 | 0.0155633 | 0.03999367 |
| BCAT_GDS748_UP | 0.30869455 | 0.00040824 | 0.00933317 |
| BCAT.100_UP.V1_DN | 0.01017899 | 0.04947824 | 0.05796504 |
| BCAT.100_UP.V1_UP | 0.195729 | 0.04189831 | 0.06906918 |
| ATF2_S_UP.V1_DN | 0.02382222 | 0.03654286 | 0.04514515 |
| ATF2_S_UP.V1_UP | 9.90E−05 | 0.17664222 | 0.19474062 |
| ATF2_UP.V1_DN | 0.00410531 | 0.08009875 | 0.09019133 |
| ATF2_UP.V1_UP | 0.03661407 | 0.05483122 | 0.06970831 |
| WNT_UP.V1_DN | 0.96658922 | −0.008993 | 1.59E−05 |
| WNT_UP.V1_UP | 0.44151287 | −0.0036148 | 0.00534605 |
| ATM_DN.V1_DN | 0.01631208 | 0.08417786 | 0.10237917 |
| ATM_DN.V1_UP | 0.01313611 | 0.09183435 | 0.11267681 |
| P53_DN.V2_DN | 0.4481751 | 0.01335996 | 0.03116482 |
| P53_DN.V2_UP | 0.00100748 | 0.1408451 | 0.16054536 |
| RELA_DN.V1_DN | 0.96260459 | −0.0089889 | 1.99E−05 |
| RELA_DN.V1_UP | 0.19862116 | 0.00596566 | 0.01484097 |
| P53_DN.V1_DN | 0.1789892 | 0.00734517 | 0.01620816 |

TABLE 17-continued

GSE76040 ENDORSE: oncogenic (C6) signature pathway generalized additive model summary

| Pathway | P-value | R-squared | Variance explained |
|---|---|---|---|
| P53_DN.V1_UP | 0.0061625 | 0.05716467 | 0.06558284 |
| BCAT_BILD_ET_AL_DN | 0.04196279 | 0.10088249 | 0.14661311 |
| BCAT_BILD_ET_AL_UP | 0.05250556 | 0.07156983 | 0.09671823 |
| E2F3_UP.V1_DN | 0.20116339 | 0.0057986 | 0.0146754 |
| E2F3_UP.V1_UP | 0.30632458 | 0.00050052 | 0.00942463 |
| MYC_UP.V1_DN | 0.27912732 | 0.01874301 | 0.03441334 |
| MYC_UP.V1_UP | 0.02885763 | 0.07972172 | 0.10092572 |
| SRC_UP.V1_DN | 0.02638237 | 0.03500237 | 0.04361842 |
| SRC_UP.V1_UP | 0.03481738 | 0.07234316 | 0.09162302 |
| SNF5_DN.V1_DN | 0.29819819 | 0.0402619 | 0.07944786 |
| SNF5_DN.V1_UP | 0.57507301 | 0.00332475 | 0.01819643 |
| CAMP_UP.V1_DN | 0.13248165 | 0.01144194 | 0.02026835 |
| CAMP_UP.V1_UP | 0.00114894 | 0.14328215 | 0.16713476 |
| LTE2_UP.V1_DN | 0.54589761 | 0.00586293 | 0.02160595 |
| LTE2_UP.V1_UP | 0.27476886 | 0.00182291 | 0.01073521 |
| MEK_UP.V1_DN | 0.10425062 | 0.04669335 | 0.06533703 |
| MEK_UP.V1_UP | 0.00123806 | 0.12487679 | 0.14140091 |
| RAF_UP.V1_DN | 0.0017085 | 0.0768444 | 0.08508686 |
| RAF_UP.V1_UP | 0.93988705 | −0.0089571 | 5.15E−05 |
| PRC1_BMI_UP.V1_DN | 0.25078882 | 0.00296125 | 0.01186338 |
| PRC1_BMI_UP.V1_UP | 0.10523077 | 0.04712732 | 0.06678259 |
| PRC2_EED_UP.V1_DN | 0.16122684 | 0.03641127 | 0.05541263 |
| PRC2_EED_UP.V1_UP | 0.88341391 | −0.0088111 | 0.00019998 |
| PRC2_EZH2_UP.V1_DN | 1.05E−13 | 0.3724598 | 0.37806356 |
| PRC2_EZH2_UP.V1_UP | 0.71806707 | −0.0078194 | 0.00117895 |
| PRC2_SUZ12_UP.V1_DN | 0.02152677 | 0.07483959 | 0.09234349 |
| PRC2_SUZ12_UP.V1_UP | 0.13229709 | 0.04712905 | 0.06963184 |
| JNK_DN.V1_DN | 0.09404904 | 0.03985204 | 0.05559999 |
| JNK_DN.V1_UP | 0.30029736 | 0.01359213 | 0.02755185 |
| BRCA1_DN.V1_DN | 0.20967944 | 0.02584391 | 0.04214059 |
| BRCA1_DN.V1_UP | 3.36E−05 | 0.20396532 | 0.2245365 |
| CTIP_DN.V1_DN | 0.50950674 | 0.00543623 | 0.02020419 |
| CTIP_DN.V1_UP | 0.01578003 | 0.089374 | 0.10981309 |
| PKCA_DN.V1_DN | 0.23757186 | 0.02290083 | 0.03914351 |
| PKCA_DN.V1_UP | 0.84253527 | −0.0060323 | 0.00512964 |
| MTOR_UP.N4.V1_DN | 0.02840425 | 0.03389023 | 0.04251621 |
| MTOR_UP.N4.V1_UP | 0.0624785 | 0.09997048 | 0.16632806 |
| PTEN_DN.V2_DN | 0.61214411 | −0.0066644 | 0.00232365 |
| PTEN_DN.V2_UP | 0.12379331 | 0.04161385 | 0.05970421 |
| DCA_UP.V1_DN | 0.52955912 | 0.00336837 | 0.01713798 |
| DCA_UP.V1_UP | 0.10263531 | 0.04913137 | 0.06815402 |
| ESC_J1_UP_EARLY.V1_DN | 0.0936827 | 0.0163185 | 0.02510137 |
| ESC_J1_UP_EARLY.V1_UP | 0.90452962 | −0.0088777 | 0.00013018 |
| ESC_J1_UP_LATE.V1_DN | 0.04735772 | 0.02625497 | 0.03494913 |
| ESC_J1_UP_LATE.V1_UP | 0.65017366 | −0.0071326 | 0.00185962 |
| ESC_V6.5_UP_EARLY.V1_DN | 0.00010057 | 0.16524278 | 0.18068622 |
| ESC_V6.5_UP_EARLY.V1_UP | 0.00768669 | 0.11717884 | 0.14849588 |
| ESC_V6.5_UP_LATE.V1_DN | 0.01148354 | 0.14094949 | 0.19899746 |
| ESC_V6.5_UP_LATE.V1_UP | 0.21141034 | 0.03081982 | 0.05309592 |
| ALK_DN.V1_DN | 0.00448847 | 0.12055852 | 0.14539266 |
| ALK_DN.V1_UP | 0.00042995 | 0.13181911 | 0.14566894 |
| BMI1_DN_MEL18_DN.V1_DN | 0.58766762 | 0.00175043 | 0.01588514 |
| BMI1_DN_MEL18_DN.V1_UP | 0.30961645 | 0.00037259 | 0.00929784 |
| BMI1_DN.V1_DN | 0.1441852 | 0.01027462 | 0.01911145 |
| BMI1_DN.V1_UP | 0.21874695 | 0.01004326 | 0.020314 |
| MEL18_DN.V1_DN | 0.1856106 | 0.0165408 | 0.02778132 |
| MEL18_DN.V1_UP | 0.12646559 | 0.02859185 | 0.04157309 |
| PTEN_DN.V1_DN | 0.00607257 | 0.15260712 | 0.21314449 |
| PTEN_DN.V1_UP | 0.00593386 | 0.10362432 | 0.1223478 |
| NOTCH_DN.V1_DN | 0.63951769 | 0.01568492 | 0.05379971 |
| NOTCH_DN.V1_UP | 0.02100242 | 0.08157102 | 0.10332606 |
| EIF4E_DN | 0.05571981 | 0.08147355 | 0.11627152 |
| EIF4E_UP | 0.08676402 | 0.08326373 | 0.13195414 |
| CRX_DN.V1_DN | 0.16941983 | 0.00808189 | 0.0169383 |
| CRX_DN.V1_UP | 0.77760439 | −0.0050121 | 0.0061767 |
| CRX_NRL_DN.V1_DN | 2.84E−06 | 0.17163322 | 0.17902935 |
| CRX_NRL_DN.V1_UP | 0.05427956 | 0.06256592 | 0.08127154 |
| NRL_DN.V1_DN | 0.00020354 | 0.10919151 | 0.11714516 |
| NRL_DN.V1_UP | 0.09613354 | 0.03385426 | 0.04706229 |
| RB_DN.V1_DN | 0.00038976 | 0.0993772 | 0.10741848 |
| RB_DN.V1_UP | 0.58102906 | −0.0062317 | 0.0027525 |
| RB_P107_DN.V1_DN | 0.007937 | 0.10253247 | 0.1227145 |
| RB_P107_DN.V1_UP | 0.01704792 | 0.04161399 | 0.05017101 |
| RB_P130_DN.V1_DN | 0.01788969 | 0.08069249 | 0.09888757 |

TABLE 17-continued

GSE76040 ENDORSE: oncogenic (C6) signature pathway generalized additive model summary

| Pathway | P-value | R-squared | Variance explained |
|---|---|---|---|
| RB_P130_DN.V1_UP | 0.23950808 | 0.00354364 | 0.01244058 |
| CAHOY_ASTROCYTIC | 0.1320853 | 0.02819295 | 0.04171465 |
| CAHOY_ASTROGLIAL | 0.00193968 | 0.07489978 | 0.0831596 |
| CAHOY_NEURONAL | 0.1005759 | 0.04606152 | 0.06431527 |
| CAHOY_OLIGODENDROCUTIC | 0.18274766 | 0.02082925 | 0.03338184 |
| RPS14_DN.V1_DN | 2.04E−07 | 0.20793554 | 0.21500755 |
| RPS14_DN.V1_UP | 0.87953199 | −0.0082102 | 0.00126977 |
| IL15_UP.V1_DN | 0.00035084 | 0.16845724 | 0.18957601 |
| IL15_UP.V1_UP | 0.75113774 | −0.003397 | 0.0090192 |
| IL2_UP.V1_DN | 0.02312998 | 0.08403234 | 0.10555568 |
| IL2_UP.V1_UP | 0.87488232 | −0.0087826 | 0.00022435 |
| IL21_UP.V1_DN | 0.04211188 | 0.06680088 | 0.08572457 |
| IL21_UP.V1_UP | 0.00304058 | 0.12239018 | 0.14243489 |
| PDGF_ERK_DN.V1_DN | 2.58E−05 | 0.13987637 | 0.14755605 |
| PDGF_ERK_DN.V1_UP | 0.56469576 | 0.01982866 | 0.05886687 |
| PDGF_UP.V1_DN | 0.00858866 | 0.10099772 | 0.12049142 |
| PDGF_UP.V1_UP | 0.00160001 | 0.14690475 | 0.17734819 |
| TGFB_UP.V1_DN | 0.141911 | 0.01049303 | 0.01932791 |
| TGFB_UP.V1_UP | 0.08227285 | 0.0273102 | 0.03780052 |
| YAP1_DN | 0.73295181 | −0.0051514 | 0.00545521 |
| YAP1_UP | 0.93431417 | −0.008947 | 6.15E−05 |
| SIRNA_EIF4GI_DN | 0.29669928 | 0.03297781 | 0.0605509 |
| SIRNA_EIF4GI_UP | 0.00067316 | 0.13519398 | 0.1523409 |
| HOXA9_DN.V1_DN | 0.22286181 | 0.05721541 | 0.10430091 |
| HOXA9_DN.V1_UP | 0.00766775 | 0.08234422 | 0.09678927 |
| SINGH_KRAS_DEPENDENCY_SIGNATURE | 0.4233942 | −0.0031742 | 0.00578272 |
| STK33_DN | 0.82323341 | −0.0085534 | 0.0004515 |
| STK33_NOMO_DN | 0.1447443 | 0.01022151 | 0.01905881 |
| STK33_NOMO_UP | 0.23957157 | 0.00354027 | 0.01243724 |
| STK33_SKM_DN | 0.02828632 | 0.08264695 | 0.10438573 |
| STK33_SKM_UP | 0.20446518 | 0.00558525 | 0.01446395 |
| STK33_UP | 0.3456608 | −0.0009215 | 0.00801528 |
| KRAS.AMP.LUNG_UP.V1_DN | 0.01772079 | 0.07767933 | 0.09535208 |
| KRAS.AMP.LUNG_UP.V1_UP | 0.00221933 | 0.12789807 | 0.14731392 |
| KRAS.DF.V1_DN | 0.31398096 | 0.00020566 | 0.00913239 |
| KRAS.DF.V1_UP | 0.07860729 | 0.01883772 | 0.0275981 |
| TBK1.DF_DN | 0.19682669 | 0.03006901 | 0.04756594 |
| TBK1.DF_UP | 0.02023569 | 0.1050527 | 0.14429227 |
| TBK1.DN.48HRS_DN | 0.07120628 | 0.05634538 | 0.0751403 |
| TBK1.DN.48HRS_UP | 0.00711399 | 0.10737403 | 0.12847481 |
| NFE2L2.V2 | 0.01566377 | 0.09551194 | 0.12101774 |
| CORDENONSI_YAP_CONSERVED_SIGNATURE | 0.37010449 | 0.02541864 | 0.05305181 |
| JAK2_DN.V1_DN | 0.08295204 | 0.05460843 | 0.07802421 |
| JAK2_DN.V1_UP | 0.00672964 | 0.1058537 | 0.12554906 |
| KRAS.300_UP.V1_DN | 0.00247781 | 0.12493175 | 0.14461165 |
| KRAS.300_UP.V1_UP | 0.09026795 | 0.03946179 | 0.05484285 |
| KRAS.50_UP.V1_DN | 0.06405221 | 0.06112282 | 0.08153679 |
| KRAS.50_UP.V1_UP | 0.0135649 | 0.09090141 | 0.11215898 |
| KRAS.600_UP.V1_DN | 0.00120756 | 0.13822897 | 0.15766746 |
| KRAS.600_UP.V1_UP | 0.00728378 | 0.14074558 | 0.19353291 |
| KRAS.600.LUNG.BREAST_UP.V1_DN | 0.06013 | 0.05813725 | 0.07648781 |
| KRAS.600.LUNG.BREAST_UP.V1_UP | 0.00157836 | 0.13304676 | 0.15220549 |
| KRAS.BREAST_UP.V1_DN | 0.18549852 | 0.03719938 | 0.05895782 |
| KRAS.BREAST_UP.V1_UP | 0.03017167 | 0.06953586 | 0.08721489 |
| KRAS.KIDNEY_UP.V1_DN | 0.01784517 | 0.08343858 | 0.10232527 |
| KRAS.KIDNEY_UP.V1_UP | 0.20840972 | 0.03103261 | 0.04906357 |
| KRAS.LUNG_UP.V1_DN | 0.01136928 | 0.09282028 | 0.11174233 |
| KRAS.LUNG_UP.V1_UP | 0.00237315 | 0.12834843 | 0.14832363 |
| KRAS.LUNG.BREAST_UP.V1_DN | 0.32656306 | 0.01808233 | 0.03495986 |
| KRAS.LUNG.BREAST_UP.V1_UP | 0.00794443 | 0.0995288 | 0.11865255 |
| KRAS.PROSTATE_UP.V1_DN | 0.00022622 | 0.20338947 | 0.24567827 |
| KRAS.PROSTATE_UP.V1_UP | 0.00256381 | 0.15334188 | 0.18944385 |
| LEF1_UP.V1_DN | 0.12879022 | 0.02939915 | 0.04354342 |
| LEF1_UP.V1_UP | 0.11979295 | 0.06962494 | 0.10995269 |

TABLE 18

| GSE124647 ENDORSE: hallmark signature pathway generalized additive model summary | | | |
|---|---|---|---|
| Pathway | P-value | R-squared | Variance explained |
| HALLMARK_TNFA_SIGNALING_VIA_NFKB | 0.002388028 | 0.058051925 | 0.06482853 |
| HALLMARK_HYPOXIA | 0.010694133 | 0.039341855 | 0.046253065 |
| HALLMARK_CHOLESTEROL_HOMEOSTASIS | 0.956120468 | −0.0072242 | 2.20E−05 |
| HALLMARK_MITOTIC_SPINDLE | 3.90E−10 | 0.282036045 | 0.294632311 |
| HALLMARK_WNT_BETA_CATENIN_SIGNALING | 0.13185462 | 0.042530275 | 0.064505481 |
| HALLMARK_TGF_BETA_SIGNALING | 0.000168835 | 0.093065511 | 0.099719911 |
| HALLMARK_IL6_JAK_STAT3_SIGNALING | 0.321524507 | −7.36E−05 | 0.00712121 |
| HALLMARK_DNA_REPAIR | 0.000392217 | 0.134457593 | 0.157034997 |
| HALLMARK_G2M_CHECKPOINT | 8.15E−49 | 0.682780153 | 0.688142264 |
| HALLMARK_APOPTOSIS | 6.34E−05 | 0.103158856 | 0.109610951 |
| HALLMARK_NOTCH_SIGNALING | 0.007543967 | 0.063594612 | 0.073335073 |
| HALLMARK_ADIPOGENESIS | 0.004301169 | 0.063052736 | 0.071185213 |
| HALLMARK_ESTROGEN_RESPONSE_EARLY | 3.84E−11 | 0.304738968 | 0.31573794 |
| HALLMARK_ESTROGEN_RESPONSE_LATE | 0.000238613 | 0.086799903 | 0.093369688 |
| HALLMARK_ANDROGEN_RESPONSE | 5.94E−05 | 0.129717902 | 0.138227279 |
| HALLMARK_MYOGENESIS | 9.66E−07 | 0.193269751 | 0.206765306 |
| HALLMARK_PROTEIN_SECRETION | 0.003757713 | 0.106826397 | 0.132564373 |
| HALLMARK_INTERFERON_ALPHA_RESPONSE | 0.308872987 | 0.036668436 | 0.075200851 |
| HALLMARK_INTERFERON_GAMMA_RESPONSE | 0.556840758 | 0.017383981 | 0.052249701 |
| HALLMARK_APICAL_JUNCTION | 0.000223482 | 0.087612686 | 0.094176623 |
| HALLMARK_APICAL_SURFACE | 0.040355611 | 0.023064865 | 0.030093176 |
| HALLMARK_HEDGEHOG_SIGNALING | 0.031622162 | 0.026013661 | 0.033020757 |
| HALLMARK_COMPLEMENT | 0.197160365 | 0.004862952 | 0.012022211 |
| HALLMARK_UNFOLDED_PROTEIN_RESPONSE | 0.007689189 | 0.043442685 | 0.050324392 |
| HALLMARK_PI3K_AKT_MTOR_SIGNALING | 7.47E−05 | 0.101144101 | 0.10761069 |
| HALLMARK_MTORC1_SIGNALING | 3.77E−06 | 0.137281445 | 0.143488053 |
| HALLMARK_E2F_TARGETS | 2.21E−40 | 0.642272674 | 0.648151837 |
| HALLMARK_MYC_TARGETS_V1 | 1.41E−14 | 0.369790728 | 0.38071163 |
| HALLMARK_MYC_TARGETS_V2 | 8.75E−05 | 0.119812517 | 0.127695375 |
| HALLMARK_EPITHELIAL_MESENCHYMAL_TRANSITION | 0.000173046 | 0.090782228 | 0.097323363 |
| HALLMARK_INFLAMMATORY_RESPONSE | 0.167604458 | 0.006604781 | 0.013751509 |
| HALLMARK_XENOBIOTIC_METABOLISM | 0.165884522 | 0.049003338 | 0.081966798 |
| HALLMARK_FATTY_ACID_METABOLISM | 0.066877423 | 0.039639007 | 0.053066192 |
| HALLMARK_OXIDATIVE_PHOSPHORYLATION | 0.238771327 | 0.021976789 | 0.036308177 |
| HALLMARK_GLYCOLYSIS | 0.506573481 | −0.004020051 | 0.003203114 |
| HALLMARK_REACTIVE_OXYGEN_SPECIES_PATHWAY | 0.686953634 | −0.006057415 | 0.001180408 |
| HALLMARK_P53_PATHWAY | 6.44E−05 | 0.102964796 | 0.109418287 |
| HALLMARK_UV_RESPONSE_UP | 0.533410862 | −0.004408945 | 0.002817018 |
| HALLMARK_UV_RESPONSE_DN | 3.99E−08 | 0.222595853 | 0.230779083 |
| HALLMARK_ANGIOGENESIS | 8.04E−07 | 0.213501374 | 0.232428333 |
| HALLMARK_HEME_METABOLISM | 0.077562001 | 0.047649724 | 0.065538387 |
| HALLMARK_COAGULATION | 0.006792062 | 0.080786868 | 0.096481215 |
| HALLMARK_IL2_STAT5_SIGNALING | 0.170005918 | 0.050867035 | 0.088027314 |
| HALLMARK_BILE_ACID_METABOLISM | 0.016755768 | 0.074501044 | 0.094022681 |
| HALLMARK_PEROXISOME | 0.001411716 | 0.064630746 | 0.071360021 |
| HALLMARK_ALLOGRAFT_REJECTION | 0.404008306 | −0.002158317 | 0.005051455 |
| HALLMARK_SPERMATOGENESIS | 1.01E−15 | 0.354242883 | 0.358888618 |
| HALLMARK_KRAS_SIGNALING_UP | 0.067348444 | 0.016965445 | 0.024037636 |
| HALLMARK_KRAS_SIGNALING_DN | 0.888238984 | −0.007101715 | 0.000143621 |
| HALLMARK_PANCREAS_BETA_CELLS | 0.689468505 | −0.006077476 | 0.001160491 |

TABLE 19

| GSE124647 ENDORSE: oncogenic (C6) signature pathway generalized additive model summary | | | |
|---|---|---|---|
| Pathway | P-value | R-squared | Variance explained |
| GLI1_UP.V1_DN | 0.54367385 | −0.0045486 | 0.00267837 |
| GLI1_UP.V1_UP | 0.87584242 | −0.0070676 | 0.00017752 |
| E2F1_UP.V1_DN | 5.92E−07 | 0.15900212 | 0.16505247 |
| E2F1_UP.V1_UP | 4.88E−16 | 0.39489474 | 0.40490649 |
| EGFR_UP.V1_DN | 0.00191867 | 0.10666433 | 0.12588464 |
| EGFR_UP.V1_UP | 0.00130895 | 0.0655764 | 0.07229887 |
| ERBB2_UP.V1_DN | 0.66308175 | −0.005857 | 0.00137941 |
| ERBB2_UP.V1_UP | 1.66E−08 | 0.19928713 | 0.20504765 |
| GCNP_SHH_UP_EARLY.V1_DN | 0.02557612 | 0.0663865 | 0.08611666 |
| GCNP_SHH_UP_EARLY.V1_UP | 8.51E−12 | 0.31737292 | 0.3291787 |
| GCNP_SHH_UP_LATE.V1_DN | 0.07794777 | 0.03976281 | 0.05601823 |
| GCNP_SHH_UP_LATE.V1_UP | 7.85E−23 | 0.49415361 | 0.50321033 |
| RAPA_EARLY_UP.V1_DN | 0.02467217 | 0.02903719 | 0.03602254 |

TABLE 19-continued

GSE124647 ENDORSE: oncogenic (C6) signature pathway generalized additive model summary

| Pathway | P-value | R-squared | Variance explained |
|---|---|---|---|
| RAPA_EARLY_UP.V1_UP | 1.08E−05 | 0.17465673 | 0.19062221 |
| HINATA_NFKB_IMMU_INF | 0.64337983 | 0.00699609 | 0.02749277 |
| HINATA_NFKB_MATRIX | 0.06729121 | 0.01697544 | 0.02404756 |
| CYCLIN_D1_KE_.V1_DN | 0.43161375 | −0.0027261 | 0.00448777 |
| CYCLIN_D1_KE_.V1_UP | 0.15620587 | 0.00737248 | 0.01451369 |
| CYCLIN_D1_UP.V1_DN | 0.04037609 | 0.02305876 | 0.03008711 |
| CYCLIN_D1_UP.V1_UP | 0.31421814 | 0.0001455 | 0.0073387 |
| CSR_EARLY_UP.V1_DN | 0.0007428 | 0.07265873 | 0.07933025 |
| CSR_EARLY_UP.V1_UP | 0.0039626 | 0.05171617 | 0.05853836 |
| CSR_LATE_UP.V1_DN | 0.00644469 | 0.10572369 | 0.13706617 |
| CSR_LATE_UP.V1_UP | 1.29E−21 | 0.50238145 | 0.52092814 |
| AKT_UP_MTOR_DN.V1_DN | 0.08609193 | 0.04716041 | 0.06911671 |
| AKT_UP_MTOR_DN.V1_UP | 6.17E−06 | 0.13140453 | 0.13765342 |
| AKT_UP.V1_DN | 7.24E−06 | 0.12948108 | 0.13574381 |
| AKT_UP.V1_UP | 0.00770291 | 0.04342049 | 0.05030236 |
| MTOR_UP.V1_DN | 1.76E−05 | 0.11880369 | 0.12514324 |
| MTOR_UP.V1_UP | 1.31E−10 | 0.32042181 | 0.34163008 |
| PGF_UP.V1_DN | 0.68303694 | 0.00282975 | 0.02180016 |
| PGF_UP.V1_UP | 0.11676281 | 0.01061192 | 0.01772982 |
| VEGF_A_UP.V1_DN | 8.86E−15 | 0.37445729 | 0.38494315 |
| VEGF_A_UP.V1_UP | 0.00213871 | 0.05943202 | 0.0661987 |
| BCAT_GDS748_DN | 0.177182 | 0.00600415 | 0.0131552 |
| BCAT_GDS748_UP | 0.16659729 | 0.0066702 | 0.01381646 |
| BCAT.100_UP.V1_DN | 0.01316701 | 0.03676414 | 0.0436939 |
| BCAT.100_UP.V1_UP | 0.00067226 | 0.09803386 | 0.10734192 |
| ATF2_S_UP.V1_DN | 2.83E−05 | 0.13870877 | 0.14681915 |
| ATF2_S_UP.V1_UP | 0.01379916 | 0.0361841 | 0.04311803 |
| ATF2_UP.V1_DN | 2.56E−05 | 0.11425505 | 0.12062731 |
| ATF2_UP.V1_UP | 0.00153569 | 0.09732322 | 0.11050381 |
| WNT_UP.V1_DN | 0.21694858 | 0.00385785 | 0.01102434 |
| WNT_UP.V1_UP | 0.44302787 | 0.01673081 | 0.04019958 |
| ATM_DN.V1_DN | 0.42498846 | −0.0025948 | 0.00461808 |
| ATM_DN.V1_UP | 0.89485087 | −0.0071184 | 0.00012704 |
| P53_DN.V2_DN | 0.00189967 | 0.08232223 | 0.09314157 |
| P53_DN.V2_UP | 0.36375199 | −0.001222 | 0.00598099 |
| RELA_DN.V1_DN | 0.82490255 | −0.0068879 | 0.00035593 |
| RELA_DN.V1_UP | 0.00114794 | 0.06721817 | 0.07392883 |
| P53_DN.V1_DN | 0.00024573 | 0.08643529 | 0.0930077 |
| P53_DN.V1_UP | 0.00222352 | 0.05894529 | 0.06571547 |
| BCAT_BILD_ET_AL_DN | 0.07567817 | 0.01559879 | 0.02268081 |
| BCAT_BILD_ET_AL_UP | 0.0113185 | 0.04268667 | 0.05007088 |
| E2F3_UP.V1_DN | 0.33880901 | 0.0091118 | 0.02001559 |
| E2F3_UP.V1_UP | 4.54E−05 | 0.10726507 | 0.11368762 |
| MYC_UP.V1_DN | 0.12933925 | 0.03551194 | 0.05405399 |
| MYC_UP.V1_UP | 0.1717929 | 0.00633743 | 0.01348608 |
| SRC_UP.V1_DN | 0.00030515 | 0.15273829 | 0.18041194 |
| SRC_UP.V1_UP | 0.46877702 | −0.0018599 | 0.00594746 |
| SNF5_DN.V1_DN | 0.01161491 | 0.0848575 | 0.10638389 |
| SNF5_DN.V1_UP | 0.04482288 | 0.02180329 | 0.02884068 |
| CAMP_UP.V1_DN | 0.08405905 | 0.01437634 | 0.02146715 |
| CAMP_UP.V1_UP | 0.42531137 | −0.0026013 | 0.00461166 |
| LTE2_UP.V1_DN | 0.00157578 | 0.06325501 | 0.06999418 |
| LTE2_UP.V1_UP | 0.00970145 | 0.0405514 | 0.04745391 |
| MEK_UP.V1_DN | 0.00025362 | 0.13970384 | 0.16117273 |
| MEK_UP.V1_UP | 3.68E−05 | 0.10981599 | 0.11622019 |
| RAF_UP.V1_DN | 4.90E−11 | 0.25967616 | 0.26500223 |
| RAF_UP.V1_UP | 0.15312446 | 0.03897917 | 0.06198336 |
| PRC1_BMI_UP.V1_DN | 0.00641034 | 0.06972608 | 0.08162156 |
| PRC1_BMI_UP.V1_UP | 0.6090157 | −0.00533 | 0.0019039 |
| PRC2_EED_UP.V1_DN | 0.72804079 | −0.006361 | 0.00087901 |
| PRC2_EED_UP.V1_UP | 6.57E−05 | 0.1027217 | 0.10917694 |
| PRC2_EZH2_UP.V1_DN | 1.55E−19 | 0.44292905 | 0.44987492 |
| PRC2_EZH2_UP.V1_UP | 0.0061185 | 0.08771614 | 0.10658698 |
| PRC2_SUZ12_UP.V1_DN | 0.41930585 | 0.02068777 | 0.04415488 |
| PRC2_SUZ12_UP.V1_UP | 0.03067127 | 0.02638448 | 0.0333889 |
| JNK_DN.V1_DN | 0.11514289 | 0.03573404 | 0.05070729 |
| JNK_DN.V1_UP | 0.41250349 | −0.002339 | 0.00487208 |
| BRCA1_DN.V1_DN | 0.85126179 | −0.0069889 | 0.00025567 |
| BRCA1_DN.V1_UP | 0.43210374 | 0.01645993 | 0.0372143 |
| CTIP_DN.V1_DN | 0.11480144 | 0.01080346 | 0.01791998 |
| CTIP_DN.V1_UP | 0.09381099 | 0.05805458 | 0.08625731 |
| PKCA_DN.V1_DN | 0.20262255 | 0.02120124 | 0.03437014 |
| PKCA_DN.V1_UP | 0.06200165 | 0.04287377 | 0.05725003 |
| MTOR_UP.N4.V1_DN | 0.00494269 | 0.12487503 | 0.1677162 |

TABLE 19-continued

GSE124647 ENDORSE: oncogenic (C6) signature pathway generalized additive model summary

| Pathway | P-value | R-squared | Variance explained |
|---|---|---|---|
| MTOR_UP.N4.V1_UP | 0.16882568 | 0.00652605 | 0.01367335 |
| PTEN_DN.V2_DN | 0.00122587 | 0.06639671 | 0.07311328 |
| PTEN_DN.V2_UP | 0.00032125 | 0.08310604 | 0.0897024 |
| DCA_UP.V1_DN | 0.33497269 | −0.0004602 | 0.00673735 |
| DCA_UP.V1_UP | 0.73634473 | −0.0064163 | 0.00082413 |
| ESC_J1_UP_EARLY.V1_DN | 0.00580486 | 0.07865206 | 0.09230667 |
| ESC_J1_UP_EARLY.V1_UP | 7.66E−05 | 0.14661655 | 0.16321891 |
| ESC_J1_UP_LATE.V1_DN | 0.07869629 | 0.04131466 | 0.05600468 |
| ESC_J1_UP_LATE.V1_UP | 3.31E−06 | 0.16564378 | 0.17575306 |
| ESC_V6.5_UP_EARLY.V1_DN | 1.94E−05 | 0.11761471 | 0.1239628 |
| ESC_V6.5_UP_EARLY.V1_UP | 1.13E−07 | 0.17793933 | 0.18385343 |
| ESC_V6.5_UP_LATE.V1_DN | 0.17630872 | 0.02538676 | 0.03915473 |
| ESC_V6.5_UP_LATE.V1_UP | 0.00027741 | 0.14939521 | 0.1765268 |
| ALK_DN.V1_DN | 0.68972884 | −0.0060795 | 0.00115844 |
| ALK_DN.V1_UP | 0.14714761 | 0.00802895 | 0.01516543 |
| BMI1_DN_MEL18_DN.V1_DN | 0.00030026 | 0.08394599 | 0.09053631 |
| BMI1_DN_MEL18_DN.V1_UP | 0.0026181 | 0.05690077 | 0.06368566 |
| BMI1_DN.V1_DN | 0.00183364 | 0.10962643 | 0.13039197 |
| BMI1_DN.V1_UP | 0.00038866 | 0.17036503 | 0.21591005 |
| MEL18_DN.V1_DN | 0.00028068 | 0.08478389 | 0.09136818 |
| MEL18_DN.V1_UP | 2.89E−05 | 0.11275421 | 0.11913727 |
| PTEN_DN.V1_DN | 0.15452597 | 0.04955112 | 0.07883609 |
| PTEN_DN.V1_UP | 0.31555556 | 0.02766552 | 0.05306372 |
| NOTCH_DN.V1_DN | 0.08223788 | 0.01463058 | 0.02171956 |
| NOTCH_DN.V1_UP | 0.25210131 | 0.00231521 | 0.0094928 |
| EIF4E_DN | 3.64E−07 | 0.16461696 | 0.17062691 |
| EIF4E_UP | 0.02110931 | 0.03094709 | 0.0379187 |
| CRX_DN.V1_DN | 0.00921278 | 0.04119364 | 0.04809152 |
| CRX_DN.V1_UP | 0.36949901 | −0.0013644 | 0.00583967 |
| CRX_NRL_DN.V1_DN | 1.61E−06 | 0.19596942 | 0.21175712 |
| CRX_NRL_DN.V1_UP | 0.65982068 | −0.0054111 | 0.00202771 |
| NRL_DN.V1_DN | 0.00207355 | 0.0598193 | 0.06658319 |
| NRL_DN.V1_UP | 0.85535294 | −0.007003 | 0.00024165 |
| RB_DN.V1_DN | 0.00011324 | 0.09602287 | 0.1025263 |
| RB_DN.V1_UP | 2.25E−05 | 0.14313413 | 0.15229941 |
| RB_P107_DN.V1_DN | 0.00738638 | 0.07433614 | 0.08772062 |
| RB_P107_DN.V1_UP | 7.10E−18 | 0.42793156 | 0.43703167 |
| RB_P130_DN.V1_DN | 4.01E−05 | 0.10876435 | 0.11517612 |
| RB_P130_DN.V1_UP | 2.05E−09 | 0.2217121 | 0.2273113 |
| CAHOY_ASTROCYTIC | 0.69384145 | −0.0001046 | 0.01169253 |
| CAHOY_ASTROGLIAL | 0.00396062 | 0.05172245 | 0.05854459 |
| CAHOY_NEURONAL | 0.00438923 | 0.13022412 | 0.17629034 |
| CAHOY_OLIGODENDROCUTIC | 0.15214098 | 0.00766165 | 0.01480077 |
| RPS14_DN.V1_DN | 2.88E−15 | 0.38349913 | 0.39201601 |
| RPS14_DN.V1_UP | 0.09708613 | 0.01271383 | 0.01981661 |
| IL15_UP.V1_DN | 0.05220401 | 0.01998113 | 0.02703162 |
| IL15_UP.V1_UP | 0.07227709 | 0.01613657 | 0.02321472 |
| IL2_UP.V1_DN | 0.00423048 | 0.05089847 | 0.05772654 |
| IL2_UP.V1_UP | 0.19855799 | 0.00517423 | 0.01243591 |
| IL21_UP.V1_DN | 0.05441626 | 0.05453971 | 0.07230879 |
| IL21_UP.V1_UP | 0.0613617 | 0.06083023 | 0.08394093 |
| PDGF_ERK_DN.V1_DN | 0.08717035 | 0.01395532 | 0.02104917 |
| PDGF_ERK_DN.V1_UP | 0.00047193 | 0.078318 | 0.0849488 |
| PDGF_UP.V1_DN | 0.00178378 | 0.09748652 | 0.11223923 |
| PDGF_UP.V1_UP | 0.14644179 | 0.00808199 | 0.01521809 |
| TGFB_UP.V1_DN | 2.96E−06 | 0.23166108 | 0.26695257 |
| TGFB_UP.V1_UP | 0.00043344 | 0.07937804 | 0.08600122 |
| YAP1_DN | 0.1786901 | 0.05375319 | 0.09640351 |
| YAP1_UP | 0.14373546 | 0.02030646 | 0.03046731 |
| SIRNA_EIF4GI_DN | 0.08293216 | 0.01453295 | 0.02162264 |
| SIRNA_EIF4GI_UP | 0.06289683 | 0.01777116 | 0.02483755 |
| HOXA9_DN.V1_DN | 4.05E−09 | 0.26635979 | 0.28035911 |
| HOXA9_DN.V1_UP | 6.62E−06 | 0.17325301 | 0.18663787 |
| SINGH_KRAS_DEPENDENCY_SIGNATURE | 0.03903739 | 0.04349368 | 0.05562243 |
| STK33_DN | 0.03270103 | 0.07851007 | 0.10535323 |
| STK33_NOMO_DN | 0.08727105 | 0.06454022 | 0.09625015 |
| STK33_NOMO_UP | 5.00E−07 | 0.16095315 | 0.16698946 |
| STK33_SKM_DN | 0.02491513 | 0.09953275 | 0.14311934 |
| STK33_SKM_UP | 1.10E−05 | 0.13630174 | 0.14316199 |
| STK33_UP | 2.34E−08 | 0.19548235 | 0.20127025 |
| KRAS.AMP.LUNG_UP.V1_DN | 0.69862601 | −0.0058928 | 0.0014815 |
| KRAS.AMP.LUNG_UP.V1_UP | 0.50029968 | −0.0039239 | 0.00329853 |
| KRAS.DF.V1_DN | 0.04783779 | 0.0688254 | 0.09505742 |
| KRAS.DF.V1_UP | 9.08E−06 | 0.12677383 | 0.13305603 |

TABLE 19-continued

GSE124647 ENDORSE: oncogenic (C6) signature pathway generalized additive model summary

| Pathway | P-value | R-squared | Variance explained |
|---|---|---|---|
| TBK1.DF_DN | 0.61998584 | −0.0054468 | 0.00178666 |
| TBK1.DF_UP | 0.00318623 | 0.0544434 | 0.06124597 |
| TBK1.DN.48HRS_DN | 0.43878046 | −0.0028647 | 0.00435015 |
| TBK1.DN.48HRS_UP | 0.43475456 | −0.0027873 | 0.00442703 |
| NFE2L2.V2 | 0.04607484 | 0.07253499 | 0.10381796 |
| CORDENONSI_YAP_CONSERVED_SIGNATURE | 0.00017975 | 0.13073192 | 0.14465309 |
| JAK2_DN.V1_DN | 0.21856804 | 0.0037804 | 0.01094745 |
| JAK2_DN.V1_UP | 0.0463315 | 0.07260246 | 0.10123861 |
| KRAS.300_UP.V1_DN | 0.42974864 | 0.01279047 | 0.02794305 |
| KRAS.300_UP.V1_UP | 0.09257917 | 0.01326037 | 0.02035922 |
| KRAS.50_UP.V1_DN | 0.01536042 | 0.07566372 | 0.09218527 |
| KRAS.50_UP.V1_UP | 0.0539119 | 0.0195979 | 0.02665115 |
| KRAS.600_UP.V1_DN | 0.00357952 | 0.11008106 | 0.13265283 |
| KRAS.600_UP.V1_UP | 0.11250792 | 0.01103202 | 0.0181469 |
| KRAS.600.LUNG.BREAST_UP.V1_DN | 0.20069412 | 0.01238131 | 0.02152372 |
| KRAS.600.LUNG.BREAST_UP.V1_UP | 0.39465721 | 0.00282638 | 0.01174183 |
| KRAS.BREAST_UP.V1_DN | 0.00331919 | 0.07969372 | 0.09157529 |
| KRAS.BREAST_UP.V1_UP | 0.14479024 | 0.05603236 | 0.09388378 |
| KRAS.KIDNEY_UP.V1_DN | 0.17142304 | 0.00636074 | 0.01350922 |
| KRAS.KIDNEY_UP.V1_UP | 0.08808045 | 0.01383521 | 0.02092992 |
| KRAS.LUNG_UP.V1_DN | 0.04622971 | 0.06956629 | 0.09605536 |
| KRAS.LUNG_UP.V1_UP | 0.23605822 | 0.00298498 | 0.01015775 |
| KRAS.LUNG.BREAST_UP.V1_DN | 0.05888047 | 0.03461683 | 0.04566108 |
| KRAS.LUNG.BREAST_UP.V1_UP | 0.29034573 | 0.01126632 | 0.02200546 |
| KRAS.PROSTATE_UP.V1_DN | 0.18503314 | 0.00553881 | 0.01269321 |
| KRAS.PROSTATE_UP.V1_UP | 0.69569749 | −0.0061263 | 0.001112 |
| LEF1_UP.V1_DN | 4.93E−13 | 0.30265483 | 0.30767171 |
| LEF1_UP.V1_UP | 0.02423577 | 0.02925538 | 0.03623915 |

TABLE 20

GSE87411 ENDORSE: hallmark signature pathway generalized additive model summary

| Pathway | Baseline P-value | R-squared | Variance explained | End of treatment P-value | R-squared | Variance explained |
|---|---|---|---|---|---|---|
| HALLMARK_TNFA_SIGNALING_VIA_NFKB | 0.464191358 | −0.004281014 | 0.005017885 | 0.078000774 | 0.019656995 | 0.028734245 |
| HALLMARK_HYPOXIA | 0.07882163 | 0.019500231 | 0.028578933 | 0.442564633 | 0.004525223 | 0.017043511 |
| HALLMARK_CHOLESTEROL_HOMEOSTASIS | 0.38752808 | 0.008889294 | 0.022699201 | 0.772116347 | −0.00855122 | 0.000787218 |
| HALLMARK_MITOTIC_SPINDLE | 1.23E−13 | 0.380948686 | 0.386680643 | 1.18E−19 | 0.540681053 | 0.553221063 |
| HALLMARK_WNT_BETA_CATENIN_SIGNALING | 0.005131272 | 0.101448787 | 0.118317427 | 0.144312749 | 0.031160813 | 0.046739455 |
| HALLMARK_TGF_BETA_SIGNALING | 0.001964429 | 0.123470633 | 0.142122129 | 0.01553108 | 0.044612568 | 0.053458748 |
| HALLMARK_IL6_JAK_STAT3_SIGNALING | 0.296702674 | 0.035870834 | 0.064627736 | 0.044631874 | 0.028140848 | 0.037139544 |
| HALLMARK_DNA_REPAIR | 2.15E−10 | 0.302022056 | 0.308484815 | 2.09E−06 | 0.229105616 | 0.243438001 |
| HALLMARK_G2M_CHECKPOINT | 4.62E−51 | 0.75385686 | 0.759518595 | 1.91E−77 | 0.82815615 | 0.834346931 |
| HALLMARK_APOPTOSIS | 0.112317421 | 0.014262795 | 0.023389991 | 0.293074696 | 0.053253416 | 0.117103349 |
| HALLMARK_NOTCH_SIGNALING | 6.67E−08 | 0.229937898 | 0.237068103 | 0.000323675 | 0.182801696 | 0.214441638 |
| HALLMARK_ADIPOGENESIS | 0.02324991 | 0.121735027 | 0.171407579 | 0.048914715 | 0.026733825 | 0.035745549 |
| HALLMARK_ESTROGEN_RESPONSE_EARLY | 0.000134281 | 0.119491265 | 0.127644123 | 9.79E−06 | 0.205456708 | 0.220214632 |
| HALLMARK_ESTROGEN_RESPONSE_LATE | 0.257011298 | 0.024512586 | 0.042170051 | 0.57920293 | 0.02185279 | 0.061604861 |
| HALLMARK_ANDROGEN_RESPONSE | 0.254021981 | 0.002908233 | 0.012140564 | 0.911694865 | −0.00922924 | 0.000115476 |
| HALLMARK_MYOGENESIS | 2.16E−05 | 0.168395278 | 0.177437337 | 0.000373381 | 0.152048572 | 0.169697819 |
| HALLMARK_PROTEIN_SECRETION | 0.396288545 | 0.005184933 | 0.017232565 | 0.525541874 | 0.014100662 | 0.040254585 |
| HALLMARK_INTERFERON_ALPHA_RESPONSE | 0.061712689 | 0.070932019 | 0.099410136 | 0.03083605 | 0.033863125 | 0.042808837 |

TABLE 20-continued

| Pathway | Baseline P-value | R-squared | Variance explained | End of treatment P-value | R-squared | Variance explained |
|---|---|---|---|---|---|---|
| GSE87411 ENDORSE: hallmark signature pathway generalized additive model summary | | | | | | |
| HALLMARK_INTERFERON_GAMMA_RESPONSE | 0.078795811 | 0.065577487 | 0.094369558 | 0.025337391 | 0.103649196 | 0.140973689 |
| HALLMARK_APICAL_JUNCTION | 0.033717606 | 0.055208518 | 0.069717782 | 0.26744308 | 0.002241284 | 0.01147979 |
| HALLMARK_APICAL_SURFACE | 0.033671363 | 0.073296659 | 0.092710626 | 0.522508935 | 0.001201886 | 0.01318305 |
| HALLMARK_HEDGEHOG_SIGNALING | 2.91E−05 | 0.142915293 | 0.150851263 | 0.037268119 | 0.052270311 | 0.065508355 |
| HALLMARK_COMPLEMENT | 0.366487597 | 0.015055258 | 0.03192167 | 0.149906761 | 0.060589232 | 0.097218039 |
| HALLMARK_UNFOLDED_PROTEIN_RESPONSE | 3.50E−05 | 0.193440928 | 0.21253635 | 2.11E−09 | 0.349678484 | 0.372652689 |
| HALLMARK_PI3K_AKT_MTOR_SIGNALING | 7.57E−06 | 0.163053356 | 0.170802862 | 0.000102999 | 0.174435589 | 0.192946233 |
| HALLMARK_MTORC1_SIGNALING | 8.03E−11 | 0.313346541 | 0.319704443 | 8.18E−12 | 0.398835654 | 0.414780747 |
| HALLMARK_E2F_TARGETS | 1.16E−53 | 0.761739532 | 0.766861878 | 1.24E−79 | 0.831516268 | 0.838100485 |
| HALLMARK_MYC_TARGETS_V1 | 4.55E−10 | 0.339448983 | 0.354223361 | 6.96E−15 | 0.467102803 | 0.481641597 |
| HALLMARK_MYC_TARGETS_V2 | 4.42E−09 | 0.265301157 | 0.272103924 | 1.98E−10 | 0.351945103 | 0.366506121 |
| HALLMARK_EPITHELIAL_MESENCHYMAL_TRANSITION | 0.011893937 | 0.069673547 | 0.081360932 | 0.007087906 | 0.153271315 | 0.216157736 |
| HALLMARK_INFLAMMATORY_RESPONSE | 0.759926277 | −0.006214053 | 0.004485341 | 0.067930083 | 0.021736077 | 0.030794076 |
| HALLMARK_XENOBIOTIC_METABOLISM | 0.014619036 | 0.045566998 | 0.05440434 | 0.524630583 | 0.010258888 | 0.031144222 |
| HALLMARK_FATTY_ACID_METABOLISM | 0.00695681 | 0.115560936 | 0.142588582 | 0.299247547 | 0.000814049 | 0.010065771 |
| HALLMARK_OXIDATIVE_PHOSPHORYLATION | 0.266073547 | 0.031221067 | 0.055659829 | 0.390159032 | −0.00237185 | 0.006909371 |
| HALLMARK_GLYCOLYSIS | 0.052159591 | 0.025750565 | 0.034771393 | 0.004620649 | 0.104634513 | 0.121744901 |
| HALLMARK_REACTIVE_OXYGEN_SPECIES_PATHWAY | 0.150819231 | 0.010022634 | 0.019189091 | 0.055122969 | 0.034085422 | 0.044643844 |
| HALLMARK_P53_PATHWAY | 0.018633515 | 0.041745207 | 0.050617936 | 0.791299439 | −0.00764536 | 0.002365192 |
| HALLMARK_UV_RESPONSE_UP | 0.000162218 | 0.116564633 | 0.12474459 | 2.57E−05 | 0.204727232 | 0.224384697 |
| HALLMARK_UV_RESPONSE_DN | 0.000275325 | 0.13927002 | 0.151373075 | 0.001400466 | 0.155874523 | 0.18952673 |
| HALLMARK_ANGIOGENESIS_ | 0.001180761 | 0.085458464 | 0.093926441 | 0.003498812 | 0.128483371 | 0.152967803 |
| HALLMARK_HEME_METABOLISM | 0.047002601 | 0.027345541 | 0.036351603 | 0.351043286 | −0.00113763 | 0.008132166 |
| HALLMARK_COAGULATION | 8.90E−05 | 0.12583146 | 0.133925613 | 0.111003394 | 0.084732356 | 0.136753492 |
| HALLMARK_IL2_STAT5_SIGNALING | 0.475901558 | 0.010069391 | 0.027174748 | 0.060133506 | 0.023582451 | 0.032623355 |
| HALLMARK_BILE_ACID_METABOLISM | 1.25E−06 | 0.189216323 | 0.196723579 | 0.001145305 | 0.12596645 | 0.141920025 |
| HALLMARK_PEROXISOME | 0.169484418 | 0.022161639 | 0.03478452 | 0.509370785 | −0.00522818 | 0.004079487 |
| HALLMARK_ALLOGRAFT_REJECTION | 0.284519898 | 0.038289731 | 0.073268531 | 0.008921355 | 0.067903886 | 0.078386851 |
| HALLMARK_SPERMATOGENESIS | 2.98E−13 | 0.37242084 | 0.378231758 | 1.63E−12 | 0.407614684 | 0.421869488 |
| HALLMARK_KRAS_SIGNALING_UP | 0.013119108 | 0.047276008 | 0.056097527 | 0.958575661 | −0.00932023 | 2.53E−05 |
| HALLMARK_KRAS_SIGNALING_DN | 0.415710366 | 0.015588206 | 0.034559055 | 0.806235919 | −0.00877576 | 0.00056476 |
| HALLMARK_PANCREAS_BETA_CELLS | 0.093621858 | 0.03470723 | 0.047753399 | 0.787335299 | −0.00362902 | 0.00964637 |

TABLE 21

GSE87411 ENDORSE: Hallmark signature pathway generalized additive model summary

| Pathway | Baseline P-value | R-squared | Variance explained | End of treatment P-value | R-squared | Variance explained |
|---|---|---|---|---|---|---|
| GLI1_UP.V1_DN | 0.58399595 | 0.00179693 | 0.0157793 | 0.28191354 | 0.00156694 | 0.01081169 |
| GLI1_UP.V1_UP | 0.180144 | 0.0610679 | 0.10101951 | 0.23683137 | 0.00382795 | 0.01305176 |
| E2F1_UP.V1_DN | 4.92E−05 | 0.13492854 | 0.14293846 | 0.06309278 | 0.02285354 | 0.03190119 |
| E2F1_UP.V1_UP | 3.85E−49 | 0.74640477 | 0.75220233 | 4.31E−69 | 0.80913 | 0.8149755 |
| EGFR_UP.V1_DN | 0.76825404 | −0.0085233 | 0.00081491 | 0.16003163 | 0.00918588 | 0.01836009 |
| EGFR_UP.V1_UP | 0.15290598 | 0.00982817 | 0.01899643 | 0.42326489 | −0.0032871 | 0.00600258 |
| ERBB2_UP.V1_DN | 0.04834505 | 0.02691343 | 0.03592349 | 0.28097836 | 0.00160921 | 0.01085357 |
| ERBB2_UP.V1_UP | 2.78E−08 | 0.24165144 | 0.24867493 | 0.0016319 | 0.08033742 | 0.08885281 |
| GCNP_SHH_UP_ EARLY.V1_DN | 0.00173018 | 0.07941094 | 0.08793492 | 0.67134899 | −0.0076411 | 0.00168896 |
| GCNP_SHH_UP_ EARLY.V1_UP | 6.82E−12 | 0.34048815 | 0.34659475 | 1.40E−15 | 0.48527728 | 0.50384354 |
| GCNP_SHH_UP_ LATE.V1_DN | 0.0292002 | 0.03471185 | 0.0436497 | 0.32353367 | 0.05663955 | 0.12064974 |
| GCNP_SHH_UP_ LATE.V1_UP | 4.33E−14 | 0.43347194 | 0.44558614 | 9.75E−22 | 0.56416322 | 0.5767687 |
| RAPA_EARLY_ UP.V1_DN | 0.07653942 | 0.01994046 | 0.02901508 | 0.3378845 | −0.0006795 | 0.00858609 |
| RAPA_EARLY_ UP.V1_UP | 0.0004051 | 0.10229963 | 0.11061167 | 0.02058596 | 0.0717699 | 0.0881606 |
| HINATA_NFKB_ IMMU_INF | 0.74858302 | −0.0033064 | 0.00976818 | 0.06777937 | 0.09713064 | 0.14950109 |
| HINATA_NFKB_ MATRIX | 0.97646866 | −0.0093375 | 8.17E−06 | 0.37134126 | −0.0018006 | 0.00747537 |
| CYCLIN_DI_KE_.V1_DN | 0.00817516 | 0.05476311 | 0.0635153 | 0.60087456 | −0.0067554 | 0.00256642 |
| CYCLIN_DI_KE_.V1_UP | 0.1742749 | 0.00799347 | 0.01717871 | 0.95622455 | −0.0093172 | 2.83E−05 |
| CYCLIN_DI_UP.V1_DN | 0.02742696 | 0.03568874 | 0.04461754 | 0.33470924 | 0.03717914 | 0.07260825 |
| CYCLIN_DI_UP.V1_UP | 0.2051206 | 0.00575399 | 0.01495997 | 0.8653502 | −0.0090733 | 0.00026994 |
| CSR_EARLY_UP.V1_DN | 0.01025266 | 0.11182718 | 0.14237086 | 3.86E−05 | 0.17120739 | 0.18413159 |
| CSR_EARLY_UP.V1_UP | 0.00644257 | 0.0743761 | 0.08494344 | 0.00277914 | 0.07189385 | 0.08048742 |
| CSR_LATE_UP.V1_DN | 1.71E−05 | 0.15094114 | 0.15880279 | 0.01594999 | 0.06512061 | 0.07695788 |
| CSR_LATE_UP.V1_UP | 7.18E−46 | 0.73737399 | 0.74706072 | 6.64E−54 | 0.76978778 | 0.77556363 |
| AKT_UP_MTOR_ DN.V1_DN | 0.00010853 | 0.12277965 | 0.13090206 | 0.02354599 | 0.10524903 | 0.14099573 |
| AKT_UP_MTOR_ DN.V1_UP | 1.46E−05 | 0.23766123 | 0.26786469 | 0.04553895 | 0.06790195 | 0.09164125 |
| AKT_UP.V1_DN | 5.15E−10 | 0.29168771 | 0.29824615 | 8.81E−05 | 0.20016711 | 0.22668371 |
| AKT_UP.V1_UP | 0.05161714 | 0.02591043 | 0.03492978 | 0.74846283 | −0.0083717 | 0.00096504 |
| MTOR_UP.V1_DN | 3.85E−07 | 0.30806497 | 0.34651214 | 8.44E−06 | 0.22984065 | 0.25254364 |
| MTOR_UP.V1_UP | 1.59E−15 | 0.4200613 | 0.4254311 | 9.01E−21 | 0.57791605 | 0.61126305 |
| PGF_UP.V1_DN | 0.39851606 | −0.0026132 | 0.00667022 | 0.63640448 | −0.0072301 | 0.00209614 |
| PGF_UP.V1_UP | 0.99746319 | −0.0093457 | 9.49E−08 | 0.88615962 | −0.0091516 | 0.00019243 |
| VEGF_A_UP.V1_DN | 3.33E−07 | 0.20791721 | 0.21525131 | 2.68E−08 | 0.3083443 | 0.32645737 |
| VEGF_A_UP.V1_UP | 0.02170667 | 0.03934807 | 0.04824299 | 0.31280109 | 0.00026299 | 0.00951981 |
| BCAT_GDS748_DN | 0.41280842 | −0.0030096 | 0.00627752 | 0.54858846 | −0.0059411 | 0.00337315 |
| BCAT_GDS748_UP | 4.62E−06 | 0.17031428 | 0.17799656 | 0.40318933 | 0.00570792 | 0.01802417 |
| BCAT.100_UP.V1_DN | 0.00252813 | 0.07339635 | 0.08197602 | 0.00019379 | 0.18741204 | 0.21514282 |
| BCAT.100_UP.V1_UP | 2.25E−10 | 0.3014568 | 0.30792479 | 7.98E−08 | 0.26269604 | 0.27442979 |
| ATF2_S_UP.V1_DN | 7.82E−06 | 0.16255705 | 0.17031115 | 0.05078827 | 0.06635564 | 0.09042676 |
| ATF2_S_UP.V1_UP | 0.18562044 | 0.00712027 | 0.0163136 | 0.05543959 | 0.09182343 | 0.13786968 |
| ATF2_UP.V1_DN | 1.36E−05 | 0.15433534 | 0.16216557 | 0.03293682 | 0.03283855 | 0.04179375 |
| ATF2_UP.V1_UP | 0.20559058 | 0.00572294 | 0.01492921 | 0.02988992 | 0.0343482 | 0.04328942 |
| WNT_UP.V1_DN | 0.01618207 | 0.10629236 | 0.13888902 | 0.56288679 | −0.0061784 | 0.00313804 |
| WNT_UP.V1_UP | 0.01791015 | 0.04236794 | 0.0512349 | 0.19646724 | 0.02969294 | 0.04719191 |
| ATM_DN.V1_DN | 0.16237711 | 0.00898147 | 0.01815756 | 0.59952169 | −0.0067361 | 0.00258552 |
| ATM_DN.V1_UP | 0.05087366 | 0.0261324 | 0.03514969 | 0.48747647 | 0.00600777 | 0.02116047 |
| P53_DN.V2_DN | 0.02288528 | 0.03851934 | 0.04742194 | 0.30490685 | 0.00058013 | 0.00983402 |
| P53_DN.V2_UP | 0.08352258 | 0.04204705 | 0.05776776 | 0.54943367 | 0.00212021 | 0.01517684 |
| RELA_DN.V1_DN | 0.0555616 | 0.03233699 | 0.04266614 | 0.53480596 | −0.0057012 | 0.00361081 |
| RELA_DN.V1_UP | 0.00712791 | 0.05693752 | 0.06566958 | 0.95090739 | −0.0093099 | 3.56E−05 |
| P53_DN.V1_DN | 0.04094898 | 0.02946759 | 0.038454 | 0.57230661 | −0.0063286 | 0.00298927 |
| P53_DN.V1_UP | 0.00026795 | 0.10876037 | 0.11701259 | 0.02722892 | 0.09853186 | 0.13336516 |
| BCAT_BILD_ET_AL_DN | 0.65236318 | −0.0074244 | 0.00190364 | 0.45938011 | 0.01469548 | 0.03858315 |
| BCAT_BILD_ET_AL_UP | 0.13307374 | 0.01180799 | 0.02095791 | 0.55605077 | −0.0060664 | 0.00324902 |
| E2F3_UP.V1_DN | 0.04838081 | 0.02690209 | 0.03591226 | 0.03571641 | 0.03158161 | 0.04054845 |
| E2F3_UP.V1_UP | 0.01241375 | 0.085003 | 0.10263942 | 0.00638427 | 0.05868614 | 0.06740201 |
| MYC_UP.V1_DN | 0.57514817 | −0.0063729 | 0.00294533 | 0.32827799 | −0.0003297 | 0.00893261 |
| MYC_UP.V1_UP | 0.01383204 | 0.0695714 | 0.08343617 | 0.00247912 | 0.16456151 | 0.20955665 |
| SRC_UP.V1_DN | 2.66E−07 | 0.21103981 | 0.218345 | 9.23E−11 | 0.39522562 | 0.42167708 |
| SRC_UP.V1_UP | 0.6928626 | −0.0078684 | 0.00146374 | 0.75424323 | −0.0084174 | 0.00091975 |
| SNF5_DN.V1_DN | 1.70E−07 | 0.21724596 | 0.22449369 | 0.00171911 | 0.14424703 | 0.17057488 |
| SNF5_DN.V1_UP | 0.00741224 | 0.05631694 | 0.06505475 | 6.87E−05 | 0.15251144 | 0.16201108 |
| CAMP_UP.V1_DN | 0.09111806 | 0.03844998 | 0.05351467 | 0.91430467 | −0.0092361 | 0.00010873 |
| CAMP_UP.V1_UP | 0.02943487 | 0.03458714 | 0.04352615 | 0.07825877 | 0.07335951 | 0.10919181 |

TABLE 21-continued

GSE87411 ENDORSE: Hallmark signature pathway generalized additive model summary

| Pathway | Baseline P-value | R-squared | Variance explained | End of treatment P-value | R-squared | Variance explained |
|---|---|---|---|---|---|---|
| LTE2_UP.V1_DN | 0.91113479 | −0.0092278 | 0.00011695 | 0.64532329 | −0.00734 | 0.00198718 |
| LTE2_UP.V1_UP | 0.00291664 | 0.07112721 | 0.07972788 | 0.20722346 | 0.02801134 | 0.04522214 |
| MEK_UP.V1_DN | 0.14832207 | 0.07669292 | 0.12498486 | 0.38018436 | −0.002074 | 0.0072045 |
| MEK_UP.V1_UP | 0.00632703 | 0.0588291 | 0.06754364 | 0.56015541 | −0.006134 | 0.00318207 |
| RAF_UP.V1_DN | 2.73E−05 | 0.14386229 | 0.1517895 | 4.51E−06 | 0.18295288 | 0.19114603 |
| RAF_UP.V1_UP | 0.15706984 | 0.00944888 | 0.01862065 | 0.25303333 | 0.00295906 | 0.01219092 |
| PRC1_BMI_UP.V1_DN | 0.02245765 | 0.03881489 | 0.04771476 | 0.17216214 | 0.01584844 | 0.02684862 |
| PRC1_BMI_UP.V1_UP | 0.14383629 | 0.01352767 | 0.02333284 | 0.64074414 | −0.0044388 | 0.00621431 |
| PRC2_EED_UP.V1_DN | 0.05937907 | 0.0237743 | 0.03281343 | 0.01561579 | 0.04452682 | 0.0533738 |
| PRC2_EED_UP.V1_UP | 0.00050844 | 0.09873611 | 0.10708115 | 0.02065783 | 0.04012505 | 0.04901278 |
| PRC2_EZH2_UP.V1_DN | 6.02E−38 | 0.67246321 | 0.67549596 | 1.30E−54 | 0.77329565 | 0.78383961 |
| PRC2_EZH2_UP.V1_UP | 0.00160029 | 0.08064726 | 0.08915979 | 0.025039 | 0.08929964 | 0.11623747 |
| PRC2_SUZ12_UP.V1_DN | 0.01306153 | 0.12417511 | 0.16528096 | 0.0304328 | 0.03406798 | 0.04301179 |
| PRC2_SUZ12_UP.V1_UP | 0.00349248 | 0.06826606 | 0.07689323 | 0.89746234 | −0.0091884 | 0.00015592 |
| JNK_DN.V1_DN | 0.54527568 | 0.00172672 | 0.01440381 | 0.27263779 | 0.0019941 | 0.0112349 |
| JNK_DN.V1_UP | 0.58144624 | 0.02129711 | 0.06192047 | 0.23840551 | 0.05814713 | 0.10570163 |
| BRCA1_DN.V1_DN | 0.04176095 | 0.02916476 | 0.03815397 | 0.21797383 | 0.02215203 | 0.03756594 |
| BRCA1_DN.V1_UP | 0.00120075 | 0.08519307 | 0.09366351 | 0.09349872 | 0.01695806 | 0.0260603 |
| CTIP_DN.V1_DN | 0.43107561 | 0.02349087 | 0.05697488 | 0.99117076 | −0.0093446 | 1.15E−06 |
| CTIP_DN.V1_UP | 0.03412727 | 0.09315932 | 0.12858035 | 0.15199803 | 0.01360482 | 0.02362377 |
| PKCA_DN.V1_DN | 0.04680273 | 0.02741095 | 0.03641641 | 0.72945546 | −0.0082128 | 0.00112248 |
| PKCA_DN.V1_UP | 0.00972642 | 0.05200951 | 0.0607872 | 0.16329785 | 0.0127341 | 0.02281247 |
| MTOR_UP.N4.V1_DN | 0.01253647 | 0.04799378 | 0.05680866 | 0.00305285 | 0.17096286 | 0.22249094 |
| MTOR_UP.N4.V1_UP | 0.00331377 | 0.12321594 | 0.14725301 | 4.71E−07 | 0.30938872 | 0.35314595 |
| PTEN_DN.V2_DN | 0.79243467 | −0.0086897 | 0.00065 | 0.15240235 | 0.00987483 | 0.01904266 |
| PTEN_DN.V2_UP | 0.00024292 | 0.11028904 | 0.1185271 | 0.34822972 | −0.0010416 | 0.00822728 |
| DCA_UP.V1_DN | 0.28802955 | 0.0440252 | 0.08166691 | 0.39128482 | 0.02392113 | 0.05563764 |
| DCA_UP.V1_UP | 0.01933968 | 0.07580578 | 0.09283478 | 0.20013207 | 0.01808011 | 0.03050179 |
| ESC_J1_UP EARLY.V1_DN | 0.05026992 | 0.02632281 | 0.03533983 | 0.4760785 | −0.0045445 | 0.00475688 |
| ESC_J1_UP EARLY.V1_UP | 3.18E−05 | 0.14155232 | 0.14950091 | 1.23E−05 | 0.1967142 | 0.21065018 |
| ESC_J1_UP LATE.V1_DN | 0.29836993 | 0.02219481 | 0.04042564 | 0.01265533 | 0.04784466 | 0.05666091 |
| ESC_J1_UP LATE.V1_UP | 1.35E−07 | 0.22039885 | 0.22761738 | 0.00126564 | 0.15666338 | 0.1853303 |
| ESC_V6.5_UP EARLY.V1_DN | 0.00046169 | 0.12668449 | 0.13961436 | 0.18884564 | 0.06210611 | 0.10715266 |
| ESC_V6.5_UP EARLY.V1_UP | 0.01651155 | 0.0436479 | 0.05250301 | 0.00586619 | 0.06002971 | 0.06873313 |
| ESC_V6.5_UP LATE.V1_DN | 0.1100237 | 0.01456407 | 0.02368848 | 0.30309565 | 0.00065439 | 0.00990759 |
| ESC_V6.5_UP LATE.V1_UP | 2.82E−06 | 0.17751905 | 0.18513461 | 0.00117102 | 0.19039058 | 0.24997647 |
| ALK_DN.V1_DN | 0.73414468 | −0.0082533 | 0.00108241 | 0.53784937 | −0.0057552 | 0.00355737 |
| ALK_DN.V1_UP | 0.81067714 | −0.0088021 | 0.00053868 | 0.07248138 | 0.02075871 | 0.02982576 |
| BMI1_DN_MEL18 DN.V1_DN | 6.27E−07 | 0.26310786 | 0.28419762 | 1.47E−06 | 0.28861809 | 0.32606437 |
| BMI1_DN_MEL18 DN.V1_UP | 0.03336532 | 0.03263782 | 0.04159488 | 0.3963562 | 0.02989564 | 0.0634107 |
| BMI1_DN.V1_DN | 1.98E−06 | 0.1826659 | 0.19023381 | 0.00011355 | 0.12208194 | 0.13021082 |
| BMI1_DN.V1_UP | 0.00586152 | 0.06004237 | 0.06874568 | 0.28630227 | 0.04505148 | 0.08640604 |
| MEL18_DN.V1_DN | 1.13E−05 | 0.19673375 | 0.21033979 | 0.00010774 | 0.21700533 | 0.25346834 |
| MEL18_DN.V1_UP | 0.19626592 | 0.03322006 | 0.05545848 | 0.63613666 | 0.00092352 | 0.01575469 |
| PTEN_DN.V1_DN | 0.01619673 | 0.04395117 | 0.05280347 | 0.9649233 | −0.0093275 | 1.82E−05 |
| PTEN_DN.V1_UP | 4.64E−05 | 0.13579535 | 0.14379725 | 0.17548919 | 0.00789696 | 0.0170831 |
| NOTCH_DN.V1_DN | 0.00197577 | 0.07730701 | 0.08585046 | 0.35354062 | −0.001222 | 0.0080486 |
| NOTCH_DN.V1_UP | 0.04765131 | 0.09651081 | 0.13957562 | 0.13196277 | 0.07772198 | 0.1389435 |
| EIF4E_DN | 0.21834392 | 0.00491079 | 0.01412458 | 0.14868543 | 0.01022461 | 0.0193892 |
| EIF4E_UP | 0.27053602 | 0.02027824 | 0.03674961 | 0.36155887 | −0.0014874 | 0.00778561 |
| CRX_DN.V1_DN | 0.00036086 | 0.10411018 | 0.11240545 | 0.4321419 | 0.00421678 | 0.01639963 |
| CRX_DN.V1_UP | 0.02142092 | 0.0395559 | 0.0484489 | 0.21821883 | 0.00491849 | 0.01413221 |
| CRX_NRL_DN.V1_DN | 0.01471856 | 0.04545996 | 0.0542983 | 0.04524441 | 0.08828131 | 0.12306362 |
| CRX_NRL_DN.V1_UP | 0.12767985 | 0.08161466 | 0.14802305 | 0.06666973 | 0.0877602 | 0.12724407 |
| NRL_DN.V1_DN | 0.00637665 | 0.0587051 | 0.06742079 | 0.13949839 | 0.06488843 | 0.10971011 |
| NRL_DN.V1_UP | 0.36312135 | 0.020418 | 0.04401147 | 0.16291715 | 0.06424536 | 0.10810325 |
| RB_DN.V1_DN | 0.00407751 | 0.06580618 | 0.07445613 | 0.10449102 | 0.07915819 | 0.12742407 |
| RB_DN.V1_UP | 1.49E−07 | 0.21900447 | 0.22623591 | 0.00047175 | 0.13863355 | 0.15373189 |
| RB_P107_DN.V1_DN | 0.99231572 | −0.0093449 | 8.71E−07 | 0.09100299 | 0.07408594 | 0.11457725 |
| RB_P107_DN.V1_UP | 3.46E−18 | 0.5050189 | 0.51378108 | 1.19E−18 | 0.54321309 | 0.56774067 |
| RB_P130_DN.V1_DN | 0.43746082 | −0.0036479 | 0.00564511 | 0.92866545 | −0.0092698 | 7.53E−05 |
| RB_P130_DN.V1_UP | 0.00064689 | 0.09495051 | 0.1033306 | 0.00276854 | 0.07195452 | 0.08054754 |
| CAHOY_ASTROCYTIC | 0.60339771 | −0.0067911 | 0.00253105 | 0.28066091 | 0.03437016 | 0.06178512 |
| CAHOY_ASTROGLIAL | 0.00144338 | 0.08228137 | 0.09077876 | 0.35779156 | −0.0013637 | 0.00790817 |

TABLE 21-continued

GSE87411 ENDORSE: Hallmark signature pathway generalized additive model summary

| Pathway | Baseline P-value | R-squared | Variance explained | End of treatment P-value | R-squared | Variance explained |
|---|---|---|---|---|---|---|
| CAHOY_NEURONAL | 0.01883482 | 0.04157628 | 0.05045057 | 0.04813456 | 0.02698035 | 0.03598979 |
| CAHOY_ OLIGODENDROCUTIC | 0.04710243 | 0.02731296 | 0.03631932 | 0.75893434 | −0.0084537 | 0.00088388 |
| RPS14_DN.V1_DN | 7.12E−18 | 0.48114157 | 0.4888773 | 8.91E−18 | 0.50316067 | 0.51472478 |
| RPS14_DN.V1_UP | 0.13420388 | 0.07720545 | 0.12665549 | 0.53796382 | −0.0057572 | 0.00355537 |
| IL15_UP.V1_DN | 3.25E−07 | 0.28459789 | 0.31111666 | 0.00404269 | 0.06594242 | 0.07459111 |
| IL15_UP.V1_UP | 0.72321675 | 0.00690298 | 0.04062148 | 0.2294856 | 0.00424575 | 0.0134657 |
| IL2_UP.V1_DN | 1.43E−12 | 0.41505307 | 0.43309508 | 2.16E−06 | 0.24542115 | 0.26593954 |
| IL2_UP.V1_UP | 0.92027633 | −0.0092509 | 9.41E−05 | 0.13429601 | 0.01167677 | 0.02082791 |
| IL21_UP.V1_DN | 4.74E−05 | 0.15354435 | 0.16256696 | 0.00026914 | 0.15747534 | 0.17449431 |
| IL21_UP.V1_UP | 0.08613328 | 0.01817599 | 0.02726696 | 0.83048804 | −0.0089116 | 0.00043022 |
| PDGF_ERK_DN.V1_DN | 0.40970783 | −0.0029253 | 0.00636102 | 0.46995771 | 0.00529208 | 0.01902056 |
| PDGF_ERK_DN.V1_UP | 0.50650275 | −0.0051723 | 0.0041349 | 0.88561672 | −0.0091497 | 0.00019429 |
| PDGF_UP.V1_DN | 0.00364119 | 0.06760377 | 0.07623707 | 0.00114681 | 0.13448728 | 0.15266106 |
| PDGF_UP.V1_UP | 0.01725293 | 0.04295628 | 0.0518178 | 0.000271 | 0.154413 | 0.17166672 |
| TGFB_UP.V1_DN | 6.88E−08 | 0.22951948 | 0.23665355 | 9.83E−06 | 0.15917069 | 0.16695615 |
| TGFB_UP.V1_UP | 0.00646423 | 0.090959 | 0.10647615 | 0.05741937 | 0.10051368 | 0.15041708 |
| YAP1_DN | 0.06877107 | 0.04388389 | 0.05902589 | 0.00111265 | 0.13891147 | 0.15981407 |
| YAP1_UP | 0.00281628 | 0.07168312 | 0.08027865 | 0.57685864 | 0.01208877 | 0.0378689 |
| SIRNA_EIF4GI_DN | 0.00407322 | 0.06582294 | 0.07447273 | 0.00261997 | 0.10000383 | 0.11382173 |
| SIRNA_EIF4GI_UP | 0.29175493 | 0.04437975 | 0.08239078 | 0.77973795 | −0.0043712 | 0.00812949 |
| HOXA9_DN.V1_DN | 1.82E−16 | 0.48725063 | 0.50081729 | 6.16E−22 | 0.55150521 | 0.56130749 |
| HOXA9_DN.V1_UP | 0.14819683 | 0.02719707 | 0.04147643 | 0.842402 | −0.0089712 | 0.0003711 |
| SINGH_KRAS_ DEPENDENCY_ SIGNATURE_ | 0.96329138 | −0.0093257 | 1.99E−05 | 0.37493541 | −0.0019128 | 0.00736421 |
| STK33_DN | 0.00011147 | 0.12236739 | 0.13049362 | 0.06314108 | 0.02284194 | 0.0318897 |
| STK33_NOMO_DN | 0.00146888 | 0.0820041 | 0.09050406 | 0.14457512 | 0.01062294 | 0.01978384 |
| STK33_NOMO_UP | 0.02685595 | 0.03601712 | 0.04494289 | 0.26255545 | 0.00247932 | 0.01171562 |
| STK33_SKM_DN | 3.26E−07 | 0.20847292 | 0.21581271 | 0.01562125 | 0.04452131 | 0.05336834 |
| STK33_SKM_UP | 0.23952732 | 0.00367848 | 0.01290368 | 0.35831261 | −0.0013809 | 0.00789112 |
| STK33_UP | 0.03394399 | 0.03237091 | 0.04133044 | 0.14320819 | 0.01075821 | 0.01991785 |
| KRAS.AMP.LUNG_UP.V1_DN | 0.10764311 | 0.01488404 | 0.02400548 | 0.01520396 | 0.08287237 | 0.10048962 |
| KRAS.AMP.LUNG_UP.V1_UP | 0.96724635 | −0.0093298 | 1.58E−05 | 0.40211468 | −0.002715 | 0.00656945 |
| KRAS.DF.V1_DN | 0.39296217 | −0.0024536 | 0.00682835 | 0.35427463 | −0.0012466 | 0.00802419 |
| KRAS.DF.V1_UP | 0.31746752 | 0.03353901 | 0.0689486 | 0.95154374 | −0.0093108 | 3.47E−05 |
| TBK1.DF_DN | 0.16913237 | 0.00841084 | 0.01759222 | 0.83456444 | −0.0089325 | 0.00040948 |
| TBK1.DF_UP | 0.93160483 | −0.009276 | 6.92E−05 | 0.71101631 | −0.0080457 | 0.00128802 |
| TBK1.DN.48 HRS_DN | 0.09017821 | 0.03577105 | 0.04908091 | 0.13644486 | 0.03385338 | 0.04998104 |
| TBK1.DN.48 HRS_UP | 0.03654562 | 0.03122609 | 0.04019622 | 0.00543132 | 0.06125275 | 0.06994485 |
| NFE2L2.V2 | 0.09460539 | 0.04965858 | 0.06951749 | 0.00027228 | 0.10851042 | 0.11676495 |
| CORDENONSI_YAP_ CONSERVED_SIGNATURE | 0.07231249 | 0.08930553 | 0.13488396 | 0.01023288 | 0.11253695 | 0.14368339 |
| JAK2_DN.V1_DN | 0.24443155 | 0.00341171 | 0.01263938 | 0.70286763 | −0.0079677 | 0.0013653 |
| JAK2_DN.V1_UP | 0.0249017 | 0.06198423 | 0.07676019 | 0.16606522 | 0.03550368 | 0.05364933 |
| KRAS.300_UP.V1_DN | 0.10772067 | 0.0148735 | 0.02399504 | 0.78198386 | −0.0086203 | 0.00071881 |
| KRAS.300_UP.V1_UP | 0.02153924 | 0.08542795 | 0.10946524 | 0.06234337 | 0.04314015 | 0.05694894 |
| KRAS.50_UP.V1_DN | 0.64278405 | −0.0073091 | 0.00201784 | 0.49152006 | 0.01239501 | 0.03549445 |
| KRAS.50_UP.V1_UP | 0.00122298 | 0.18746839 | 0.23396581 | 0.0288147 | 0.07190084 | 0.09143929 |
| KRAS.600_UP.V1_DN | 0.01053282 | 0.05074831 | 0.05953768 | 0.37562159 | 0.00846127 | 0.02155201 |
| KRAS.600_UP.V1_UP | 0.01984198 | 0.04075772 | 0.04963959 | 0.35697511 | 0.00298248 | 0.01365077 |
| KRAS.600.LUNG.BREAST_ UP.V1_DN | 0.00191862 | 0.07777239 | 0.08631153 | 0.19139983 | 0.01588376 | 0.0273592 |
| KRAS.600.LUNG.BREAST_ UP.V1_UP | 0.12677194 | 0.01250625 | 0.02164971 | 0.69650745 | −0.007905 | 0.00142742 |
| KRAS.BREAST_UP.V1_DN | 9.76E−06 | 0.15927067 | 0.1670552 | 0.01278364 | 0.07606124 | 0.091142 |
| KRAS.BREAST_UP.V1_UP | 0.06815162 | 0.02168692 | 0.03074538 | 0.9925028 | −0.009345 | 8.29E−07 |
| KRAS.KIDNEY_UP.V1_DN | 0.06353718 | 0.02274718 | 0.03179582 | 0.91323198 | −0.0092333 | 0.00011148 |
| KRAS.KIDNEY_UP.V1_UP | 2.26E−06 | 0.18072275 | 0.18830865 | 0.00237144 | 0.07441168 | 0.08298194 |
| KRAS.LUNG_UP.V1_DN | 0.0171666 | 0.04303525 | 0.05189604 | 0.20520606 | 0.00574834 | 0.01495437 |
| KRAS.LUNG_UP.V1_UP | 0.33122561 | 0.00958082 | 0.02212512 | 0.41463888 | 0.01203861 | 0.02859198 |
| KRAS.LUNG.BREAST_ UP.V1_DN | 0.00090597 | 0.0896427 | 0.09807194 | 0.06899383 | 0.03558902 | 0.04721018 |
| KRAS.LUNG.BREAST_ UP.V1_UP | 0.35269165 | 0.01020024 | 0.02363041 | 0.35748382 | −0.0013535 | 0.00791826 |
| KRAS.PROSTATE_ UP.V1_DN | 0.00025272 | 0.1096729 | 0.11791667 | 0.11685606 | 0.01368588 | 0.02281842 |
| KRAS.PROSTATE_ UP.V1_UP | 0.01402906 | 0.04621707 | 0.05504839 | 0.56199577 | −0.0055263 | 0.00404307 |
| LEF1_UP.V1_DN | 4.92E−10 | 0.32167381 | 0.32905505 | 7.20E−08 | 0.33940138 | 0.37874912 |
| LEF1_UP.V1_UP | 0.00716758 | 0.08234849 | 0.09541241 | 0.799821 | −0.0087366 | 0.00060359 |

TABLE 22

| ANOVA analysis of METABRIC ENDORSE scores vs. single-nucleotide variants | | | |
|---|---|---|---|
| | Gene | P-value | FDR |
| 1 | TP53 | 1.63E−26 | 1.80E−25 |
| 2 | GATA3 | 0.000346014 | 0.000951538 |
| 3 | PIK3CA | 3.50E−07 | 1.92E−06 |
| 4 | MAP3K1 | 0.000567754 | 0.001249059 |
| 5 | AKT1 | 0.573426767 | 0.733318378 |
| 6 | CDH1 | 0.945743555 | 0.945743555 |
| 7 | CBFB | 1.22E−06 | 4.47E−06 |
| 8 | NOTCH1 | 0.189548944 | 0.347506397 |
| 9 | KMT2C | 0.94475775 | 0.945743555 |
| 10 | TBX3 | 0.448134521 | 0.70421139 |
| 11 | PDE4DIP | 0.599987764 | 0.733318378 |

TABLE 23

| ANOVA analysis of METABRIC ENDORSE scores vs. copy number gains | | | | |
|---|---|---|---|---|
| | Gene | P-value | FDR | Cytoband |
| 1 | CCND1 | 3.76E−13 | 3.04E−12 | 11q13.3 |
| 2 | FGF19 | 1.36E−13 | 1.52E−12 | 11q13.3 |
| 3 | FGF3 | 7.16E−13 | 5.31E−12 | 11q13.3 |
| 4 | FGF4 | 9.71E−13 | 6.65E−12 | 11q13.3 |
| 5 | PAK1 | 5.77E−05 | 0.000171204 | 11q13.5-q14.1 |
| 6 | GAB2 | 1.05E−06 | 3.59E−06 | 11q14.1 |
| 7 | BCL9 | 0.020228901 | 0.047378215 | 1q21.2 |
| 8 | PDE4DIP | 0.004619418 | 0.011420227 | 1q21.2 |
| 9 | SDHC | 0.013782384 | 0.033152222 | 1q23.3 |
| 10 | DKK4 | 0.000388563 | 0.001047943 | 8p11.21 |
| 11 | HOOK3 | 0.002073361 | 0.005272261 | 8p11.21 |
| 12 | IKBKB | 0.000103491 | 0.00029712 | 8p11.21 |
| 13 | KAT6A | 0.000226216 | 0.000629164 | 8p11.21 |
| 14 | SFRP1 | 1.26E−05 | 3.86E−05 | 8p11.21 |
| 15 | FGFR1 | 4.13E−06 | 1.31E−05 | 8p11.23 |
| 16 | ZNF703 | 1.11E−06 | 3.65E−06 | 8p11.23 |
| 17 | PRKDC | 0.000666894 | 0.001745694 | 8q11.21 |
| 18 | SOX17 | 1.61E−07 | 5.97E−07 | 8q11.23 |
| 19 | TCEA1 | 7.01E−07 | 2.50E−06 | 8q11.23 |
| 20 | CHCHD7 | 1.60E−08 | 6.20E−08 | 8q12.1 |
| 21 | LYN | 1.21E−08 | 4.88E−08 | 8q12.1 |
| 22 | PLAG1 | 6.39E−09 | 2.71E−08 | 8q12.1 |
| 23 | PREX2 | 2.27E−09 | 1.01E−08 | 8q13.2 |
| 24 | NCOA2 | 5.08E−10 | 2.51E−09 | 8q13.3 |
| 25 | PRDM14 | 9.26E−10 | 4.34E−09 | 8q13.3 |
| 26 | HEY1 | 3.00E−12 | 1.78E−11 | 8q21.13 |
| 27 | PAG1 | 1.26E−11 | 6.99E−11 | 8q21.13 |
| 28 | NBN | 4.73E−14 | 6.65E−13 | 8q21.3 |
| 29 | RUNX1T1 | 1.00E−14 | 2.23E−13 | 8q21.3 |
| 30 | UBR5 | 1.67E−15 | 4.97E−14 | 8q22.3 |
| 31 | EIF3E | 2.53E−13 | 2.25E−12 | 8q23.1 |
| 32 | RSPO2 | 2.47E−13 | 2.25E−12 | 8q23.1 |
| 33 | EXT1 | 1.63E−14 | 2.89E−13 | 8q24.11 |
| 34 | RAD21 | 9.07E−18 | 8.07E−16 | 8q24.11 |
| 35 | MYC | 3.45E−17 | 1.54E−15 | 8q24.21 |
| 36 | NDRG1 | 1.28E−12 | 8.11E−12 | 8q24.22 |
| 37 | AGO2 | 1.63E−11 | 8.53E−11 | 8q24.3 |
| 38 | RECQL4 | 5.23E−14 | 6.65E−13 | 8q24.3 |

Example 6: mTOR Signature Response for mTor Inhibitor Response in Estrogen-Receptor Positive Breast Cancers The mTOR inhibitor response prediction signature has 97 genes and combines in vitro everolimus+exemestane response genes with clinical everolimus+exemestane response genes developed using the GSE119262 (gene set enrichment) expression datasets. The stratification in SPOCK will be performed based on a machine-learning classifier (random forest). A random forest model using a combination of cell line signature genes and clinical response genes filtered using symmetrical uncertainty performed the best in a LOOCV analysis. The feature selection for the evaluation purposes was performed within the LOOCV loop, instead of on the full data for honest performance evaluation.

Figure 16:
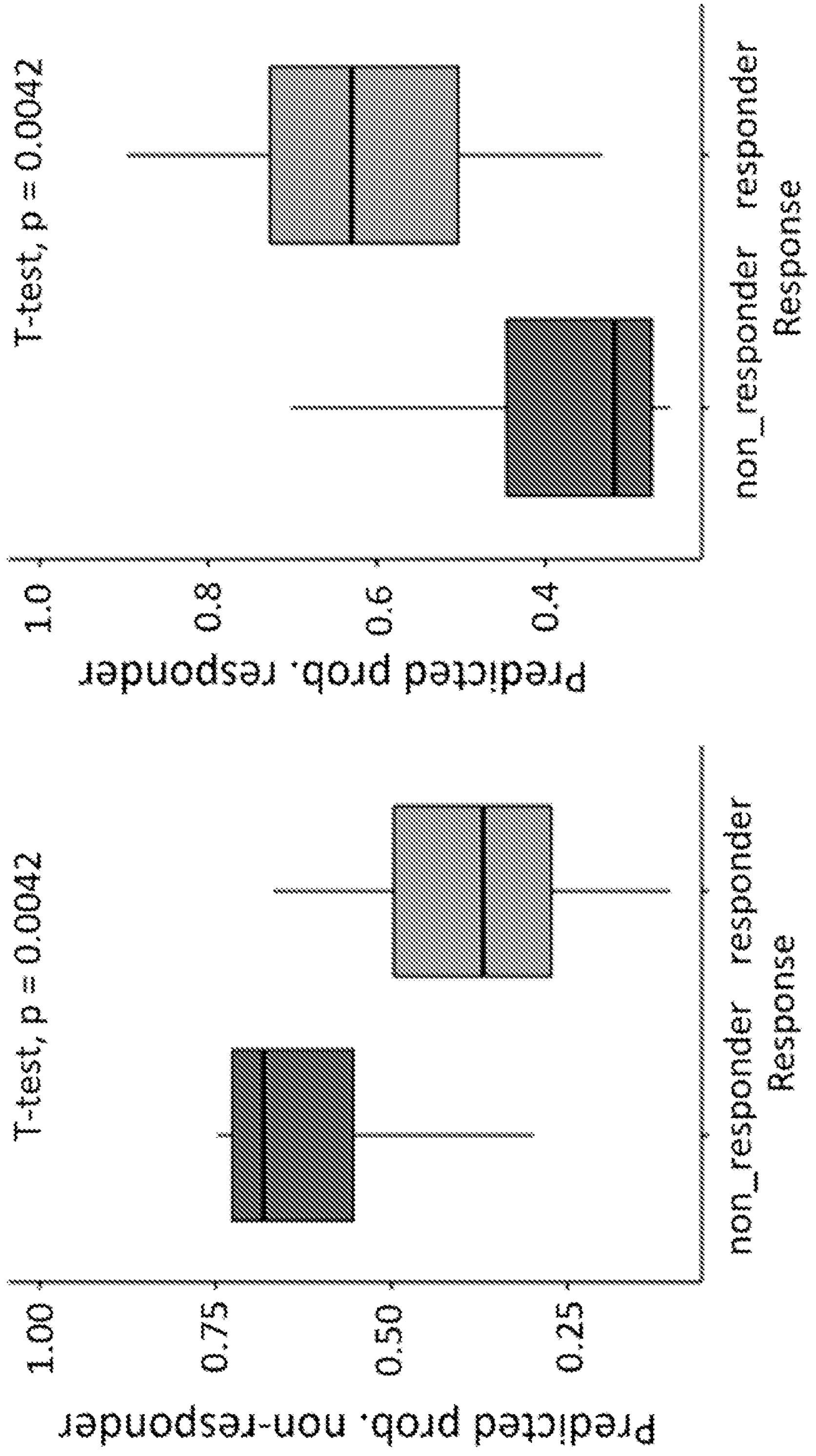
FIG. 16. The probability that a patient is sensitive to mTOR inhibitor. The predicted probability of a sample to be a non-responder (Y-axis) vs. the actual response class and the predicted probability of a responder, shown in left and right panels, respectively. The p-values in both are the same for plots, since substantially the same information is displayed in both plots.

The class-probabilities predicted using this approach are shown in FIG. 16. The final list of mTOR sensitivity genes is as listed in Table 24, and was based on the model described above, but was constructed with the full data set (final model has a cross-validation accuracy of 95%).

For the SPOCK trial, the response probability threshold was set at 0.7 for selecting the patients that are recommended to receive everolimus+exemestane, while the remaining patients receive fulvestrant.

REFERENCES: EXAMPLES 1-4

1. Harvey, J. M., Clark, G. M., Osborne, C. K. & Allred, D. C. Estrogen receptor status by immunohistochemistry is superior to the ligand-binding assay for predicting response to adjuvant endocrine therapy in breast cancer. *J Clin. Oncol.* 17, 1474-1481 (1999).
2. Rugo, H. S. et al. Endocrine Therapy for Hormone Receptor-Positive Metastatic Breast Cancer: American Society of Clinical Oncology Guideline. *JCO* 34, 3069-3103 (2016).
3. Allison, K. H. et al. Estrogen and Progesterone Receptor Testing in Breast Cancer: ASCO/CAP Guideline Update. *JCO* 38, 1346-1366 (2020).
4. Musgrove, E. A. & Sutherland, R. L. Biological determinants of endocrine resistance in breast cancer. *Nature Reviews Cancer* 9, 631-643 (2009).
5. Spoerke, J. M. et al. Heterogeneity and clinical significance of ESR1 mutations in ER-positive metastatic breast cancer patients receiving fulvestrant. *Nature Communications* 7, 1-10 (2016).
6. Parker, J. S. et al. Supervised Risk Predictor of Breast Cancer Based on Intrinsic Subtypes. *J Clin Oncol* 27, 1160-1167 (2009).
7. Paik, S. et al. A multigene assay to predict recurrence of tamoxifen-treated, node-negative breast cancer. *N. Engl. J. Med.* 351, 2817-2826 (2004).
8. Cardoso, F. et al. 70-Gene Signature as an Aid to Treatment Decisions in Early-Stage Breast Cancer. https://doi.org/10.1056/NEJMoa1602253 https://www.nejm.org/doi/10.1056/NEJMoa1602253 (2016) doi: 10.1056/NEJMoa1602253.
9. Witten, D. M. & Tibshirani, R. Survival analysis with high-dimensional covariates. *Stat Methods Med Res* 19, 29-51 (2010).
10. Taylor, J. M. G., Ankerst, D. P. & Andridge, R. R. Validation of Biomarker-Based Risk Prediction Models. *Clin Cancer Res* 14, 5977-5983 (2008).
11. Tibshirani, R. The lasso method for variable selection in the Cox model. *Stat Med* 16, 385-395 (1997).
12. Bild, A. H. et al. Oncogenic pathway signatures in human cancers as a guide to targeted therapies. *Nature* 439, 353-357 (2006).
13. Curtis, C. et al. The genomic and transcriptomic architecture of 2,000 breast tumours reveals novel subgroups. *Nature* 486, 346-352 (2012).
14. Pereira, B. et al. The somatic mutation profiles of 2,433 breast cancers refine their genomic and transcriptomic landscapes. *Nature Communications* 7, 1-16 (2016).
15. Liberzon, A. et al. Molecular signatures database (MSigDB) 3.0. *Bioinformatics* 27, 1739-1740 (2011).

16. Liberzon, A. et al. The Molecular Signatures Database Hallmark Gene Set Collection. *Cell Systems* 1, 417-425 (2015).
17. Hanzelmann, S., Castelo, R. & Guinney, J. GSVA: gene set variation analysis for microarray and RNA-Seq data. *BMC Bioinformatics* 14, 7 (2013).
18. Barbie, D. A. et al. Systematic RNA interference reveals that oncogenic KRAS-driven cancers require TBK1. *Nature* 462, 108-112 (2009).
19. Ali, H. R. et al. Genome-driven integrated classification of breast cancer validated in over 7,500 samples. *Genome Biology* 15, 431 (2014).
20. Sinn, B. V. et al. $SET_{ER/PR}$: a robust 18-gene predictor for sensitivity to endocrine therapy for metastatic breast cancer. *NPJ Breast Cancer* 5, 16 (2019).
21. Ellis, M. J. et al. Ki67 Proliferation Index as a Tool for Chemotherapy Decisions During and After Neoadjuvant Aromatase Inhibitor Treatment of Breast Cancer: Results From the American College of Surgeons Oncology Group Z1031 Trial (Alliance). *J. Clin. Oncol.* 35, 1061-1069 (2017).
22. Jeselsohn, R. et al. TransCONFIRM: Identification of a Genetic Signature of Response to Fulvestrant in Advanced Hormone Receptor-Positive Breast Cancer. *Clin. Cancer Res.* 22, 5755-5764 (2016).
23. Venet, D., Dumont, J. E. & Detours, V. Most Random Gene Expression Signatures Are Significantly Associated with Breast Cancer Outcome. *PLOS Computational Biology* 7, e1002240 (2011).
24. Kjallquist, U. et al. Exome sequencing of primary breast cancers with paired metastatic lesions reveals metastasis-enriched mutations in the A-kinase anchoring protein family (AKAPs). *BMC Cancer* 18, 174 (2018).
25. Sparano, J. A. et al. Adjuvant Chemotherapy Guided by a 21-Gene Expression Assay in Breast Cancer. *New England Journal of Medicine* 379, 111-121 (2018).
26. Sotiriou, C. et al. Breast cancer classification and prognosis based on gene expression profiles from a population-based study. *PNAS* 100, 10393-10398 (2003).
27. Paul, D., Bair, E., Hastie, T. & Tibshirani, R. "Preconditioning" for feature selection and regression in high-dimensional problems. *Ann. Statist.* 36, 1595-1618 (2008).
28. Cattoretti, G., Rilke, F., Andreola, S., D'Amato, L. & Delia, D. P53 expression in breast cancer. *International Journal of Cancer* 41, 178-183 (1988).
29. Elledge, R. M. et al. Prognostic significance of p53 gene alterations in node-negative breast cancer. *Breast Cancer Res Tr* 26, 225-235 (1993).
30. Ungerleider, N. A. et al. Breast cancer survival predicted by TP53 mutation status differs markedly depending on treatment. *Breast Cancer Research* 20, 115 (2018).
31. Bosco, E. E. et al. The retinoblastoma tumor suppressor modifies the therapeutic response of breast cancer. *J Clin Invest* 117, 218-228 (2007).
32. Witkiewicz, A. K. & Knudsen, E. S. Retinoblastoma tumor suppressor pathway in breast cancer: prognosis, precision medicine, and therapeutic interventions. *Breast Cancer Research* 16, 207 (2014).
33. Creighton, C. J., Chang, J. C. & Rosen, J. M. Epithelial-Mesenchymal Transition (EMT) in Tumor-Initiating Cells and Its Clinical Implications in Breast Cancer. *J Mammary Gland Biol Neoplasia* 15, 253-260 (2010).
34. Deblois, G. et al. Genome-wide identification of direct target genes implicates estrogen-related receptor alpha as a determinant of breast cancer heterogeneity. *Cancer Res.* 69, 6149-6157 (2009).
35. Manna, S. et al. ERRα is a marker of tamoxifen response and survival in triple-negative breast cancer. *Clin Cancer Res* 22, 1421-1431 (2016).
36. Bergamaschi, A. et al. Extracellular matrix signature identifies breast cancer subgroups with different clinical outcome. *The Journal of Pathology* 214, 357-367 (2008).
37. Giussani, M., Merlino, G., Cappelletti, V., Tagliabue, E. & Daidone, M. G. Tumor-extracellular matrix interactions: Identification of tools associated with breast cancer progression. *Seminars in Cancer Biology* 35, 3-10 (2015).
38. Gao, J. et al. Integrative analysis of complex cancer genomics and clinical profiles using the cBioPortal. *Sci Signal* 6, p11 (2013).
39. Tibshirani, R. Regression Shrinkage and Selection Via the Lasso. *Journal of the Royal Statistical Society: Series B (Methodological)* 58, 267-288 (1996).
40. Friedman, J. H., Hastie, T. & Tibshirani, R. Regularization Paths for Generalized Linear Models via Coordinate Descent. *Journal of Statistical Software* 33, 1-22 (2010).
41. Simon, N., Friedman, J. H., Hastie, T. & Tibshirani, R. Regularization Paths for Cox's Proportional Hazards Model via Coordinate Descent. *Journal of Statistical Software* 39, 1-13 (2011).
42. Ramaker, R. C. et al. RNA sequencing-based cell proliferation analysis across 19 cancers identifies a subset of proliferation-informative cancers with a common survival signature. *Oncotarget* 8, 38668-38681 (2017).
43. Barbie, D. A. et al. Systematic RNA interference reveals that oncogenic KRAS-driven cancers require TBK1. *Nature* 462, 108-112 (2009).
44. Hanzelmann, S., Castelo, R. & Guinney, J. GSVA: gene set variation analysis for microarray and RNA-Seq data. *BMC Bioinformatics* 14, 7 (2013).
45. Sambrook, et al., Molecular Cloning: A Laboratory Manual (3rd Edition, 2001)
46. Sambrook, et al., Molecular Cloning: A Laboratory Manual (2nd Edition, 1989)
47. Maniatis et al., Molecular Cloning: A Laboratory Manual (1982); Ausubel et al.
48. Current Protocols in Molecular Biology (John Wiley and Sons, updated July 2008)
49. Short Protocols in Molecular Biology: A Compendium of Methods from Current Protocols in Molecular Biology, Greene Pub. Associates and Wiley-Interscience
50. Glover, DNA Cloning: A Practical Approach, vol. I & II (IRL Press, Oxford, 1985)
51. Anand, Techniques for the Analysis of Complex Genomes, (Academic Press, New York, 1992)
52. Hames, B. S. Higgins, S. Transcription and Translation (Eds., 1984)

REFERENCES: EXAMPLE 5

1. Sung, H. et al. Global Cancer Statistics 2020: GLOBOCAN Estimates of Incidence and Mortality Worldwide for 36 Cancers in 185 Countries. *CA A Cancer J Clin* 71, 209-249 (2021).
2. Harvey, J. M., Clark, G. M., Osborne, C. K. & Allred, D. C. Estrogen receptor status by immunohistochemistry is superior to the ligand-binding assay for predicting response to adjuvant endocrine therapy in breast cancer. *J. Clin. Oncol.* 17, 1474-1481 (1999).
3. Kohler, B. A. et al. Annual Report to the Nation on the Status of Cancer, 1975-2011, Featuring Incidence of Breast Cancer Subtypes by Race/Ethnicity, Poverty, and State. *JNCI: Journal of the National Cancer Institute* 107, (2015).

4. Waks, A. G. & Winer, E. P. Breast Cancer Treatment: A Review. *JAMA* 321, 288 (2019).
5. McDonnell, D. P. & Wardell, S. E. The molecular mechanisms underlying the pharmacological actions of ER modulators: implications for new drug discovery in breast cancer. *Current Opinion in Pharmacology* 10, 620-628 (2010).
6. Smith, I. E. & Dowsett, M. Aromatase Inhibitors in Breast Cancer. *N Engl J Med* 348, 2431-2442 (2003).
7. Cardoso, F. et al. 70-Gene Signature as an Aid to Treatment Decisions in Early-Stage Breast Cancer. https: doi.org 10.1056/NEJMoaJ602253 https://www.nejm.org/doi/10.1056/NEJMoa1602253 (2016) doi:10.1056/NEJMoa1602253.
8. Sparano, J. A. et al. Adjuvant Chemotherapy Guided by a 21-Gene Expression Assay in Breast Cancer. *New England Journal ofMedicine* 379, 111-121 (2018).
9. Krop, I. et al. Use of Biomarkers to Guide Decisions on Adjuvant Systemic Therapy for Women With Early-Stage Invasive Breast Cancer: American Society of Clinical Oncology Clinical Practice Guideline Focused Update. *JCO* 35, 2838-2847 (2017).
10. Duffy, M. J. et al. Clinical use of biomarkers in breast cancer: Updated guidelines from the European Group on Tumor Markers (EGTM). *European Journal of Cancer* 75, 284-298 (2017).
11. McAndrew, N. P. & Finn, R. S. Management of ER positive metastatic breast cancer. *Seminars in Oncology* 47, 270-277 (2020).
12. Andre, F. et al. Alpelisib for PIK3CA-Mutated, Hormone Receptor-Positive Advanced Breast Cancer. *New England Journal of Medicine* 380, 1929-1940 (2019).
13. Baselga, J. et al. Everolimus in Postmenopausal Hormone-Receptor-Positive Advanced Breast Cancer. *N Engl J Med* 366, 520-529 (2012).
14. Rugo, H. S. et al. Endocrine Therapy for Hormone Receptor-Positive Metastatic Breast Cancer: American Society of Clinical Oncology Guideline. *JCO* 34, 3069-3103 (2016).
15. Gradishar, W. J. et al. NCCN Guidelines Insights: Breast Cancer, *Version* 1.2017. *J Natl Compr Canc Netw* 15, 433-451 (2017).
16. Gradishar, W. J. et al. Breast Cancer, Version 3.2020, NCCN Clinical Practice Guidelines in Oncology. *Journal of the National Comprehensive Cancer Network* 18, 452-478 (2020).
17. Cardoso, F. et al. 5th ESO-ESMO international consensus guidelines for advanced breast cancer (ABC 5). *Annals of Oncology* 31, 1623-1649 (2020).
18. Sinn, B. V. et al. $SET_{ER/PR}$: a robust 18-gene predictor for sensitivity to endocrine therapy for metastatic breast cancer. *NPJ Breast Cancer* 5, 16 (2019).
19. Jeselsohn, R. et al. TransCONFIRM: Identification of a Genetic Signature of Response to Fulvestrant in Advanced Hormone Receptor-Positive Breast Cancer. *Clin. Cancer Res.* 22, 5755-5764 (2016).
20. Boutros, P. C. The path to routine use of genomic biomarkers in the cancer clinic. *Genome Res* 25, 1508-1513 (2015).
21. Witten, D. M. & Tibshirani, R. Survival analysis with high-dimensional covariates. *Stat Methods Med Res* 19, 29-51 (2010).
22. Taylor, J. M. G., Ankerst, D. P. & Andridge, R. R. Validation of Biomarker-Based Risk Prediction Models. *Clin Cancer Res* 14, 5977-5983 (2008).
23. Pereira, B. et al. The somatic mutation profiles of 2,433 breast cancers refine their genomic and transcriptomic landscapes. *Nature Communications* 7, 1-16 (2016).
24. Curtis, C. et al. The genomic and transcriptomic architecture of 2,000 breast tumours reveals novel subgroups. *Nature* 486, 346-352 (2012).
25. Liberzon, A. et al. The Molecular Signatures Database Hallmark Gene Set Collection. *Cell Systems* 1, 417-425 (2015).
26. Venet, D., Dumont, J. E. & Detours, V. Most Random Gene Expression Signatures Are Significantly Associated with Breast Cancer Outcome. *PLOS Computational Biology* 7, e1002240 (2011).
27. Ramaker, R. C. et al. RNA sequencing-based cell proliferation analysis across 19 cancers identifies a subset of proliferation-informative cancers with a common survival signature. *Oncotarget* 8, 38668-38681 (2017).
28. Nielsen, T. O. et al. A Comparison of PAM50 Intrinsic Subtyping with Immunohistochemistry and Clinical Prognostic Factors in Tamoxifen-Treated Estrogen Receptor-Positive Breast Cancer. *Clin Cancer Res* 16, 5222-5232 (2010).
29. Dawson, S.-J., Rueda, O. M., Aparicio, S. & Caldas, C. A new genome-driven integrated classification of breast cancer and its implications. *EMBO J* 32, 617-628 (2013).
30. Paik, S. et al. A multigene assay to predict recurrence of tamoxifen-treated, node-negative breast cancer. *N. Engl. J. Med.* 351, 2817-2826 (2004).
31. Ellis, M. J. et al. Ki67 Proliferation Index as a Tool for Chemotherapy Decisions During and After Neoadjuvant Aromatase Inhibitor Treatment of Breast Cancer: Results From the American College of Surgeons Oncology Group Z1031 Trial (Alliance). *J Clin. Oncol.* 35, 1061-1069 (2017).
32. Allison, K. H. et al. Estrogen and Progesterone Receptor Testing in Breast Cancer: ASCO/CAP Guideline Update. *JCO* 38, 1346-1366 (2020).
33. Musgrove, E. A. & Sutherland, R. L. Biological determinants of endocrine resistance in breast cancer. *Nature Reviews Cancer* 9, 631-643 (2009).
34. Spoerke, J. M. et al. Heterogeneity and clinical significance of ESR1 mutations in ER-positive metastatic breast cancer patients receiving fulvestrant. *Nature Communications* 7, 1-10 (2016).
35. Parker, J. S. et al. Supervised Risk Predictor of Breast Cancer Based on Intrinsic Subtypes. *J Clin Oncol* 27, 1160-1167 (2009).
36. Hart, C. D. et al. Challenges in the management of advanced, ER-positive, HER2-negative breast cancer. *Nat Rev Clin Oncol* 12, 541-552 (2015).
37. Sotiriou, C. et al. Breast cancer classification and prognosis based on gene expression profiles from a population-based study. *PNAS* 100, 10393-10398 (2003).
38. Paul, D., Bair, E., Hastie, T. & Tibshirani, R. "Preconditioning" for feature selection and regression in high-dimensional problems. *Ann. Statist.* 36, 1595-1618 (2008).
39. Hollern, D. P., Honeysett, J., Cardiff, R. D. & Andrechek, E. R. The E2F Transcription Factors Regulate Tumor Development and Metastasis in a Mouse Model of Metastatic Breast Cancer. *Molecular and Cellular Biology* 34, 3229-3243 (2014).
40. Hollern, D. P. et al. E2F1 Drives Breast Cancer Metastasis by Regulating the Target Gene FGF13 and Altering Cell Migration. *Sci Rep* 9, 10718 (2019).

41. Bosco, E. E. et al. The retinoblastoma tumor suppressor modifies the therapeutic response of breast cancer. *J Clin Invest* 117, 218-228 (2007).

42. Witkiewicz, A. K. & Knudsen, E. S. Retinoblastoma tumor suppressor pathway in breast cancer: prognosis, precision medicine, and therapeutic interventions. *Breast Cancer Research* 16, 207 (2014).

43. Cattoretti, G., Rilke, F., Andreola, S., D'Amato, L. & *Delia*, D. P53 expression in breast cancer. *International Journal of Cancer* 41, 178-183 (1988).

44. Elledge, R. M. et al. Prognostic significance of p53 gene alterations in node-negative breast cancer. *Breast Cancer Res Tr* 26, 225-235 (1993).

45. Ungerleider, N. A. et al. Breast cancer survival predicted by TP53 mutation status differs markedly depending on treatment. *Breast Cancer Research* 20, 115 (2018).

46. Baslan, T. et al. Novel insights into breast cancer copy number genetic heterogeneity revealed by single-cell genome sequencing. *eLife* 9, e51480 (2020).

47. Lundgren, K., Holm, K., Nordenskjold, B., Borg, Å. & Landberg, G. Gene products of chromosome 11q and their association with CCND1 gene amplification and tamoxifen resistance in premenopausal breast cancer. *Breast Cancer Res* 10, R81 (2008).

48. Hortobagyi, G. N. et al. Ribociclib as First-Line Therapy for HR-Positive, Advanced Breast Cancer. *N Engl J Med* 375, 1738-1748 (2016).

49. Gao, J. et al. Integrative analysis of complex cancer genomics and clinical profiles using the cBioPortal. *Sci Signal* 6, p11 (2013).

50. Tibshirani, R. Regression Shrinkage and Selection Via the Lasso. *Journal of the Royal Statistical Society: Series B* (*Methodological*) 58, 267-288 (1996).

51. Friedman, J. H., Hastie, T. & Tibshirani, R. Regularization Paths for Generalized Linear Models via Coordinate Descent. *Journal of Statistical Software* 33, 1-22 (2010).

52. Simon, N., Friedman, J. H., Hastie, T. & Tibshirani, R. Regularization Paths for Cox's Proportional Hazards Model via Coordinate Descent. *Journal of Statistical Software* 39, 1-13 (2011).

53. Hanzelmann, S., Castelo, R. & Guinney, J. GSVA: gene set variation analysis for microarray and RNA-Seq data. *BMC Bioinformatics* 14, 7 (2013).

54. Barbie, D. A. et al. Systematic RNA interference reveals that oncogenic KRAS-driven cancers require TBK1. *Nature* 462, 108-112 (2009).

55. Vuong, Q. H. Likelihood Ratio Tests for Model Selection and Non-Nested Hypotheses. *Econometrica* 57, 307 (1989).

56. Leek, J. T., Johnson, W. E., Parker, H. S., Jaffe, A. E. & Storey, J. D. The sva package for removing batch effects and other unwanted variation in high-throughput experiments. *Bioinformatics* 28, 882-883 (2012).

57. Liberzon, A. et al. Molecular signatures database (MSigDB) 3.0. *Bioinformatics* 27, 1739-1740 (2011).

What is claimed is:

1. A method of treating cancer in a metastatic estrogen receptor positive breast cancer subject, the method comprising:

(a) measuring an expression level of a transcriptome set of RNA transcripts in a plurality of cells obtained from a tumor from a metastatic estrogen receptor positive breast cancer subject, wherein the transcriptome set of RNA transcripts comprises RNA transcripts expressed from:

(i) an endocrine signaling negative gene set, wherein said endocrine signaling negative gene set comprises at least 5 genes selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25;

(ii) an endocrine signaling positive gene set, wherein said endocrine signaling positive gene set comprises at least 5 genes selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1; and (iii) a remainder gene set, wherein said remainder gene set consists of all genes expressing said transcriptome set of RNA transcripts except said endocrine signaling positive gene set and said endocrine signaling negative gene set;

(b) determining a first aggregate rank of the expression level of RNA transcripts from the endocrine signaling negative gene set relative to the expression level of RNA transcripts from said remainder gene set and calculating an empirical gene set enrichment score ($GES_{emp}$);

(c) determining a second aggregate rank of the expression level of RNA transcripts from an endocrine signaling positive gene set relative to the expression level of RNA transcripts from said remainder gene set and calculating an estrogen response gene set enrichment score ($GES_{er}$);

(d) calculating a risk score according to according to the function:

$$\exp(1.54 \times GES_{emp} + -2.72 \times GES_{er})$$

when said risk score is greater than or equal to 2, administering chemotherapy to said metastatic estrogen receptor positive breast cancer subject and not administering anticancer endocrine therapy to said metastatic estrogen receptor positive breast cancer subject, and when said risk score is less than 2, administering anticancer endocrine therapy to said metastatic estrogen receptor positive breast cancer subject and not administering chemotherapy to said metastatic estrogen receptor positive breast cancer subject.

2. The method of claim 1, wherein said endocrine signaling negative gene set comprises at least 10, at least 15, or at least 20 genes selected from ASF1B, CDCA8, HJURP, NCAPG, STIL, ASPM, CENPA, hNp95, NUSAP1, TACC3, AURKA, CENPE, KIF14, OIP5, AURKB, CENPF, KIF15, PKMYT1, TOP2A, BIRC5, CEP55, KIF20A, PLK1, TPX2, BUB1, CKAP2L, KIF23, PLK4, TRIP13, CCNA2, DLGAP5, KIF2C, POLQ, TROAP, CCNB2, E2F2, KIF4A, PRC1, TTK, CDC20, CDC25C, ESPL1, KIFC1, PTTG1, UBE2C, CDC25, EXO1, MCM10, PTTG3, TIMELESS, UBE2S, CDC45, FAM64A, MCM2, RACGAP1, ZWINT, CDCA3, FOXM1, MELK, RECQL4, CDCA5, GSK3B, MKI67, or SPC25.

3. The method of claim 1, wherein said endocrine signaling positive gene set comprises at least 10 genes, at least 15 genes, or at least 20 genes selected from GREB1, CA12, SLC9A3R1, MYB, ANXA9, IGFBP4, SYBU, NPY1R, PDZK1, NRIP1, MLPH, HSPB8, EGR3, KRT19, LRIG1, KDM4B, PGR, RHOBTB3, TPD52L1, ELOVL2, RET, TPBG, TFF1, MAPT, SCNN1A, ABAT, FLNB, XBP1, CELSR2, RAB31, MYBL1, MREG, FAM102A, MSMB, STC2, RETREG1, SIAH2, SLC27A2, FKBP4, CXCL12, TMPRSS3, RARA, IL17RB, CBFA2T3, TFF3, UGCG, CCND1, SLC22A5, WFS1, PTGES, WWC1, CCN5, MYC, ITPK1, TMEM164, ARL3, MED13L, SEMA3B, KRT18, SLC16A1, TJP3, SLC26A2, FCMR, SULT2B1, SNX24, TFAP2C, TTC39A, GJA1, PRSS23, OLFM1, RAPGEFL1, ASB13, TIPARP, ABCA3, PLAAT3, SLC7A5, MPPED2, TIAM1, CLDN7, MYOF, RBBP8, OLFML3, GFRA1, FARP1, SVIL, TGM2, DEPTOR, CYP26B1, PAPSS2, SLC1A1, DLC1, JAK2, AFF1, KLK10, P2RY2, BLVRB, CISH, GLA, ADD3, PDLIM3, MINDY1, FOS, KRT8, SLC37A1, B4GALT1, CALCR, ESRP2, IGF1R, NBL1, SFN, OPN3, TUBB2B, TBC1D30, SEC14L2, ENDOD1, HR, SCARB1, NCOR2, RHOD, INPP5F, PPIF, DHRS3, FDFT1, GAB2, UNC119, KLF10, HES1, FKBP5, SLC2A1, AMFR, NADSYN1, INHBB, BHLHE40, CALB2, FASN, CHPT1, MYBBP1A, ELOVL5, DYNLT3, ABLIM1, SOX3, SLC24A3, RAB17, MAST4, KCNK5, ELF1, RPS6KA2, ISG20L2, ZNF185, SLC19A2, SLC1A4, FHL2, BCL2, PMAIP1, AREG, OVOL2, TSKU, ADCY9, RASGRP1, MUC1, KAZN, FRK, DHRS2, AQP3, KCNK15, TGIF2, FOXC1, ELF3, REEP1, PEX11A, PODXL, KLF4, BAG1, CELSR1, ABHD2, AR, SLC39A6, SYT12, CD44, MED24, BCL11B, CANT1, KRT13, KRT15, TOB1, IL6ST, SYNGR1, SH3BP5, ALDH3B1, THSD4, CLIC3, NXT1, NAV2, RRP12, ADCY1, DHCR7, MICB, AKAP1, SLC7A2, or LAD1.

4. The method of claim 1, wherein measuring an expression level comprises sequencing, microarray, PCR, or a combination thereof.

5. The method of claim 1, wherein said chemotherapy comprises capecitabine, gemicitabine, vinorelbine, doxorubicin, epirubicin, paclitaxel, docetaxel, eribulin, cyclophosphamide, carboplatin, cisplatin, ixabepilone, fluorouracil, methotrexate, or a combination thereof.

6. The method of claim 1, wherein said breast cancer is a human epidermal growth factor receptor 2 negative breast cancer.

7. The method of claim 1, wherein said anticancer endocrine therapy comprises a selective estrogen receptor modulator (SERM), a selective estrogen receptor down-regulator (SERD), an aromatase inhibitor, or a combination thereof.

8. The method of claim 7, wherein said aromatase inhibitor is exemestane, anastrozole, or letrozole.

9. The method of claim 7, wherein said SERD is fulvestrant.

10. The method of claim 7, wherein said SERM is tamoxifen, raloxifene arzoxiphene, lasofoxifene, or toremifene.

11. The method of claim 1, further comprising steps of:

detecting a PI3 Kinase (PI3K) mutation in said plurality of cells, wherein said PI3K mutation is associated with a PI3K inhibitor sensitivity; and administering a PI3K inhibitor to said subject.

12. The method of claim 1, wherein the metastatic estrogen receptor positive breast cancer subject is a PI3K mutation negative subject, the method further comprising measuring the expression level of an mTor sensitivity gene.

13. The method of claim 12, further comprising administering to said metastatic estrogen receptor positive breast cancer subject an mTor inhibitor.

14. The method of claim 13, further comprising administering to said metastatic estrogen receptor positive breast cancer subject an aromatase inhibitor.

15. The method of claim 12, further comprising administering to said metastatic estrogen receptor positive breast cancer subject an aromatase inhibitor and not administering to said metastatic estrogen receptor positive breast cancer subject the mTor inhibitor.

16. The method of claim 12, further comprising applying a machine learning model to identify said metastatic estrogen receptor positive breast cancer subject as responsive to the mTor inhibitor or non-responsive to the mTor inhibitor.

* * * * *

SEQUENCE LISTING

```
<160> NUMBER OF SEQ ID NOS: 1

<210> SEQ ID NO 1
<211> LENGTH: 1068
<212> TYPE: PRT
<213> ORGANISM: Homo sapiens

<400> SEQUENCE: 1

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175
```

-continued

```
Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
```

-continued

```
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020
```

-continued

```
Lys Thr  Leu Ala Leu Asp Lys  Thr Glu Gln Glu Ala  Leu Glu Tyr
    1025                 1030                 1035

Phe Met  Lys Gln Met Asn Asp  Ala His His Gly Gly  Trp Thr Thr
    1040                 1045                 1050

Lys Met  Asp Trp Ile Phe His  Thr Ile Lys Gln His  Ala Leu Asn
    1055                 1060                 1065
```